United States Patent
Cook et al.

(10) Patent No.: US 11,231,430 B2
(45) Date of Patent: Jan. 25, 2022

(54) INSTRUMENT FOR ANALYZING BIOLOGICAL SAMPLES AND REAGENTS

(71) Applicant: Douglas Scientific, LLC, Alexandria, MN (US)

(72) Inventors: Darren Lynn Cook, Alexandria, MN (US); Eric Guy Johnson, Carlos, MN (US); Nathan Luther Westad, Miltona, MN (US); Andrew Richard Haug, Alexandria, MN (US); James Henry Konynenbelt, Fergus Falls, MN (US); Grant Edward Maasjo, Villard, MN (US); Jared Whittier Patterson, Alexandra, MN (US); Brent Conrad Urke, Alexandria, MN (US); Ryan John Zitzmann, Farwell, MN (US); Chad Steven Smith, Battle Lake, MN (US)

(73) Assignee: Douglas Scientific, LLC, Alexandria, MN (US)

( * ) Notice: Subject to any disclaimer, the term of this patent is extended or adjusted under 35 U.S.C. 154(b) by 0 days.

(21) Appl. No.: 16/799,584

(22) Filed: Feb. 24, 2020

(65) Prior Publication Data
US 2020/0191808 A1 Jun. 18, 2020

Related U.S. Application Data

(63) Continuation of application No. 15/500,481, filed as application No. PCT/US2015/042471 on Jul. 28, 2015, now Pat. No. 10,620,226.
(Continued)

(51) Int. Cl.
*G01N 35/00* (2006.01)
*G01N 35/10* (2006.01)
(Continued)

(52) U.S. Cl.
CPC ........ *G01N 35/00009* (2013.01); *B01L 3/502* (2013.01); *B01L 3/50851* (2013.01);
(Continued)

(58) Field of Classification Search
None
See application file for complete search history.

(56) References Cited

U.S. PATENT DOCUMENTS 5,055,263 A * 10/1991 Meltzer .............. G01N 35/1072
422/65
5,306,510 A * 4/1994 Meltzer .............. G01N 35/1072
422/561
(Continued)

FOREIGN PATENT DOCUMENTS

DE 3805808 A1 9/1989
JP 2008170332 A 7/2008
(Continued)

OTHER PUBLICATIONS

U.S. Patent and Trademark Office; PCT International Search Report, Issued in connection with PCT/US2015/042471; dated Jan. 5, 2016; 6 pages.
(Continued)

*Primary Examiner* — Brian R Gordon
(74) *Attorney, Agent, or Firm* — Greenberg Traurig, LLP

(57) ABSTRACT

An instrument for processing a biological sample includes a chassis. Connected to the chassis is a tape path along which a tape with a matrix of wells can be automatically advanced through the instrument, a dispensing assembly for dispensing the biological sample and a reagent into the matrix of wells of the tape to form a biological sample and reagent mixture, a sealing assembly for sealing the biological sample and reagent mixture in the tape, and an amplification and detection assembly for detecting a signal from the
(Continued)

biological sample and reagent mixture in the matrix of wells in the tape.

6 Claims, 113 Drawing Sheets

Related U.S. Application Data

(60) Provisional application No. 62/029,965, filed on Jul. 28, 2014, provisional application No. 62/029,959, filed on Jul. 28, 2014, provisional application No. 62/029,968, filed on Jul. 28, 2014, provisional application No. 62/029,961, filed on Jul. 28, 2014, provisional application No. 62/029,953, filed on Jul. 28, 2014, provisional application No. 62/029,954, filed on Jul. 28, 2014.

(51) Int. Cl.
*G01N 35/04* (2006.01)
*B01L 7/00* (2006.01)
*B01L 3/00* (2006.01)
*C12Q 1/686* (2018.01)

(52) U.S. Cl.
CPC ........... *B01L 7/52* (2013.01); *C12Q 1/686* (2013.01); *G01N 35/00029* (2013.01); *G01N 35/0099* (2013.01); *G01N 35/04* (2013.01); *G01N 35/10* (2013.01); *G01N 35/1004* (2013.01); *G01N 35/1065* (2013.01); *B01L 2200/0605* (2013.01); *B01L 2200/0689* (2013.01); *B01L 2200/14* (2013.01); *B01L 2300/021* (2013.01); *B01L 2300/0627* (2013.01); *B01L 2300/0812* (2013.01); *B01L 2300/0887* (2013.01); *B01L 2300/123* (2013.01); *B01L 2300/14* (2013.01); *B01L 2300/1827* (2013.01); *G01N 2035/00148* (2013.01); *G01N 2035/00346* (2013.01); *G01N 2035/00366* (2013.01); *G01N 2035/00376* (2013.01); *G01N 2035/00445* (2013.01); *G01N 2035/0405* (2013.01); *G01N 2035/0422* (2013.01); *G01N 2035/0425* (2013.01); *G01N 2035/0465* (2013.01)

(56) References Cited

U.S. PATENT DOCUMENTS

| | | | |
|---|---|---|---|
| 5,670,120 A | 9/1997 | Degenhardt et al. | |
| 6,207,031 B1* | 3/2001 | Adourian | B01L 3/0275 204/450 |
| 6,234,033 B1* | 5/2001 | Eipel | G01N 35/1011 422/417 |
| 6,589,483 B1* | 7/2003 | Maeda | B01L 3/0217 222/249 |
| 6,605,257 B1* | 8/2003 | Nakazawa | B01J 19/0046 141/21 |
| 6,632,653 B1 | 10/2003 | Astle | |
| 6,878,345 B1 | 4/2005 | Astle | |
| 6,979,425 B1* | 12/2005 | Ganz | B01J 19/0046 141/129 |
| 7,025,933 B2 | 4/2006 | Ganz et al. | |
| 7,288,228 B2* | 10/2007 | Lefebvre | G01N 30/24 422/509 |
| 7,662,339 B2* | 2/2010 | Mattila | B25J 9/023 422/67 |
| 7,790,462 B2* | 9/2010 | Fournier | B01L 9/523 436/47 |
| 8,007,741 B1* | 8/2011 | Heyes | G01N 35/0099 422/511 |
| 9,623,405 B2* | 4/2017 | Nichols | G01N 35/1065 |
| 10,173,218 B2 | 1/2019 | Peterson | |
| 2003/0026732 A1 | 2/2003 | Gordon et al. | |
| 2003/0232967 A1* | 12/2003 | Chait | C30B 29/58 506/12 |
| 2004/0042339 A1 | 3/2004 | Gebrian et al. | |
| 2004/0062686 A1* | 4/2004 | Ganz | G01N 35/1074 506/32 |
| 2004/0071599 A1 | 4/2004 | Rusch et al. | |
| 2004/0096360 A1* | 5/2004 | Toi | G01N 35/1067 422/63 |
| 2004/0157318 A1* | 8/2004 | Kuhn | B82Y 30/00 435/287.1 |
| 2005/0058577 A1* | 3/2005 | Micklash, II | B01L 3/021 422/400 |
| 2006/0002824 A1* | 1/2006 | Chang | B01L 3/0293 422/400 |
| 2006/0093530 A1 | 5/2006 | Ueda | |
| 2006/0189890 A1* | 8/2006 | Gooley | G01N 35/1016 600/562 |
| 2007/0053797 A1* | 3/2007 | Muraishi | B01L 3/021 422/400 |
| 2007/0178513 A1* | 8/2007 | Akai | C12Q 2527/127 435/6.14 |
| 2007/0184546 A1 | 8/2007 | Farrelly et al. | |
| 2007/0281359 A1* | 12/2007 | Chait | G01N 35/028 436/43 |
| 2007/0287157 A1* | 12/2007 | Nakabayashi | G01N 35/0099 435/6.14 |
| 2007/0295113 A1* | 12/2007 | Londo | G01N 35/1065 73/864.34 |
| 2008/0026483 A1 | 1/2008 | Oldenburg | |
| 2008/0156118 A1* | 7/2008 | Takaya | G01N 35/10 73/864.14 |
| 2008/0240898 A1* | 10/2008 | Manz | B25J 9/023 414/680 |
| 2009/0155123 A1* | 6/2009 | Williams | F16K 99/0001 422/65 |
| 2009/0176661 A1 | 7/2009 | Harding et al. | |
| 2009/0180931 A1* | 7/2009 | Silbert | B01L 3/0244 422/63 |
| 2010/0137165 A1* | 6/2010 | Tajima | G01N 35/0098 506/32 |
| 2010/0203573 A1 | 8/2010 | Heinonen et al. | |
| 2011/0166031 A1 | 7/2011 | Schoeneck | |
| 2011/0174435 A1 | 7/2011 | Peterson | |
| 2011/0183371 A1* | 7/2011 | Noda | C12Q 1/008 435/39 |
| 2012/0100047 A1* | 4/2012 | Brutler | G01N 35/1074 422/511 |
| 2012/0186367 A1* | 7/2012 | D'Amore | G01N 35/1016 73/864.11 |
| 2012/0195811 A1* | 8/2012 | Nelson | G01N 35/1067 422/522 |
| 2012/0211026 A1* | 8/2012 | Schoeneck | G01N 35/1004 134/10 |
| 2012/0295249 A1 | 11/2012 | Cherubini et al. | |
| 2013/0108521 A1* | 5/2013 | Ikushima | B05B 15/55 422/509 |
| 2013/0123089 A1* | 5/2013 | Johns | B65G 47/28 494/37 |
| 2013/0130369 A1* | 5/2013 | Wilson | G01N 35/1011 435/289.1 |
| 2013/0143199 A1 | 6/2013 | Wilson et al. | |
| 2013/0217105 A1 | 8/2013 | Spence et al. | |
| 2013/0243654 A1 | 9/2013 | Davis et al. | |
| 2013/0280145 A1* | 10/2013 | West | G01N 35/1065 422/509 |
| 2014/0050637 A1* | 2/2014 | Giovanoli | G01N 1/286 422/551 |
| 2014/0112839 A1* | 4/2014 | Richardson | G01N 35/1065 422/511 |
| 2014/0193826 A1* | 7/2014 | Gajewski | G01N 35/028 435/6.12 |
| 2014/0311090 A1* | 10/2014 | Weber | B25J 15/12 53/381.4 |

(56) References Cited

U.S. PATENT DOCUMENTS

| | | | |
|---|---|---|---|
| 2015/0044111 A1* | 2/2015 | Peetz | B01L 9/543 |
| | | | 422/511 |
| 2015/0210437 A1* | 7/2015 | Tajima | B01L 3/0275 |
| | | | 222/1 |
| 2015/0300931 A1* | 10/2015 | Dockrill | G01N 35/0099 |
| | | | 435/30 |
| 2016/0023213 A1* | 1/2016 | Richardson | G01N 35/109 |
| | | | 414/589 |
| 2017/0128932 A1* | 5/2017 | Ito | G01N 35/1081 |
| 2017/0253914 A1* | 9/2017 | Du | B01L 3/021 |
| 2017/0328928 A1* | 11/2017 | Brennen | G01N 35/1074 |
| 2018/0154349 A1* | 6/2018 | Habbal | B01L 3/0227 |
| 2018/0246134 A1* | 8/2018 | LaChance | B01L 3/021 |

FOREIGN PATENT DOCUMENTS

| | | |
|---|---|---|
| WO | 97/22882 | 6/1997 |
| WO | 2014110494 A1 | 7/2014 |
| WO | 2014179584 A1 | 11/2014 |
| WO | 2016018910 A1 | 2/2016 |

OTHER PUBLICATIONS

U.S. Patent and Trademark Office; PCT Written Opinion of the International Searching Authority, Issued in connection with PCT/US2015/042471; dated Jan. 5, 2016; 22 pages.

European Patent Office, Extended European Search Report for European Patent Application No. 20173320.1, dated Jul. 22, 2020, 13 pages.

\* cited by examiner

INSTRUMENT FOR ANALYZING BIOLOGICAL SAMPLES AND REAGENTS

CROSS-REFERENCE TO RELATED APPLICATIONS

This application is a continuation of U.S. application Ser. No. 15/500,481, filed Jan. 30, 2017, entitled "Instrument for Analyzing Biological Samples and Reagents", which claims priority to International Application No. PCT/US2015/042471, filed Jul. 28, 2015, entitled "Instrument for Analyzing Biological Samples and Reagents", which claims the benefit of and priority to U.S. Provisional Application No. 62/029,954, filed Jul. 28, 2014, U.S. Provisional Application No. 62/029,959, filed Jul. 28, 2014, U.S. Provisional Application No. 62/029,965, filed Jul. 28, 2014, U.S. Provisional Application No. 62/029,968, filed Jul. 28, 2014, U.S. Provisional Application No. 62/029,953, filed Jul. 28, 2014, and U.S. Provisional Application No. 62/029,961, filed Jul. 28, 2014, the entire contents of which are incorporated herein by reference.

BACKGROUND

The present invention relates to an instrument for analyzing biological samples, and in particular, to an all-in-one instrument that is capable of dispensing, amplifying, and analyzing biological samples.

A biological sample and reagent mixture can undergo amplification and analysis to detect the presence of an analyte in the mixture. Historically, biological sample and reagent mixtures were amplified and analyzed for research applications, including DNA sequencing, gene mapping, and DNA cloning, among other things. Biological sample and reagent mixture amplification and analysis is becoming increasingly popular and innovative uses are constantly being discovered, including medical applications, infectious disease applications, and forensic applications. With the increase in popularity of biological sample and reagent mixture amplification and analysis comes a need for more advanced equipment.

Equipment that is currently available to prepare, amplify, and analyze a biological sample and reagent mixture includes laboratory equipment, handheld devices, and lab-on-a-chip devices. Handheld devices and lab-on-a-chip devices are not capable of testing a large number of biological sample and reagent mixtures at the same time, thus making them unsuitable for many applications. To amplify and analyze a large number of biological sample and reagent mixtures, laboratory equipment must be used. Laboratory equipment typically involves many separate pieces of equipment, where each piece of equipment is used for a different purpose. For instance, a first piece of equipment can be used to prepare the biological sample and reagent mixture, a second piece of equipment can be used to amplify the biological sample and reagent mixture, and a third piece of equipment can be used to analyze the biological sample and reagent mixture. The different pieces of equipment take up a lot of space in laboratories and it can be costly to acquire all of the equipment needed to prepare, amplify, and analyze the biological sample and reagent mixture. Further, the amount of biological sample and the amount of reagent needed to analyze the biological sample and reagent mixture using existing laboratory equipment can be expensive due to the cost of acquiring the biological sample and the reagent.

SUMMARY

An instrument for processing a biological sample includes a chassis. Connected to the chassis is a tape path along which a tape with a matrix of wells can be automatically advanced through the instrument, a dispensing assembly for dispensing the biological sample and a reagent into the matrix of wells of the tape to form a biological sample and reagent mixture, a sealing assembly for sealing the biological sample and reagent mixture in the tape, and an amplification and detection assembly for detecting a signal from the biological sample and reagent mixture in the matrix of wells in the tape.

An instrument for amplifying and analyzing a biological sample and a reagent includes a path extending through the device for advancing a tape containing a plurality of wells through the instrument. Positioned along the path and downstream of an entrance to the path is a dispensing and sealing station with a dispensing assembly positioned adjacent to the dispensing and sealing station to dispense a biological sample and a reagent into the plurality of wells in the tape to form a biological sample and reagent mixture, and a tape sealing assembly positioned adjacent to the dispensing and sealing station to seal the biological sample and reagent mixture in the plurality of wells in the tape. Positioned along the path and downstream of the dispensing and sealing station is a holding station with a thermal unit positioned below the holding station to heat or cool the biological sample and reagent mixture in the plurality of wells in the tape. Positioned along the path and downstream of the holding station is an amplification and detection station with a thermal unit to amplify the biological sample and reagent mixture, and a detection unit to detect a signal from the biological sample and reagent mixture.

An instrument for amplifying and detecting a biological sample includes a plate rack that is capable of holding one or more plates; a plate stacker to lift a plate out of the plate rack; a plate shuttle with a platform on which the plate stacker can place the plate from the plate rack, wherein the plate shuttle can position the platform for aspirating or dispensing; a plate deck on which a plate can be placed; a dispensing assembly with a first plurality of tips and a second plurality of tips, wherein the dispensing assembly can dispense a biological sample and a reagent into the plurality of wells on the tape to form a biological sample and reagent mixture; a path extending through the instrument along which the tape is advanced through the instrument; a tape sealer that seals the plurality of wells in the tape; a thermal unit that heats the biological sample and reagent mixture in the plurality of wells in the tape; a heated pressure chamber that pressurizes an area over the tape; and a detection device that detects a signal from the biological sample and reagent mixture in the plurality of wells in the tape.

An instrument for processing a biological sample includes a tape with a plurality of wells, wherein the tape has a first matrix of wells and a second matrix of wells offset from and interlaced with the first matrix of wells. The instrument also includes a tape path extending through the instrument along which the tape with the plurality of wells can be automatically advanced. The instrument further includes a dispensing assembly for dispensing the biological sample and a reagent into the plurality of wells of the tape, wherein the dispensing assembly can dispense the biological sample or the reagent into the first matrix of wells and reposition to dispense the biological sample or the reagent into the second matrix of wells.

A method of analyzing a biological sample and reagent mixture in an instrument includes automatically advancing a tape with a matrix of wells to a first position on a tape path in the instrument using a tape infeed and a drive mechanism positioned along the tape path; automatically advancing the tape to a second position on the tape path in the instrument using the drive mechanism positioned along the tape path; dispensing a biological sample into the matrix of wells in the tape with a dispensing assembly when the tape is positioned at the second position of the tape path; dispensing a reagent into the matrix of wells in the tape with a dispensing assembly when the tape is positioned at the second position of the tape path, wherein a biological sample and reagent mixture is formed; sealing a seal over the matrix of wells in the tape with a tape sealer when the tape is positioned at the second position; automatically advancing the tape to a third position on the tape path in the instrument using the drive mechanism positioned along the tape path; automatically advancing the tape to a fourth position on the tape path in the instrument using the drive mechanism positioned along the tape path; amplifying the biological sample and reagent mixture at the fourth position of the tape path; and detecting a signal from the biological sample and reagent mixture using a camera positioned above the fourth position of the tape path.

A tape path assembly for an instrument for processing a biological sample includes a tape path having a front end, a back end, a first position downstream of the front end, a second position downstream of the first position, a third position downstream of the second position, and a fourth position between the third position and the back end. The tape path assembly also includes a tape infeed attached to the front end that automatically advances a tape with a matrix of wells to the first position of the tape path, and a drive mechanism that advances the tape along the tape path.

An instrument for processing a biological sample includes a tape path along which a tape with a matrix of wells can be automatically advanced through the instrument; a dispensing system for dispensing the biological sample and a reagent into the matrix of wells of the tape to form a biological sample and reagent mixture; a sealing system for sealing the biological sample and reagent mixture in the tape; and an amplification and detection system for detecting a signal from the biological sample in the matrix of wells in the tape, wherein the amplification and detection system includes a thermal unit positioned on the tape path that is capable of controlling the temperature of the biological sample and reagent mixture in the matrix of wells of the tape.

An apparatus for heating a plurality of wells of a tape includes a first layer with cavities that are capable of receiving wells of a tape, a second layer attached to a bottom side of the first layer, and a heat pump positioned on a bottom side of the second layer, wherein the heat pump is positioned so that heat can be exchanged between the heat pump and a biological sample and reagent mixture in the wells on the tape through the second layer and the first layer.

An apparatus includes a tape with a matrix of wells, a thermal unit positioned below the tape with a matrix of wells, and a chamber positioned on top of the tape with a matrix of wells. The chamber includes a housing and a glass cover plate, wherein the housing and the glass cover plate form an enclosed space above the matrix of wells of the tape.

An instrument for processing a biological sample includes a tape path along which a tape with a matrix of wells can be automatically advanced through the instrument. The instrument further includes a plate stacker with an arm that can rotate around and move vertically on a z-axis. The arm is configured to pick a plate out of a plate rack and place the plate on a plate shuttle. The instrument further includes a dispensing system for dispensing the biological sample and a reagent into the matrix of wells of the tape to form a biological sample and reagent mixture, a sealing system for sealing the biological sample and reagent mixture in the tape, and an amplification and detection system for detecting a signal from the biological sample and reagent mixture in the matrix of wells in the tape.

A plate stacker assembly includes a plate rack that includes a plurality of nests attached to a frame, wherein each of the plurality of nests has a plurality of corner supports that are capable of supporting a plate. The plate stacker assembly also includes a plate shuttle that includes a nest attached to a support structure, wherein the nest has a plurality of corner supports that are capable of supporting one plate. The plate stacker assembly further includes a spatula that is capable of picking a plate off of one of the plurality of nests in the plate stacker and placing it on the nest in the plate shuttle, wherein the spatula has a support member that is capable of supporting a plate and notches is each corner of the support member that correspond to the location of the corner supports on the nests in the plate stacker and the plate shuttle.

A method for moving a plate in an instrument includes picking a plate off of a nest of a plate rack using a spatula attached to an arm of a plate stacker; rotating the arm of the plate stacker around a z-axis; moving the arm of the plate stacker in a vertical direction along the z-axis; and placing the plate on a nest of a plate shuttle.

A tape sealing assembly includes a spool holder for holding a seal web, a peel plate located downstream of the spool holder, and a backer take-up mechanism downstream of the peel plate for advancing the seal web across the peel plate. The tape sealing assembly also includes an applicator positioned above the peel plate for peeling a seal from a backer of the seal web and applying the seal to a surface.

A dispensing assembly includes a gantry with an x-axis track and a y-axis track. The y-axis track of the gantry is configured to move along the x-axis track of the gantry. The dispensing assembly further includes a dispensing head attached to the y-axis track of the gantry below the y-axis track of the gantry. The dispensing head includes a contact dispensing unit and a non-contact dispensing unit with a jet tip for dispensing a liquid. The dispensing assembly further includes a dispensing enclosure attached to the y-axis track of the gantry on top of the y-axis track of the gantry. The dispensing enclosure includes a pressure reservoir. A tube connects the jet tip of the non-contact dispensing unit to the pressure reservoir of the dispensing enclosure. The contact dispensing unit is attached to the y-axis track of the gantry with a first z-axis track, and the non-contact dispensing unit is attached to the contact dispensing unit with a second z-axis track.

A method of operating a dispensing assembly includes moving a dispensing head along an x-axis track and a y-axis track of a gantry into a first aspiration position, aspirating a first liquid with a pipette tip of a contact dispensing unit of the dispensing head, moving the dispensing head along the x-axis track and the y-axis track of the gantry into a second aspiration position, aspirating a second liquid with a jet tip of a non-contact dispensing unit of the dispensing head, moving the dispensing head along the x-axis track and the y-axis track of the gantry into a first dispensing position, dispensing the first liquid into a well of a tape with a matrix of wells with the pipette tip of the contact dispensing unit, moving the dispensing head along the x-axis track and the y-axis track of the gantry into a second dispensing position, and dispensing the second liquid into a well of the tape with a matrix of wells with the jet tip of the non-contact dispensing unit. The contact dispensing unit of the dispensing head extends and retracts along a first z-axis track connected to the y-axis track of the gantry, and the non-contact dispensing unit of the dispensing head extends and retracts along a second z-axis track connected to the contact dispensing unit.

Plate Stacker Assembly

Figure 5A:
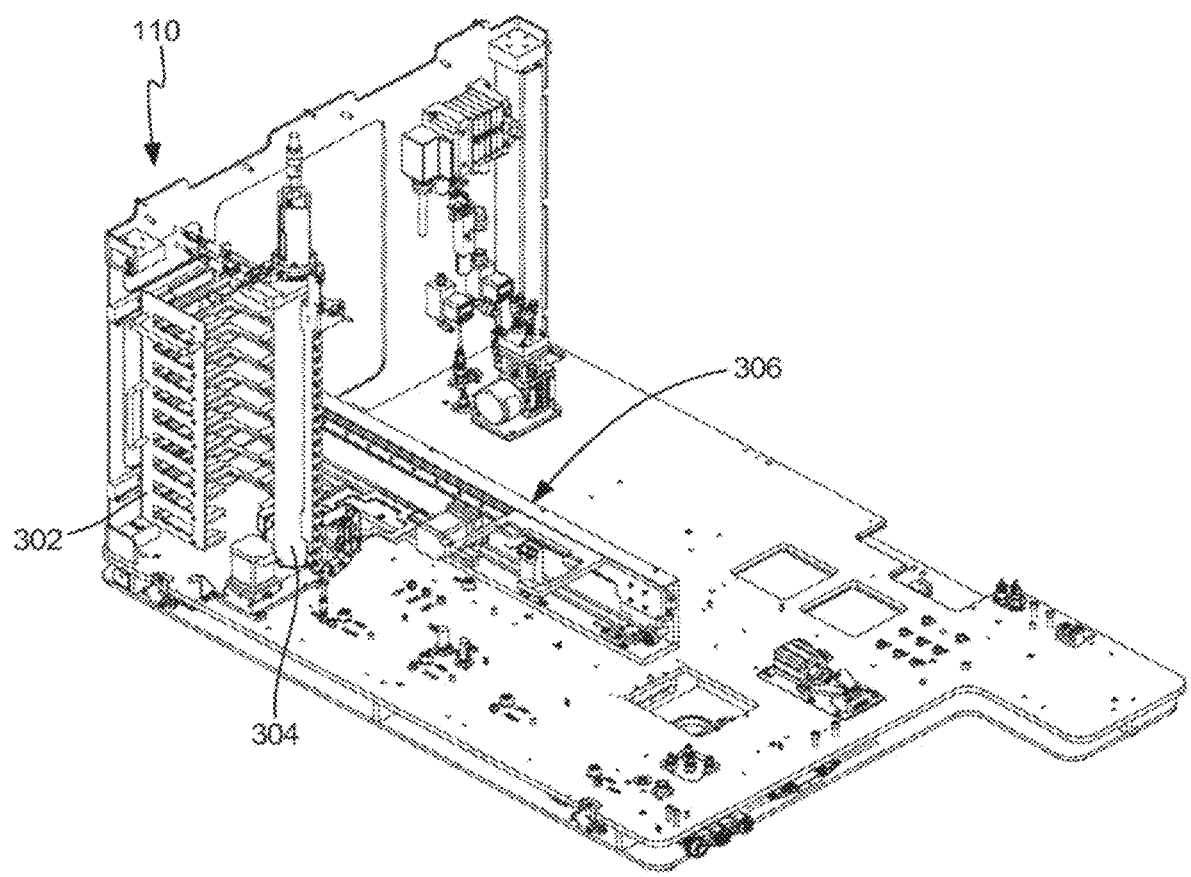

FIG. 5A is an isometric view of a plate stacker assembly in the instrument.

Figure 5B:
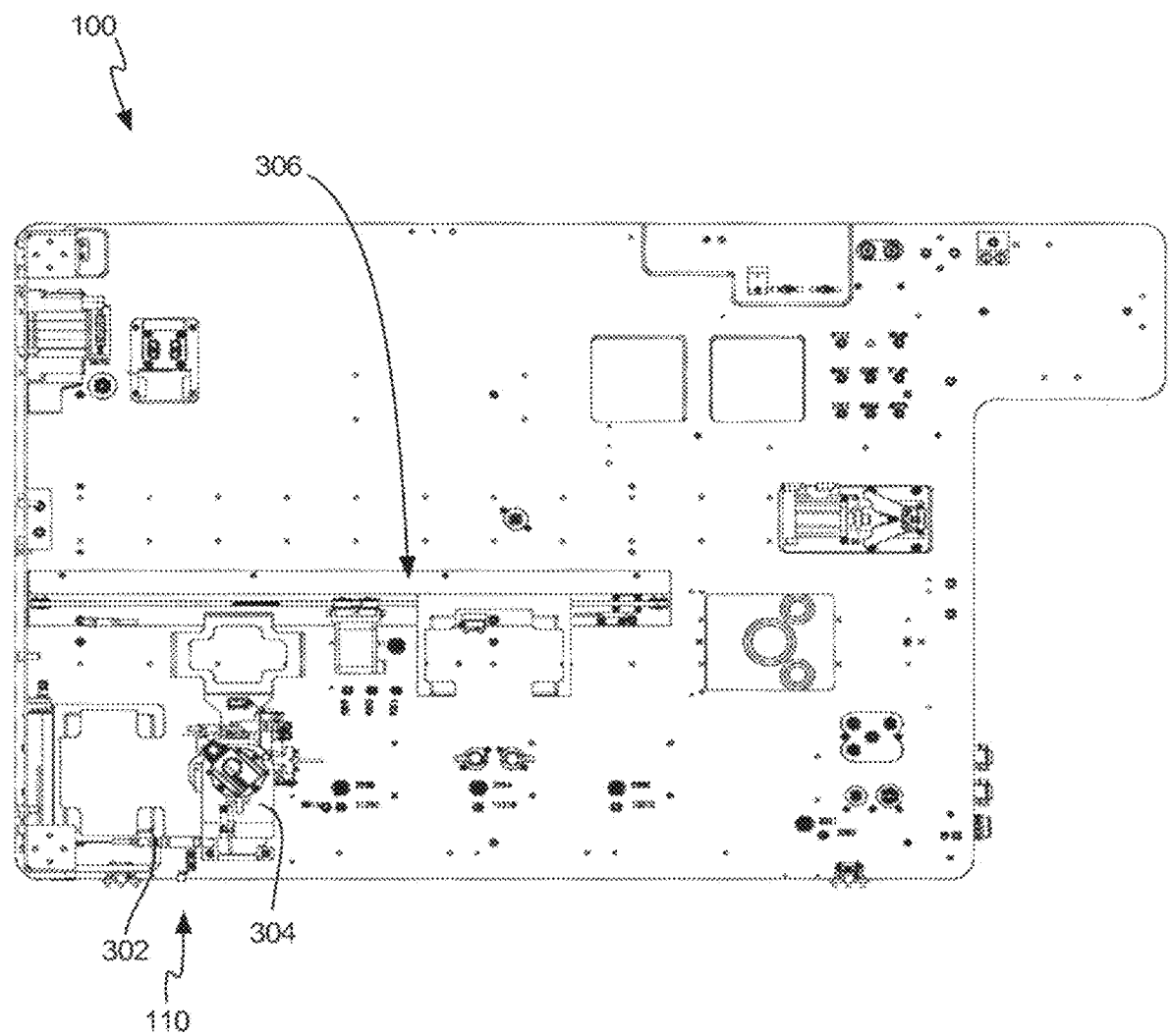

FIG. 5B is a top cut away view of the plate stacker assembly in the instrument.

Figure 5C:
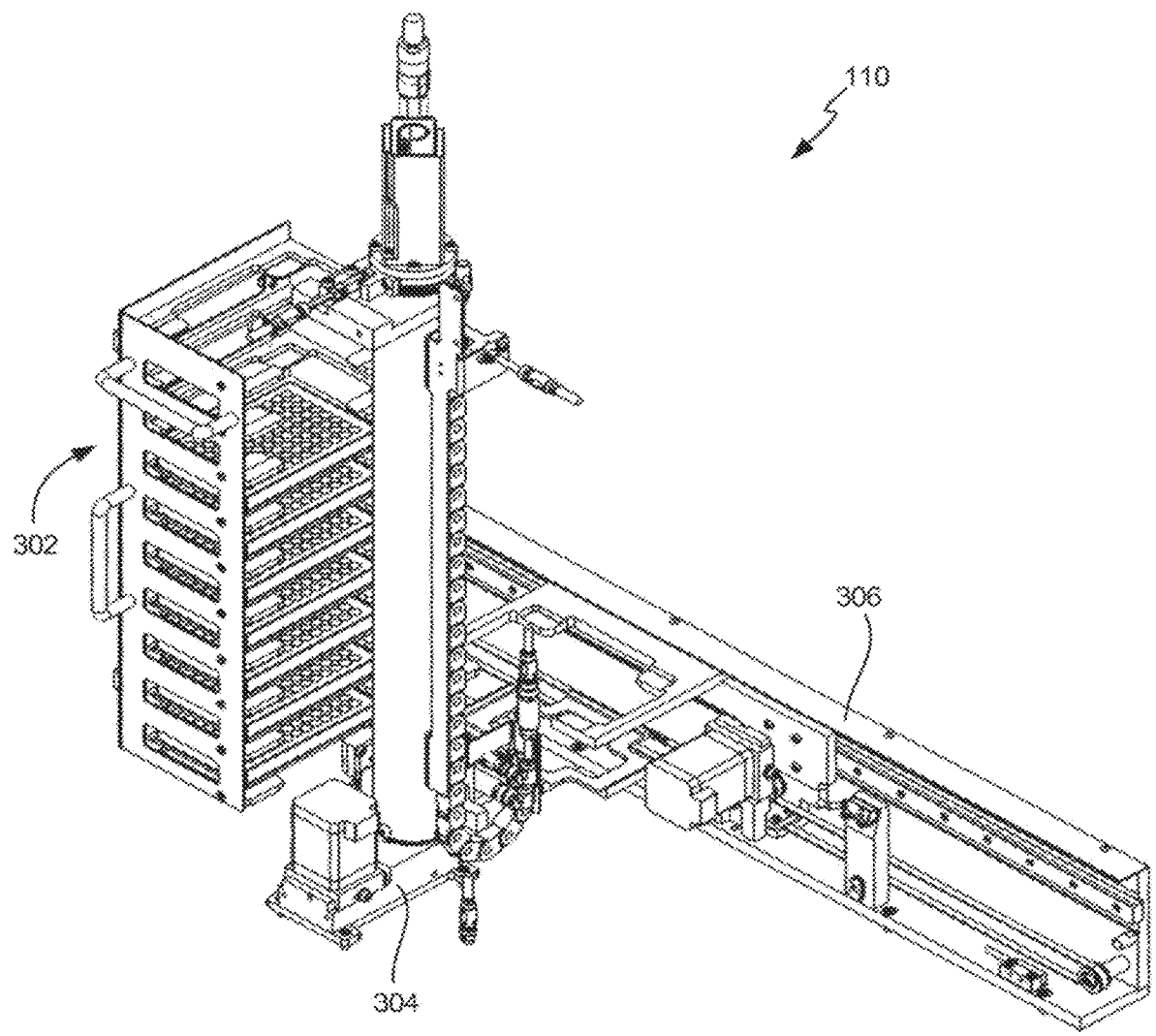

FIG. 5C is an isometric view of the plate stacker assembly.

Figure 6A:
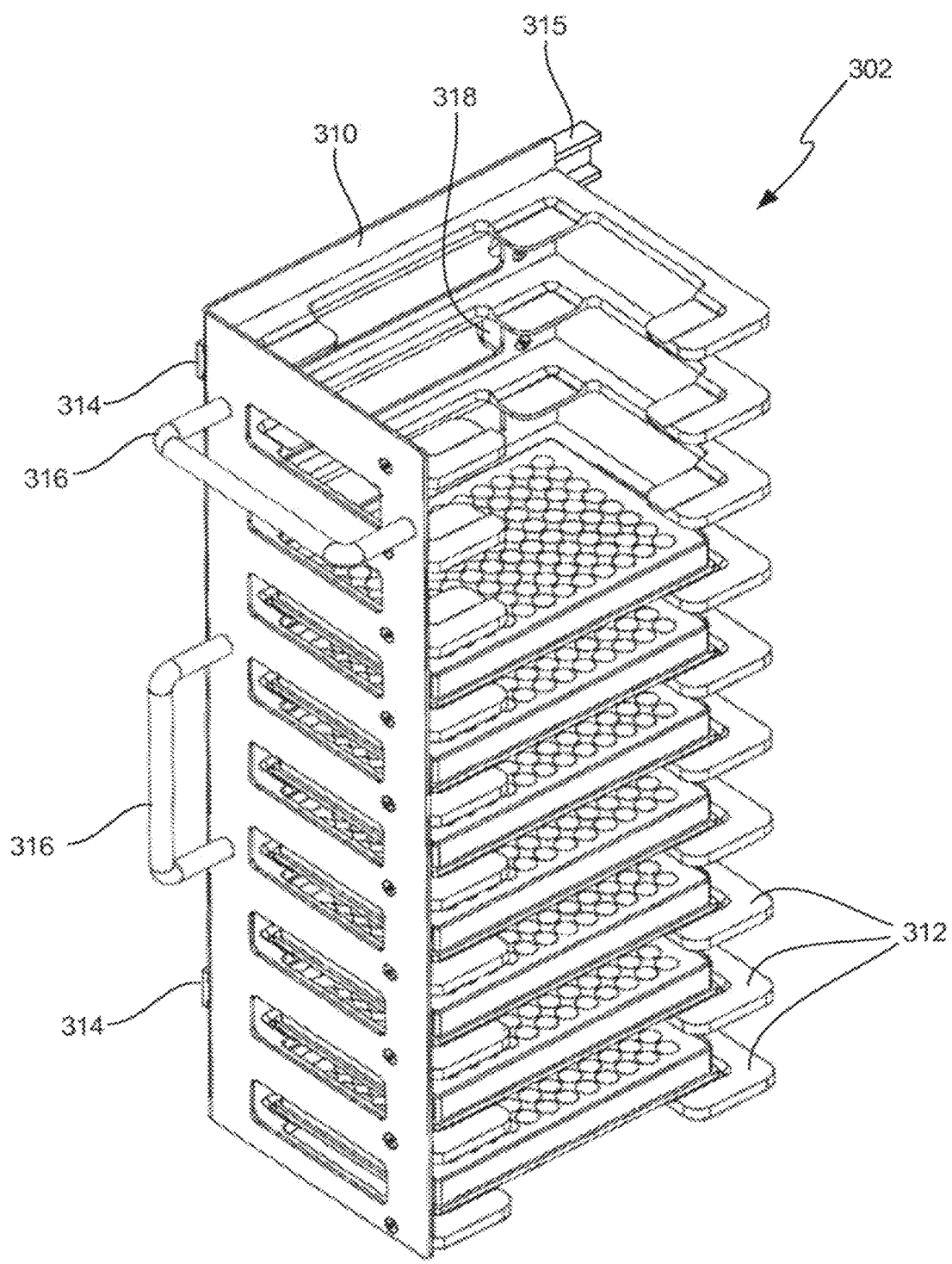

FIG. 6A is an isometric view of a plate rack.

Figure 6B:
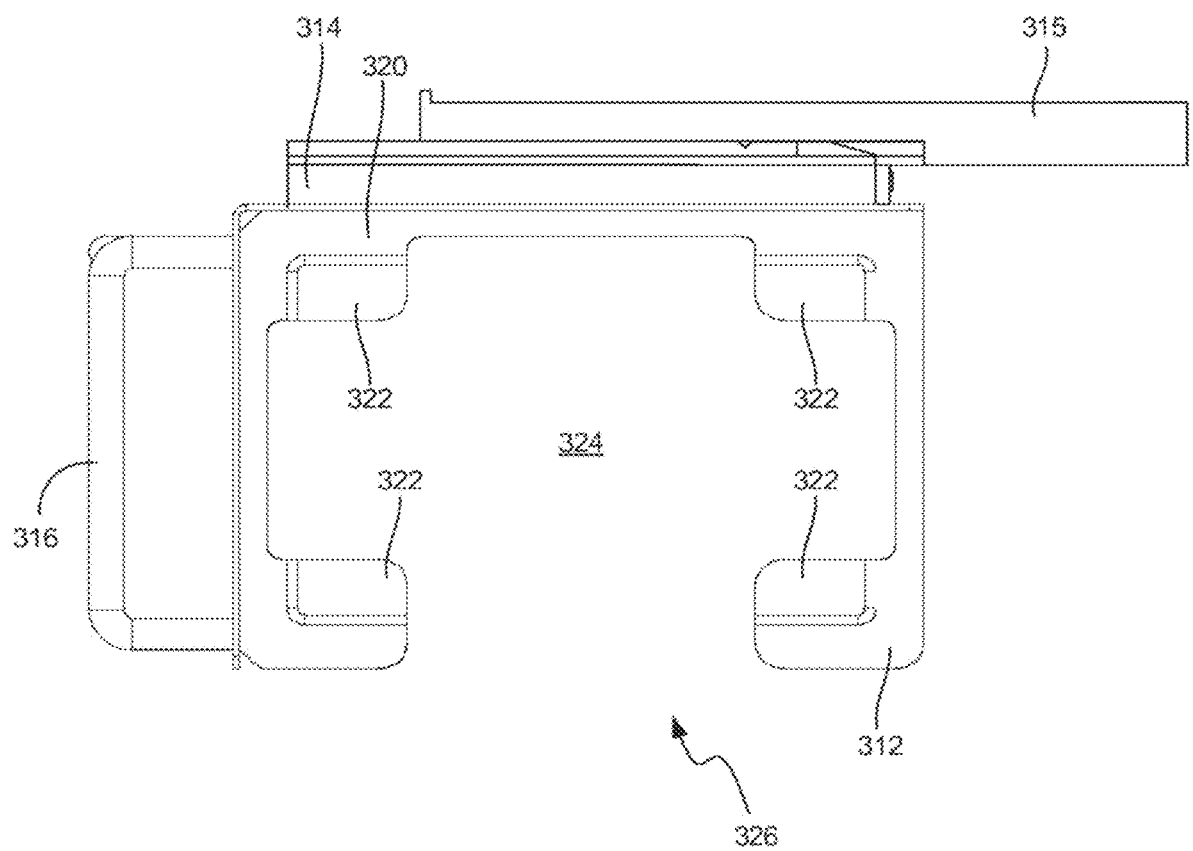

FIG. 6B is a top plan view of a nest of the plate rack.

Figure 7A:
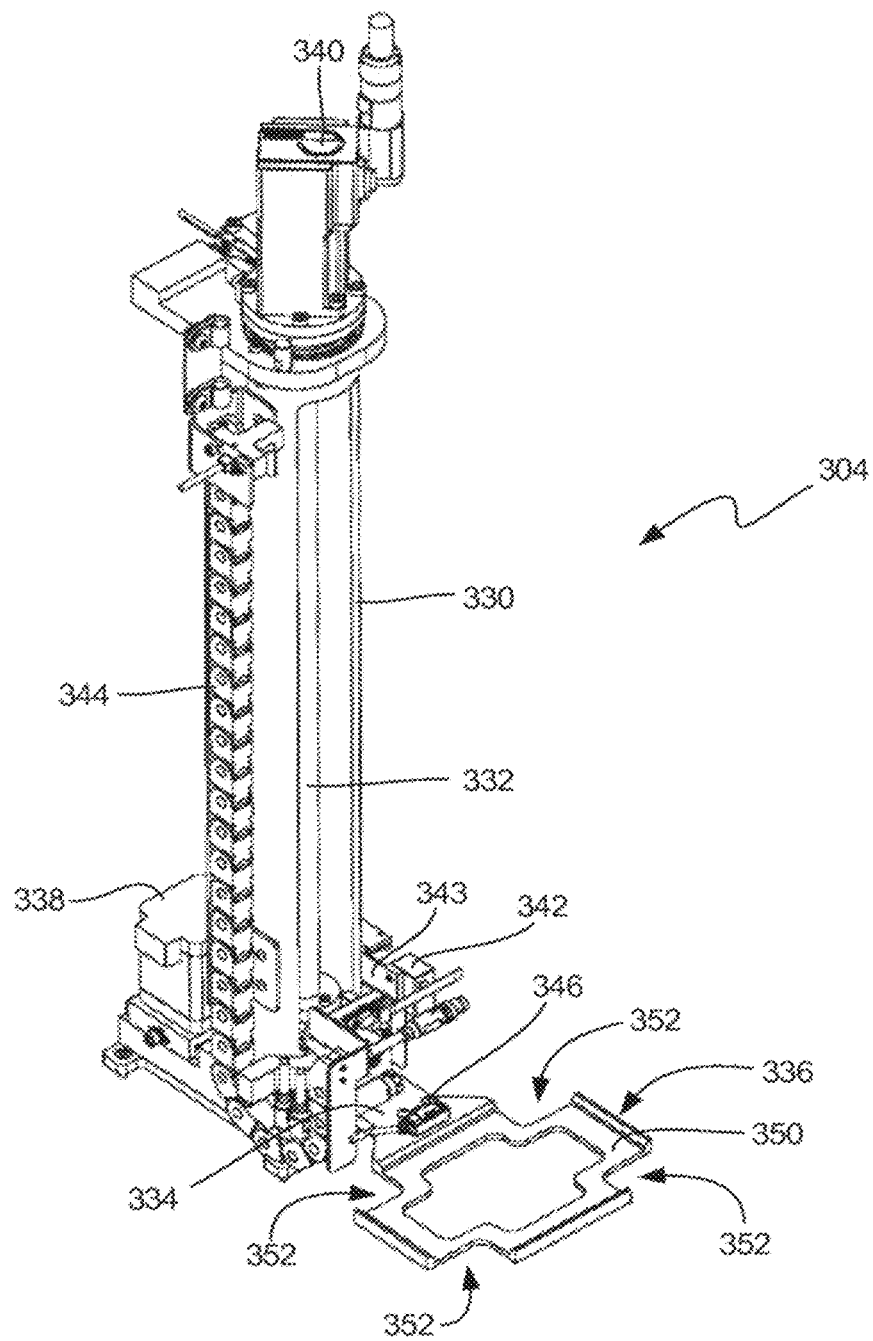

FIG. 7A is a perspective view of a plate stacker.

Figure 7B:
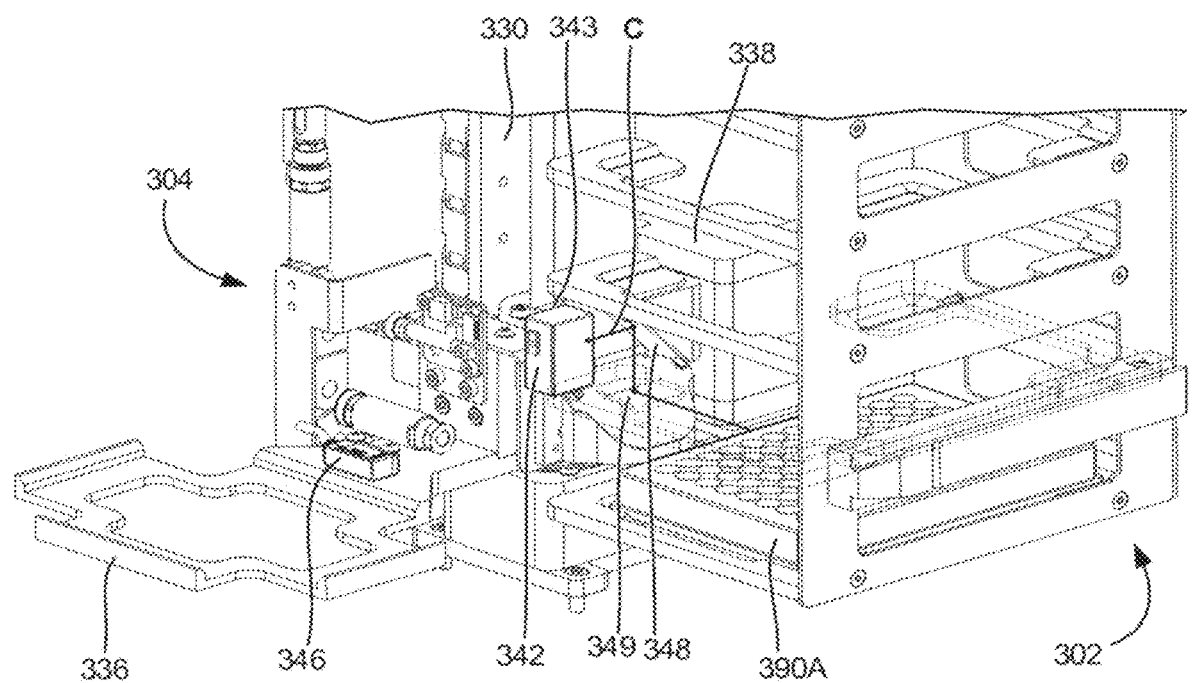

FIG. 7B is a perspective view of a portion of the plate stacker and a portion of the plate rack.

7C is an isometric view of a portion of the plate stacker seen in FIG. 7A.

Figure 8A:
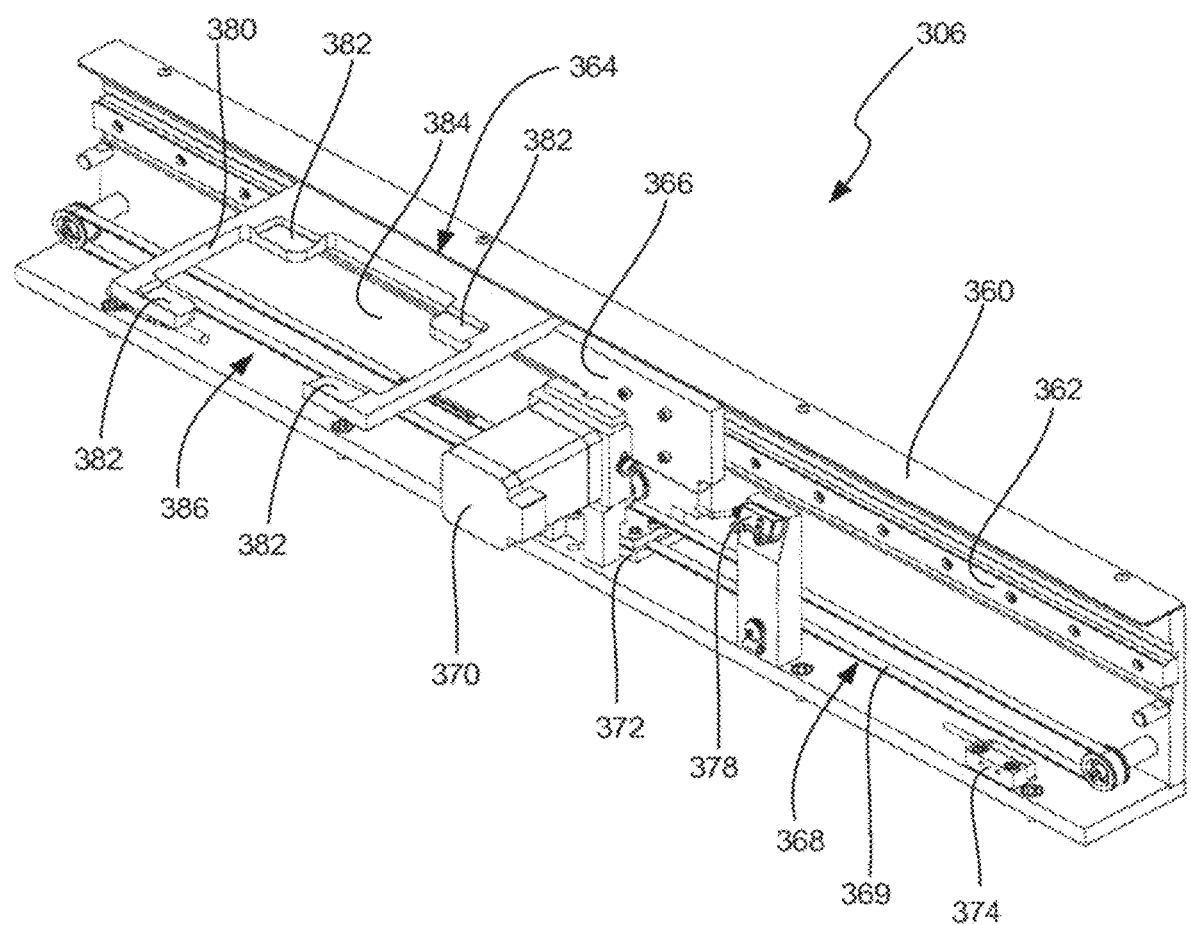

FIG. 8A is an isometric view of a plate shuttle.

Figure 8B:
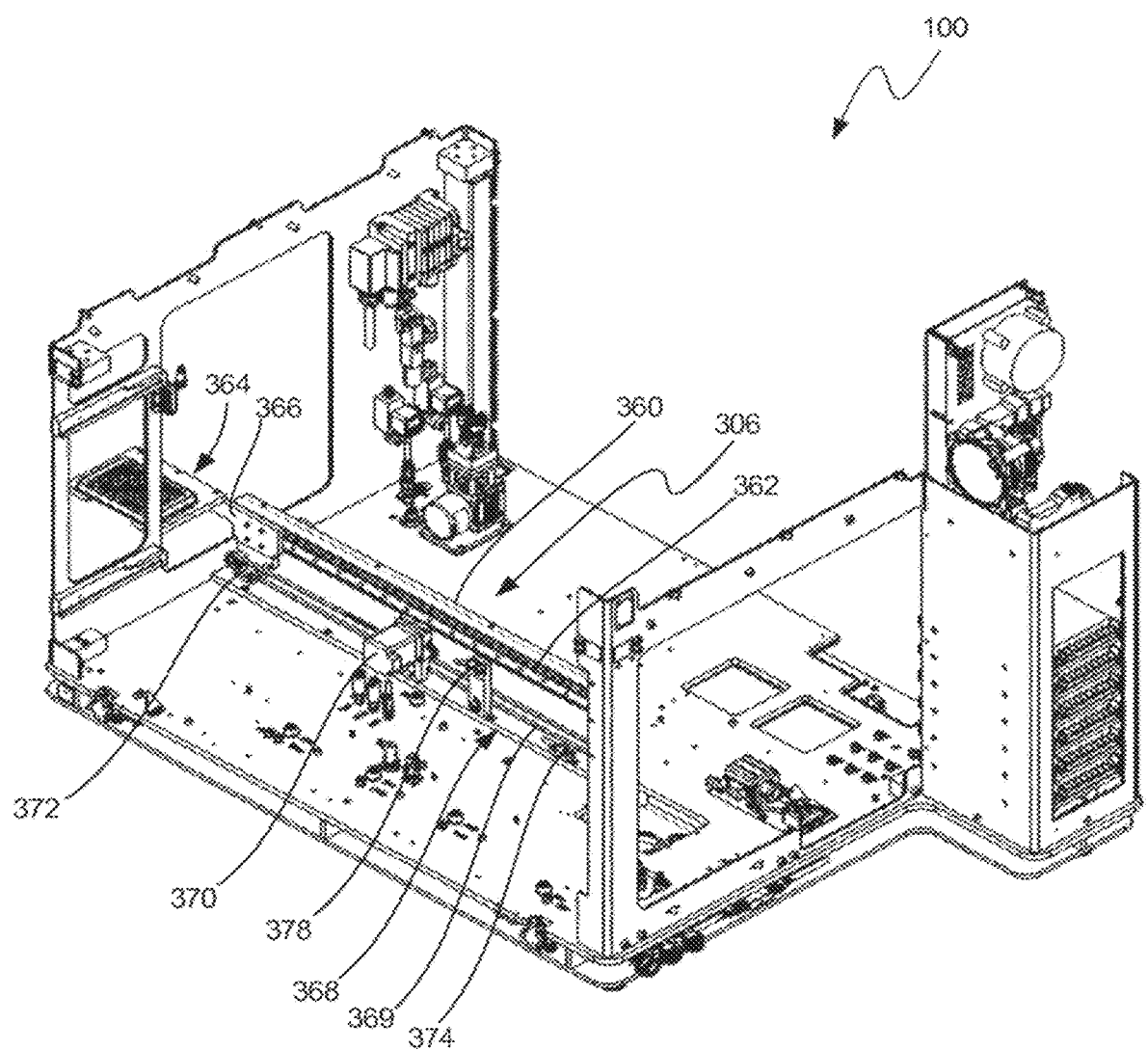

FIG. 8B is an isometric view of a plate shuttle in the instrument.

Figure 9A:
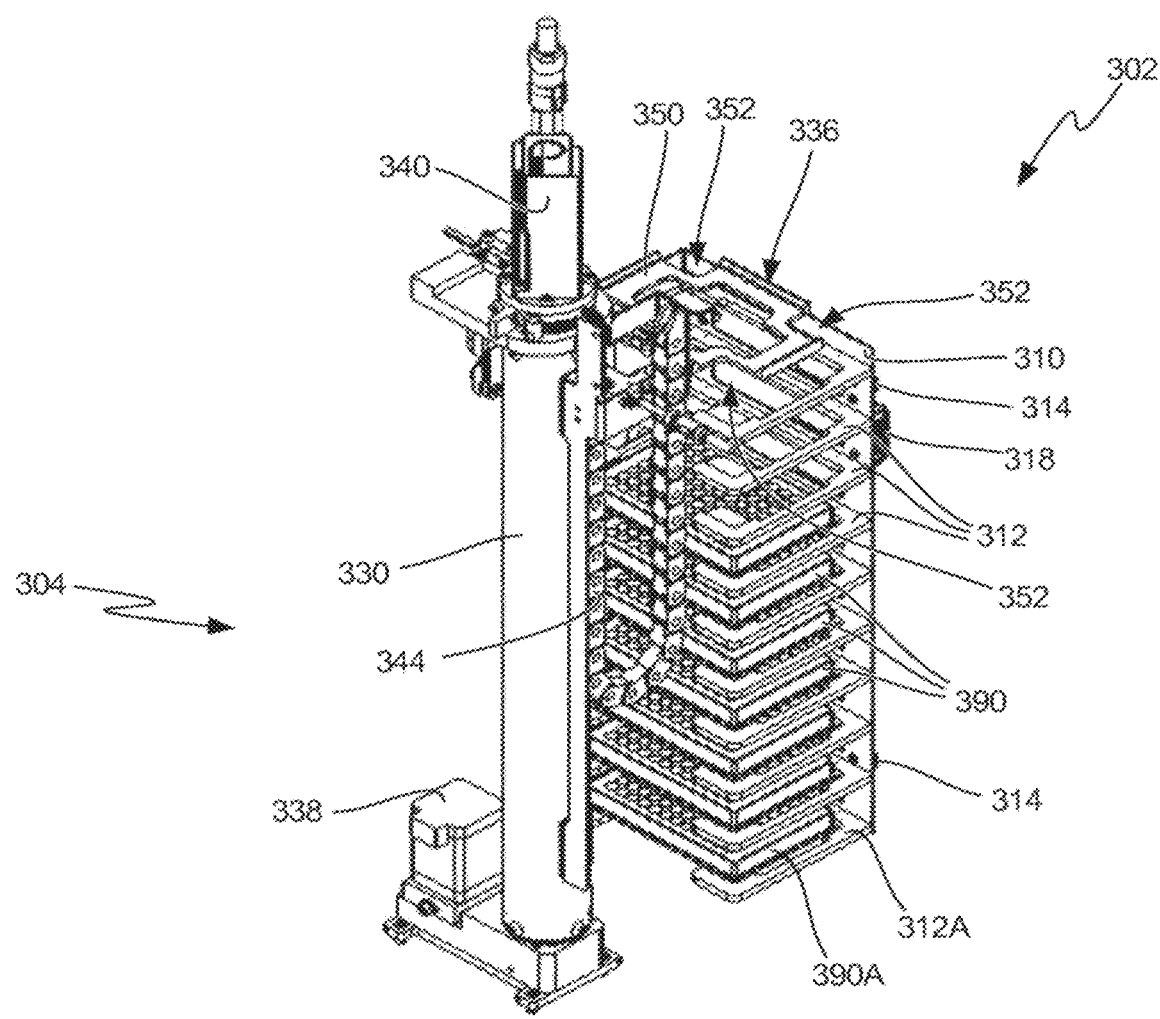
Figure 9B:
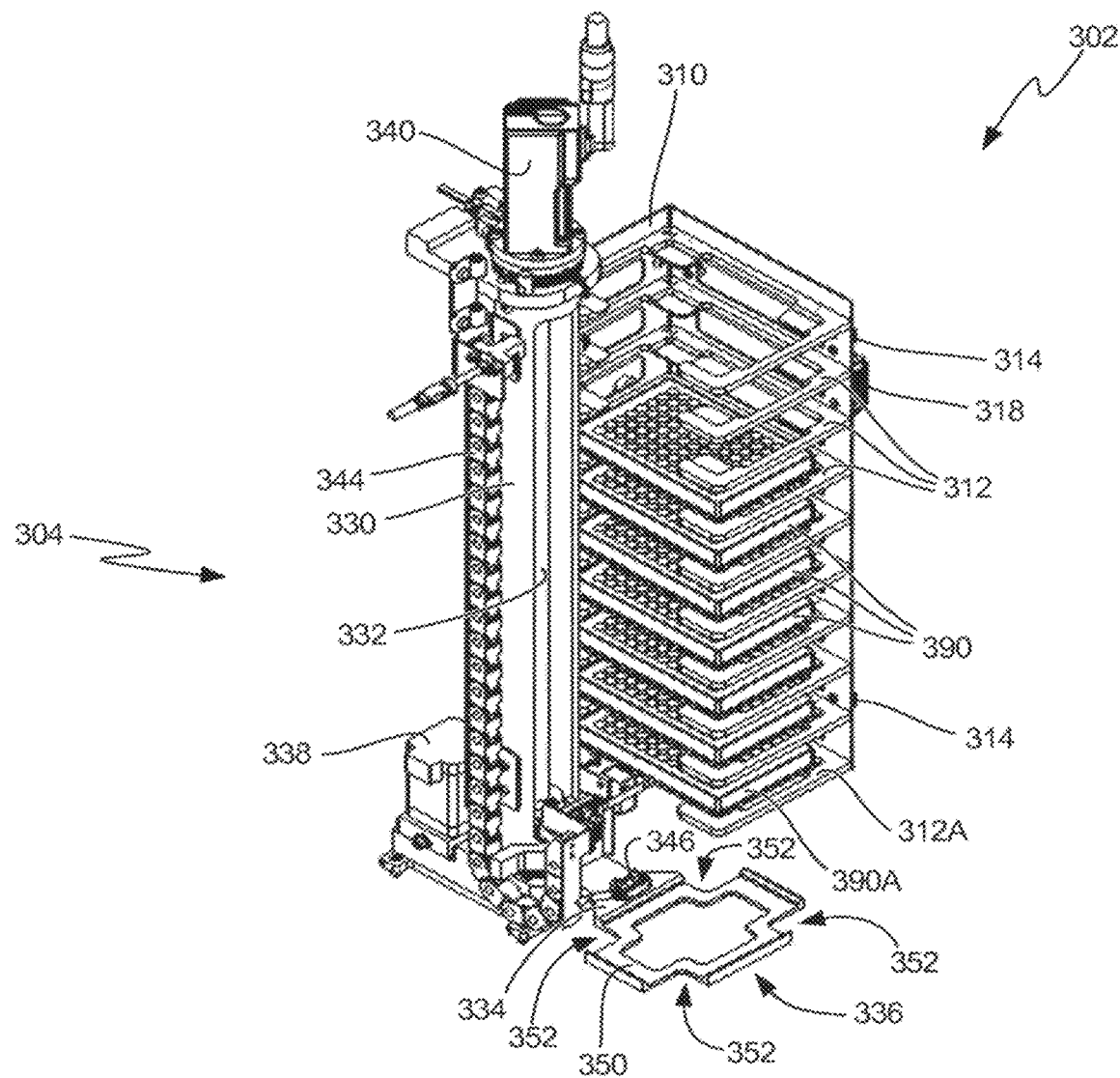

FIG. 9A is an isometric view of the plate rack and the plate stacker when a spatula is in a home position, FIG. 9B is an isometric view of the plate rack and the plate stacker when the spatula has been moved from the home position.

Figure 9C:
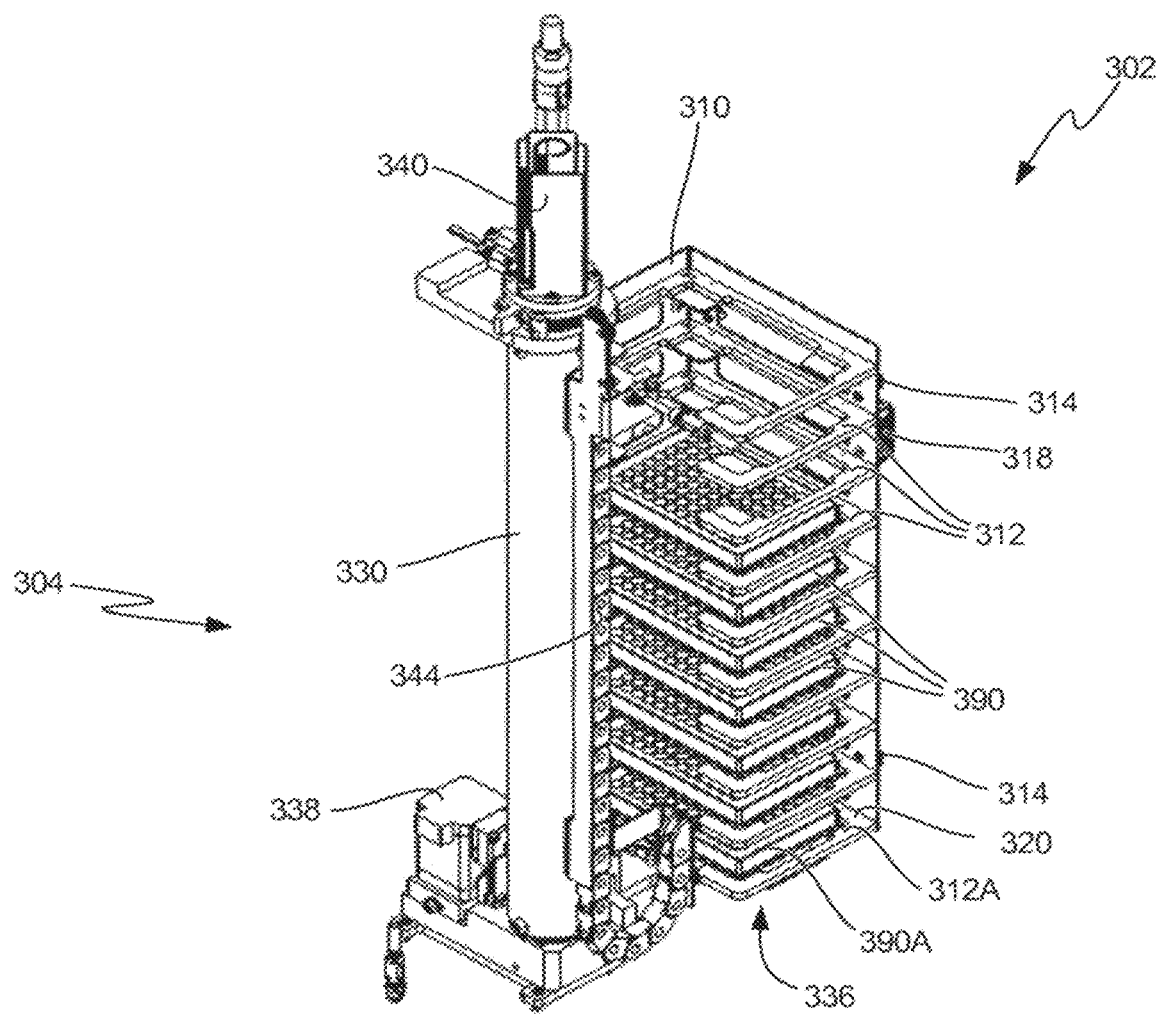

FIG. 9C is an isometric view of the plate rack and the plate stacker when the spatula is positioned to pick a plate.

Figure 9D:
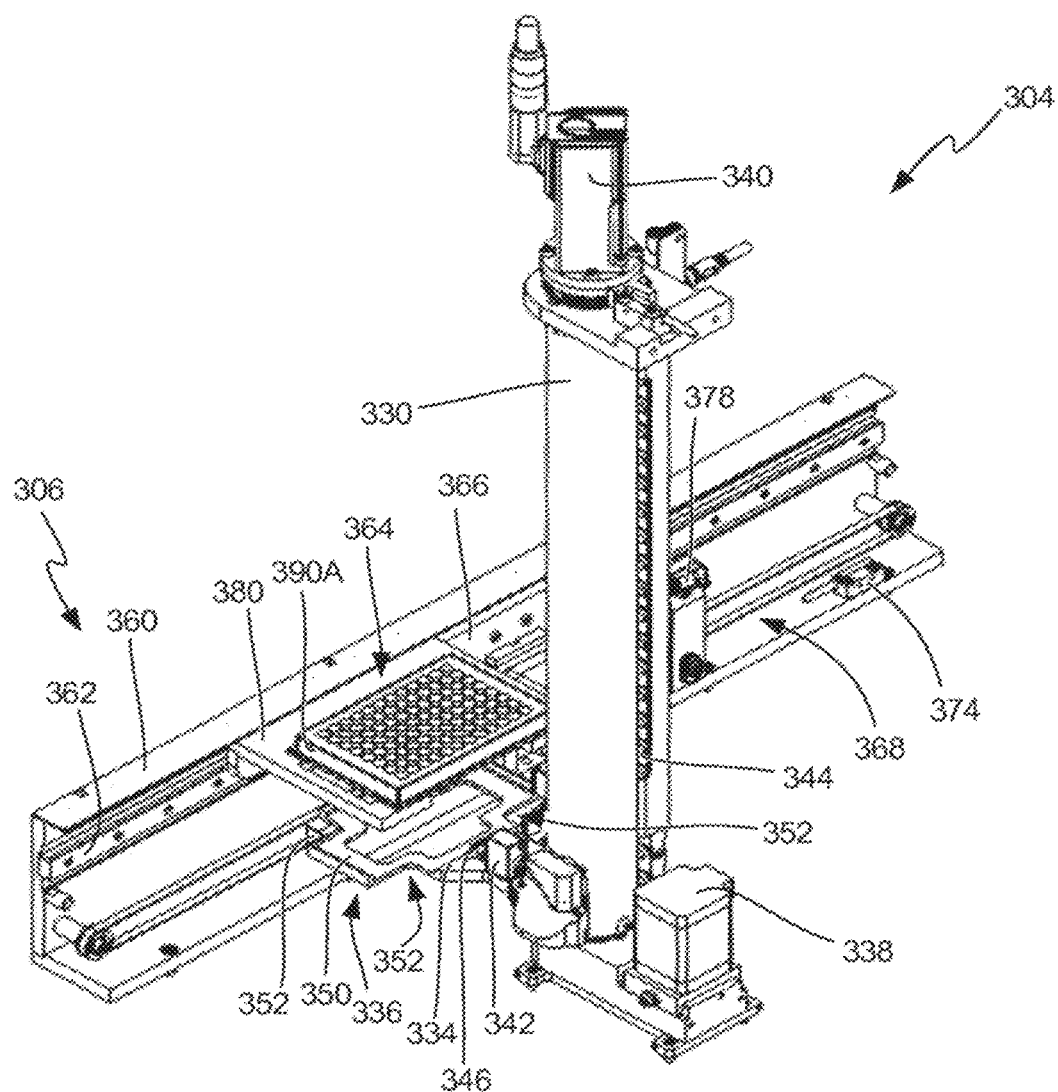

FIG. 9D is a perspective view of the plate stacker and the plate shuttle when the spatula has placed the plate in a nest of the plate shuttle.

Deck Plate Assembly

Figure 10:
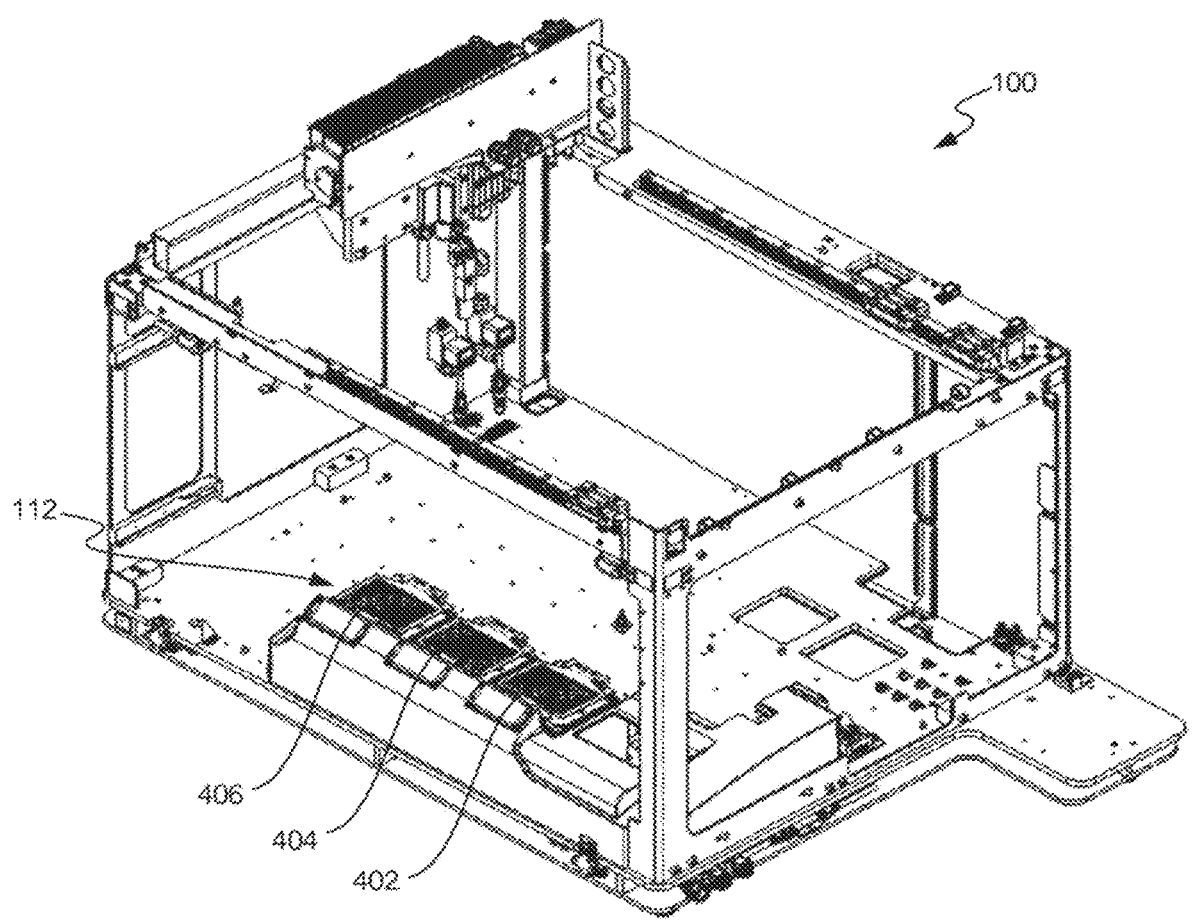

FIG. 10 is an isometric view of a deck plate assembly in the instrument.

Figure 11A:
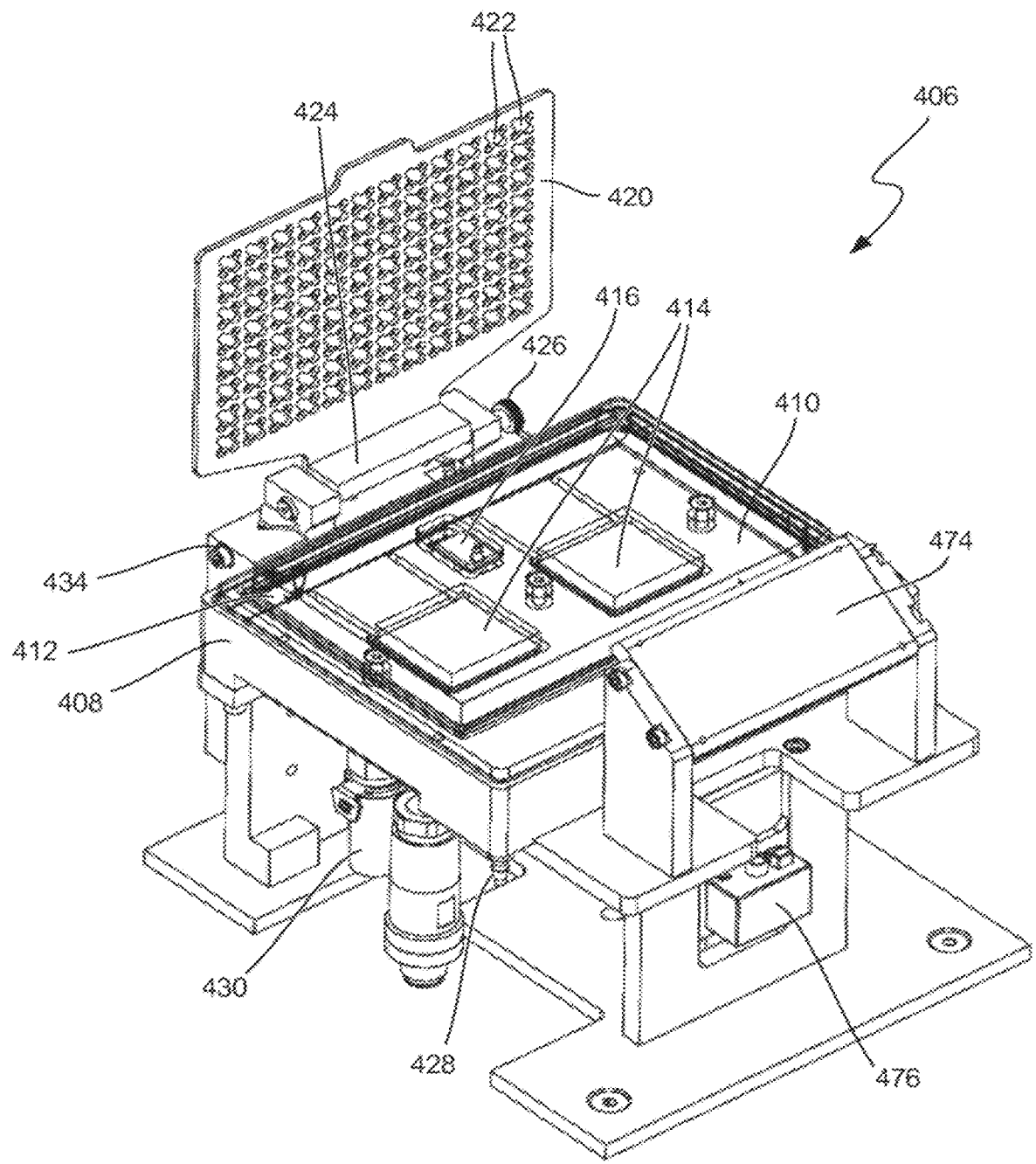

FIG. 11A is a partially transparent isometric view of a deck plate station of the deck plate assembly.

Figure 11B:
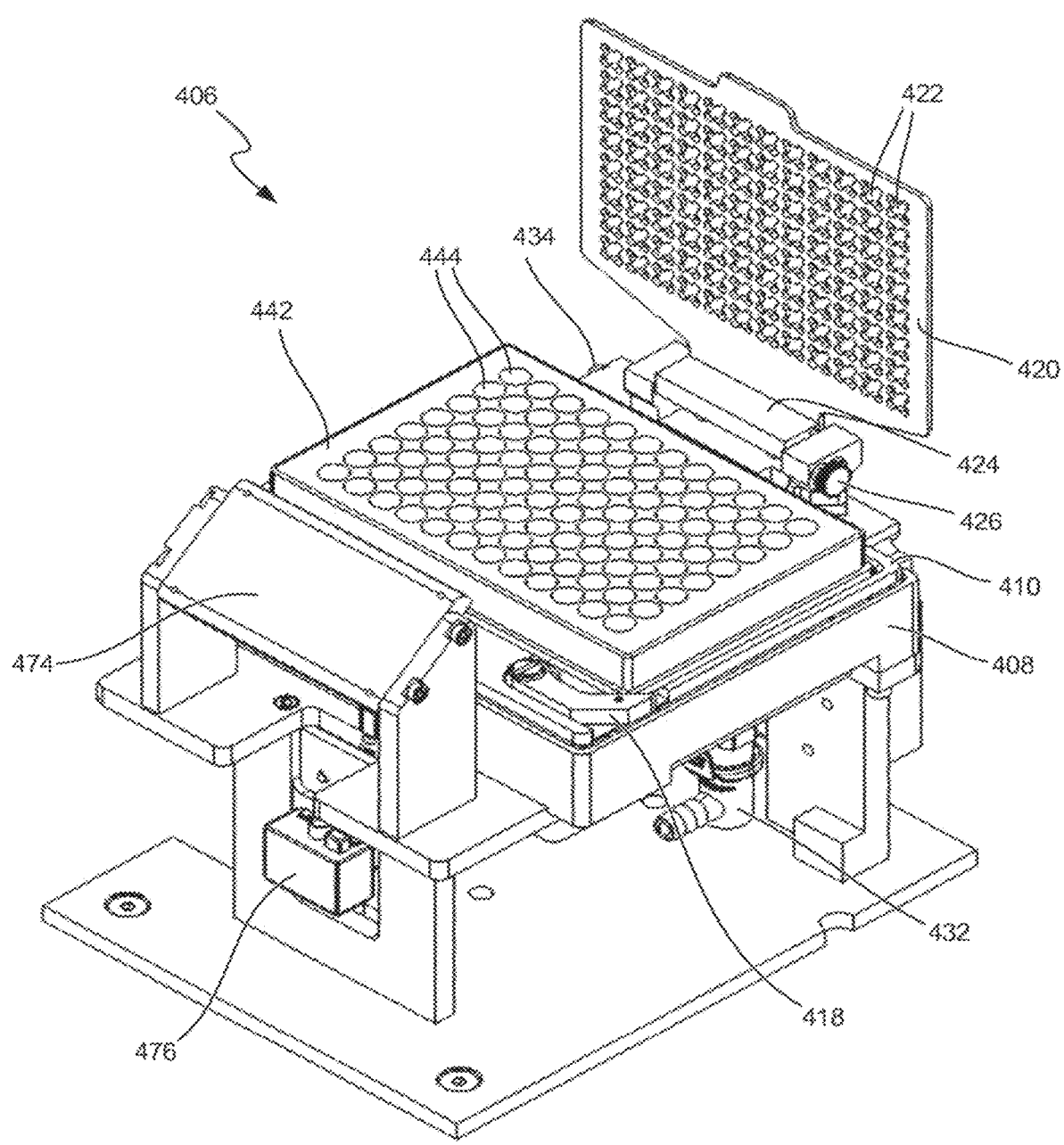
Figure 11C:
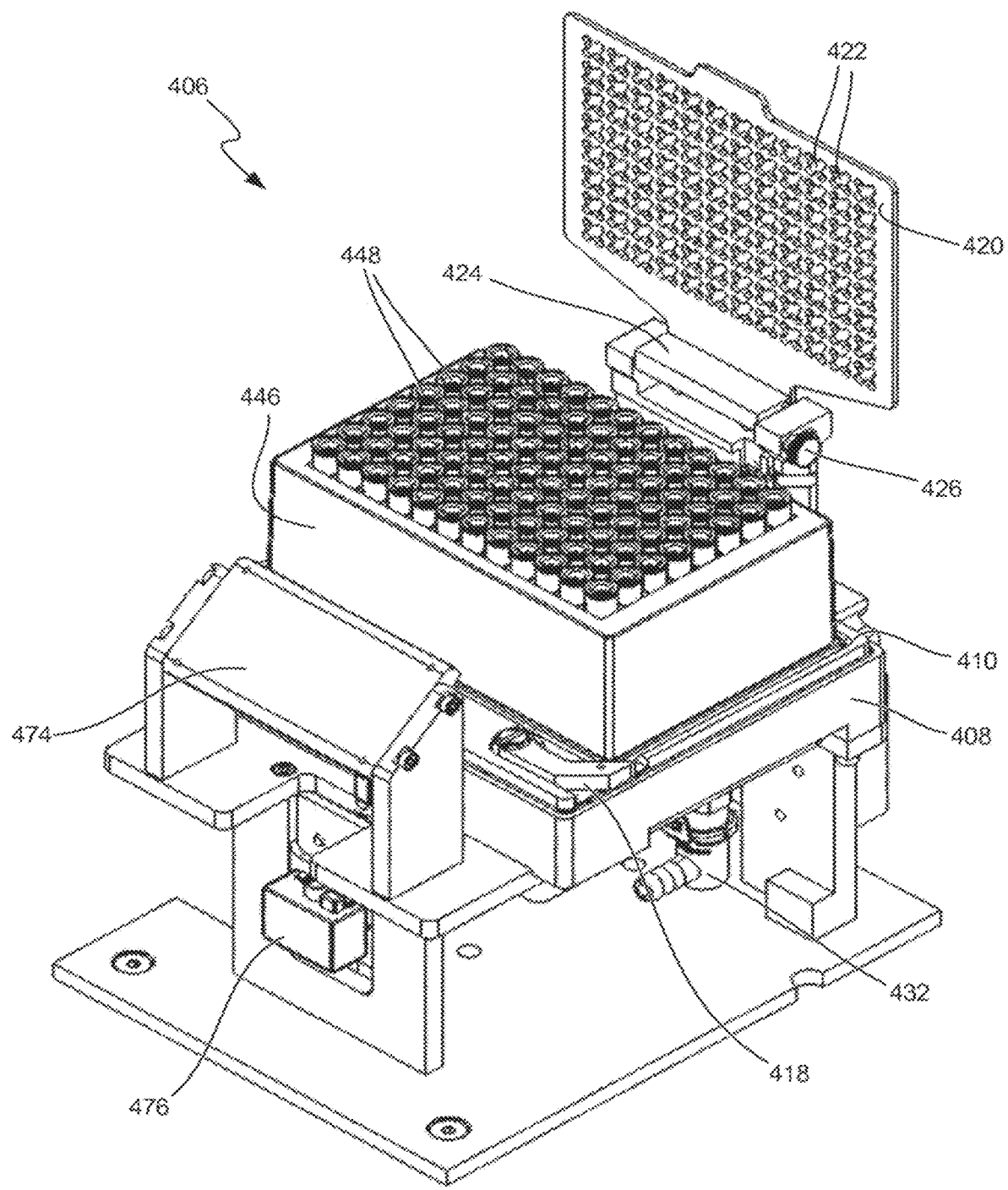
Figure 11D:
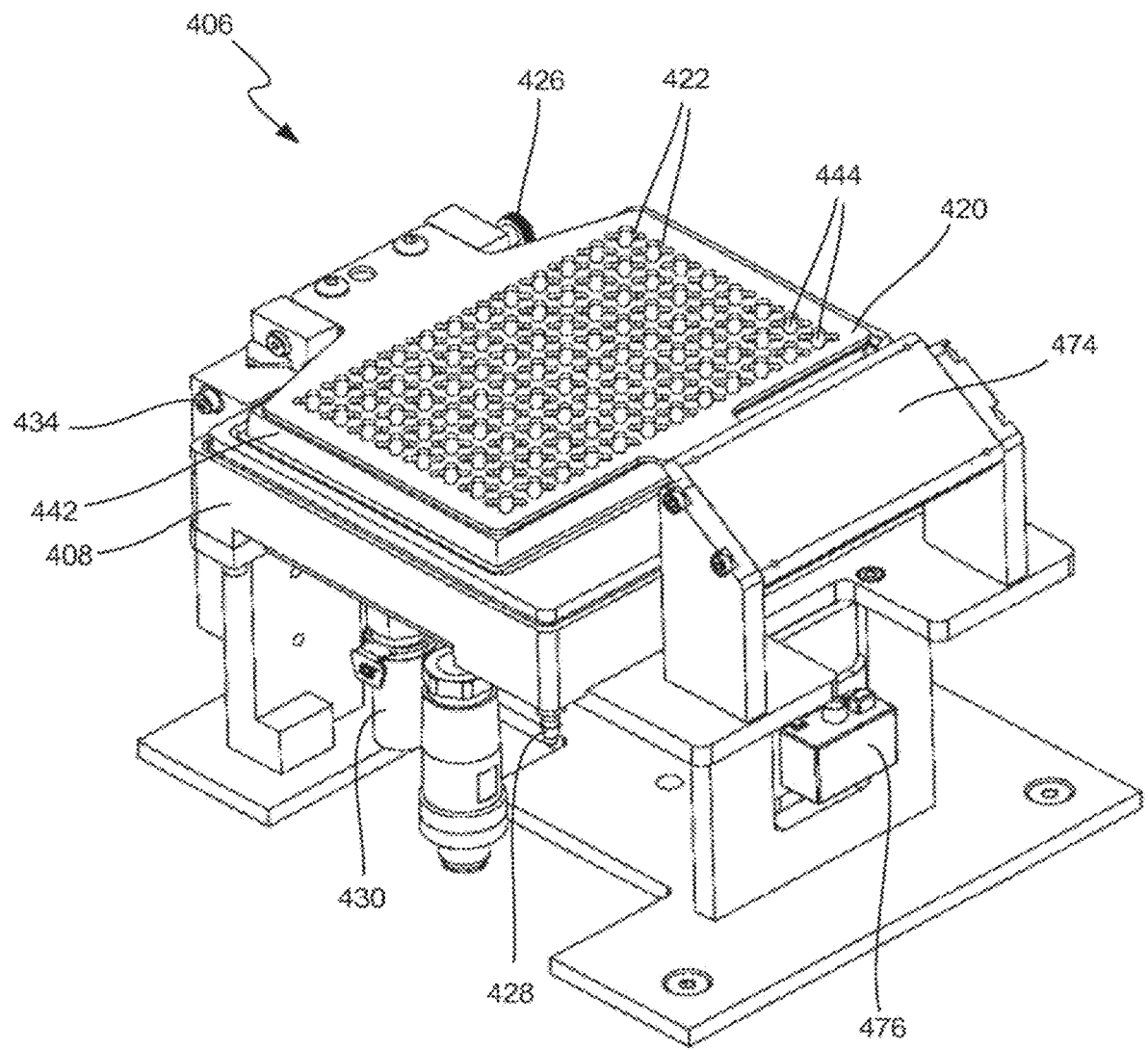

FIGS. 11B-11D are perspective views of the deck plate station seen in FIG. 11A.

Figure 12A:
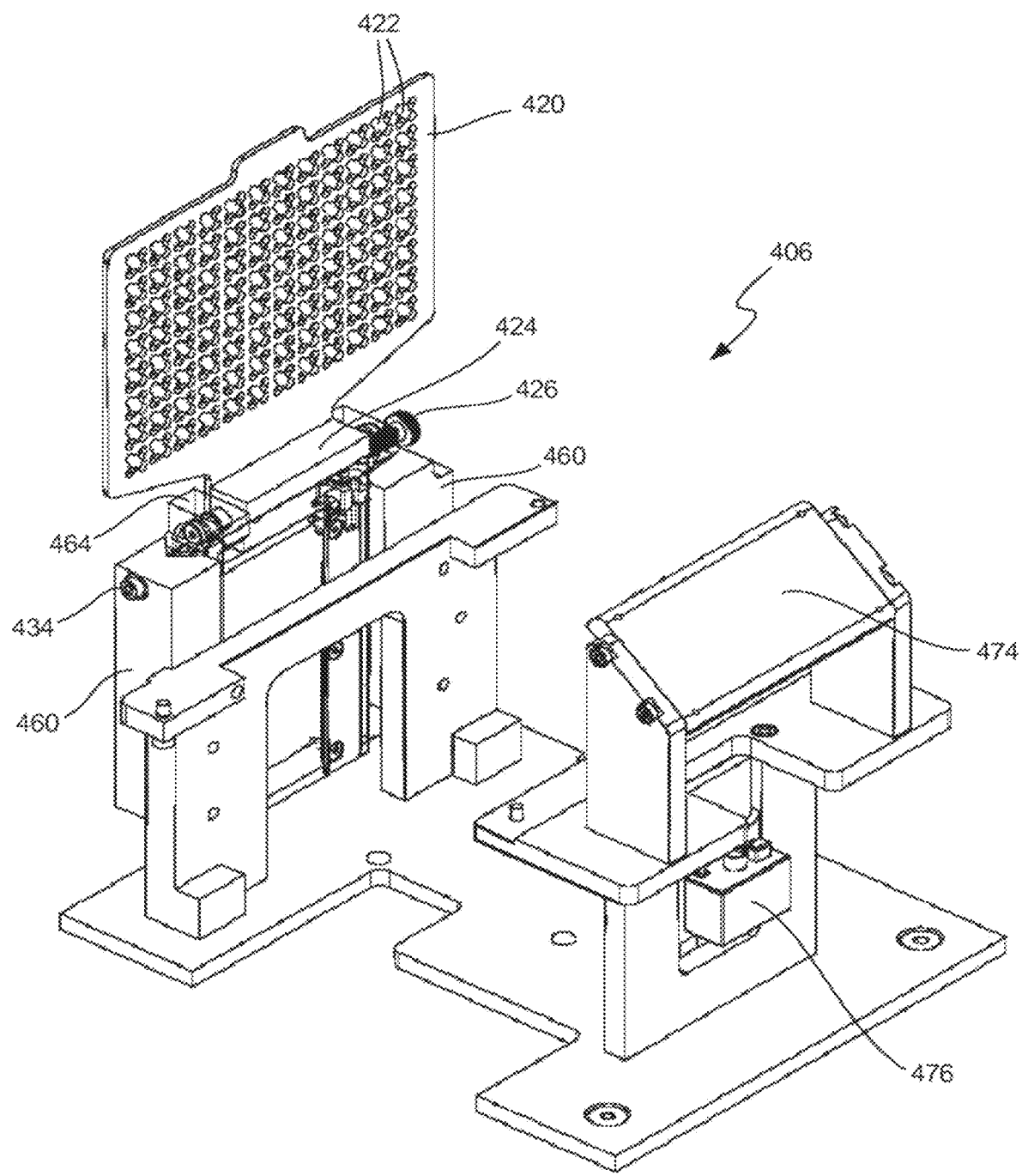
Figure 12B:
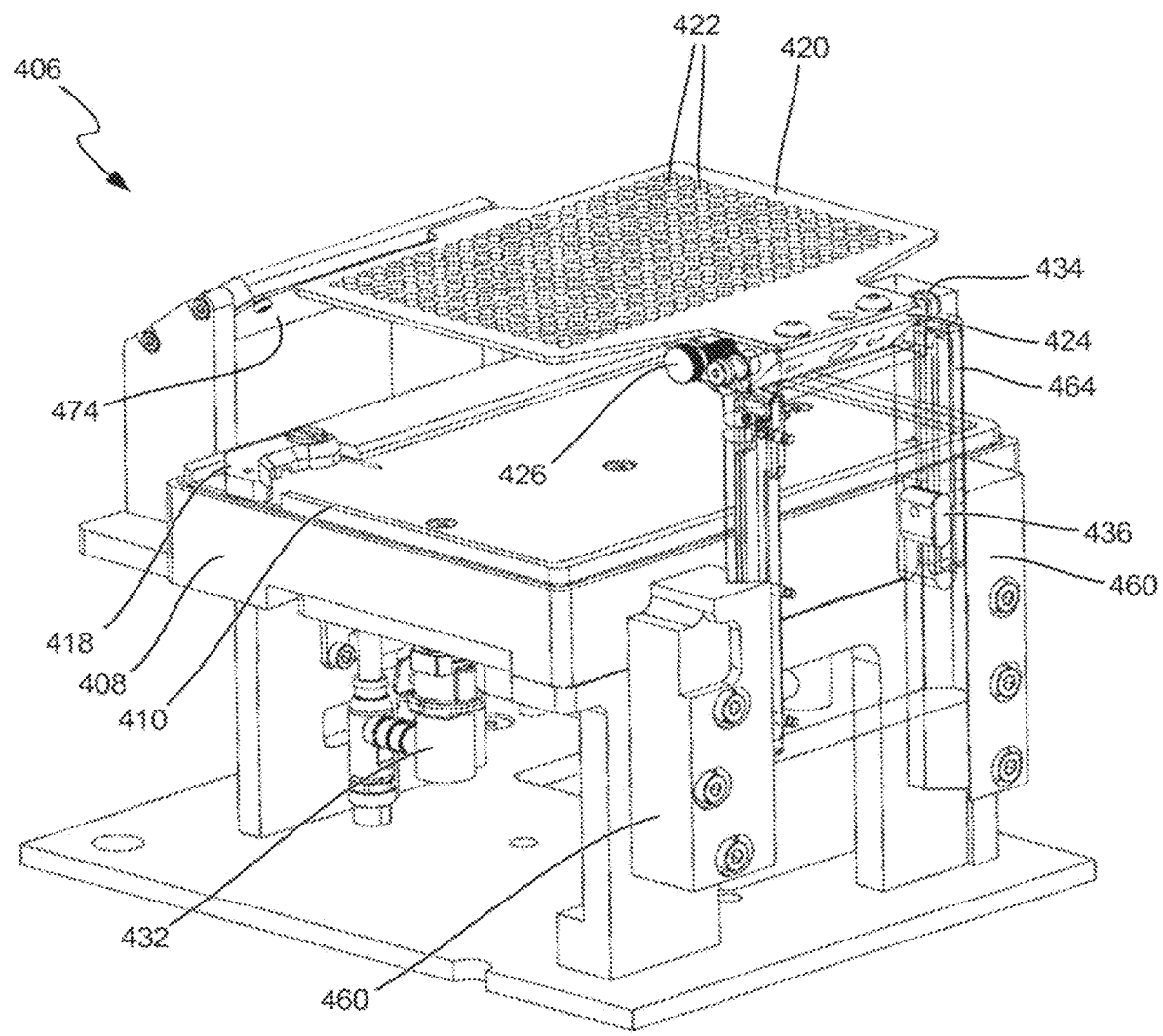

FIGS. 12A and 12B are partially transparent perspective views of the deck plate station.

Figure 13:
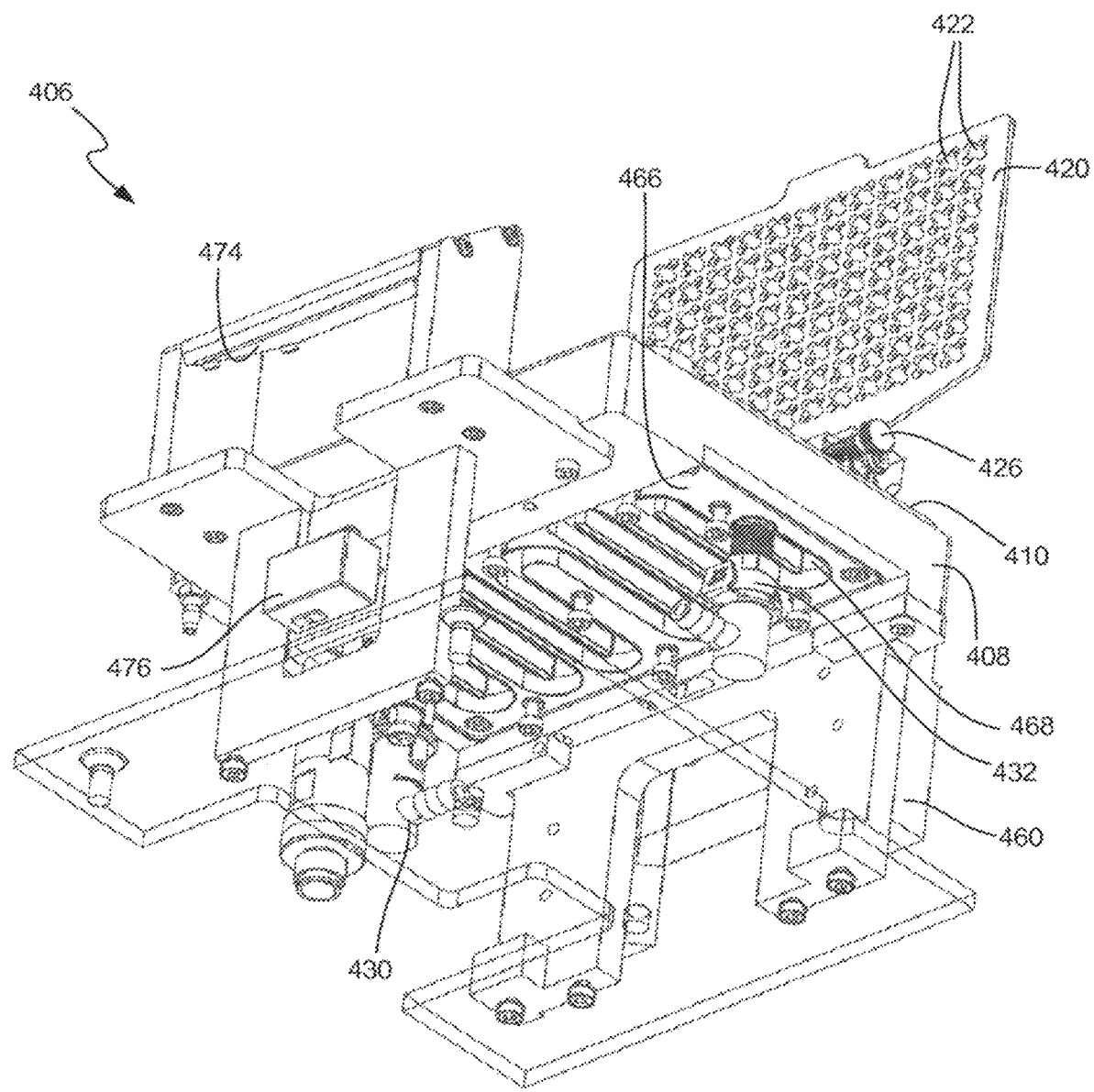

FIG. 13 is a partially transparent perspective view from underneath the deck plate station.

Figure 14:
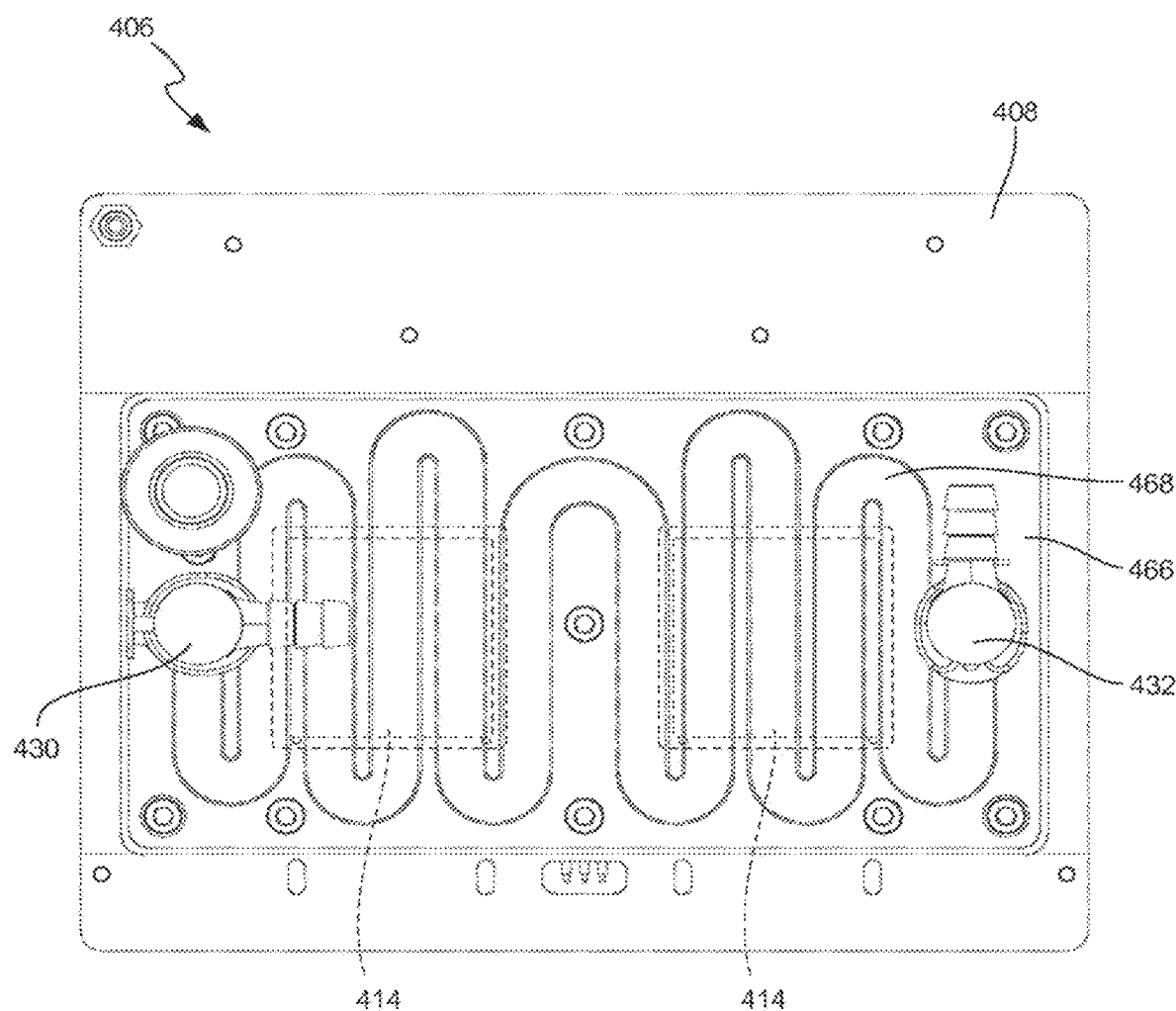

FIG. 14 is a bottom view of the deck plate station.

Figure 15:
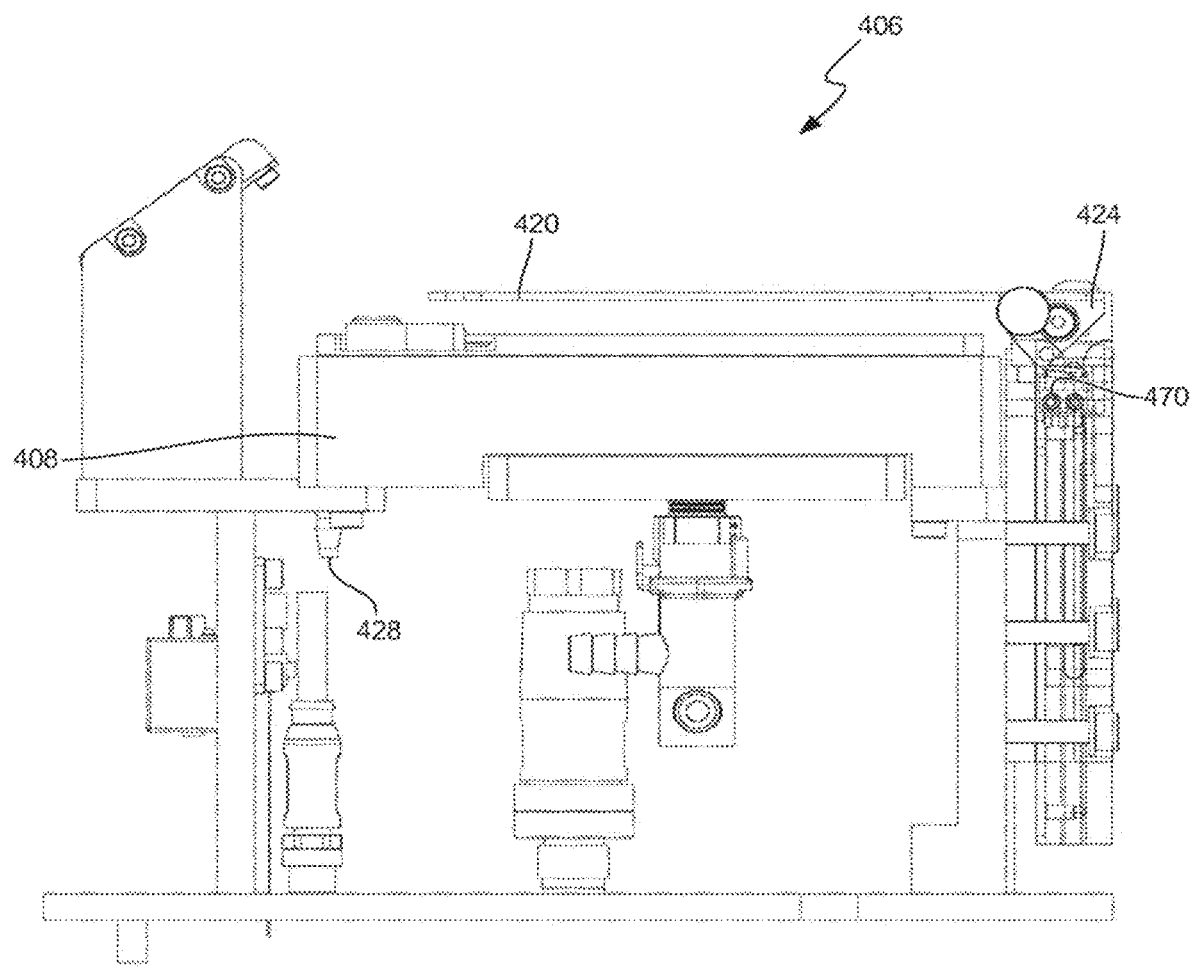

FIG. 15 is a partially transparent side view of the deck plate station.

Figure 16:
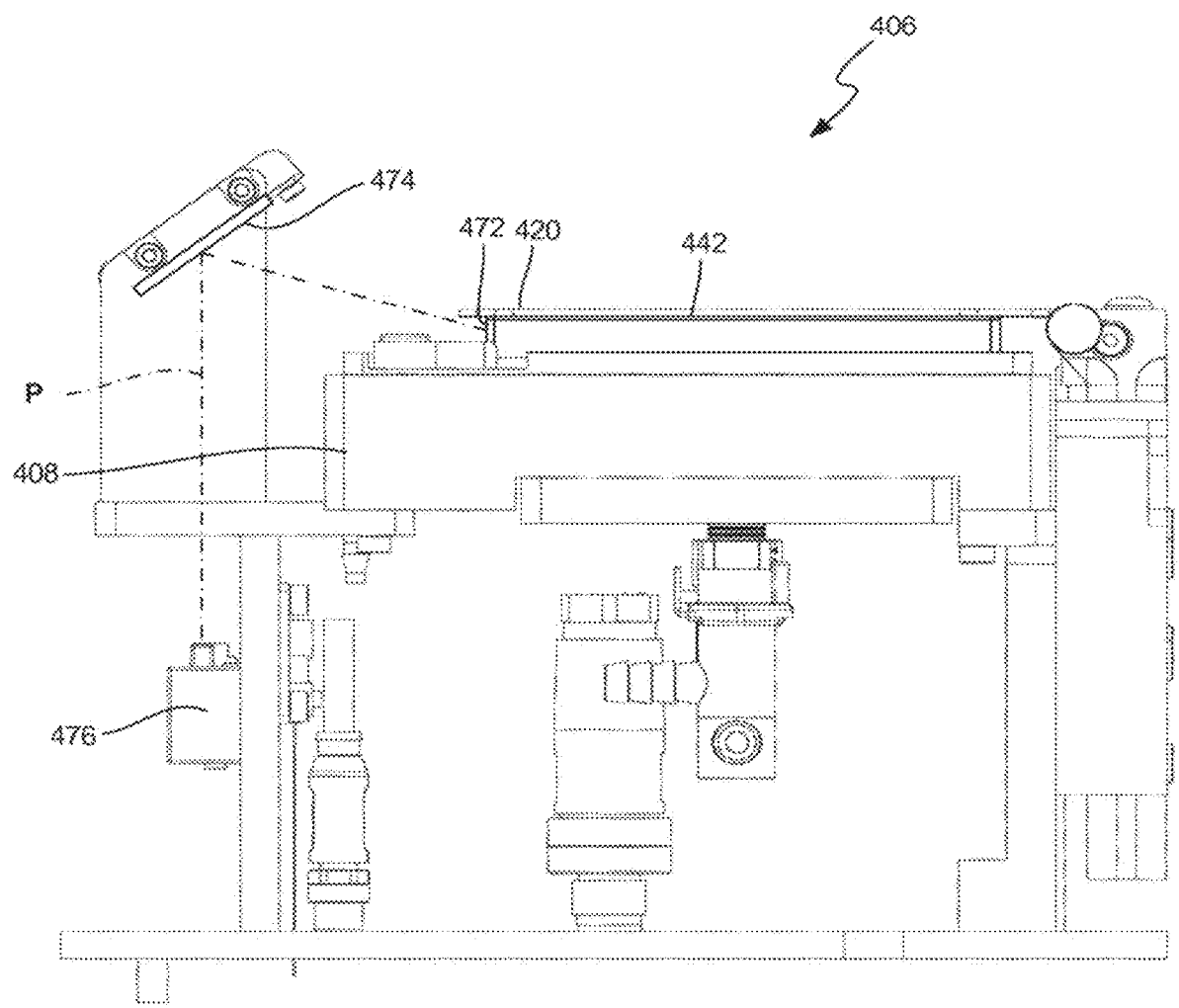

FIG. 16 is a side view of the deck plate station within the instrument.

Tape Path Assembly

Figure 17A:
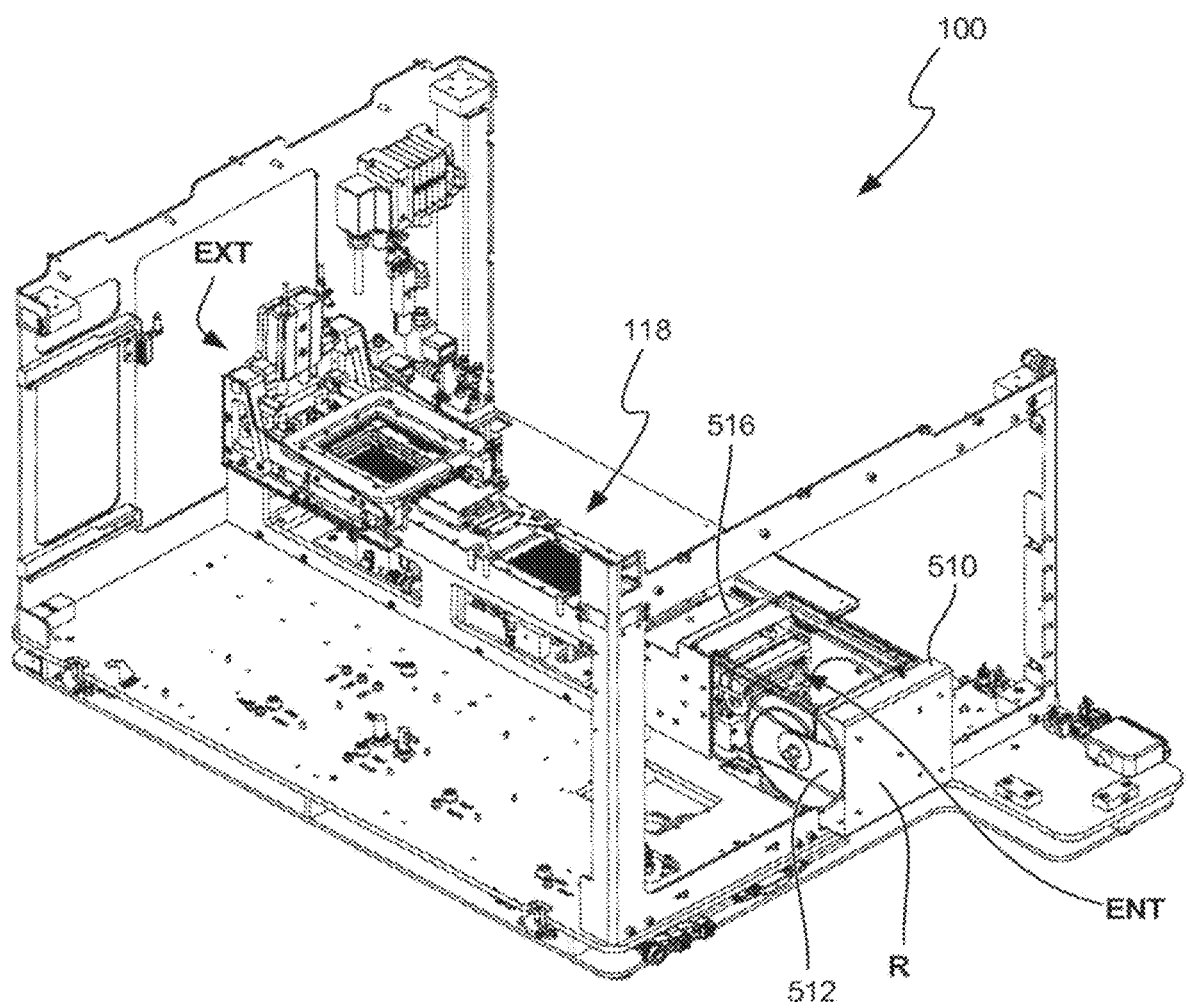

FIG. 17A is an isometric view of a tape path assembly in the instrument.

Figure 17B:
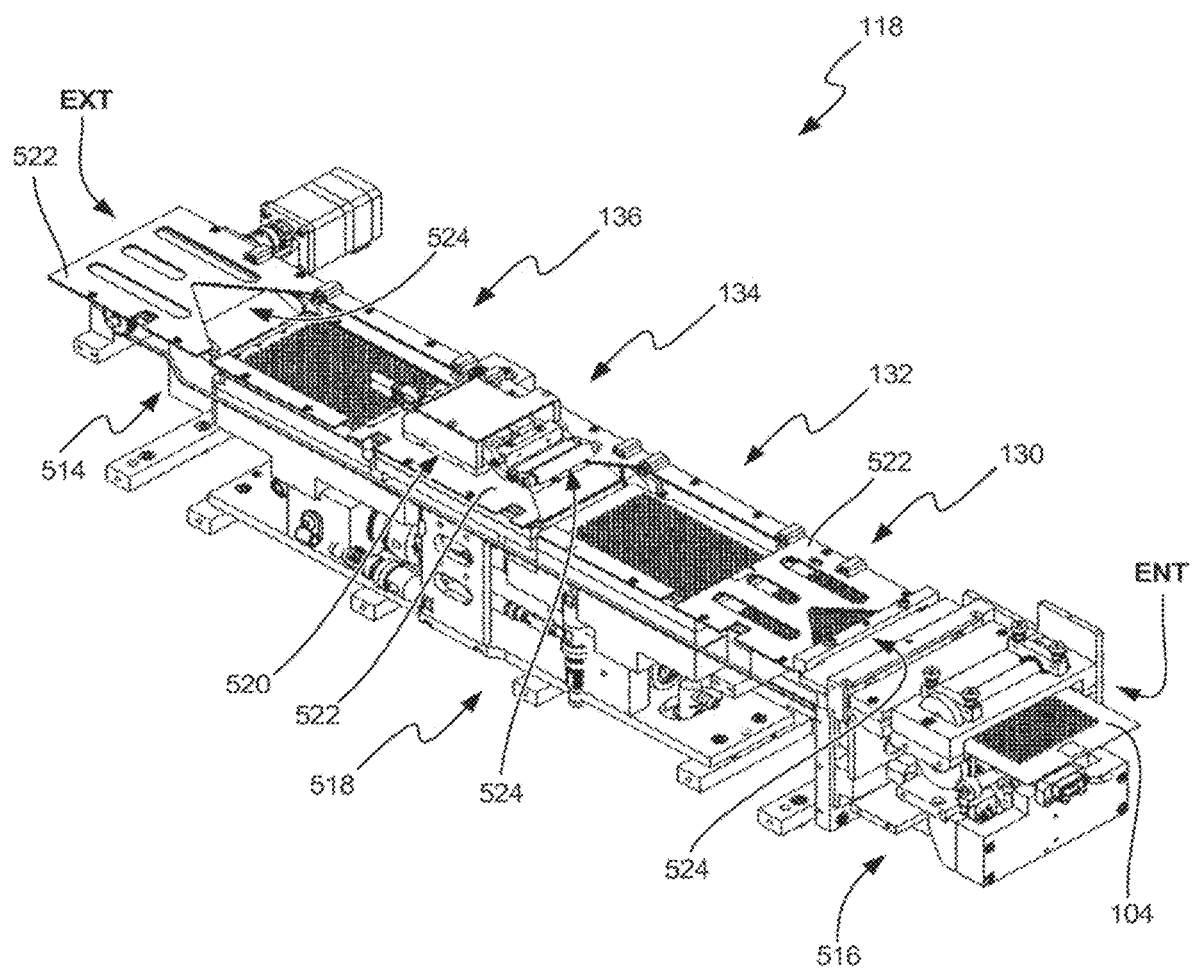

FIG. 17B is a front isometric view of the tape path assembly.

Figure 18A:
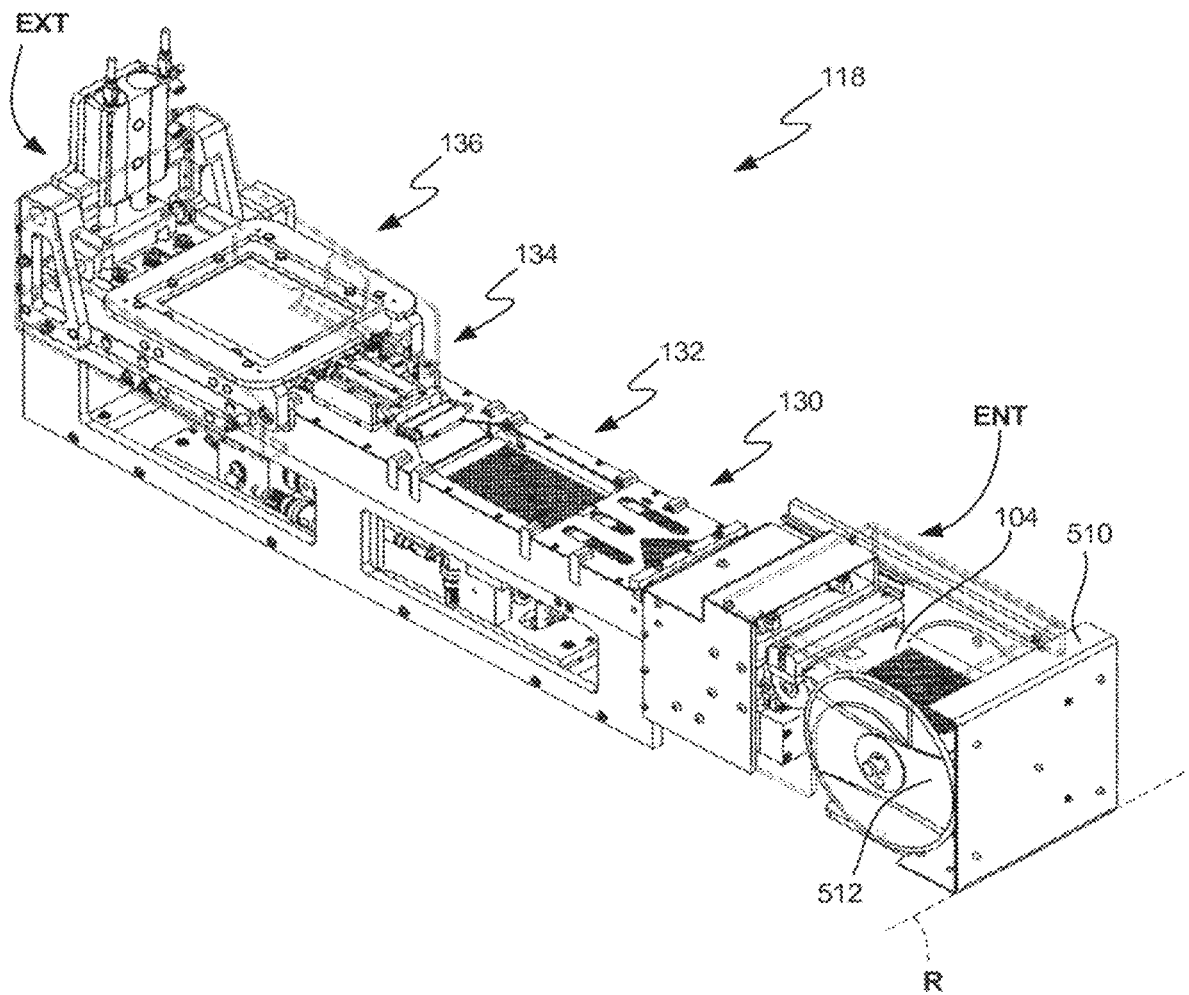

FIG. 18A is a front isometric view of the tape path assembly with a tape infeed in a retracted position.

Figure 18B:
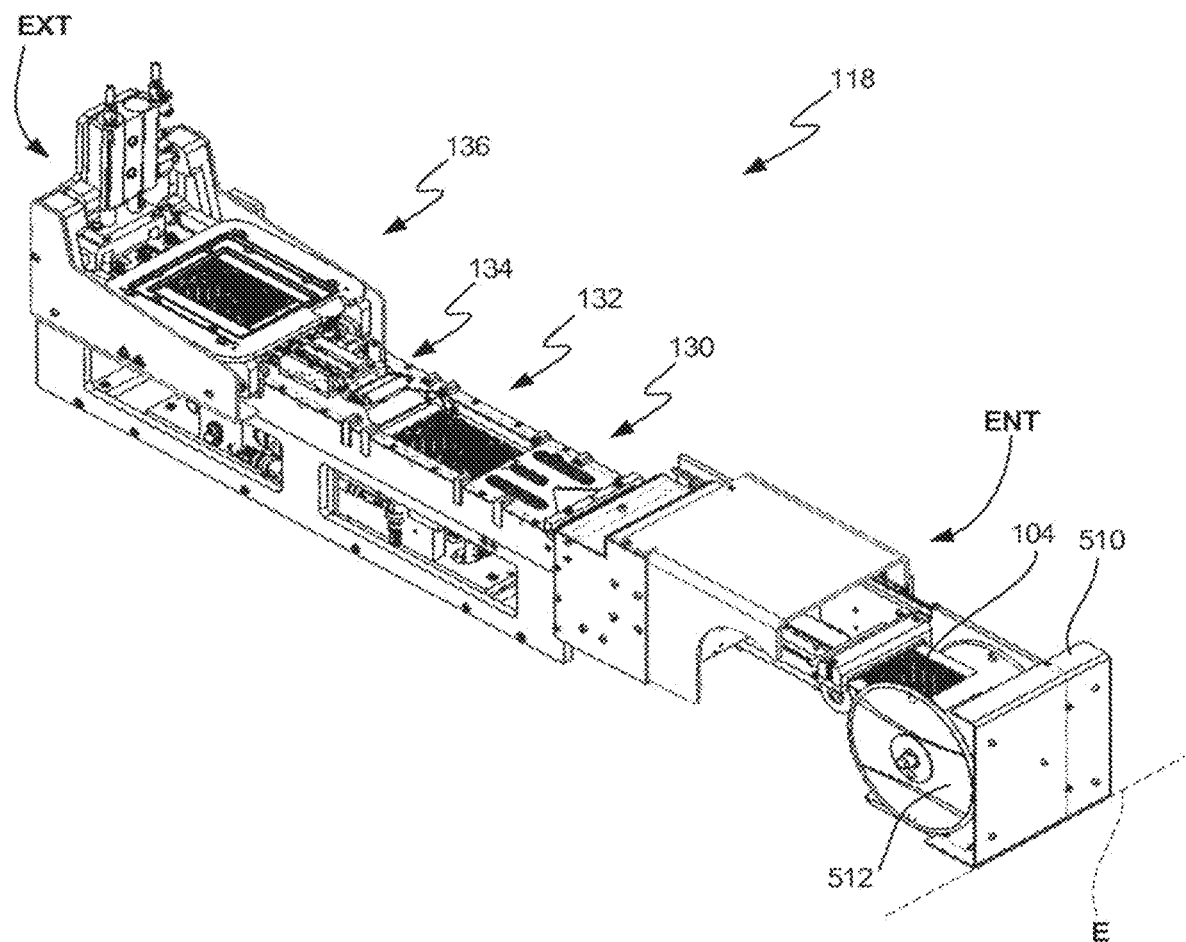
Figure 19A:
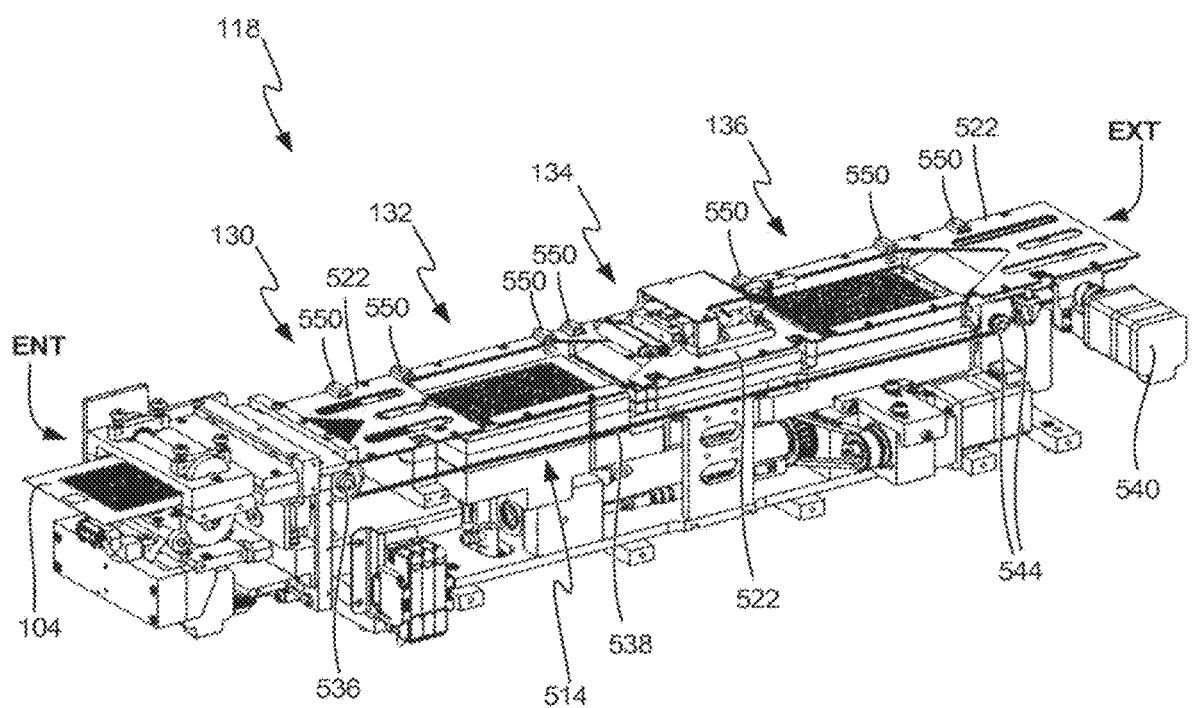

FIG. 18B is a front isometric view of the tape path assembly seen in FIG. 19A with the tape infeed in an extended position.

FIG. 19A is a back perspective view of the tape path assembly with a drive mechanism.

Figure 19B:
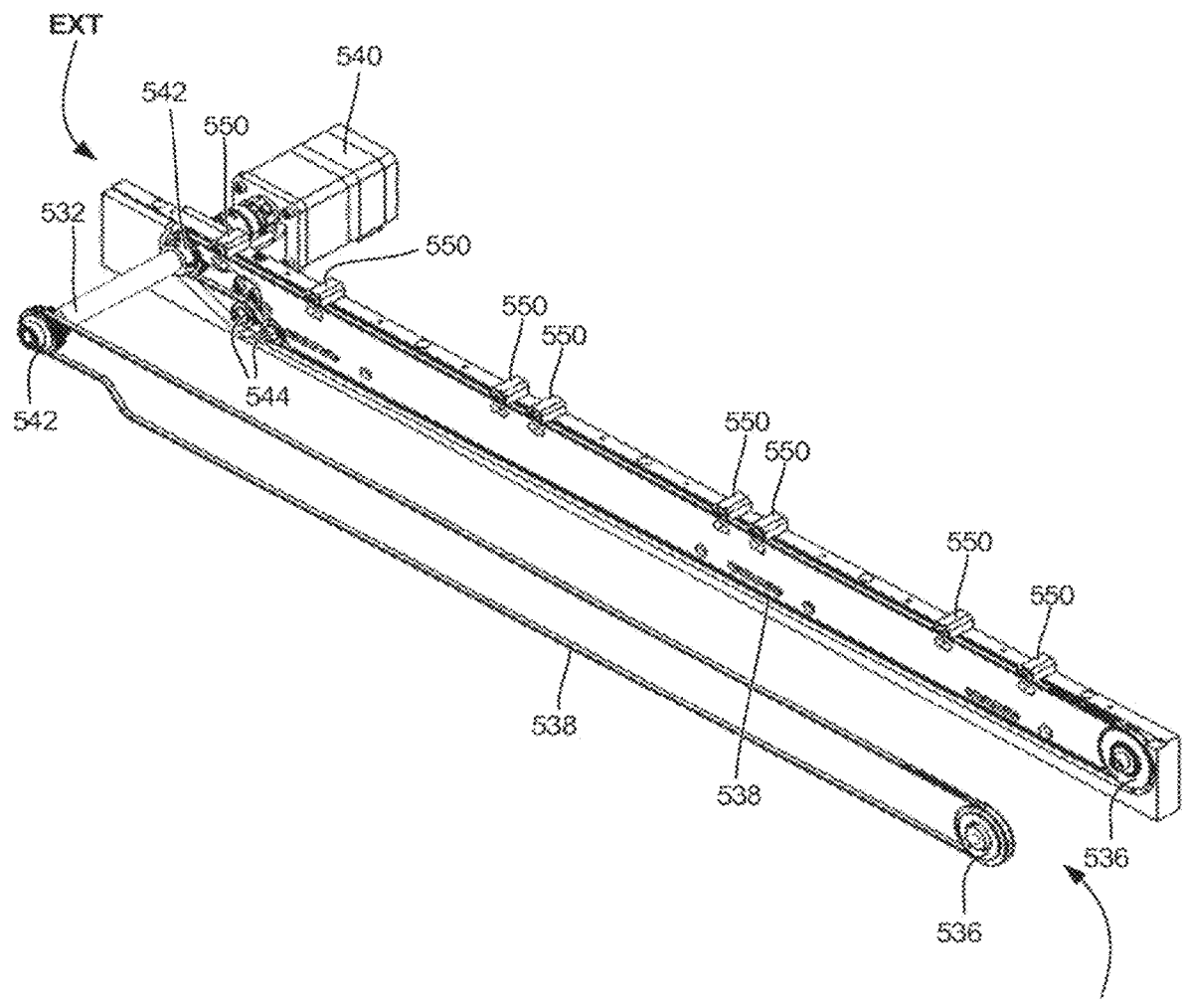

FIG. 19B is a back isometric view of the drive mechanism.

Figure 19C:
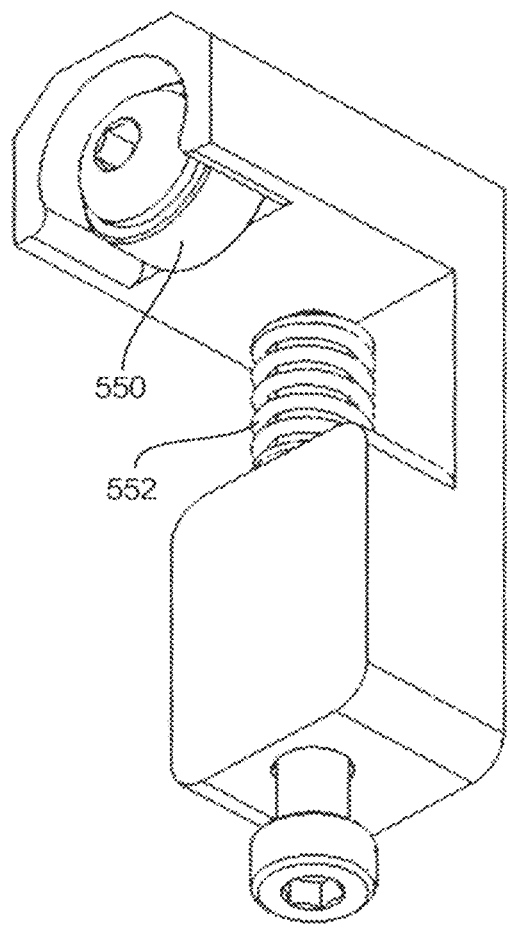

FIG. 19C is a perspective view of a roller on the tape path assembly.

Figure 20A:
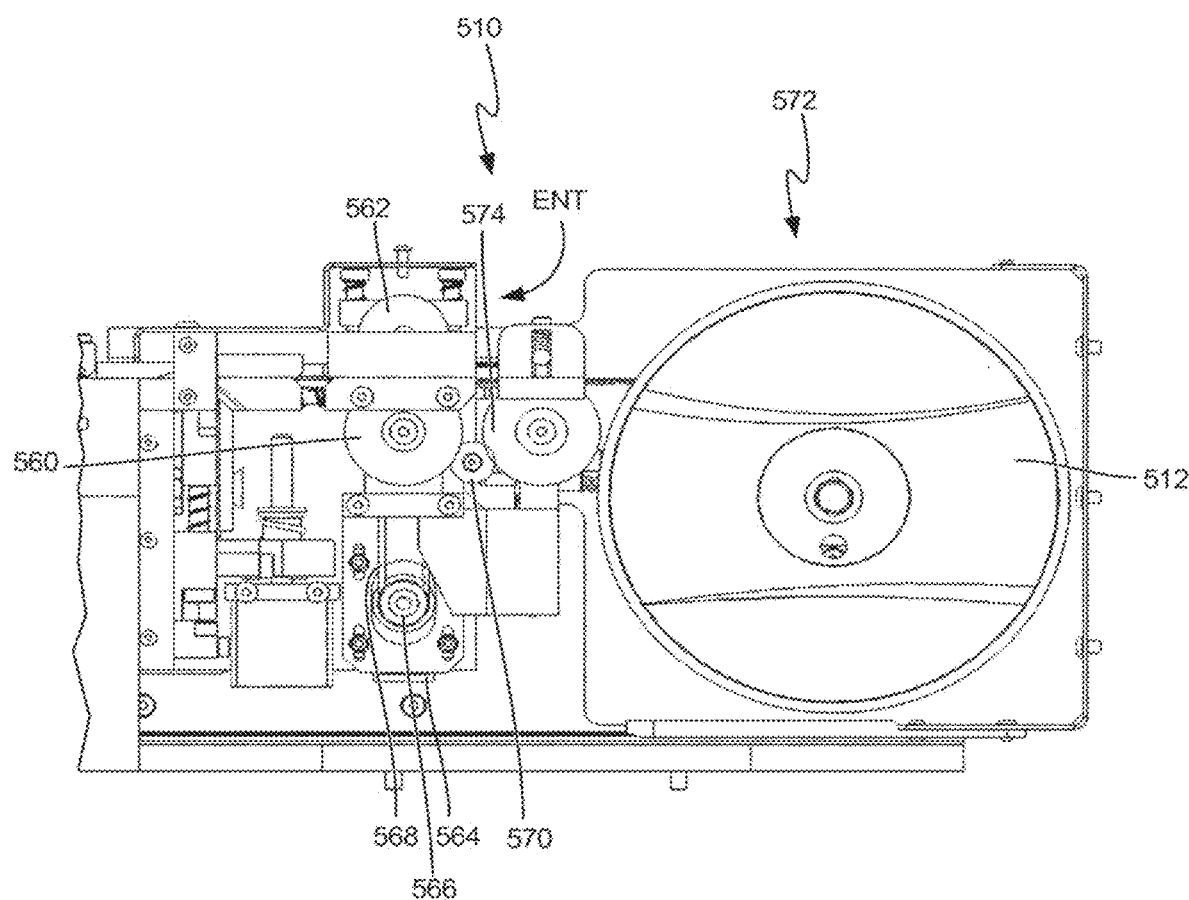

FIG. 20A is a front plan view of a tape infeed on the tape path assembly.

Figure 20B:
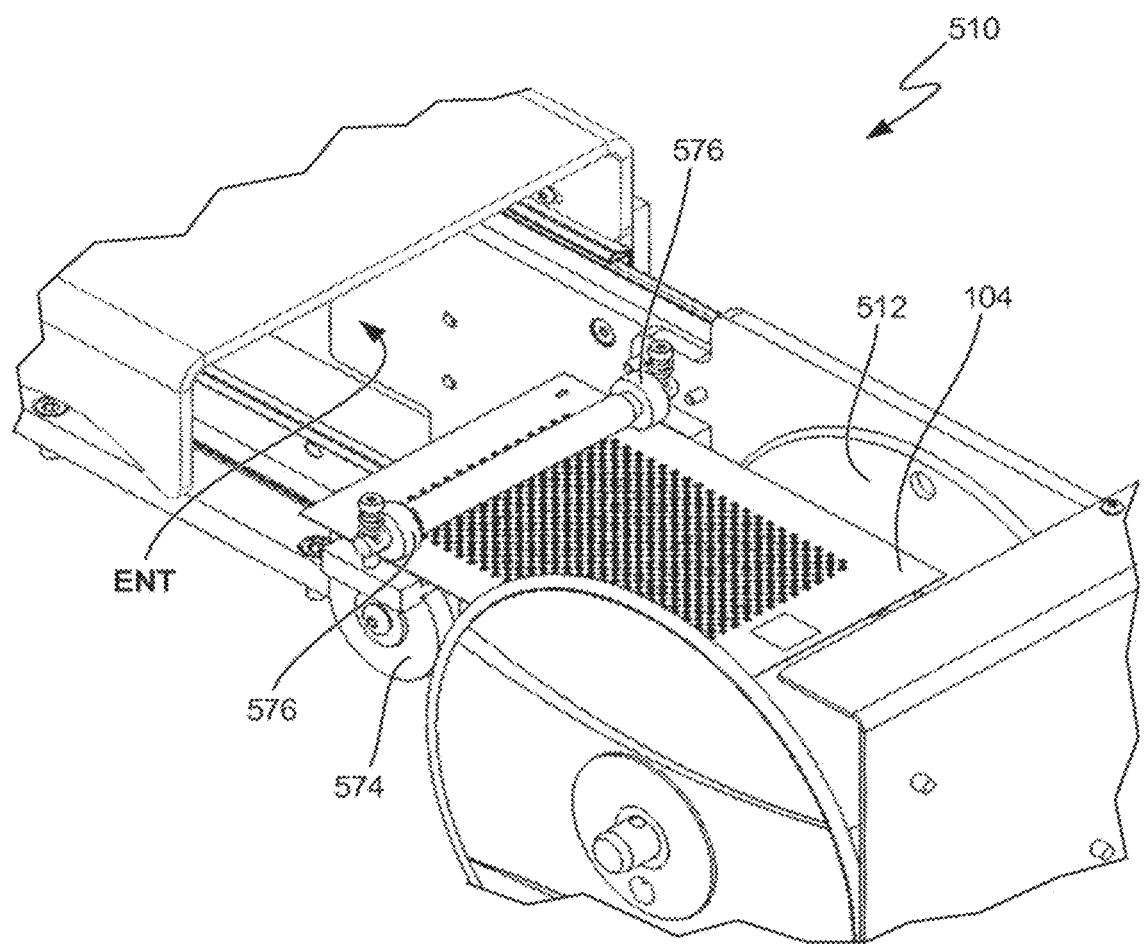

FIG. 20B is a front isometric view of the tape infeed on the tape path assembly.

Figure 21A:
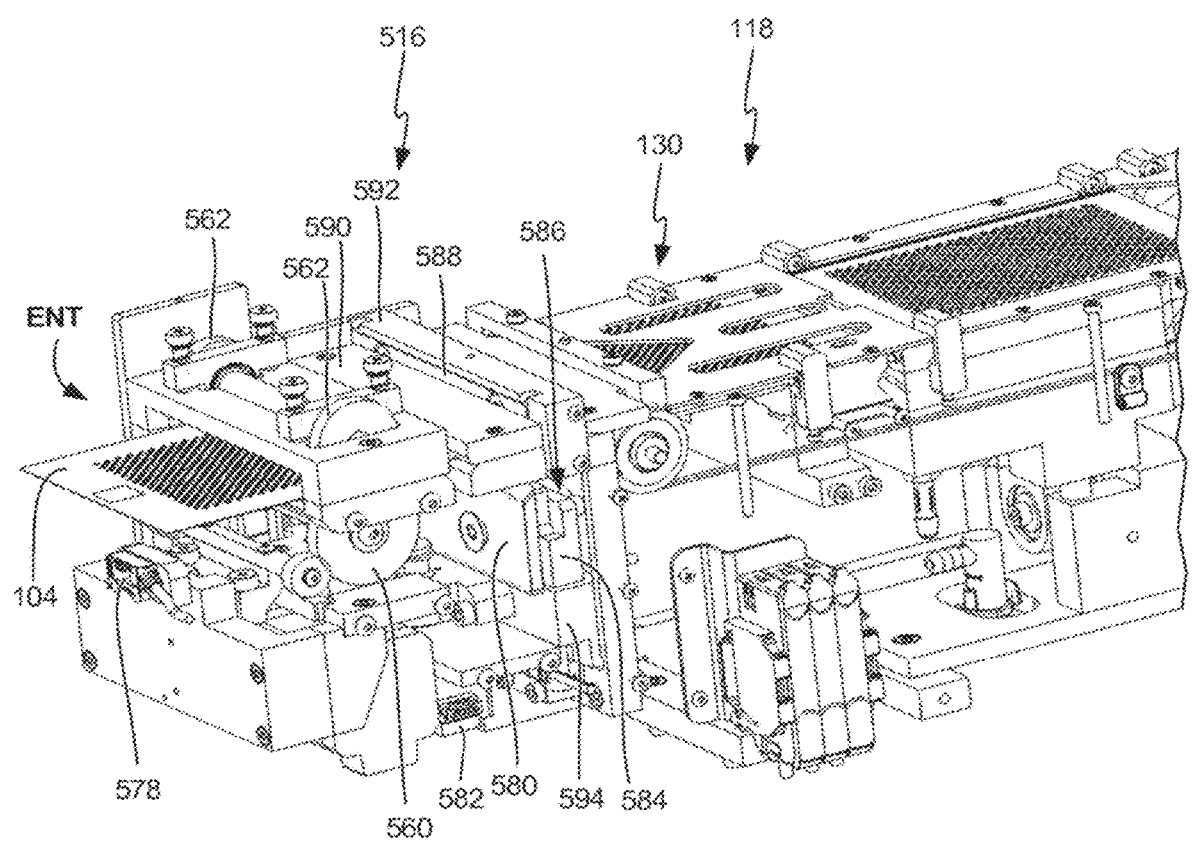

FIG. 21A is a back perspective view of a tape cutter on the tape path assembly.

Figure 21B:
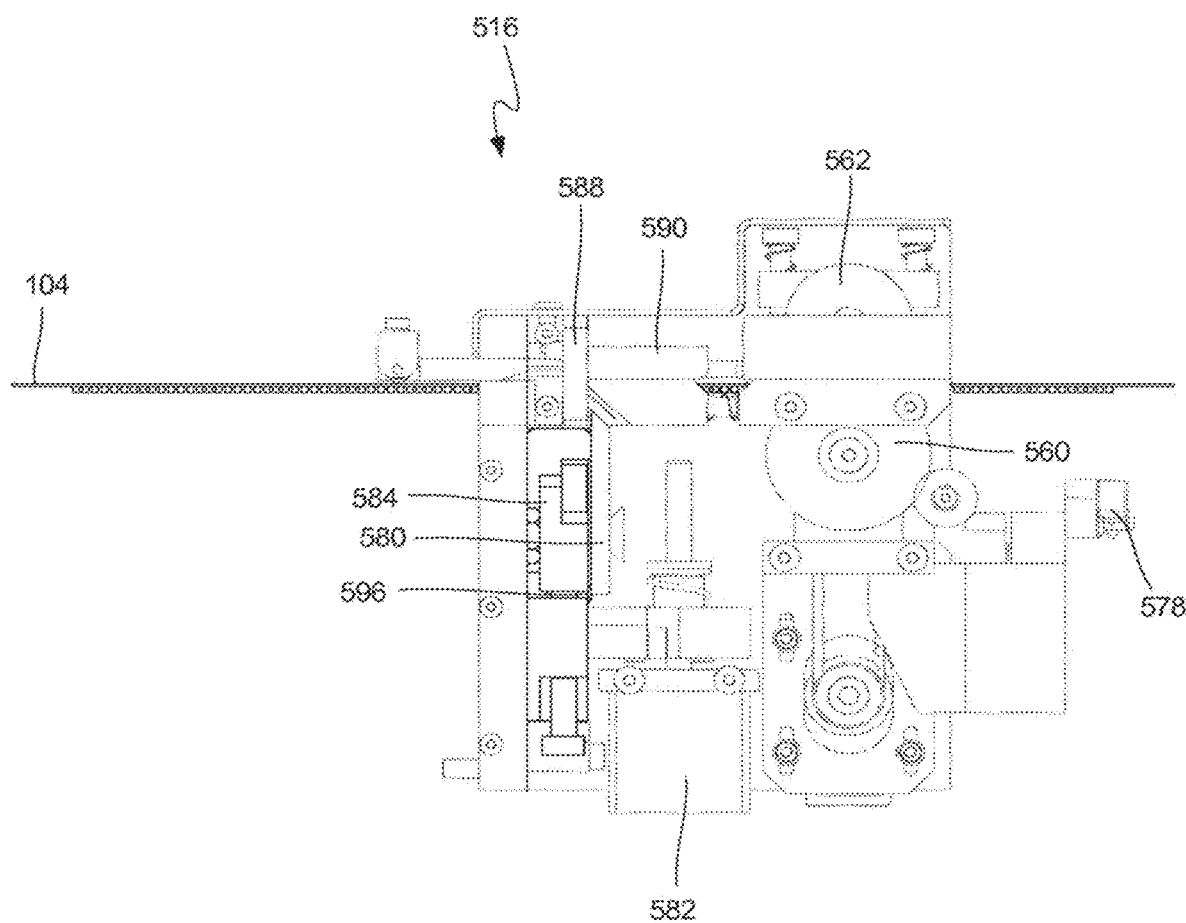

FIG. 21B is a plan view of a front side of the tape cutter having the blade in a retracted position.

Figure 21C:
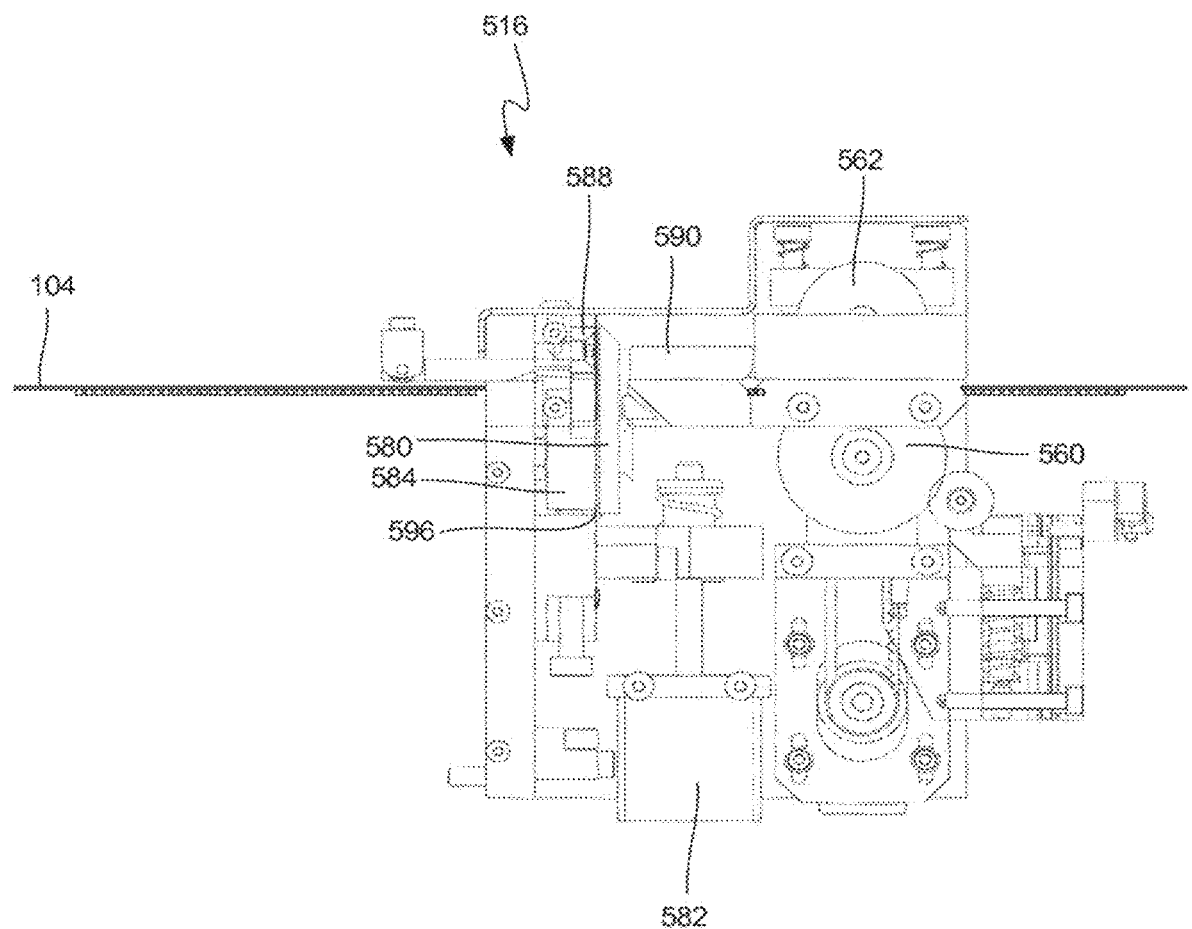

FIG. 21C is a plan view of a front side of the tape cutter having the blade in an extended position.

Figure 21D:
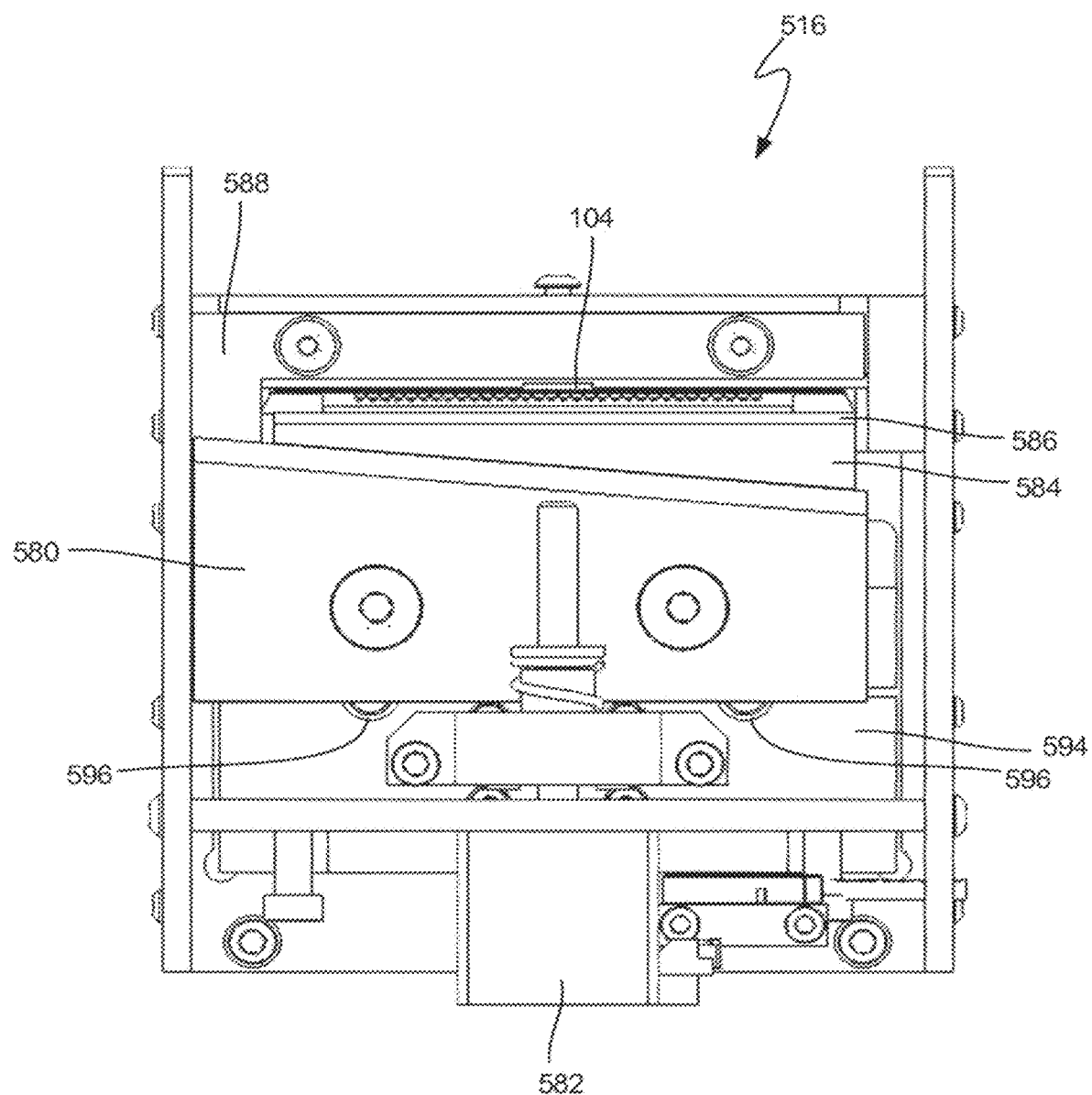

FIG. 21D is a plan view at an entrance of the tape path assembly with the tape cutter having the blade in a retracted position.

Figure 21E:
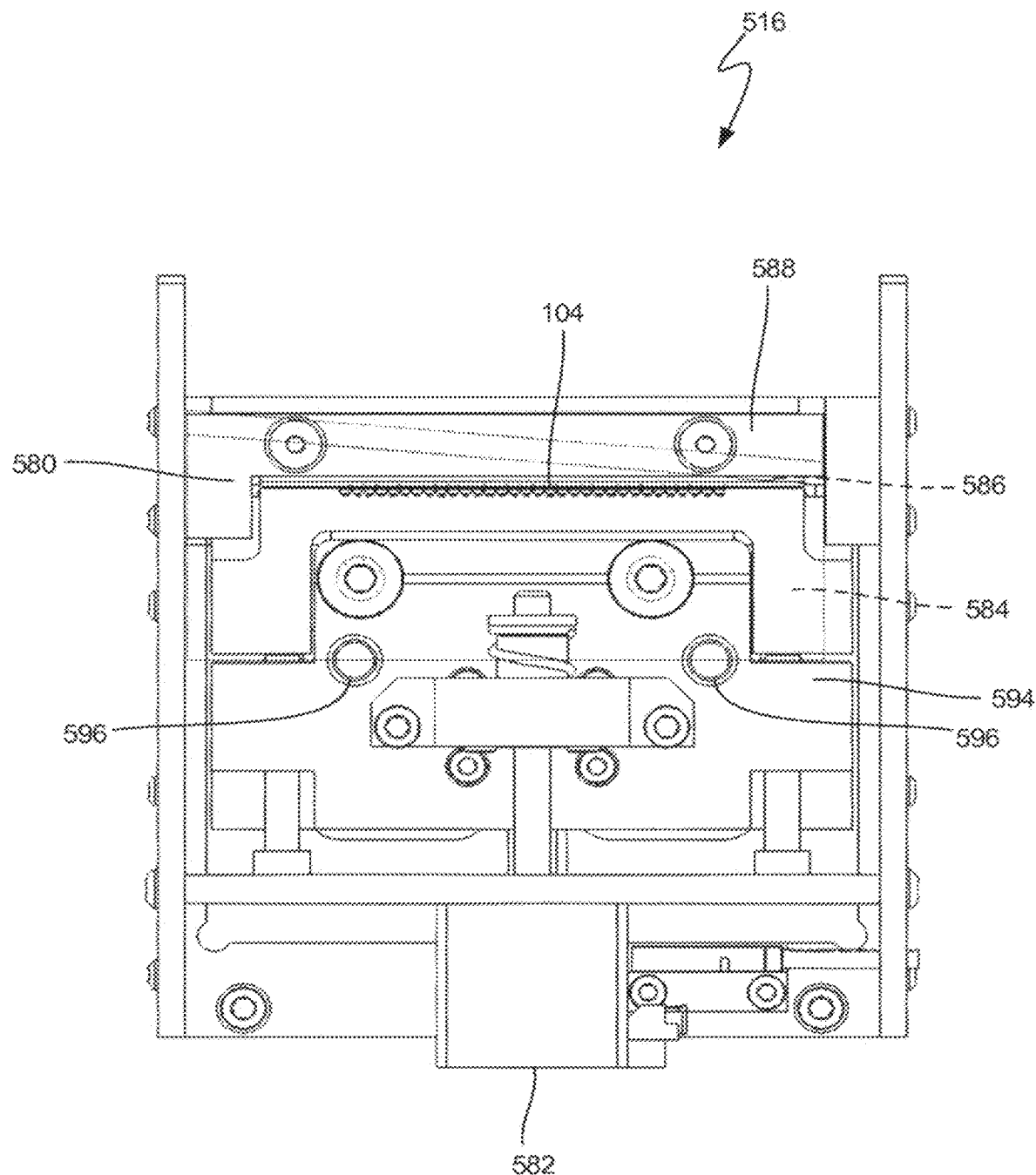

FIG. 21E is a partially transparent plan view at an entrance of the tape path assembly with the tape cutter having the blade in an extended position.

Figure 22A:
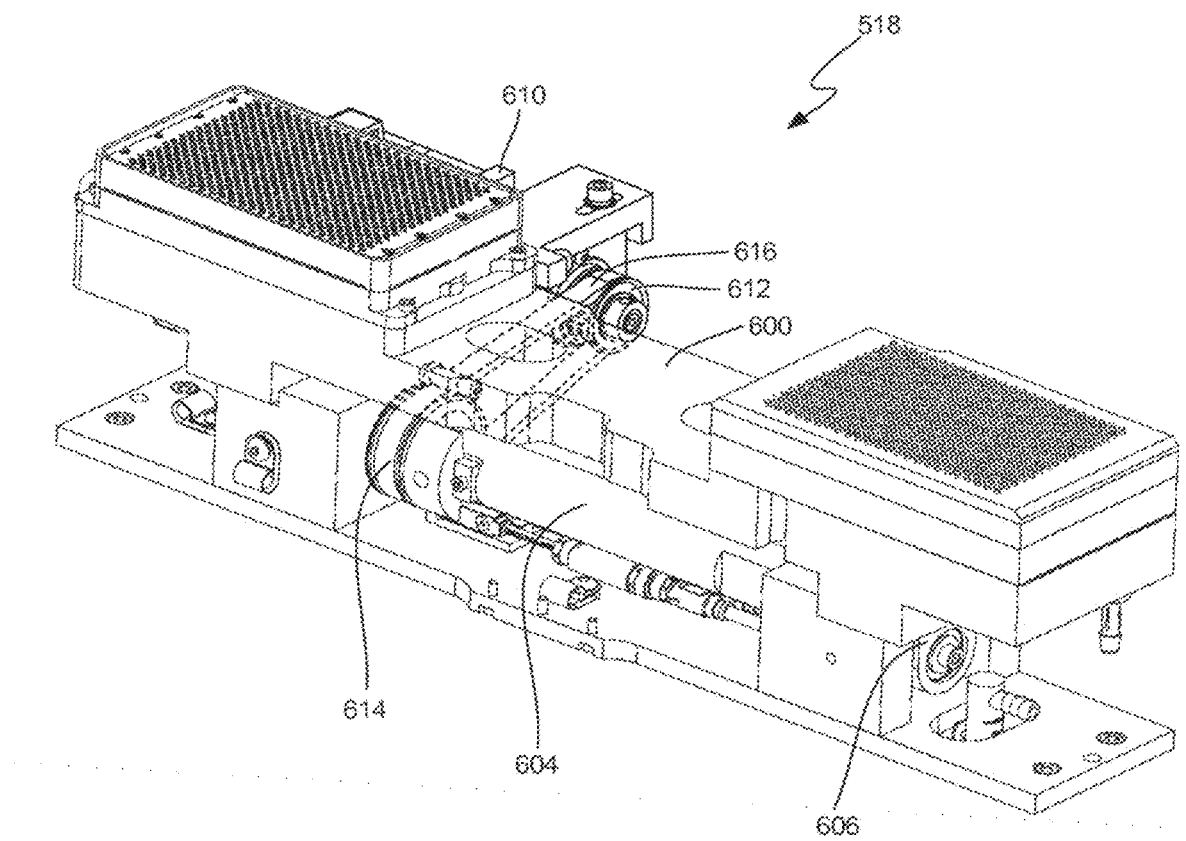

FIG. 22A is a partially transparent front perspective view of a lift mechanism.

Figure 22B:
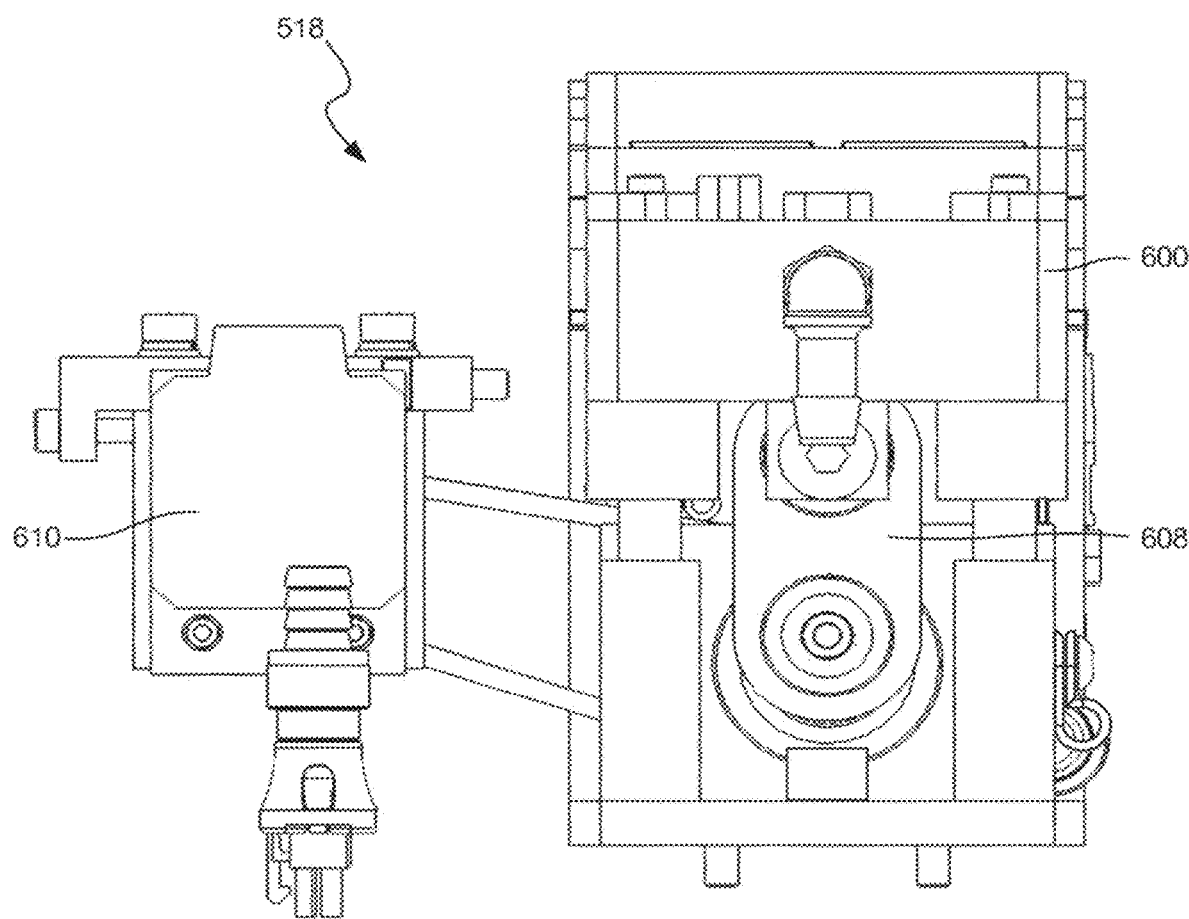

FIG. 22B is a plan view of the lift mechanism.

Figure 23A:
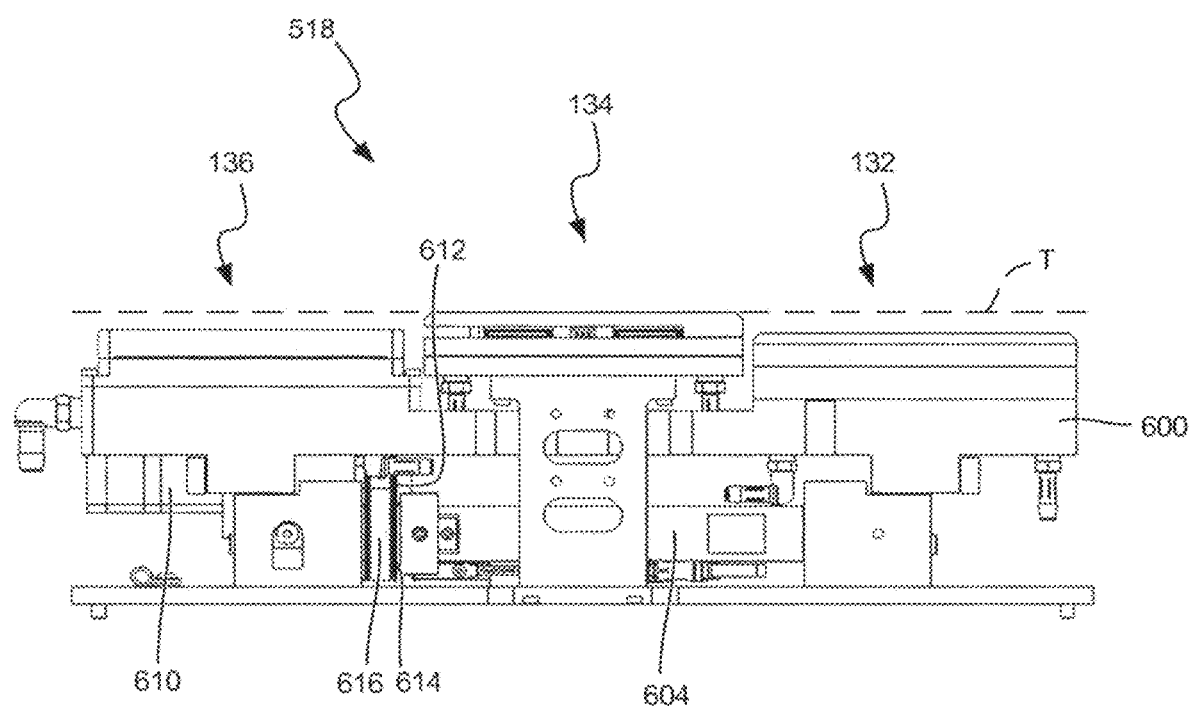

FIG. 23A is a front plan view of the lift mechanism on the tape path assembly in a retracted position.

Figure 23B:
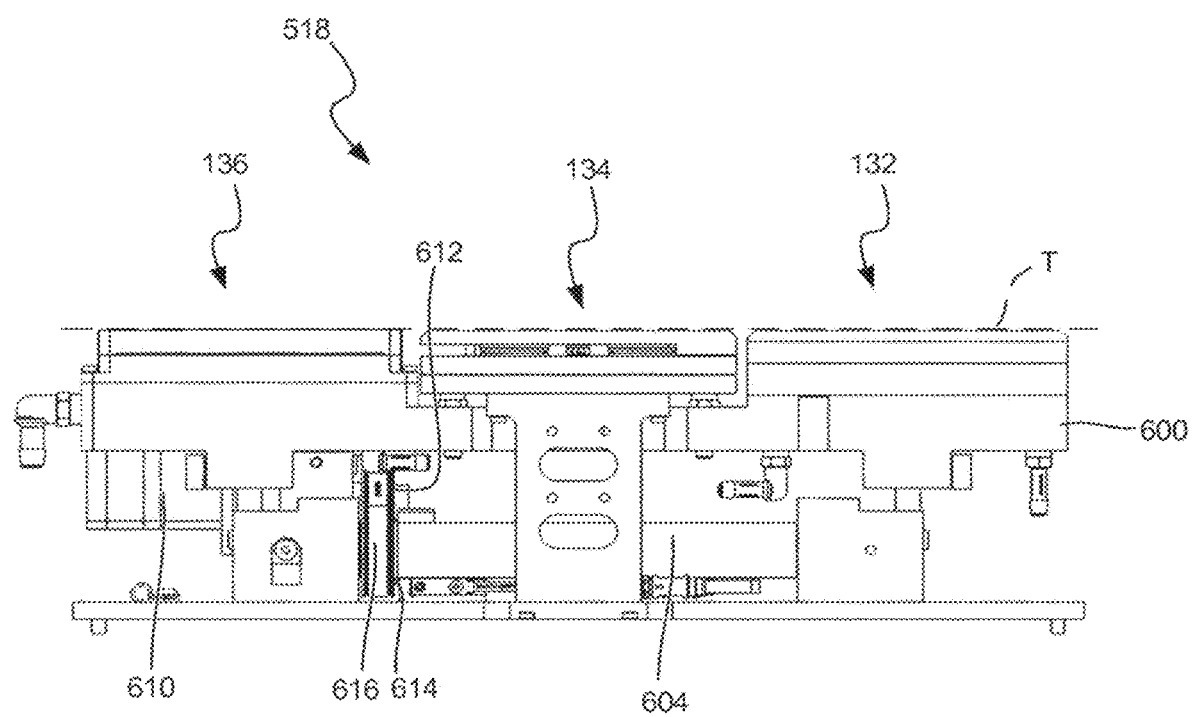

FIG. 23B is a front plan view of the lift mechanism on the tape path assembly in an extended position.

Figure 24:
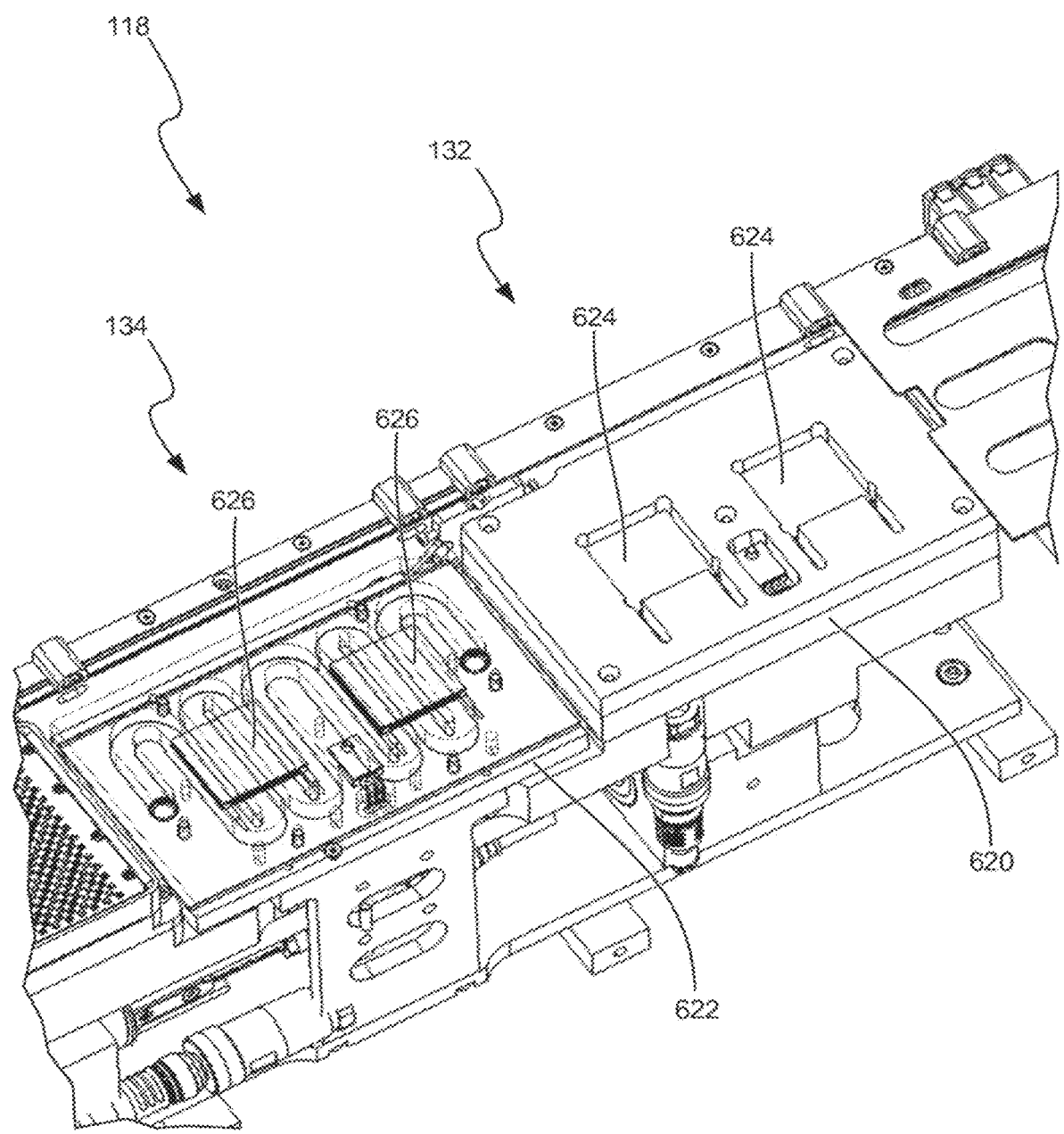

FIG. 24 is a front perspective view of thermal units on the tape path assembly.

Figure 25:
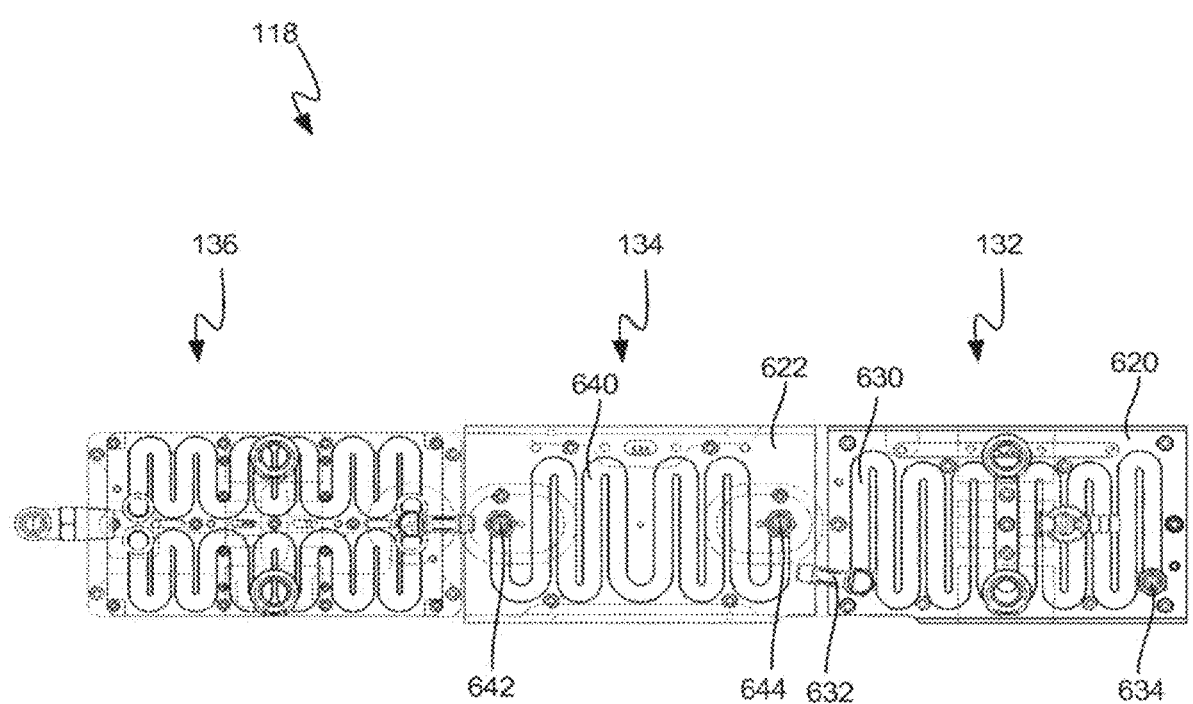

FIG. 25 is a bottom view of fluid paths on the tape path assembly.

Figure 26A:
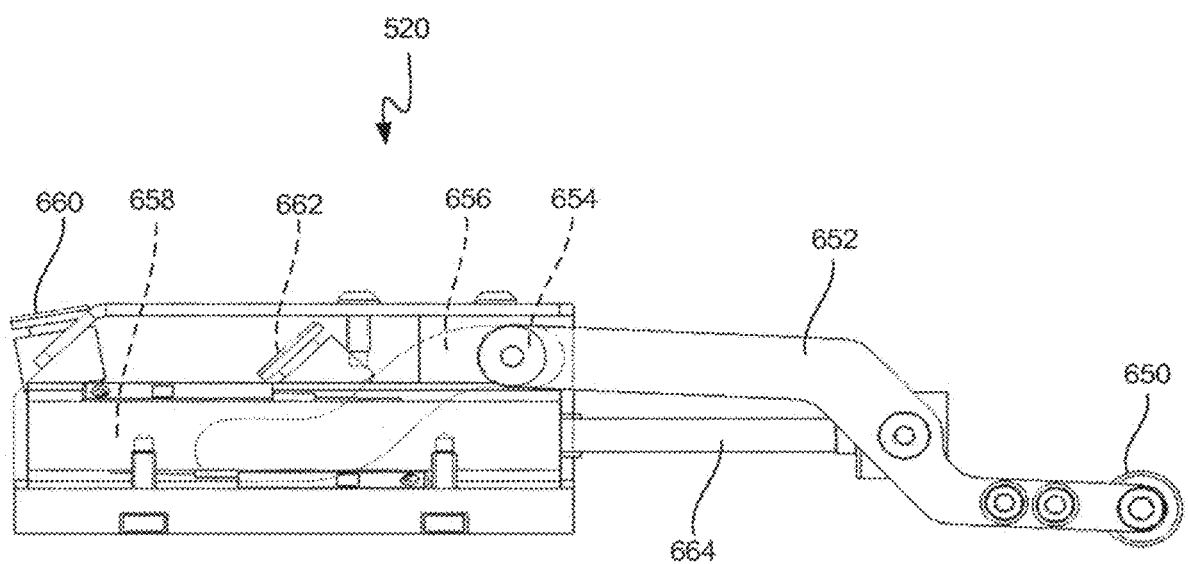

FIG. 26A is a partially transparent side view of a retractable hold down.

Figure 26B:
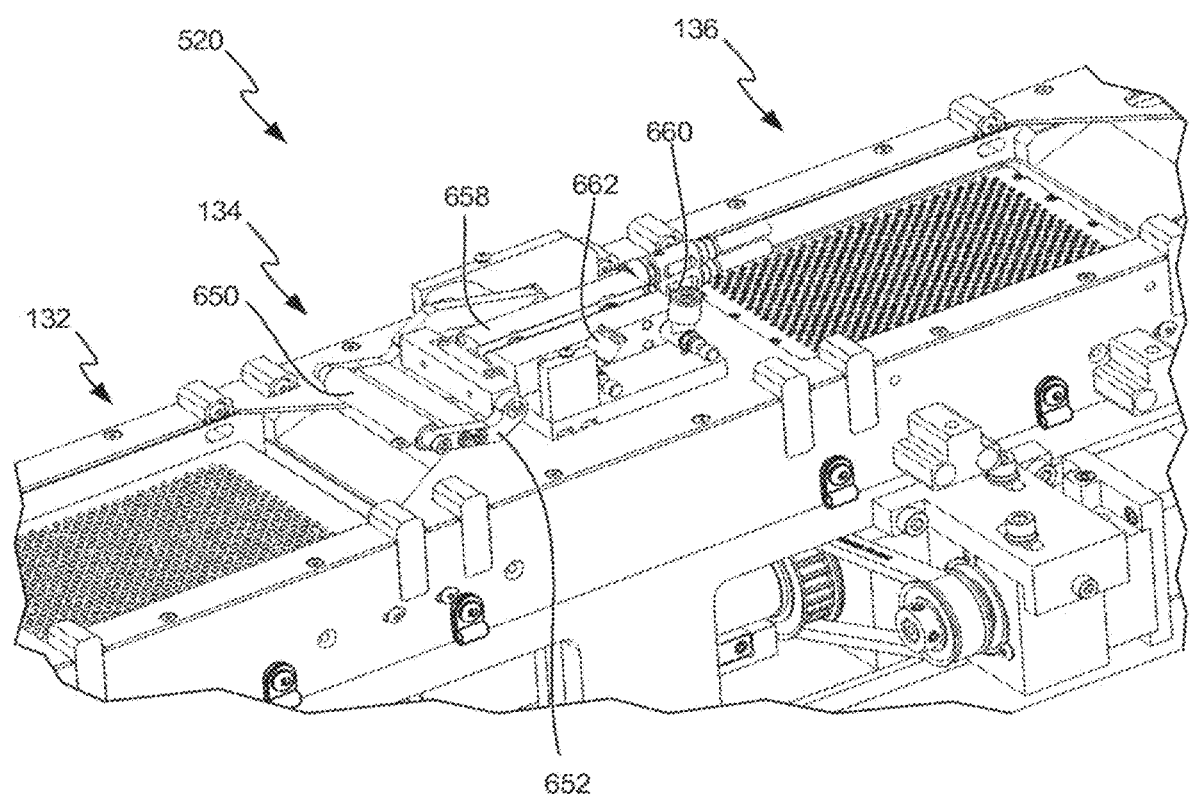

FIG. 26B is a back perspective view of the retractable hold down on the tape path assembly with the retractable hold down in a retracted position.

Figure 26C:
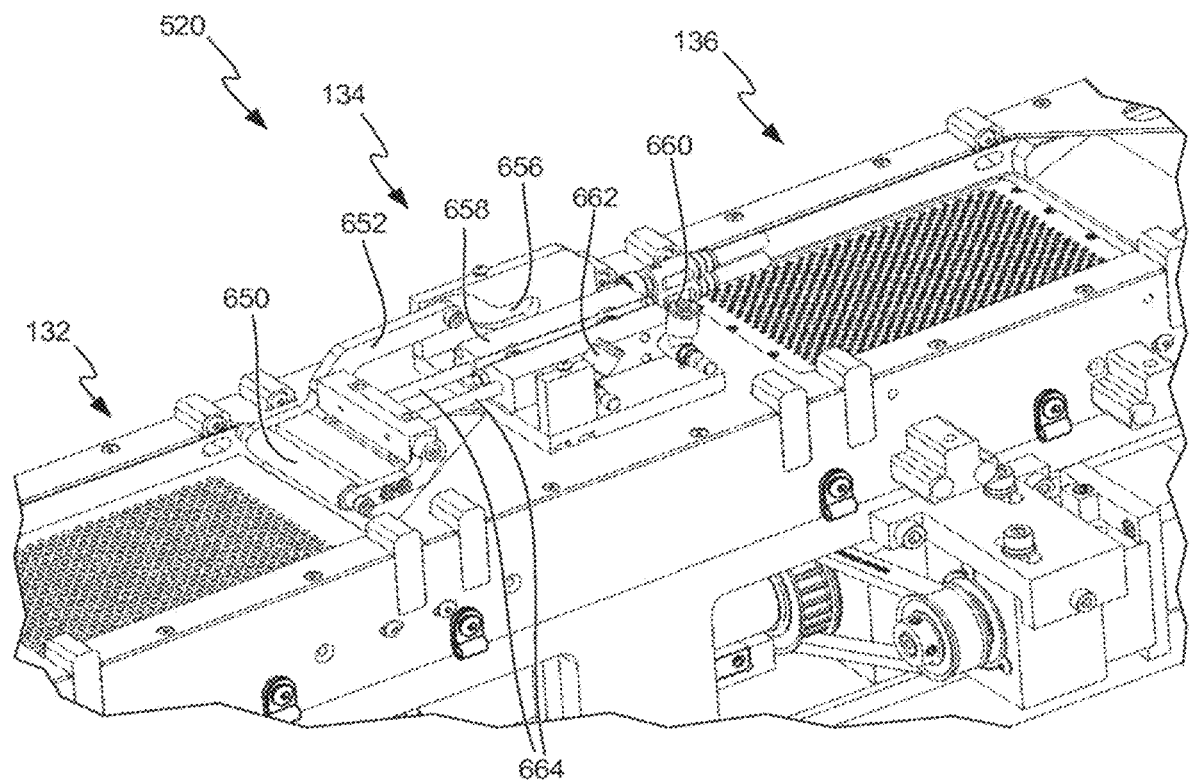

FIG. 26C is a back perspective view of the retractable hold down on the tape path assembly with the retractable hold down in an extended position.

Figure 27:
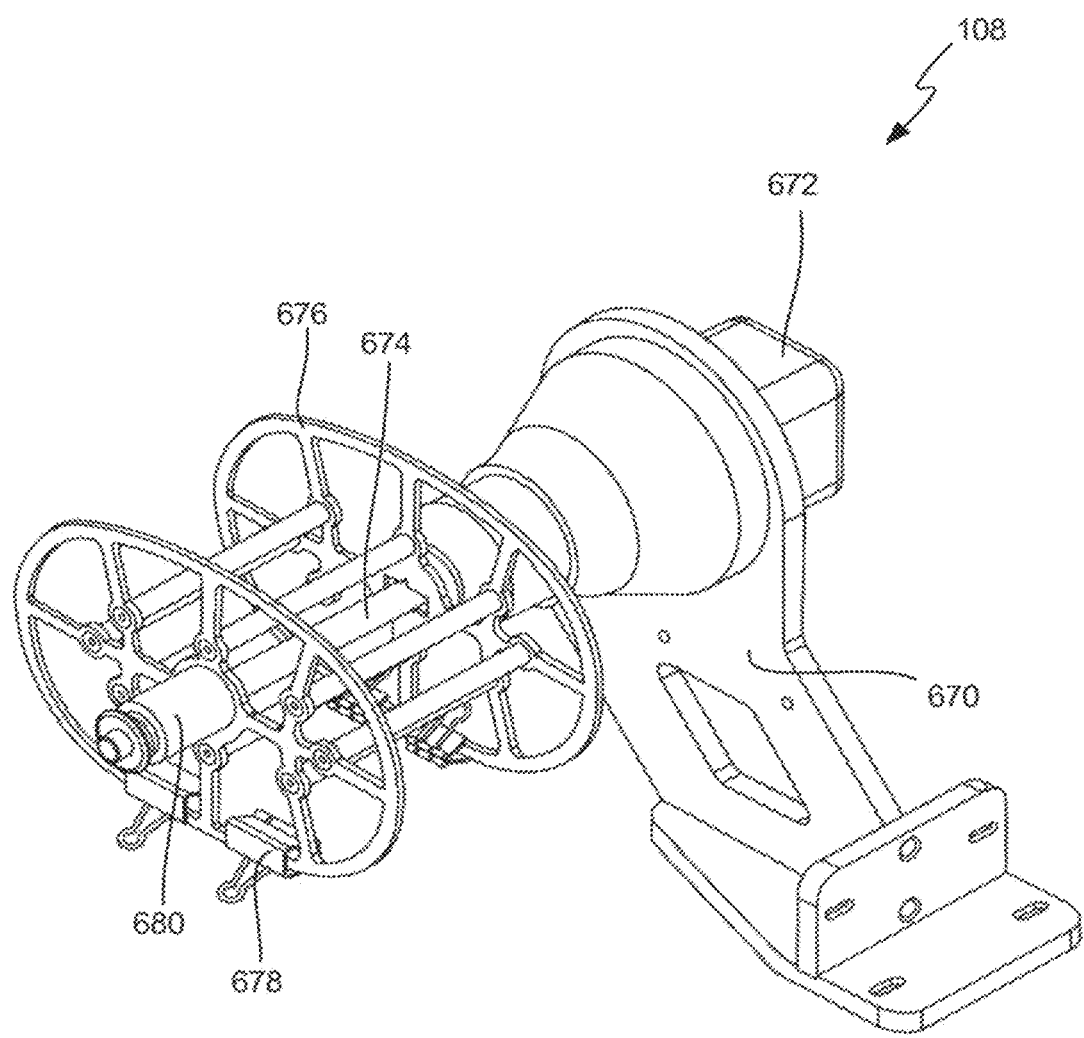

FIG. 27 is a perspective view of a rewind assembly that can accumulate processed tape leaving the tape path assembly.

Dispensing Assembly

Figure 28:
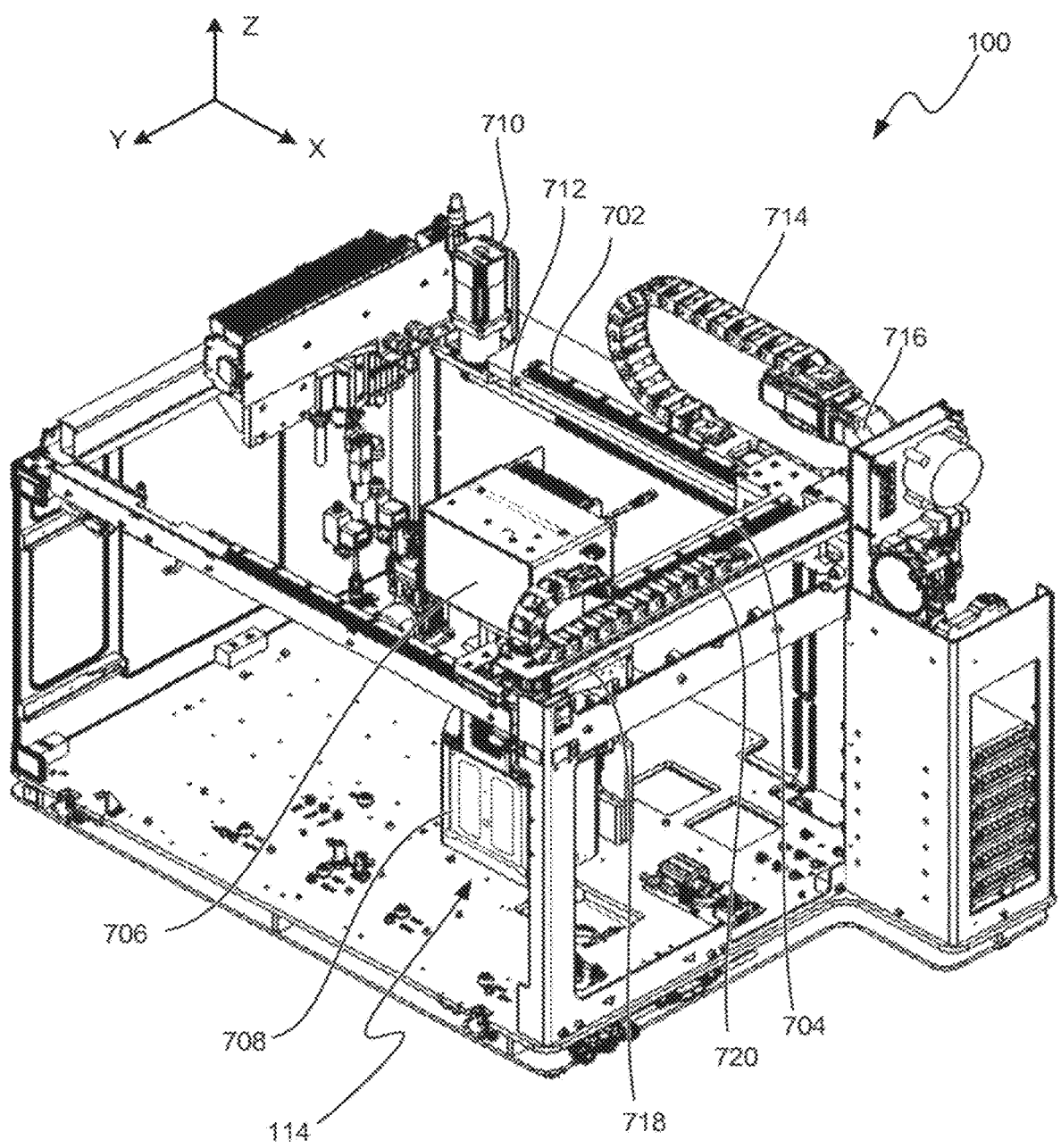

FIG. 28 is an isometric view of a dispensing assembly in the instrument.

Figure 29:
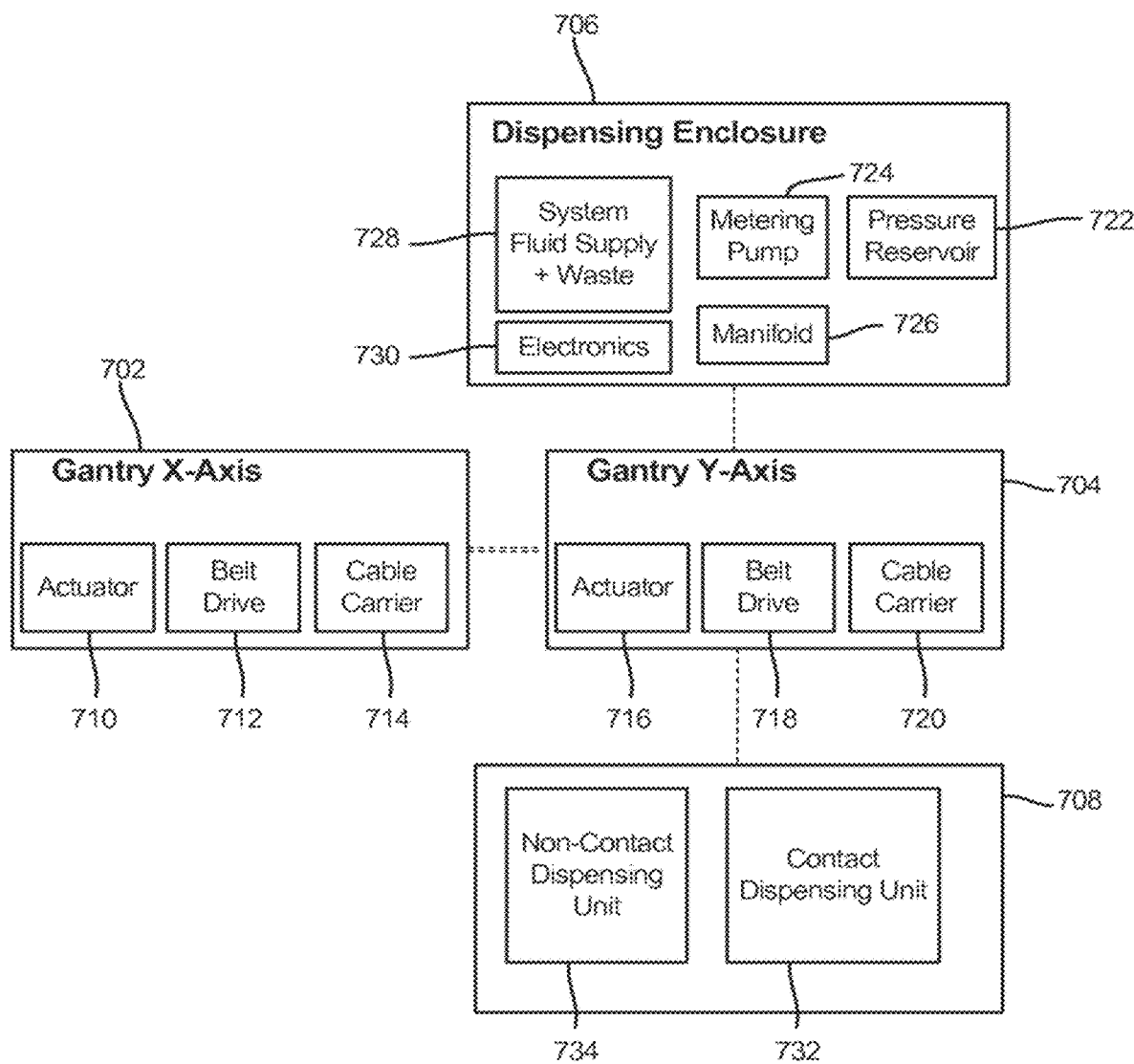

FIG. 29 is a schematic diagram of the dispensing assembly seen in FIG. 28.

Figure 30:
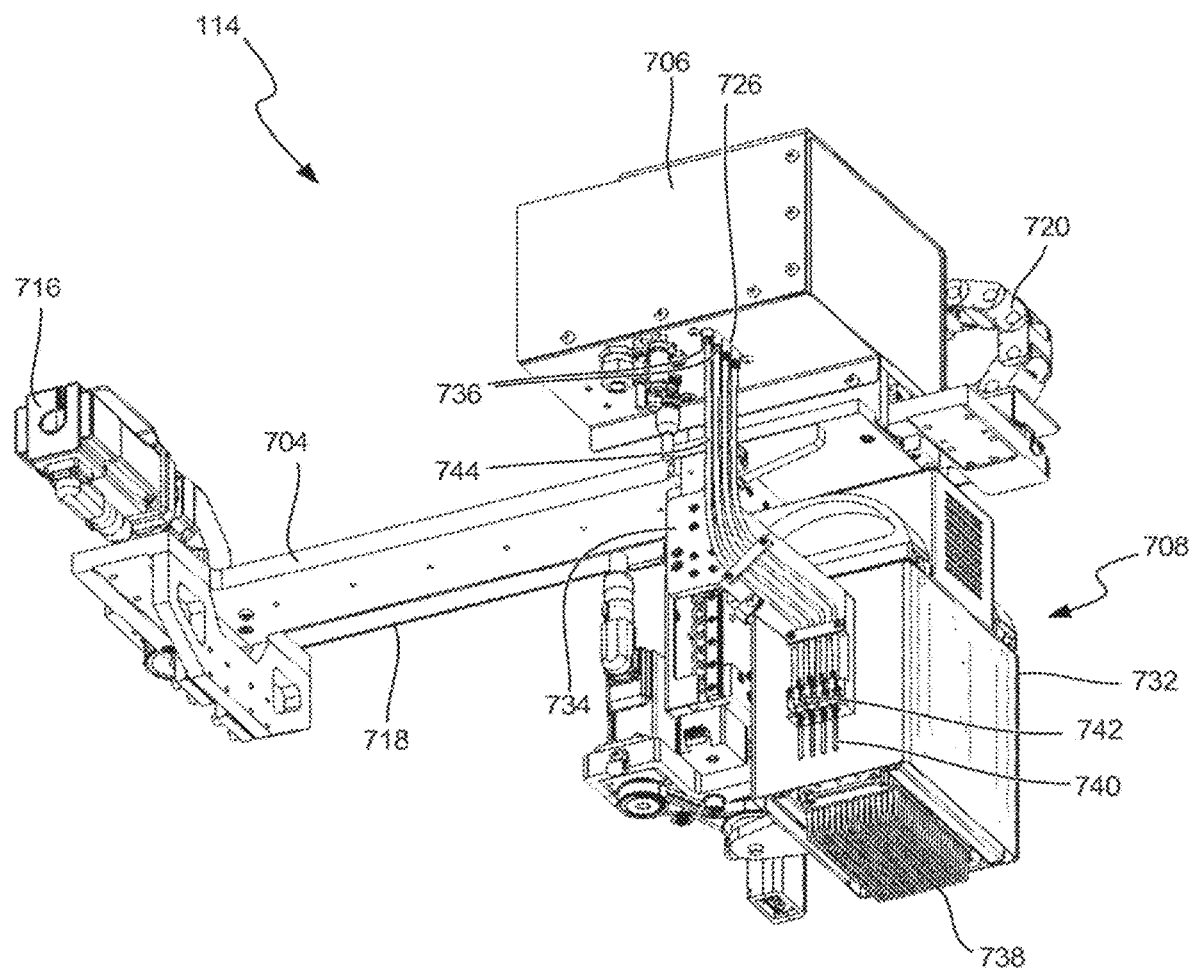

FIG. 30 is a perspective view of the y-axis gantry of the dispensing assembly seen in FIG. 28.

Figure 31A:
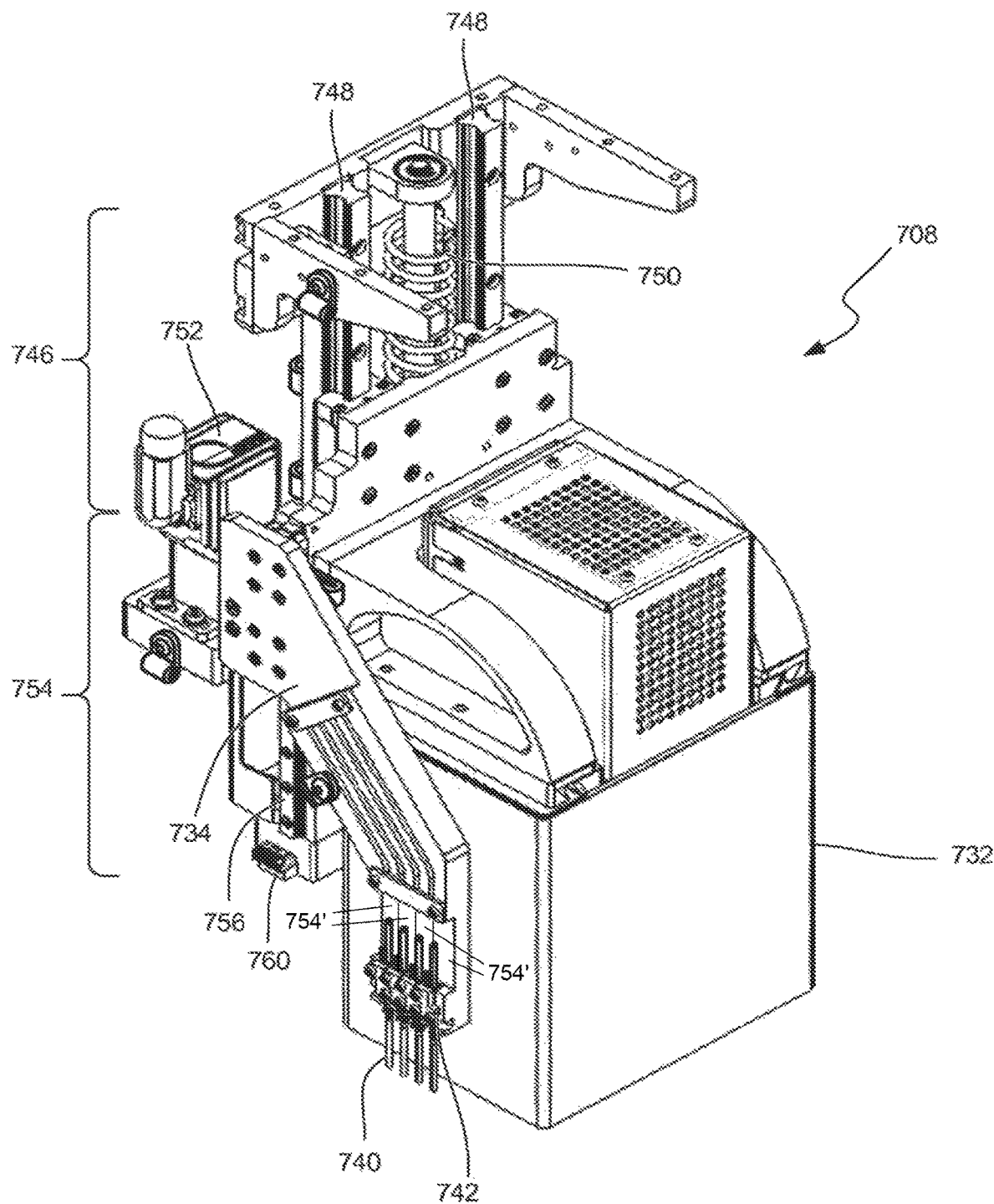
Figure 31B:
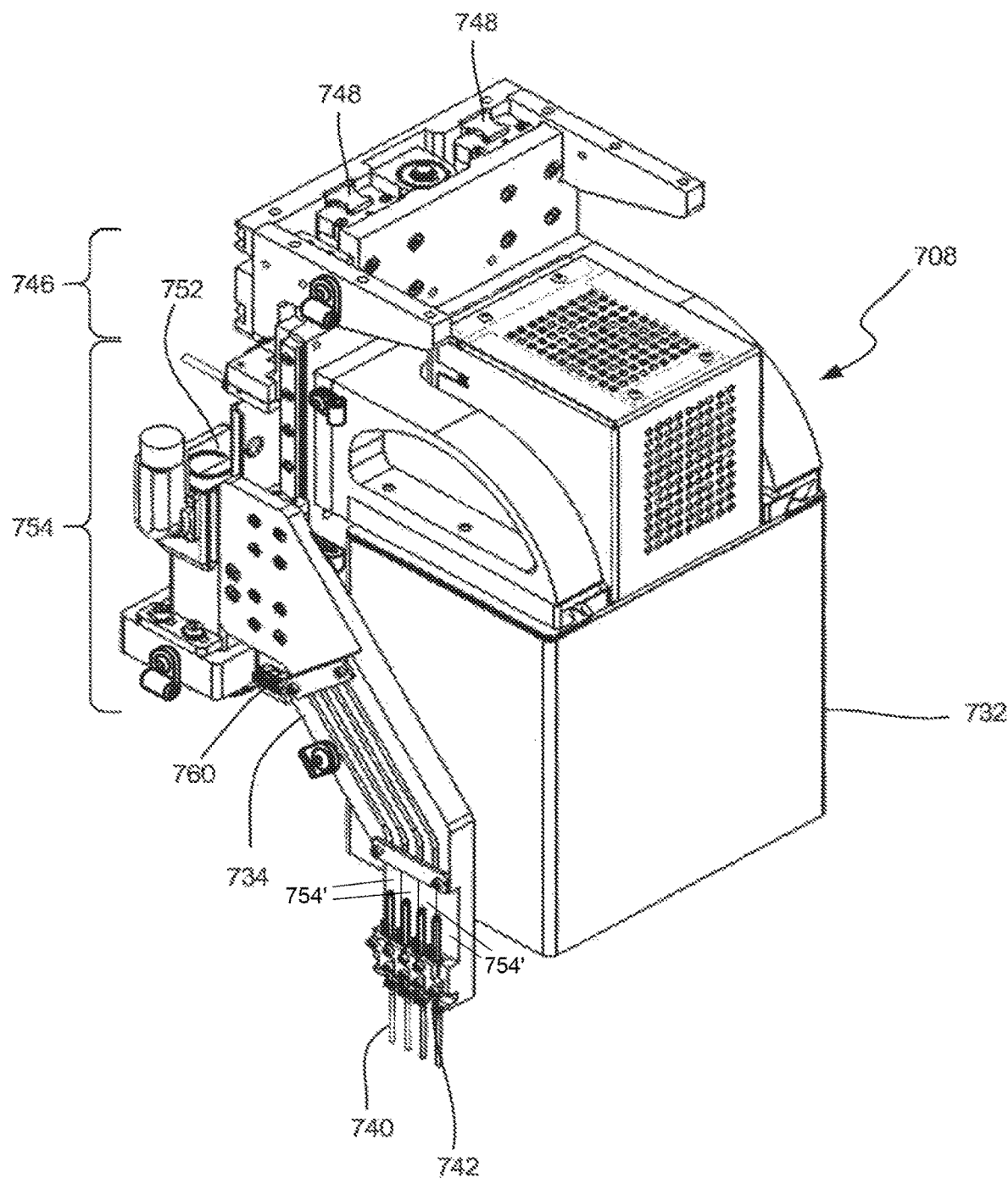

FIGS. 31A-31B are isometric views of the dispensing head of the dispensing assembly seen in FIG. 28.

Figure 31C:
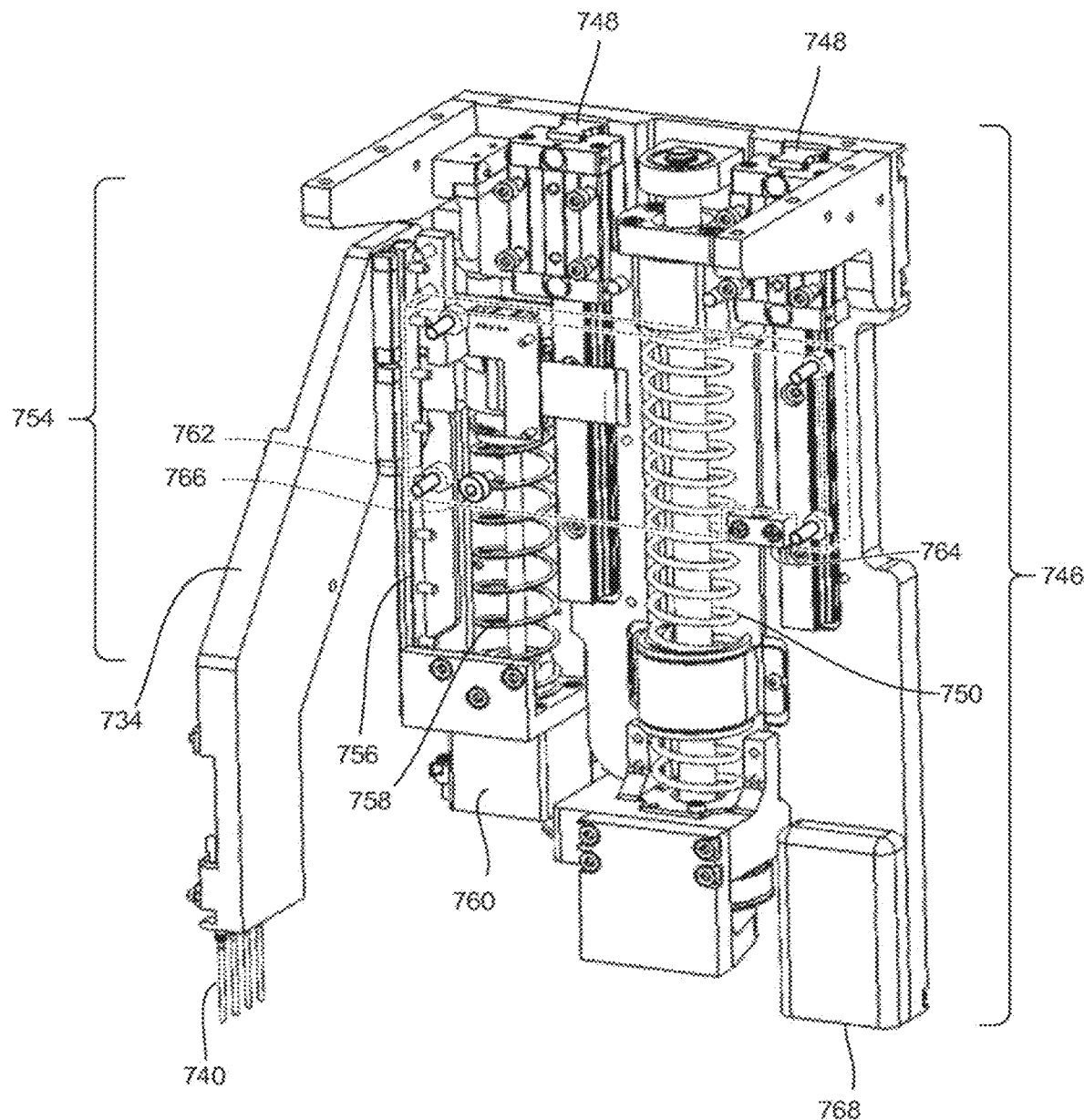

FIG. 31C is a partially transparent perspective view of two z-axes of the dispensing head seen in FIGS. 31A-31B.

Figure 32A:
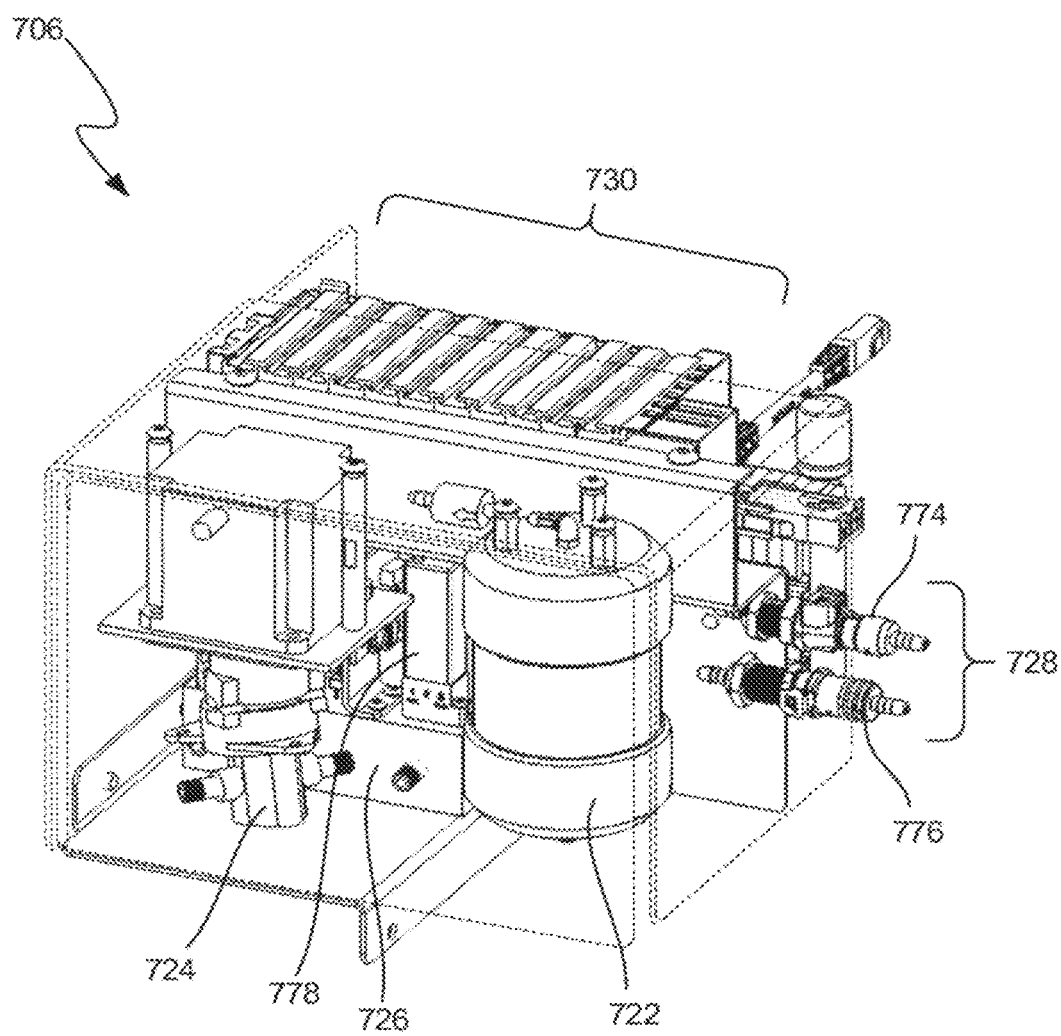

FIG. 32A is a transparent isometric view of the dispensing enclosure of the dispensing assembly seen in FIG. 28.

Figure 32B:
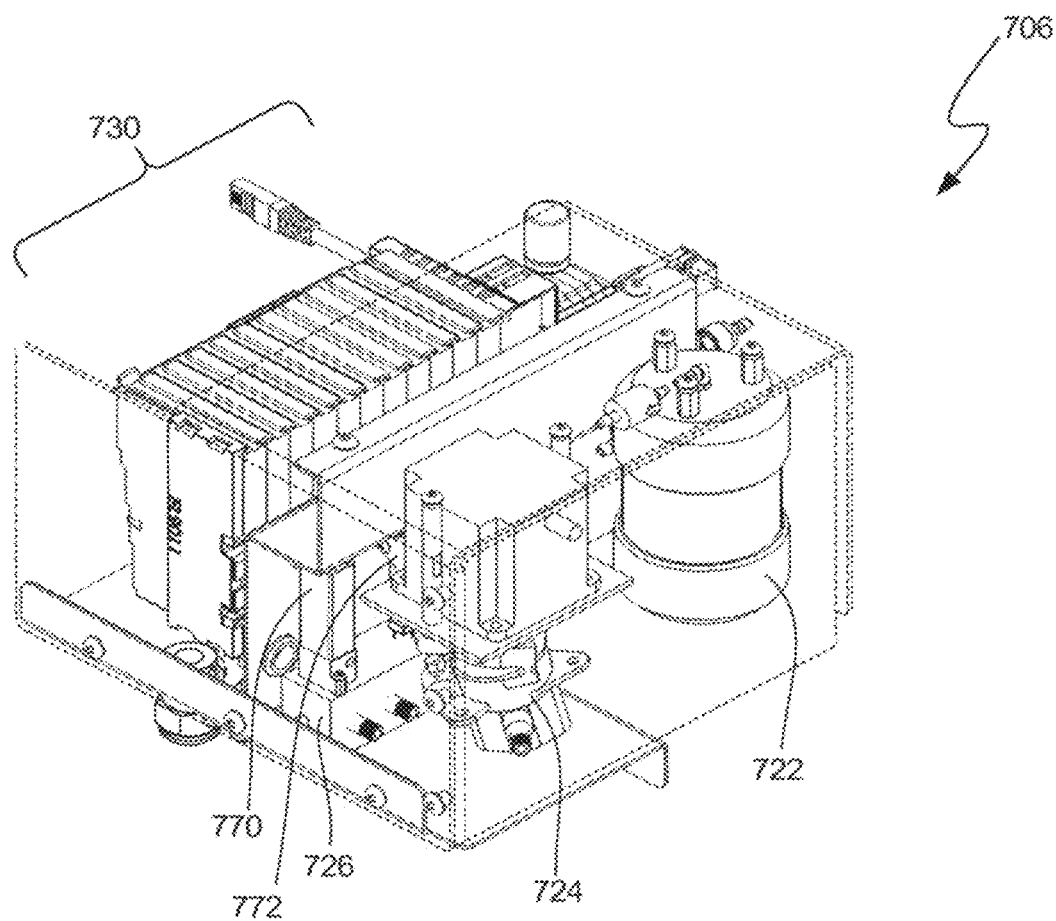

FIG. 32B is a transparent perspective view of the dispensing enclosure of the dispensing assembly seen in FIG. 28.

Figure 33:
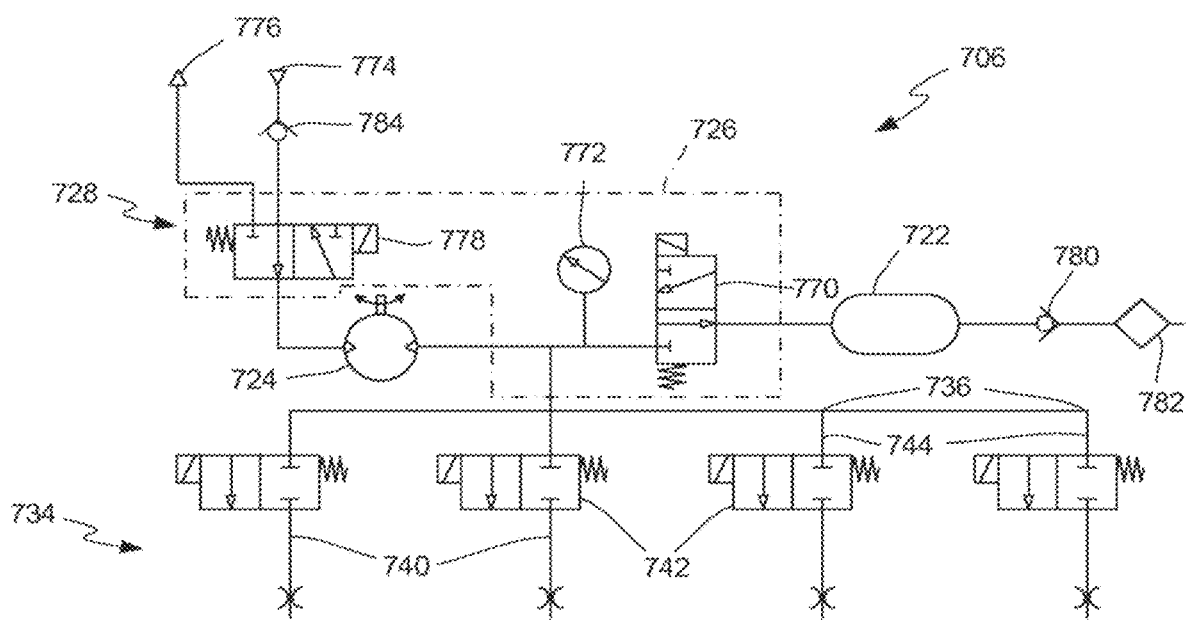

FIG. 33 is a schematic diagram of non-contact dispensing components of the dispensing enclosure and the dispensing head seen in FIGS. 31A-31C and 32A-32B.

Tape Sealing Assembly

Figure 34A:
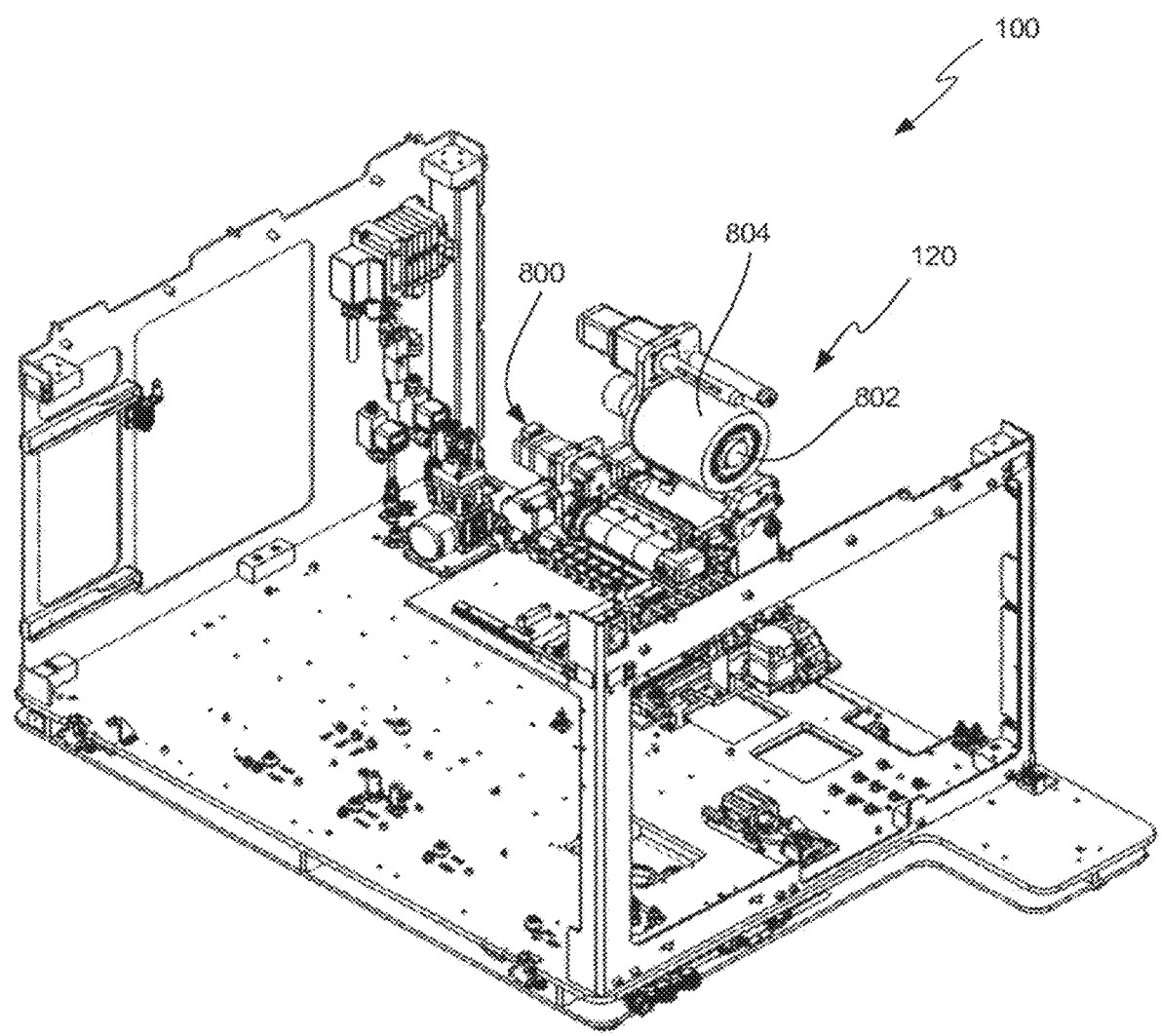

FIG. 34A is an isometric view of a tape sealing assembly in the instrument.

Figure 34B:
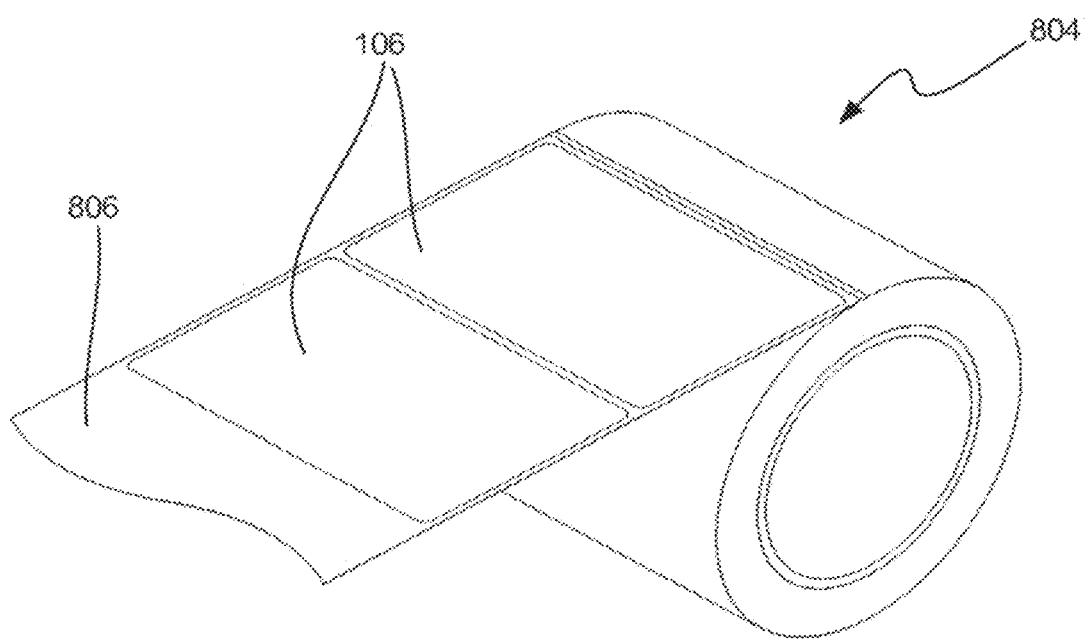

FIG. 34B is a perspective view of a seal web.

Figure 35:
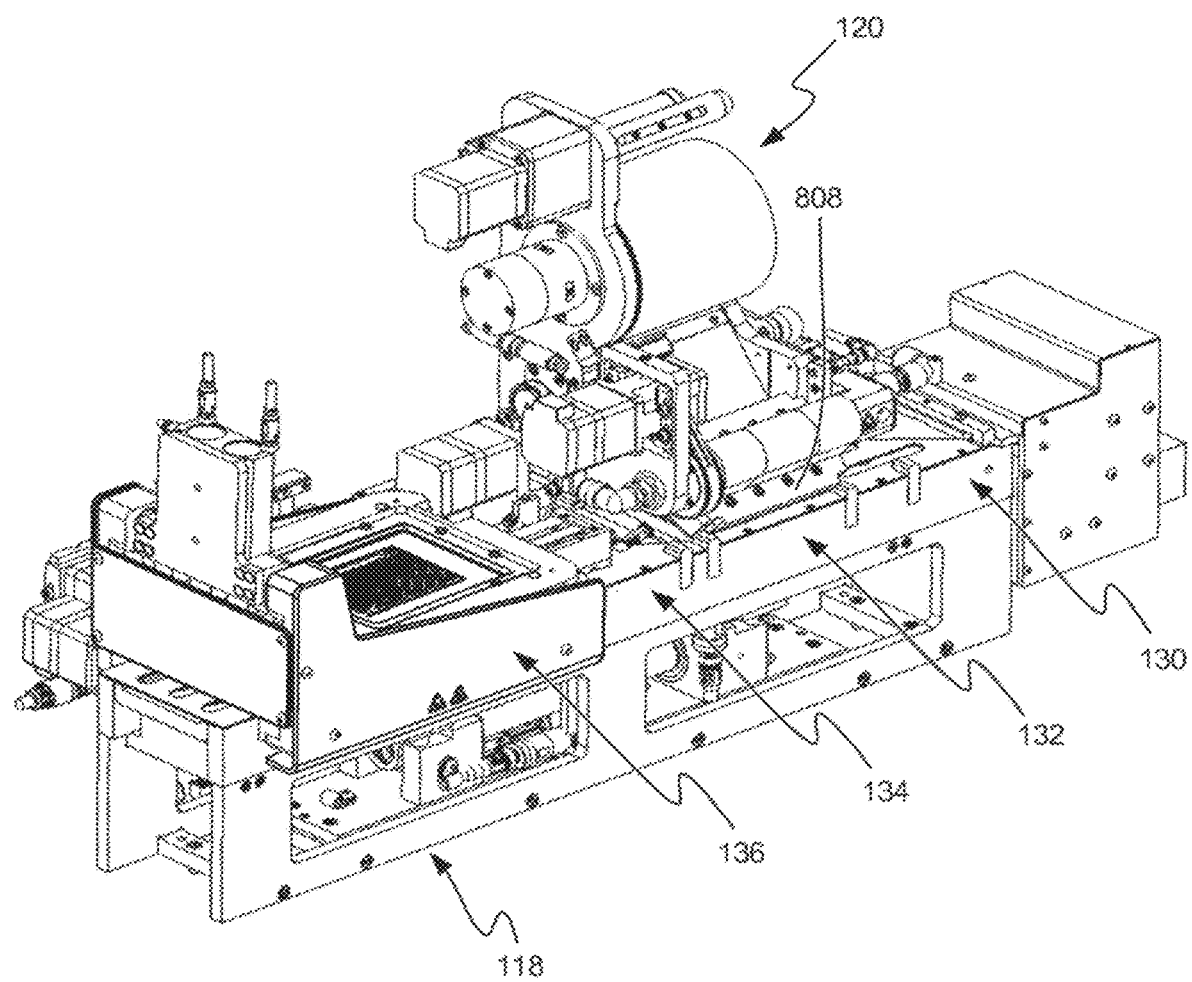

FIG. 35 is a perspective view of the tape sealing assembly positioned adjacent to a tape path assembly.

Figure 36A:
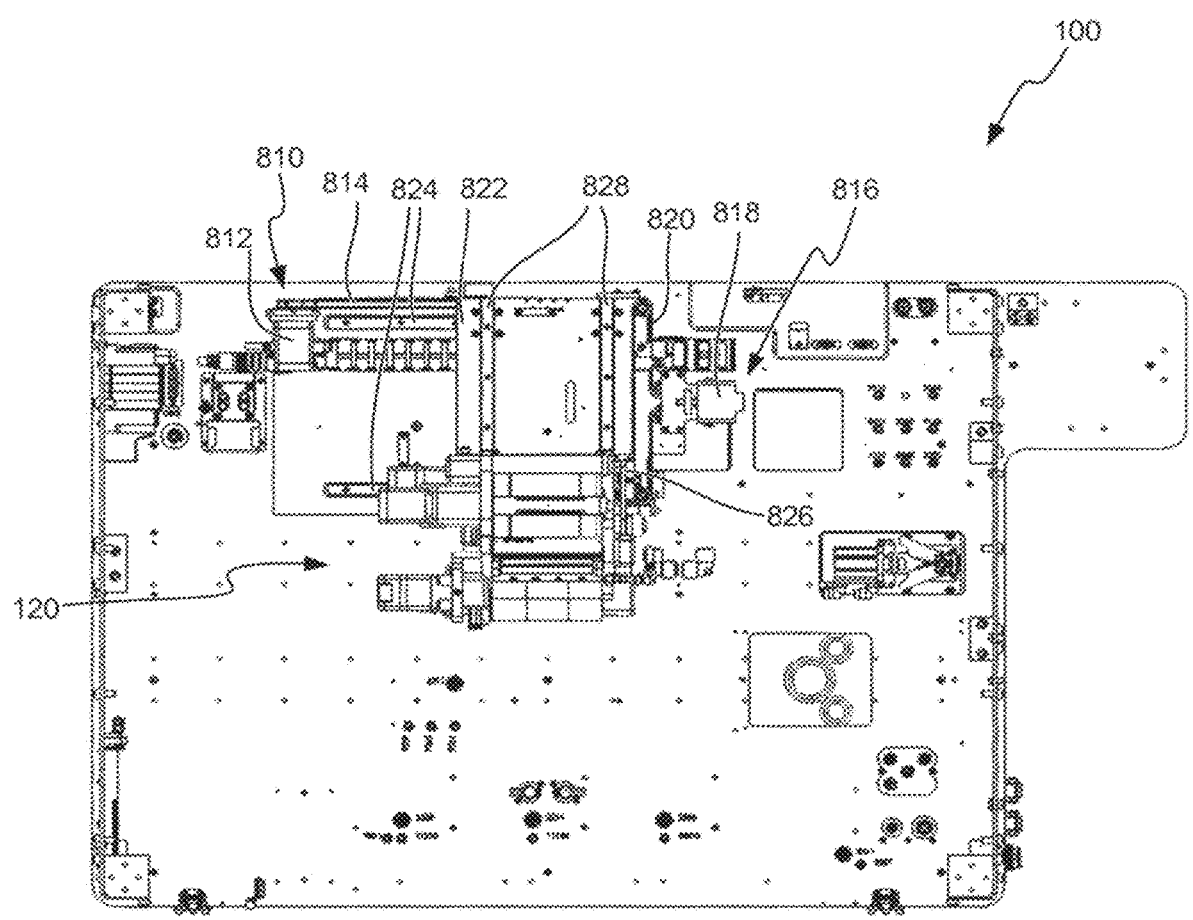

FIG. 36A is a top view of the tape sealing assembly within the instrument.

Figure 36B:
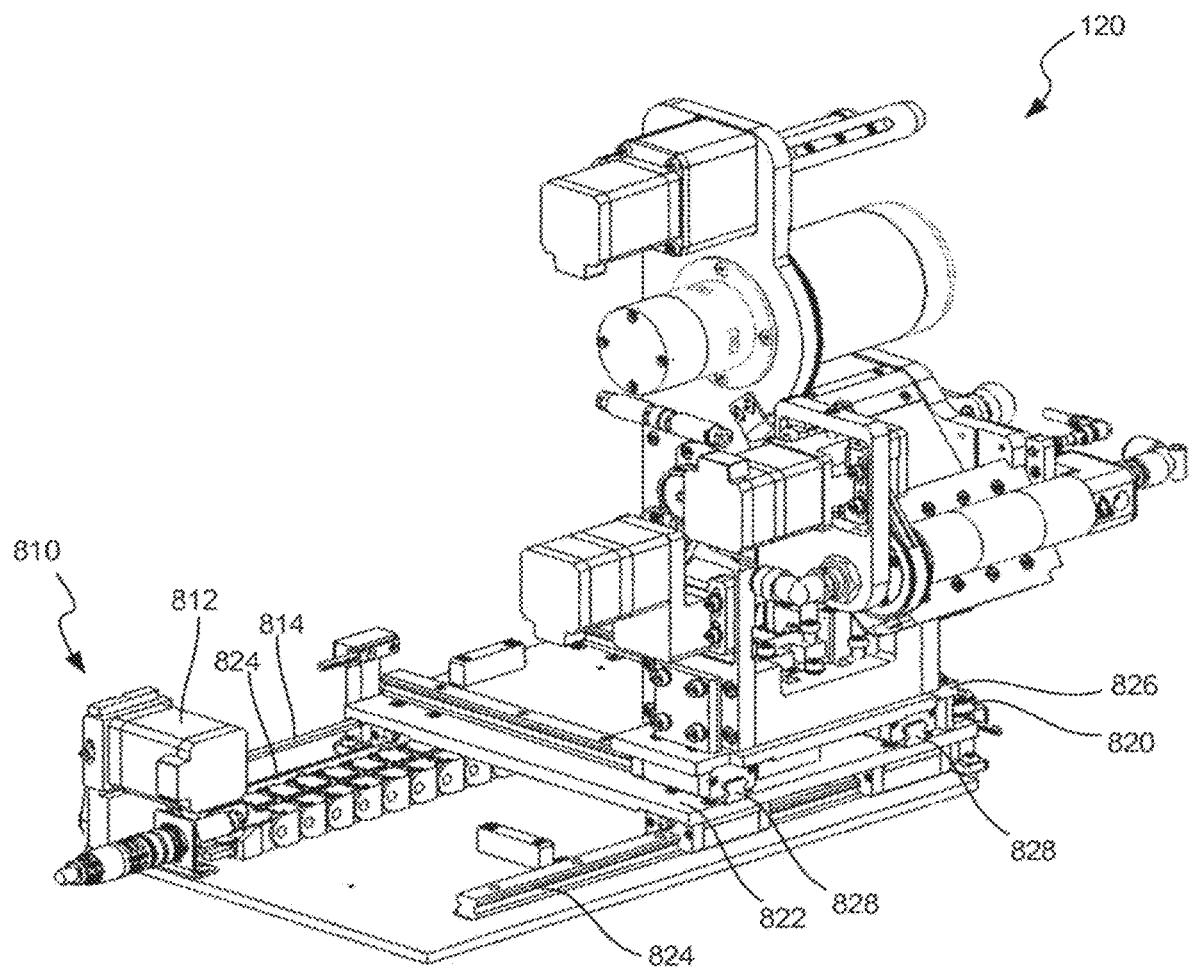
Figure 36C:
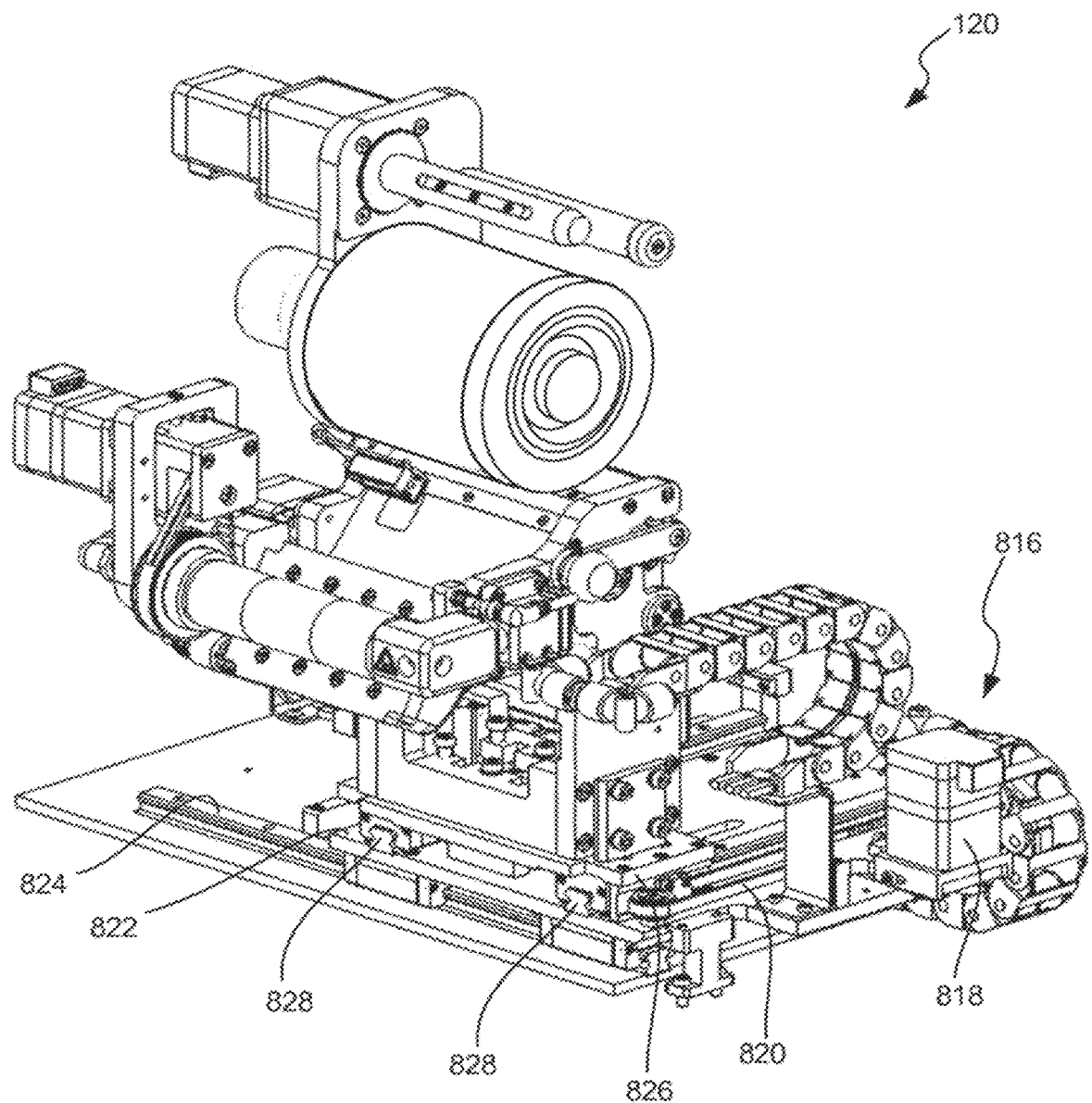

FIGS. 36B-36C are perspective views of the tape sealing assembly.

Figure 37A:
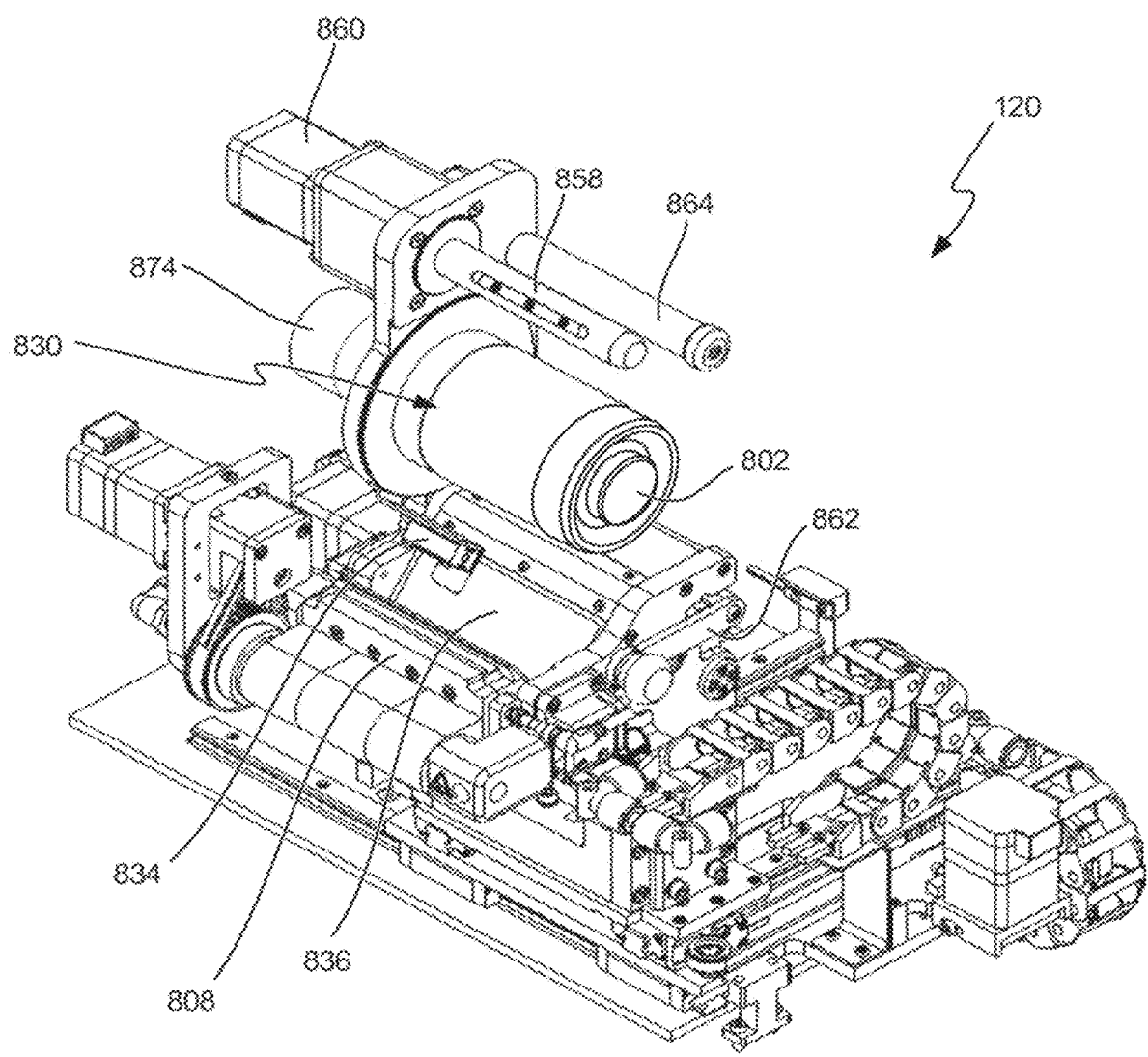

FIG. 37A is an isometric view of a portion of the tape sealing assembly.

Figure 37B:
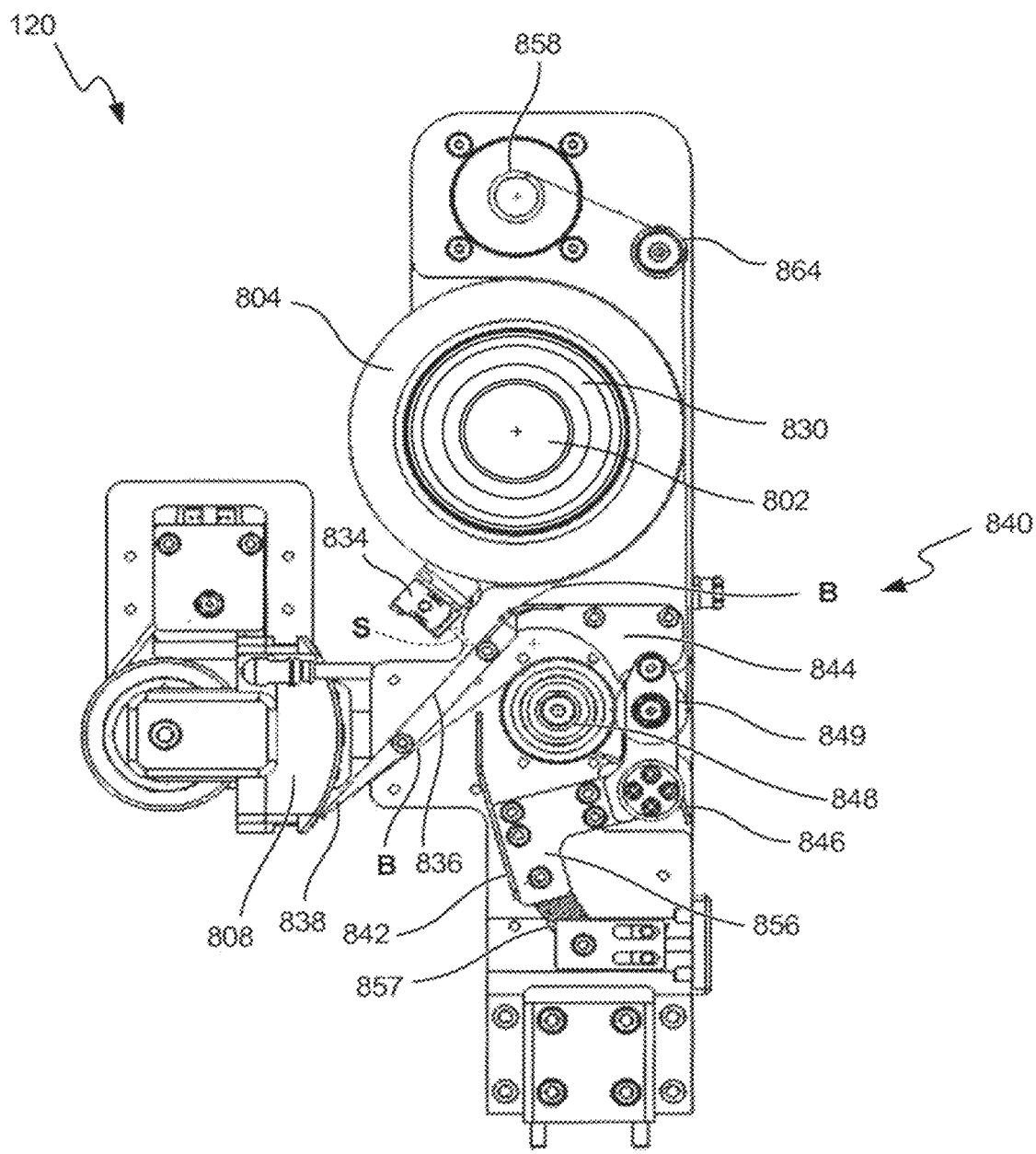

FIG. 37B is a side view of the tape sealing assembly with a seal web threading path.

Figure 38A:
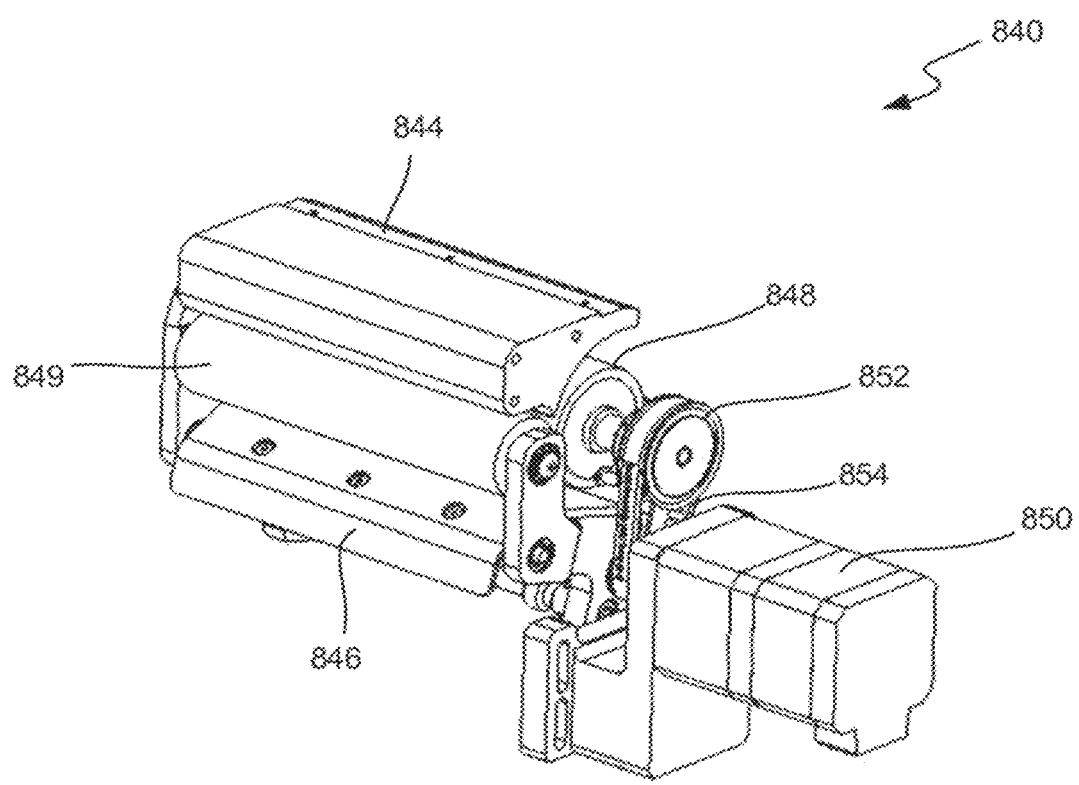

FIG. 38A is a perspective view of a backer take-up mechanism of the tape sealing assembly.

Figure 38B:
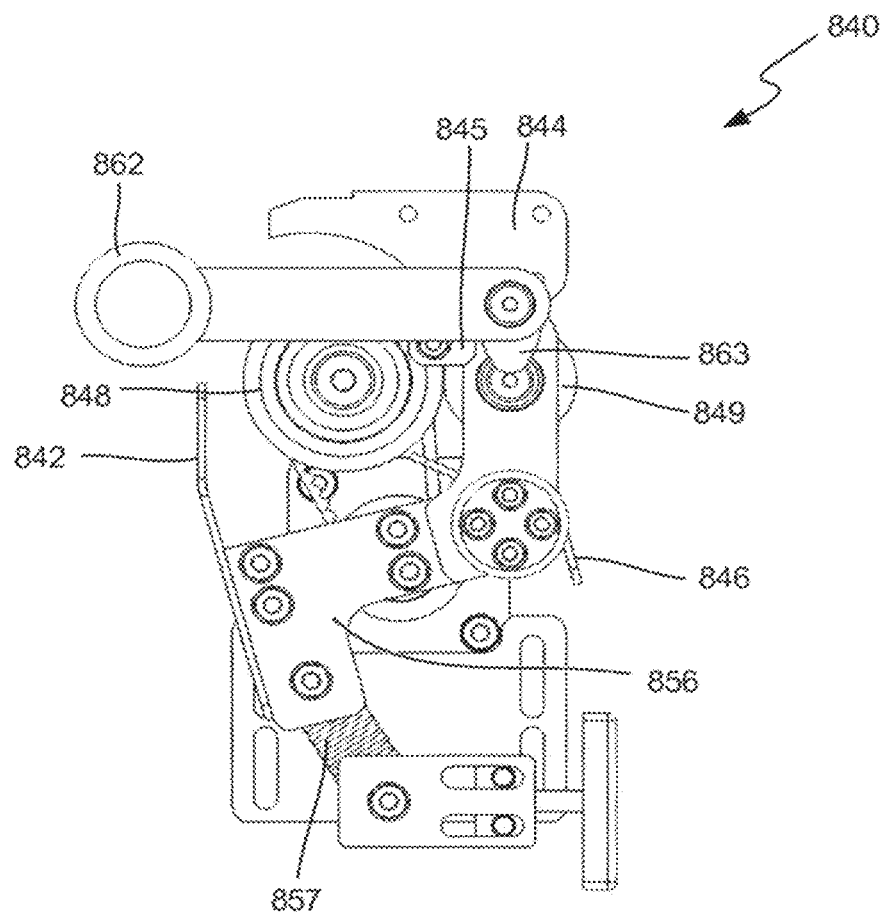
Figure 38C:
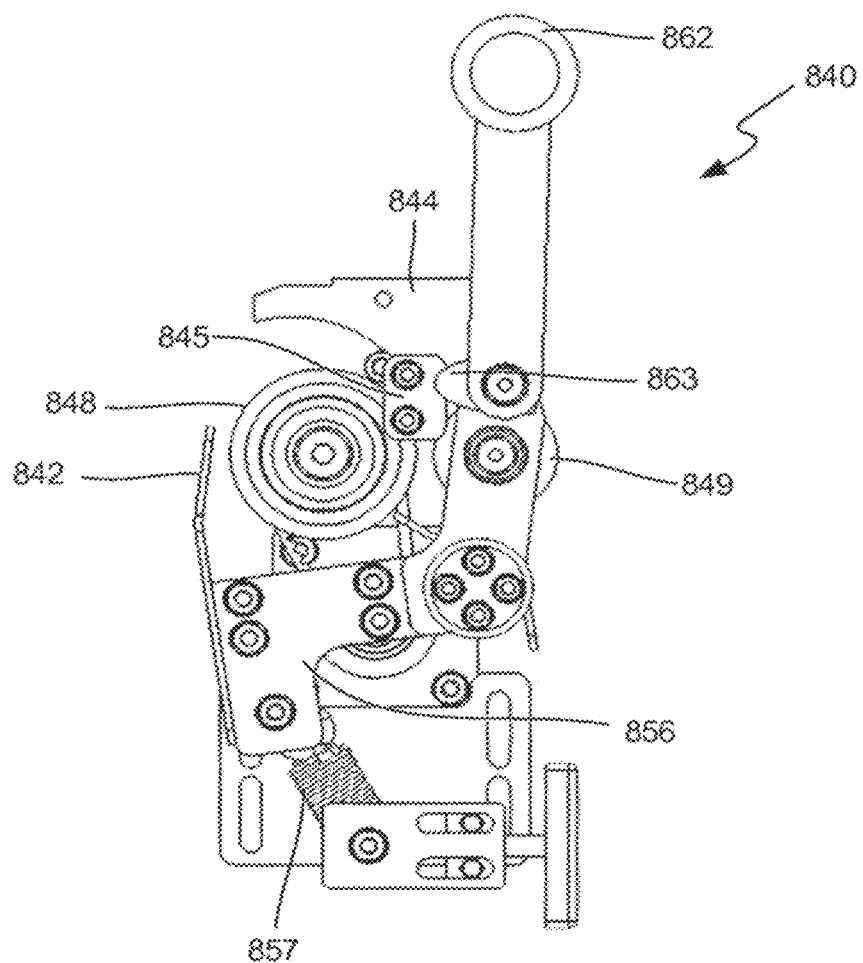
Figure 39A:
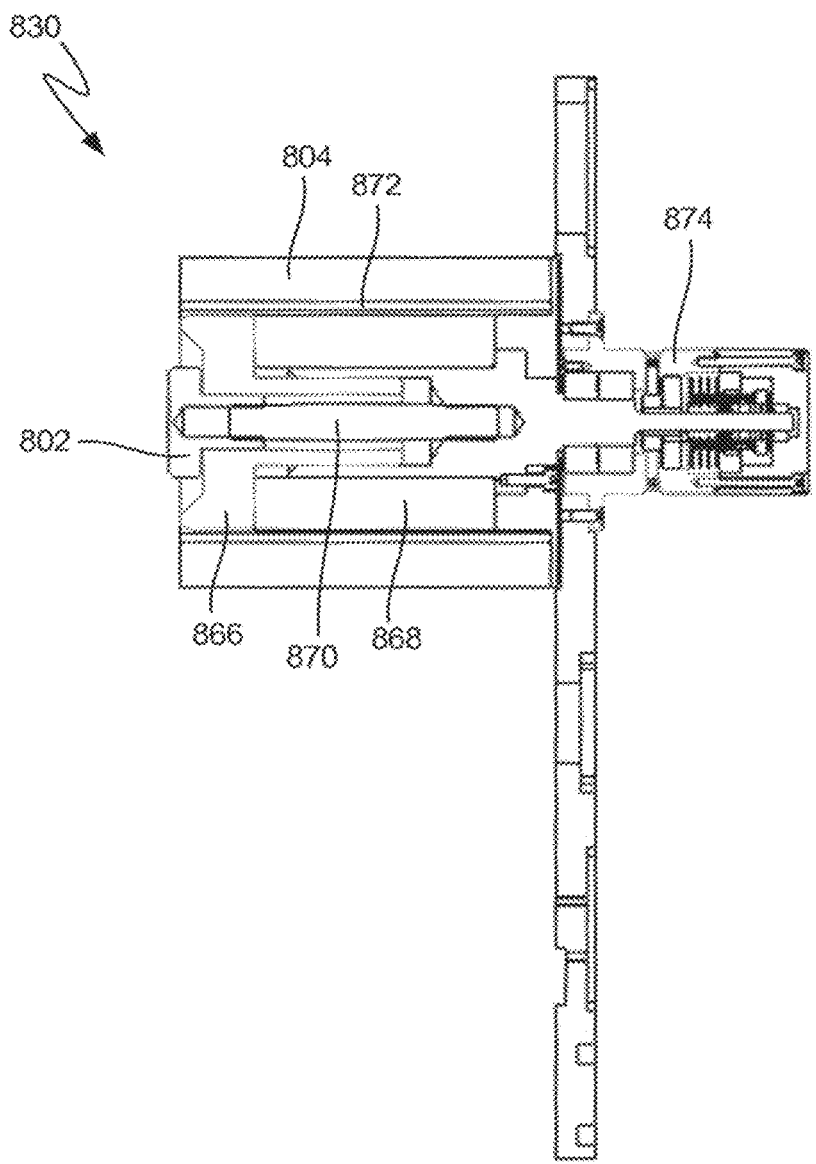

FIG. 38B is a side view of the backer taker-up mechanism in FIG. 38A with friction roller in a closed position FIG. 38C is a side view of the backer taker-up mechanism in FIG. 38A with friction roller in an open position FIG. 39A is a cross-sectional view of a locking mechanism of the tape sealing assembly in an unlocked position.

Figure 39B:
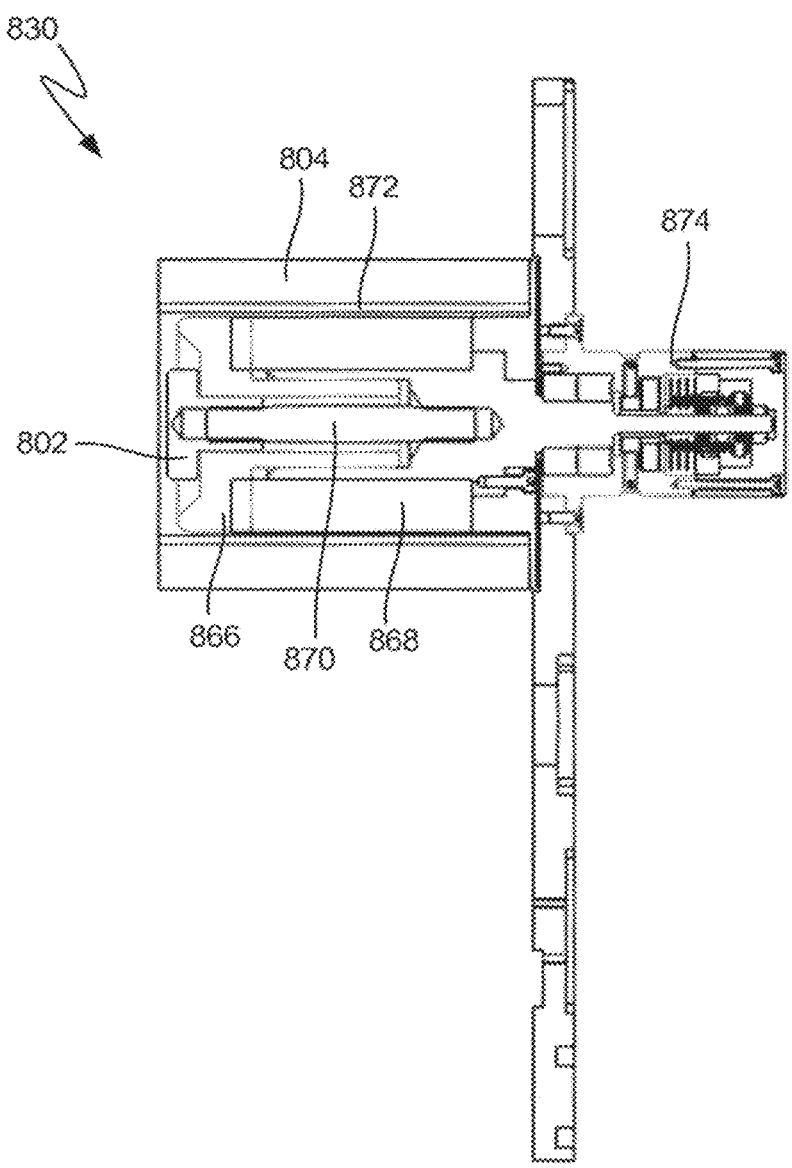

FIG. 39B is a cross-sectional view of a locking mechanism of the tape sealing assembly in a locked position.

Figure 40:
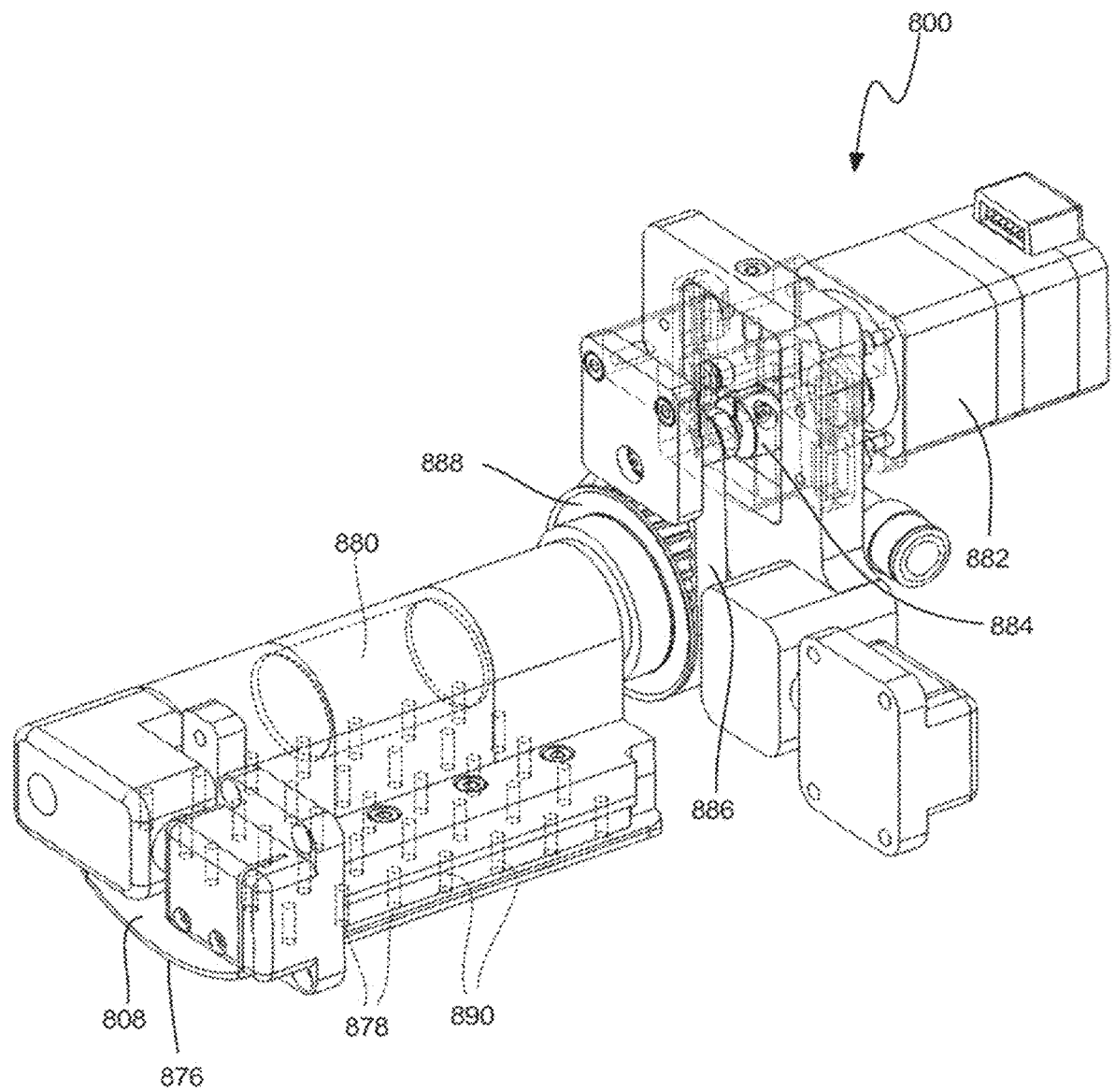

FIG. 40 is a partially transparent perspective view of an applicator of the tape sealing assembly.

Figure 41:
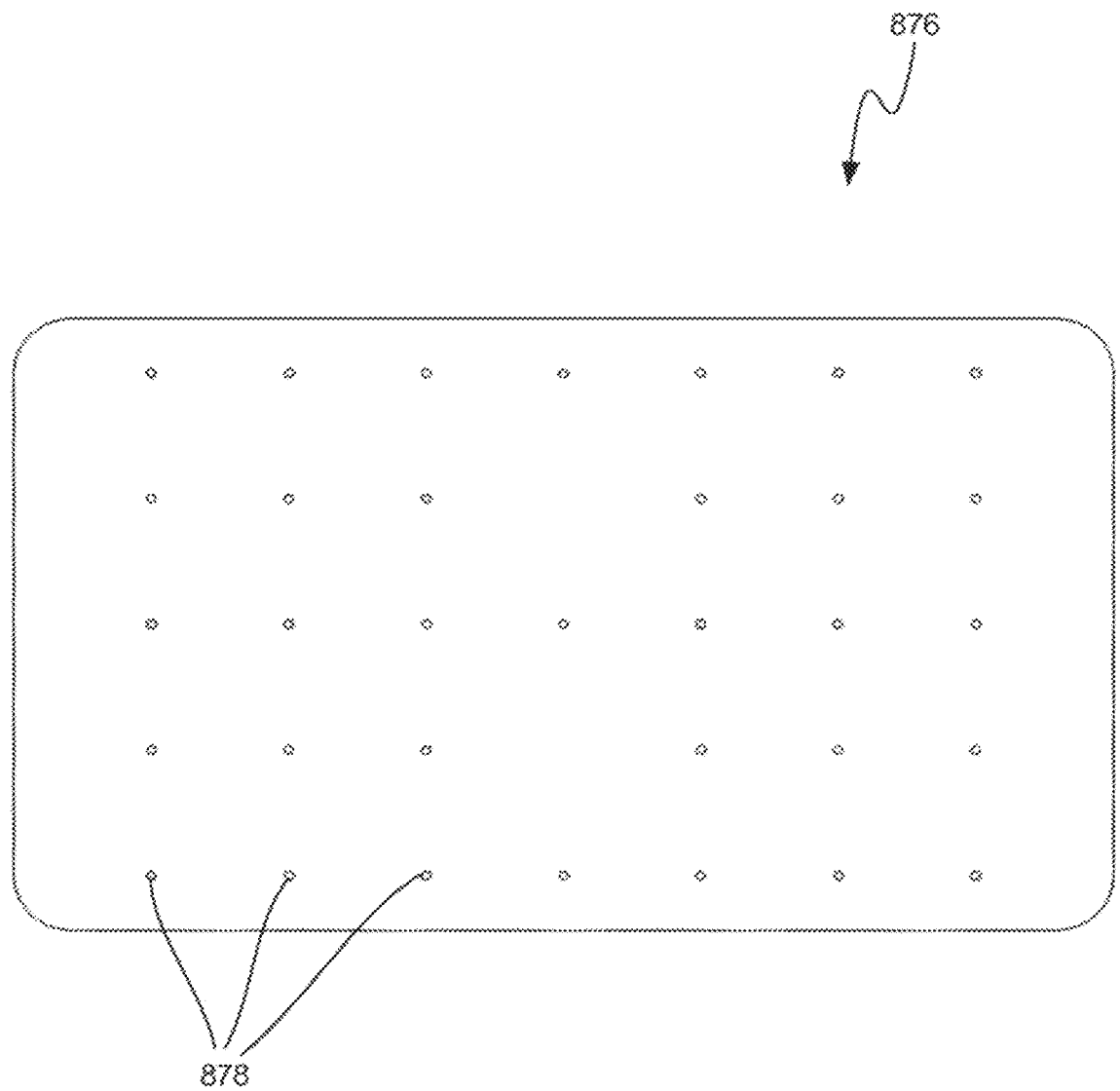

FIG. 41 is a bottom view of a pad of the applicator.

Figure 42A:
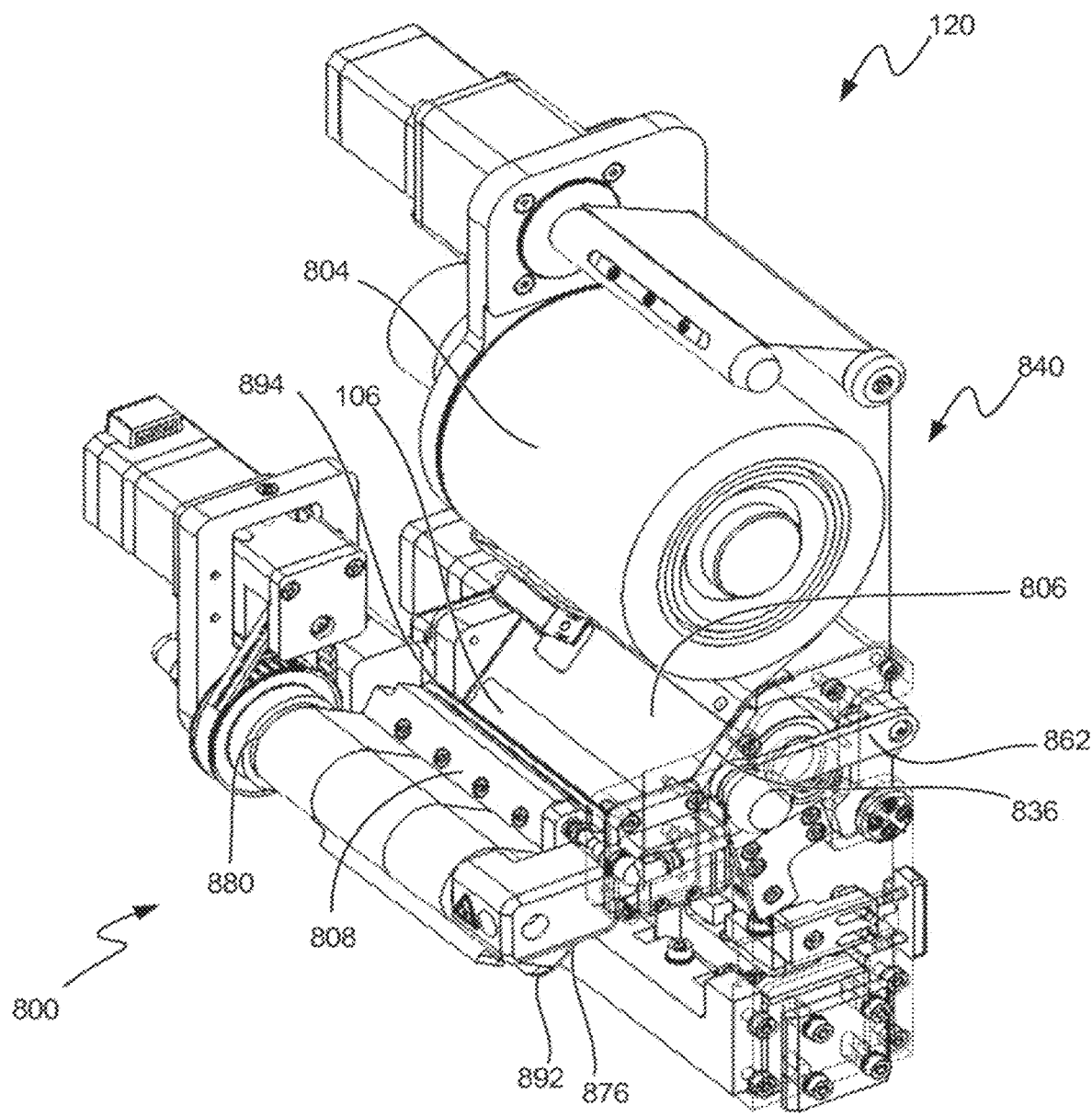
Figure 42B:
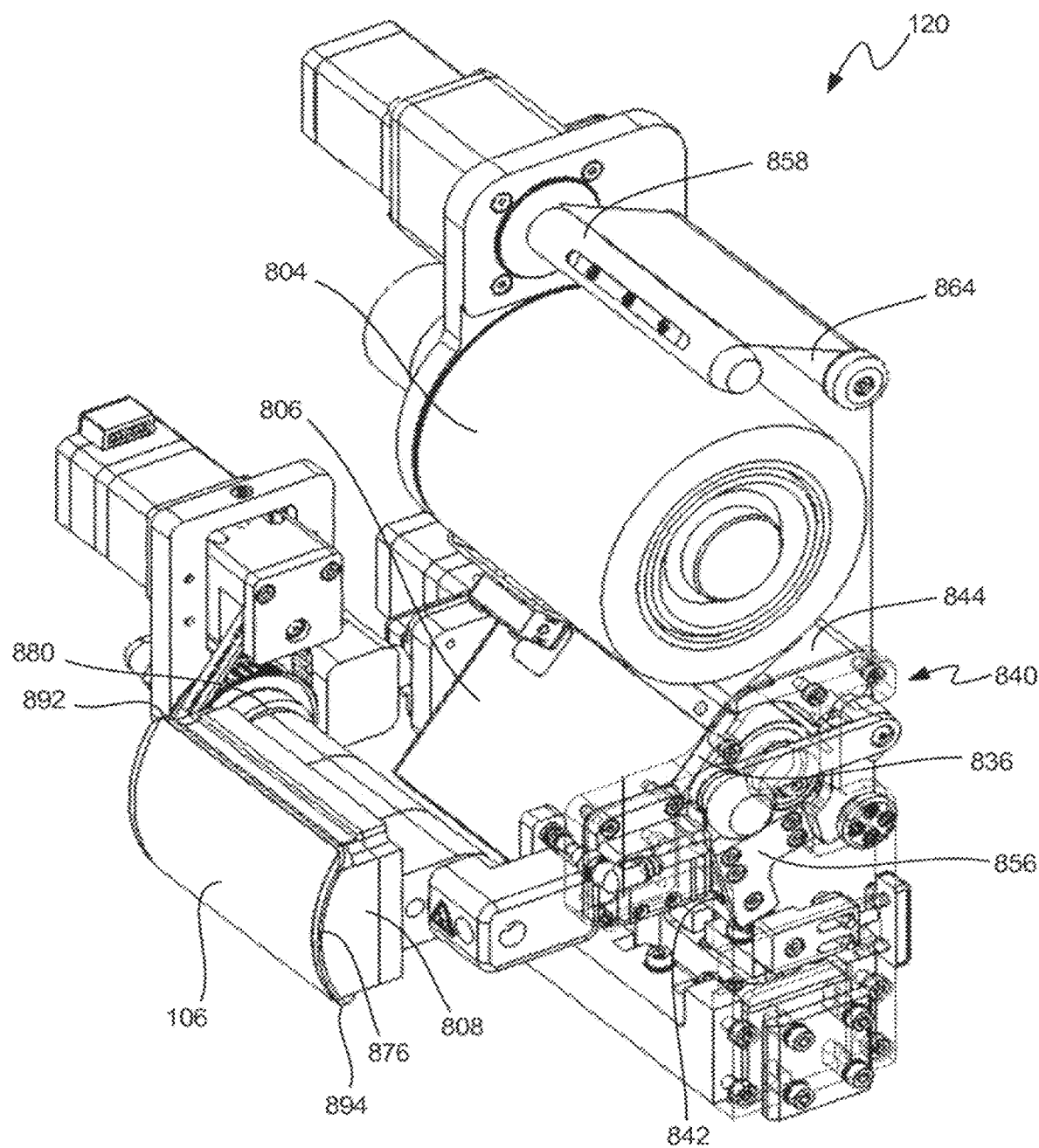

FIGS. 42A-42B are partially transparent perspective views of a portion of the tape sea ng assembly removing a seal from a backer of the seal web.

Figure 43A:
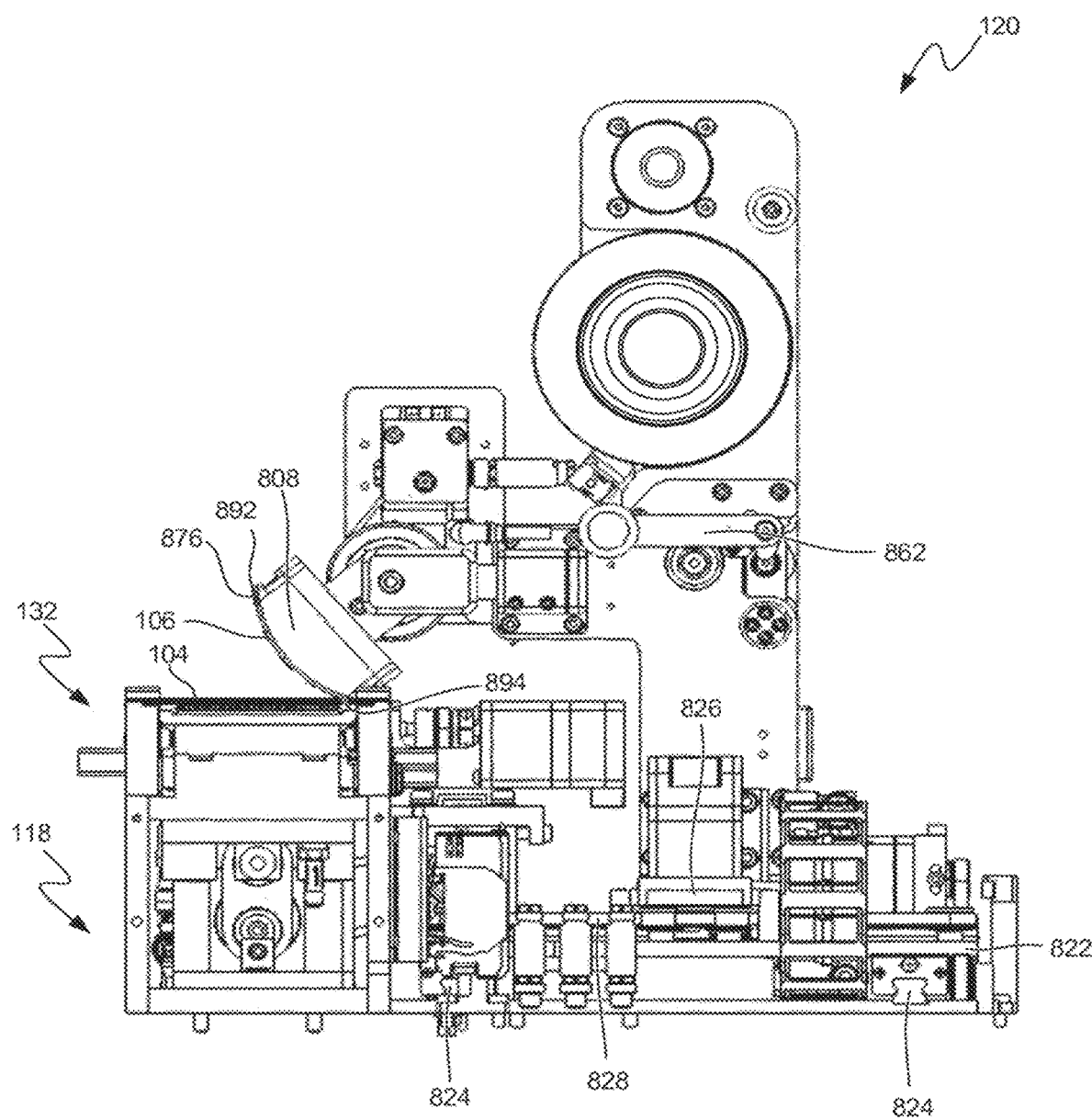
Figure 43B:
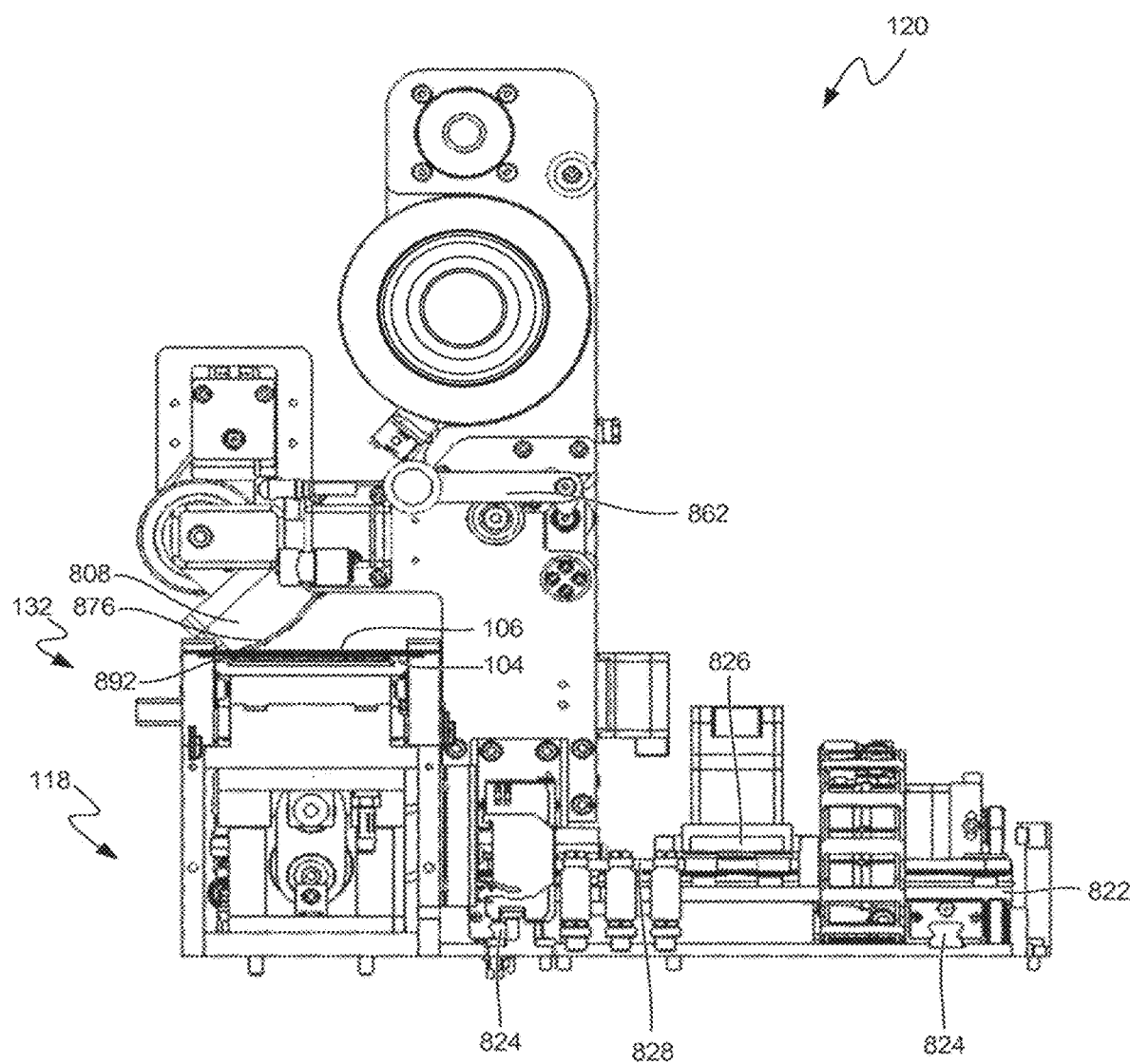

FIGS. 43A-43B are side views of the tape sealing assembly applying a seal to a tape on the tape path assembly.

Thermal Unit and Heated Pressure Chamber

Figure 44:
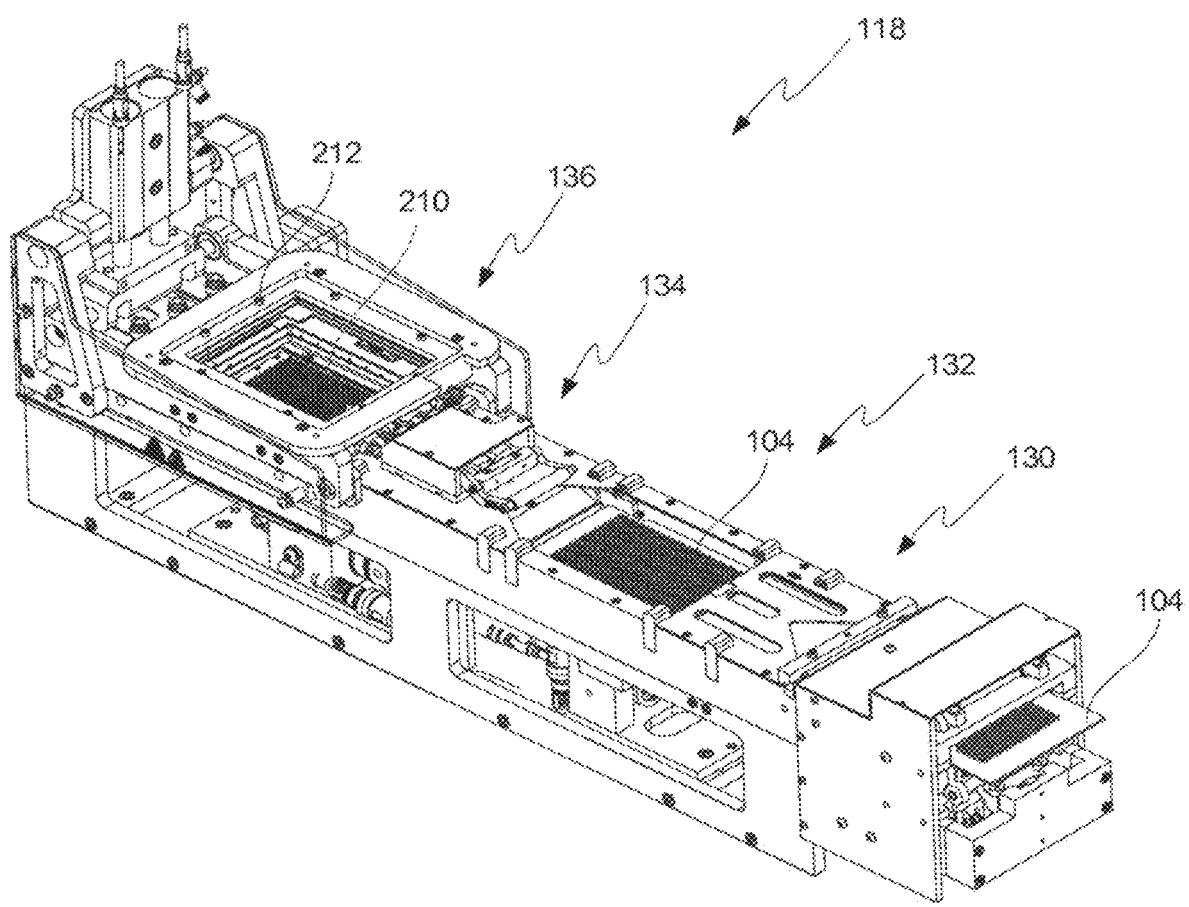
Figure 45A:
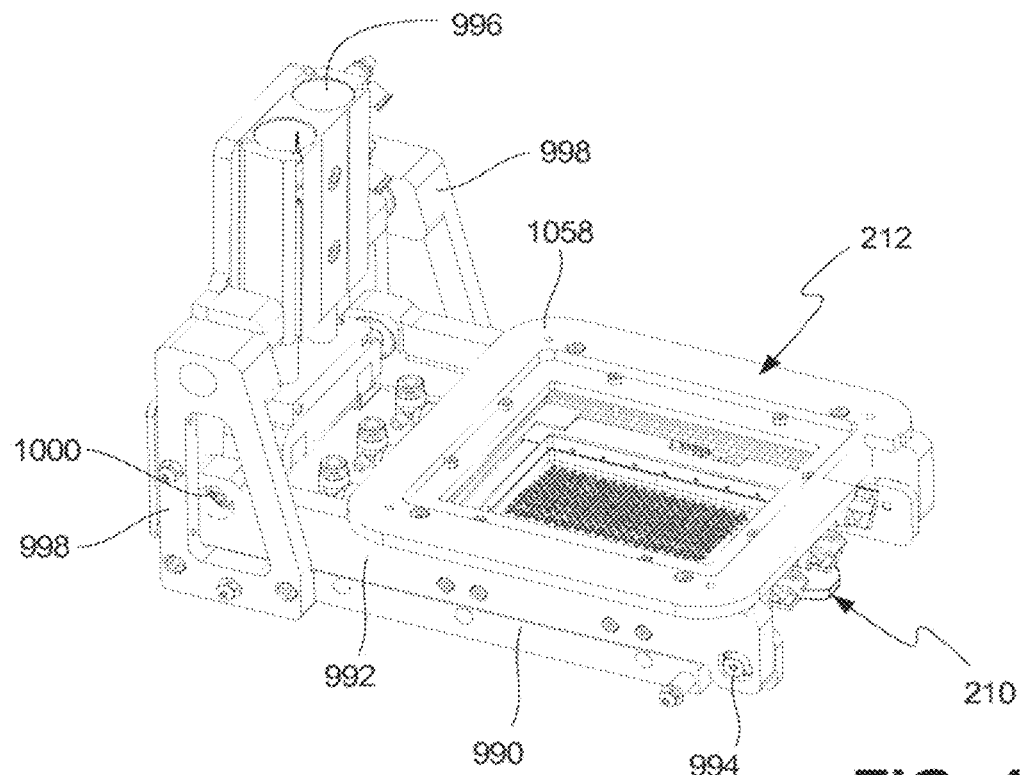

FIG. 44 is an isometric view of a tape path assembly that runs through an instrument, FIG. 45A is a perspective view of a thermal unit and a heated pressure chamber, with the heated pressure chamber in a closed position.

Figure 45B:
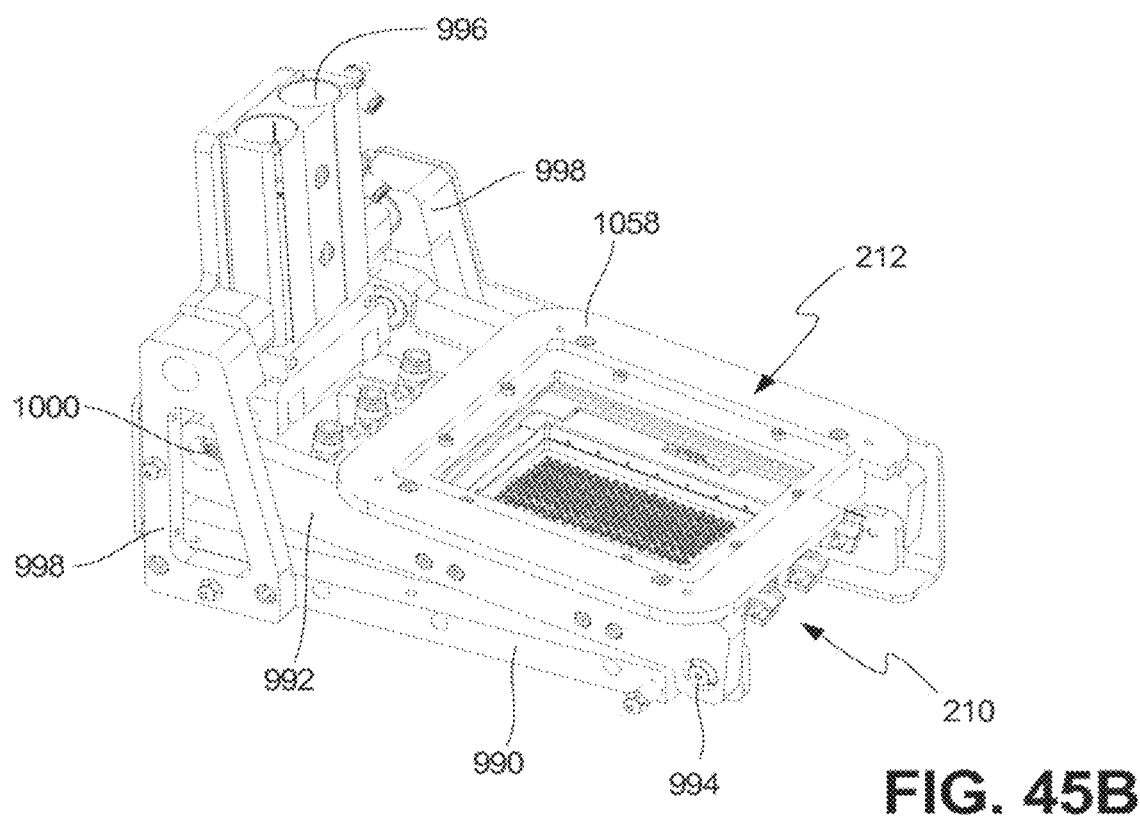

FIG. 45B is a perspective view of a thermal unit and a heated pressure chamber, with the heated pressure chamber in a closed position.

Figure 45C:
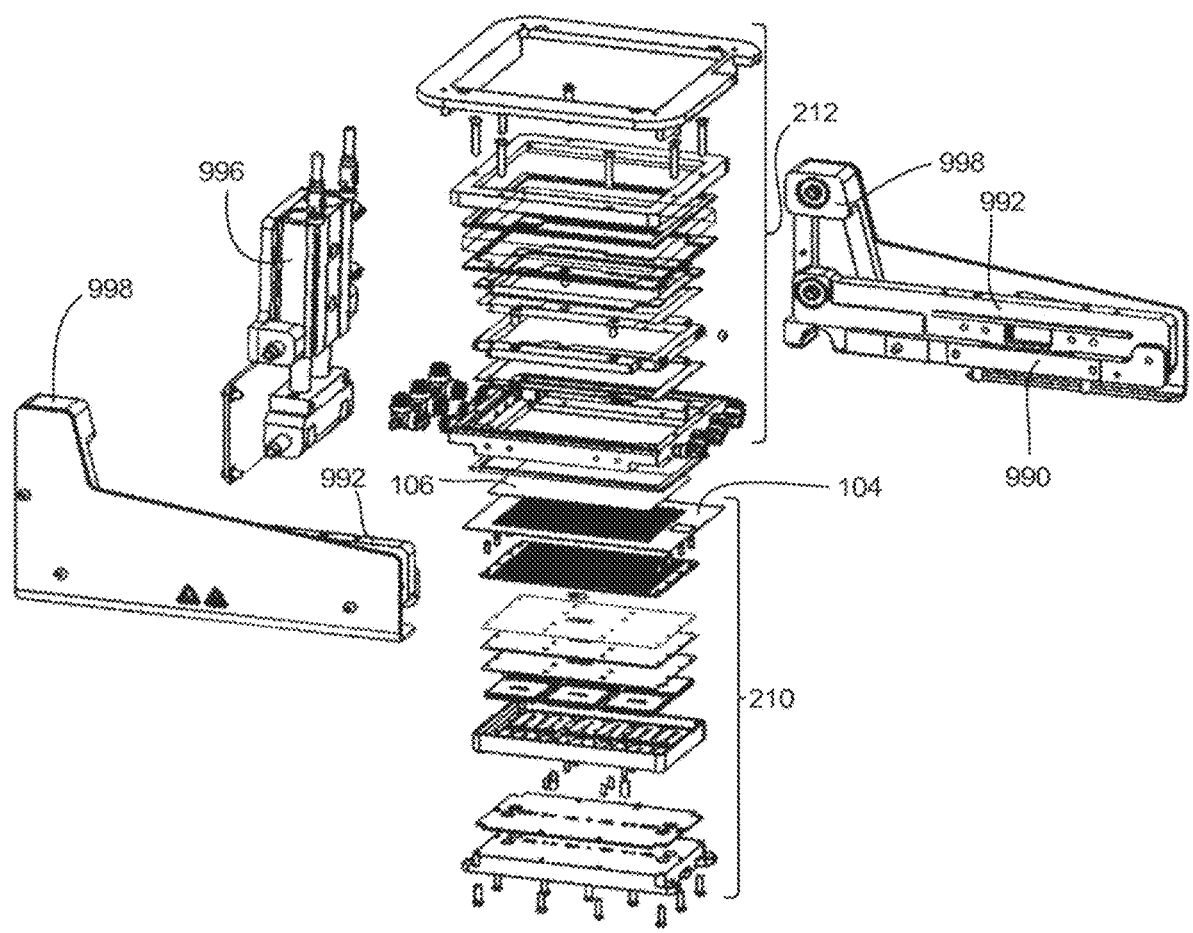

FIG. 45C is an exploded view of the thermal unit and the heated pressure chamber.

Figure 45D:
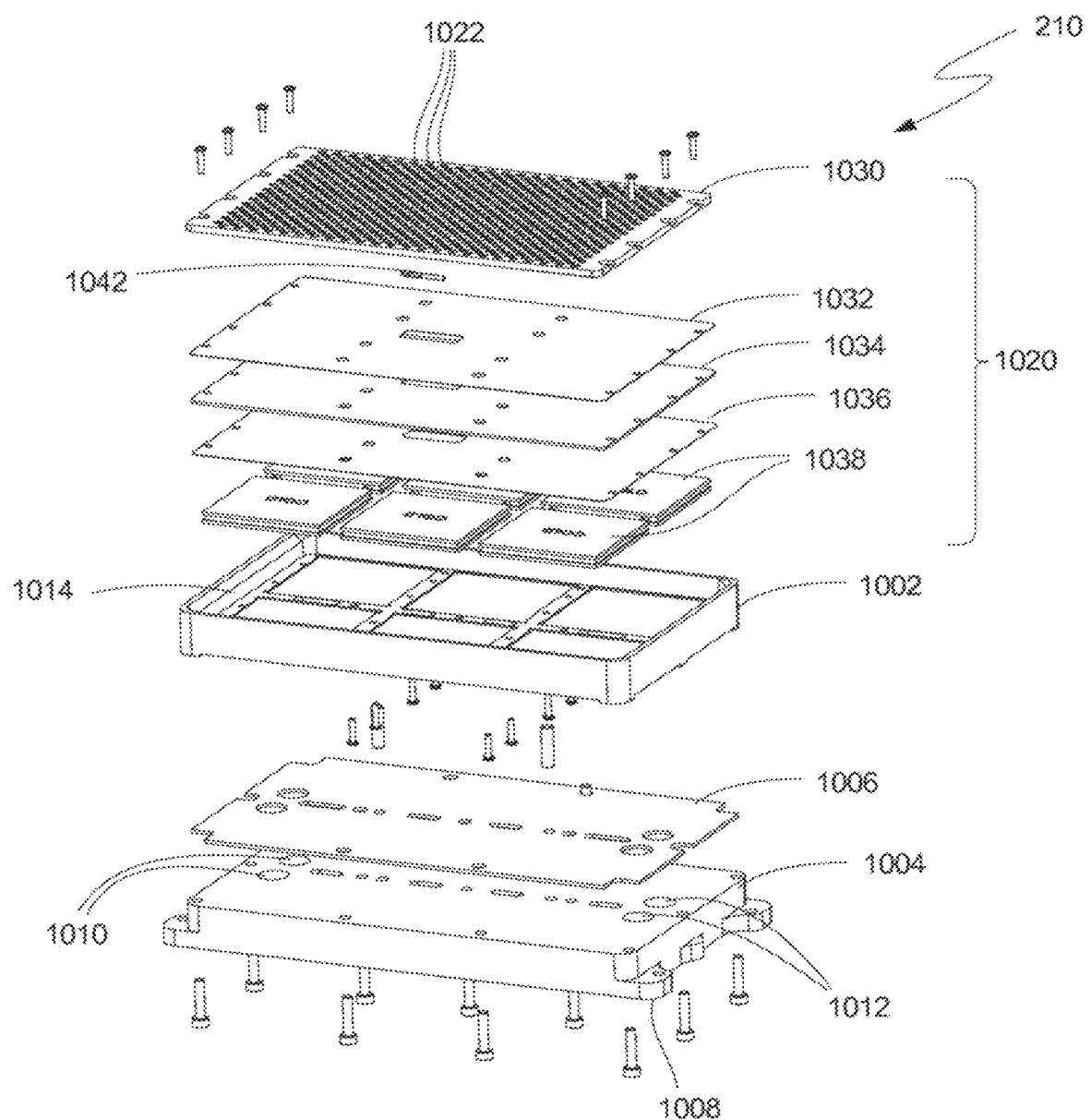

FIG. 45D is an exploded view of thermal unit.

Figure 45E:
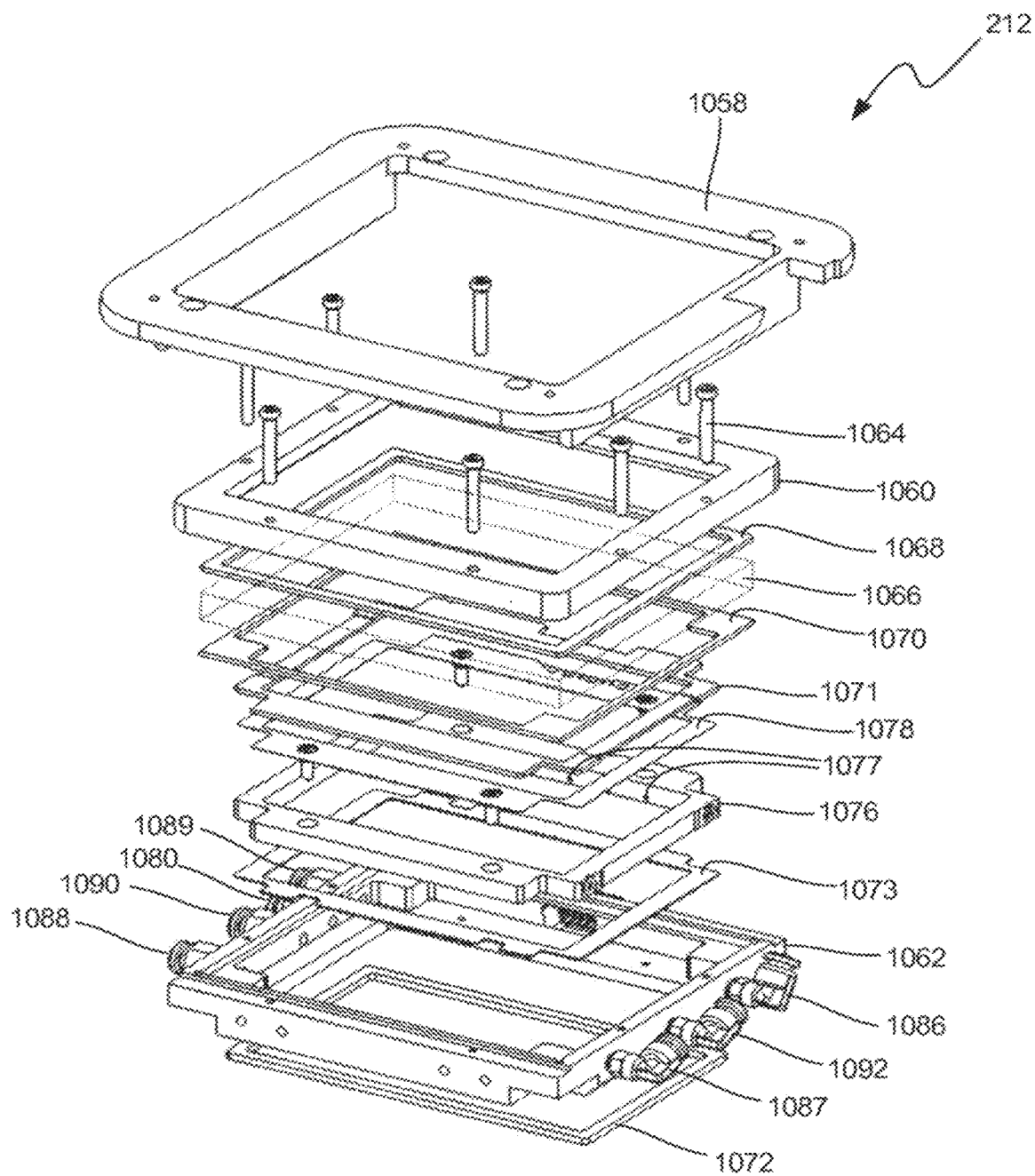

FIG. 45E is an exploded view of the heated pressure chamber.

Figure 46A:
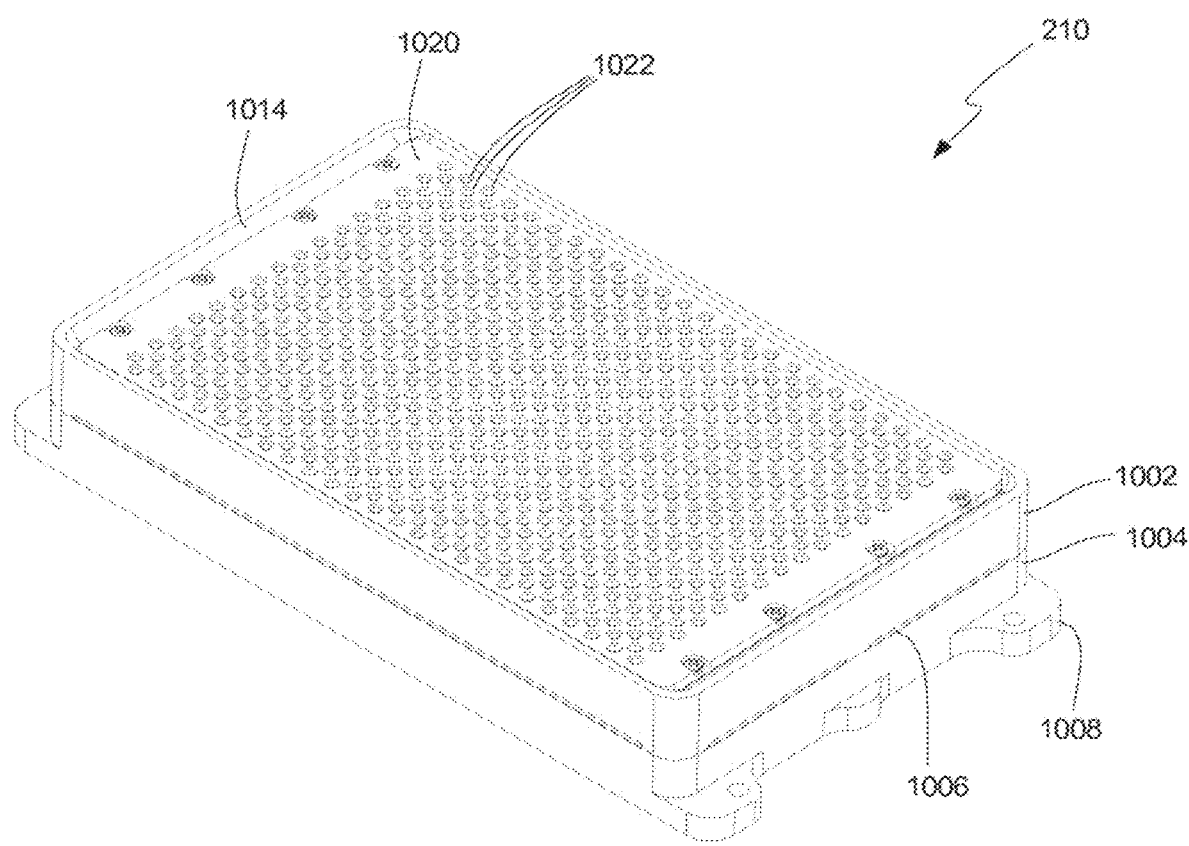

FIG. 46A is a perspective view of the thermal unit.

Figure 46B:
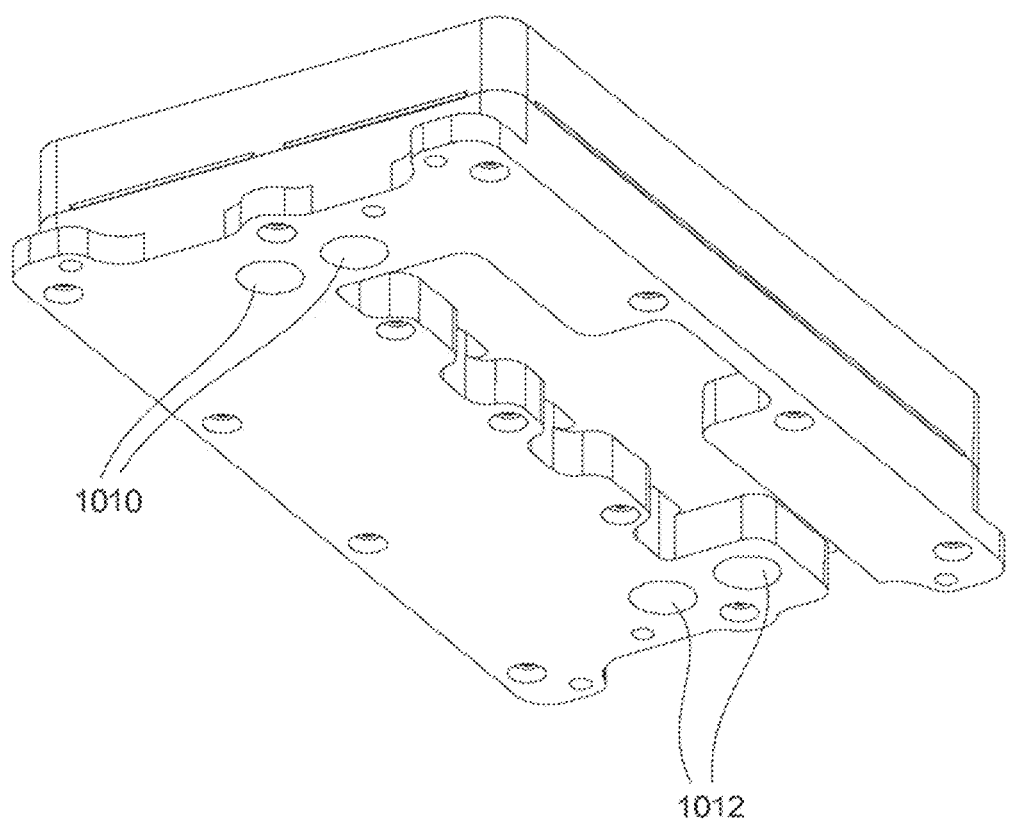

FIG. 46B is a perspective view of the bottom of the thermal unit.

Figure 46C:
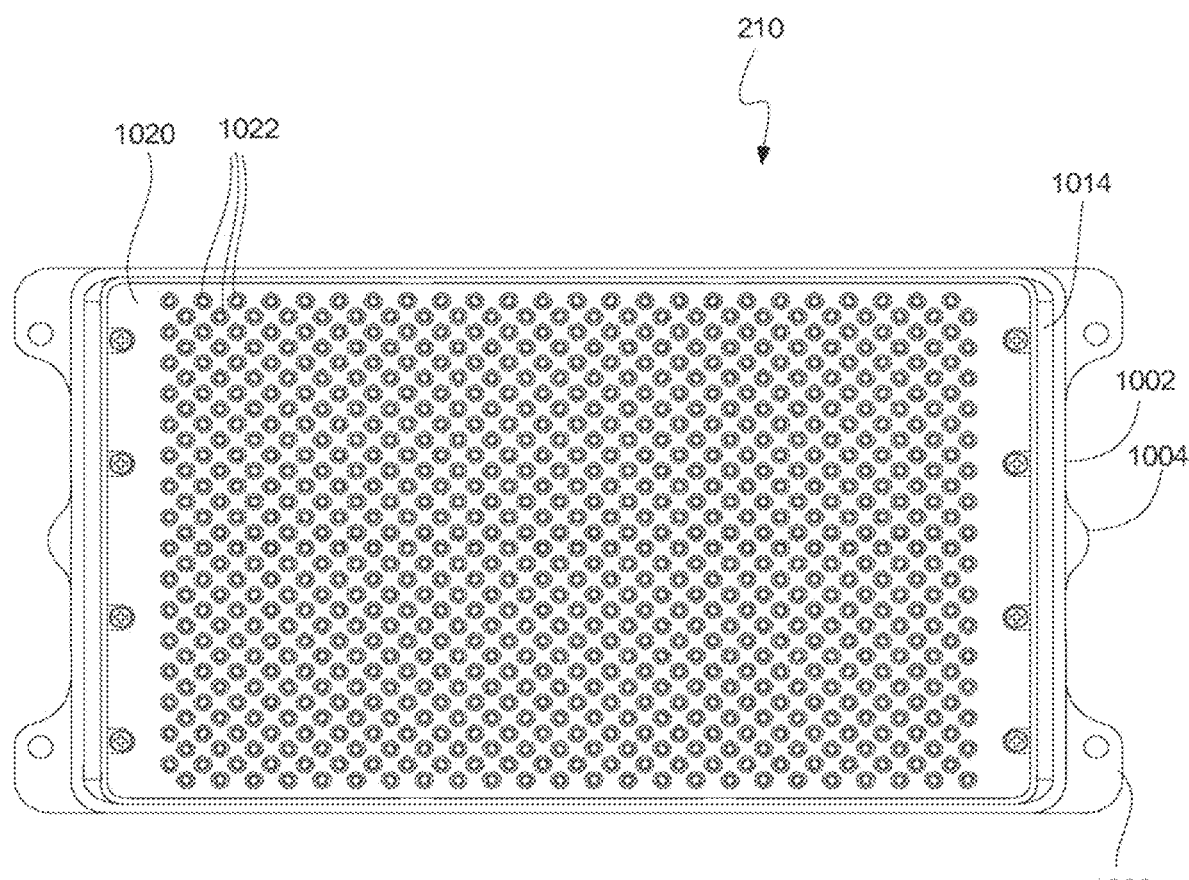

FIG. 46C is a top view of the thermal unit.

Figure 46D:
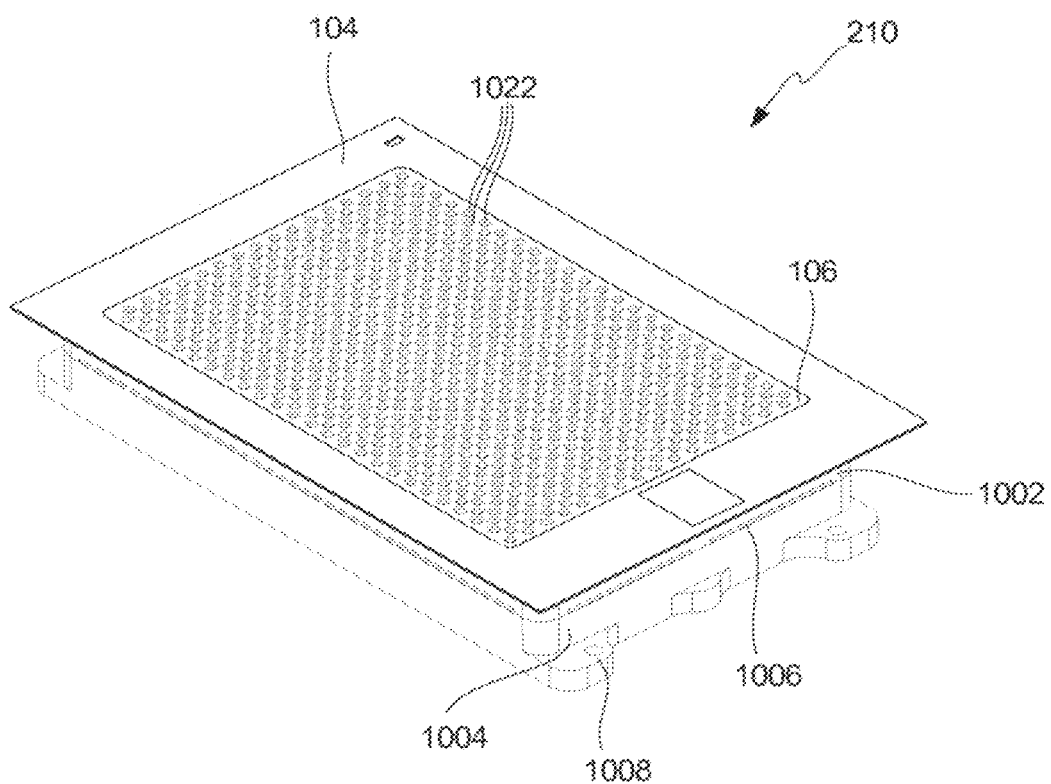

FIG. 46D is an isometric view of an array of tape on the thermal unit.

Figure 47A:
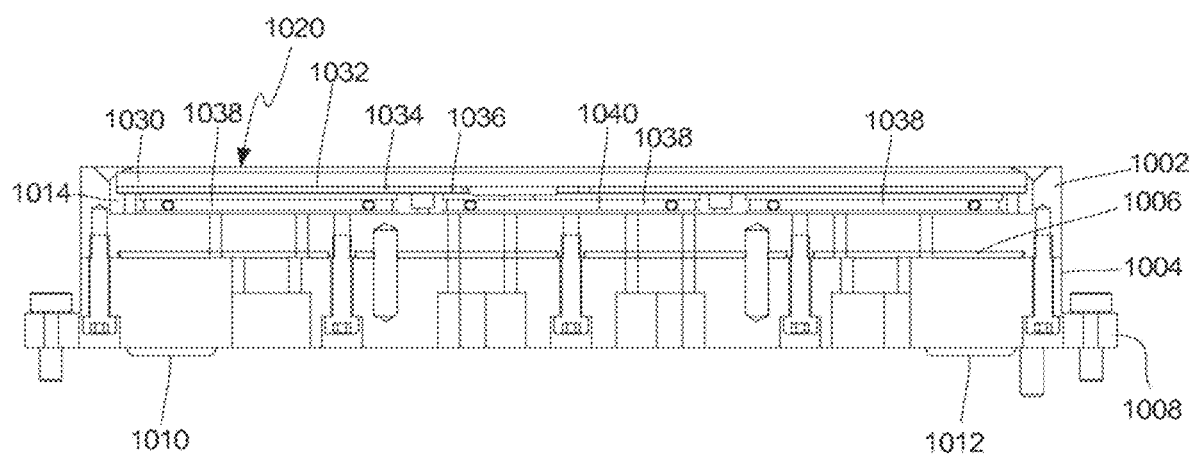

FIG. 47A is a cross-sectional side view of the thermal unit.

Figure 47B:
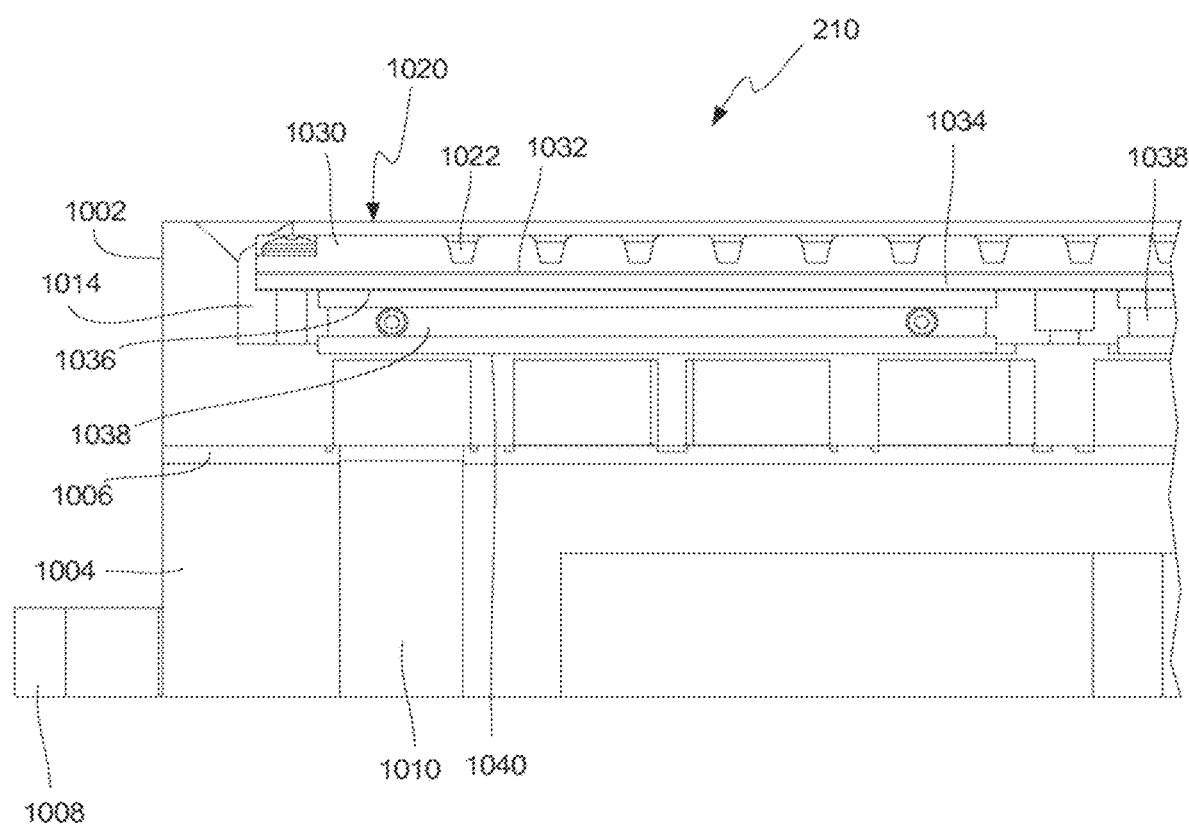

FIG. 47B is a cut-away cross-sectional side view of the thermal unit.

Figure 47C:
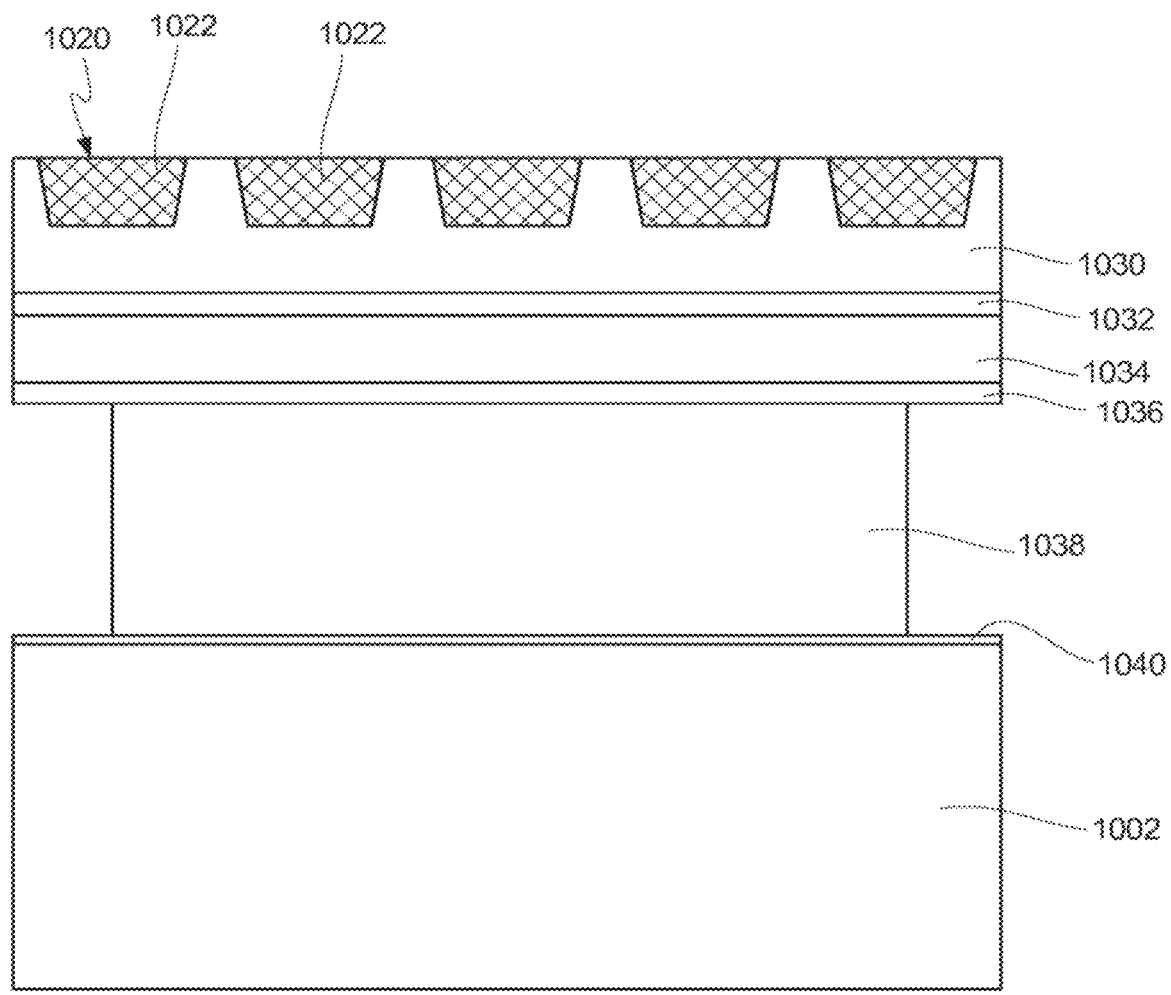

FIG. 47C is a schematic view of a cross-section of the thermal unit.

Figure 48:
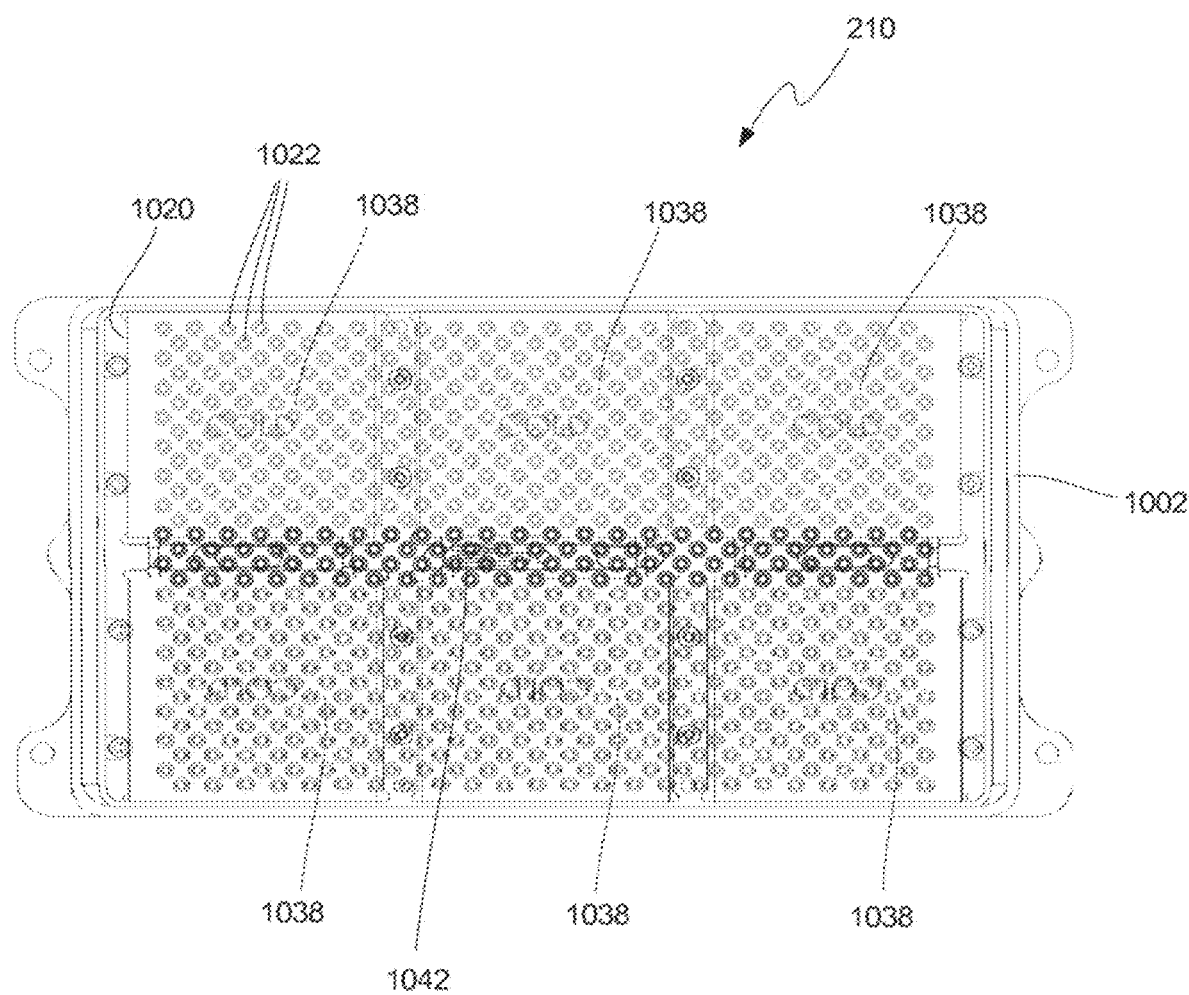
Figure 49:
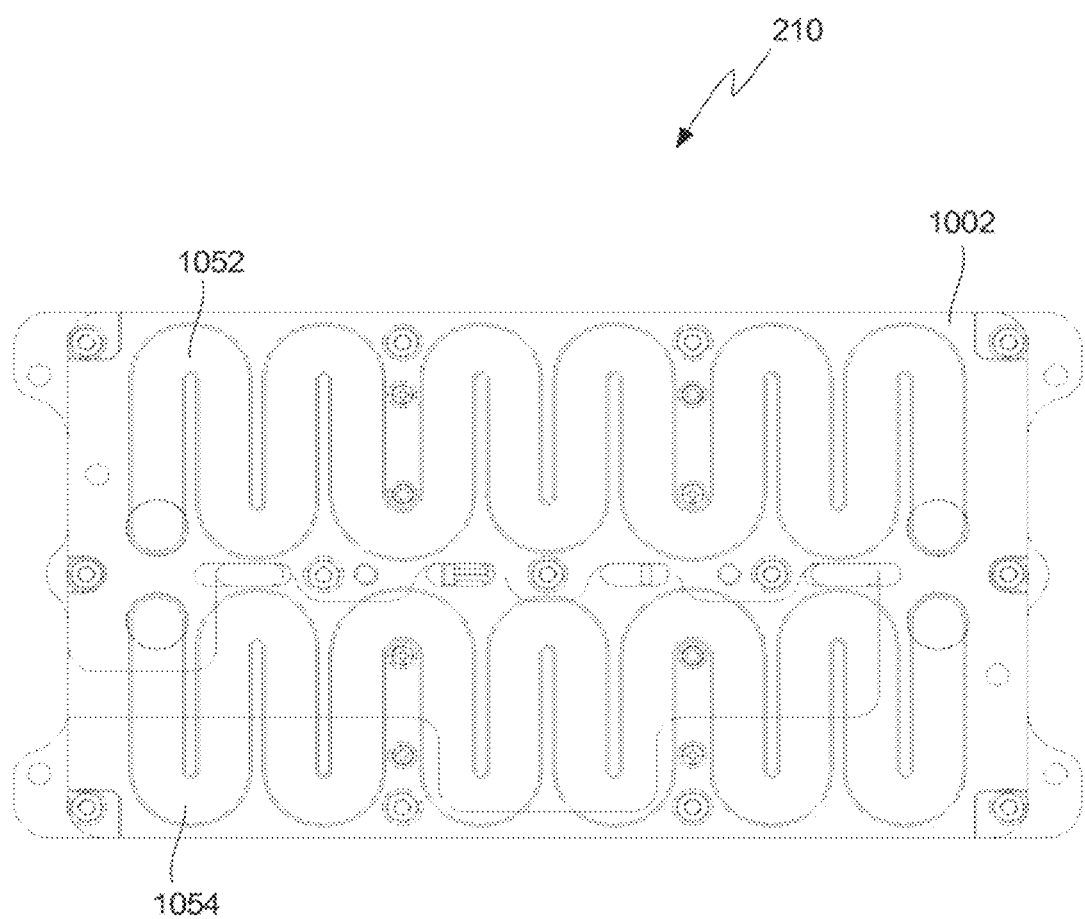

FIG. 48 is a top plan see-through view of a top side of the thermal unit,

FIG. 49 is a bottom plan see-through view of the thermal unit.

Figure 50:
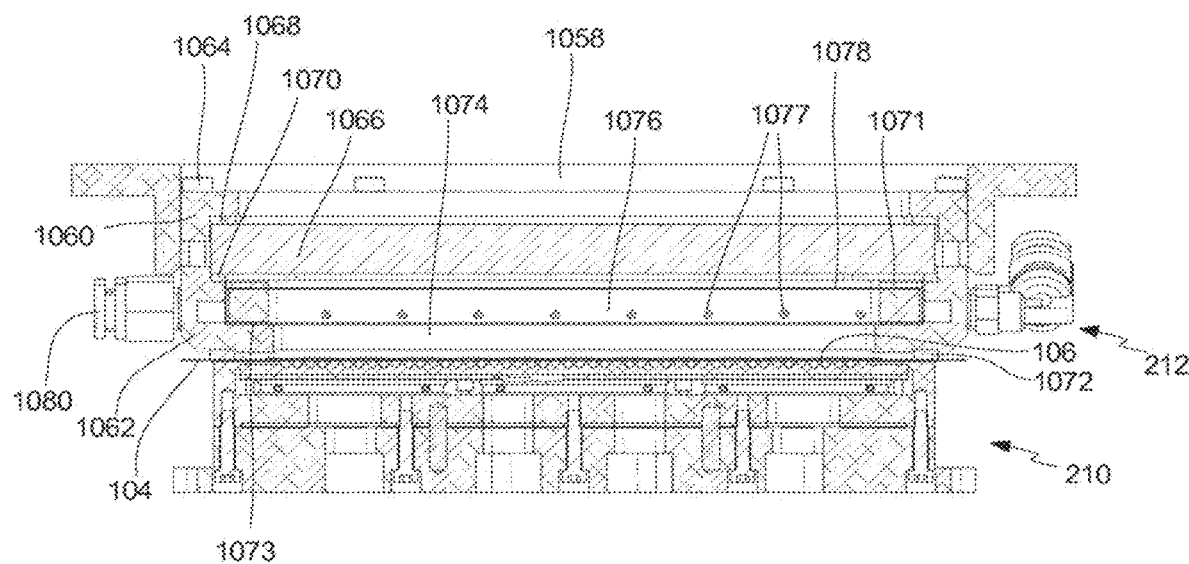

FIG. 50 is a cross-sectional view of the heated pressure chamber and thermal unit.

Figure 51:
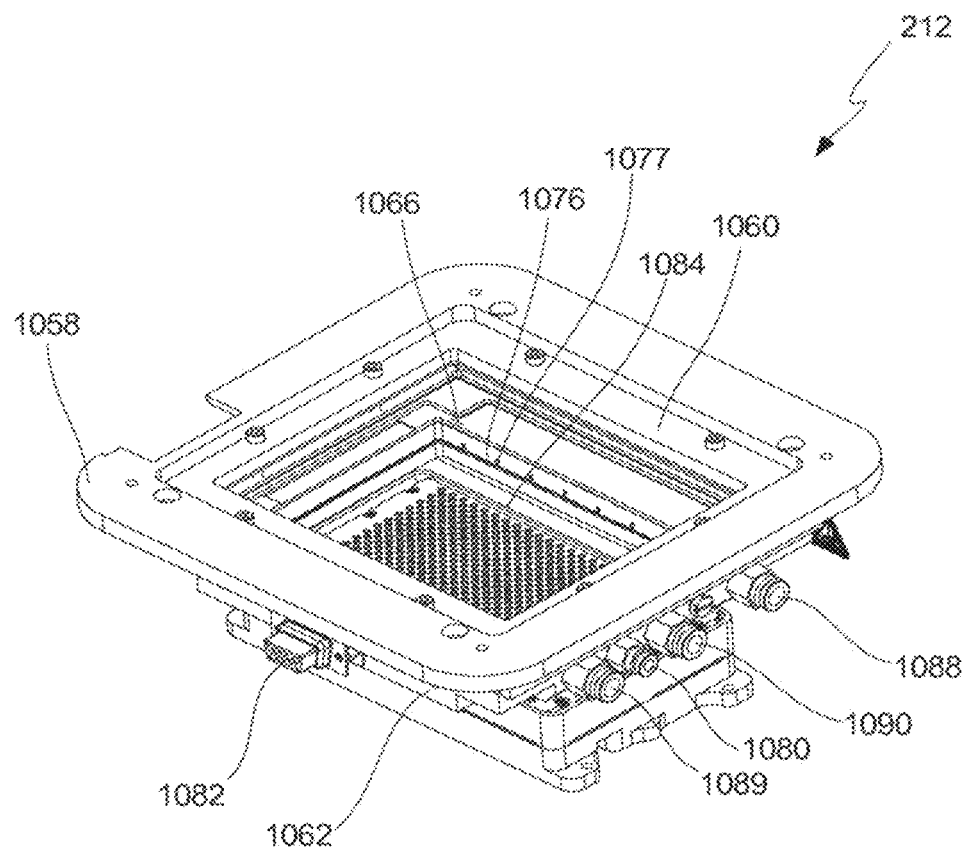

FIG. 51 is an isometric view of the heated pressure chamber.

Figure 52:
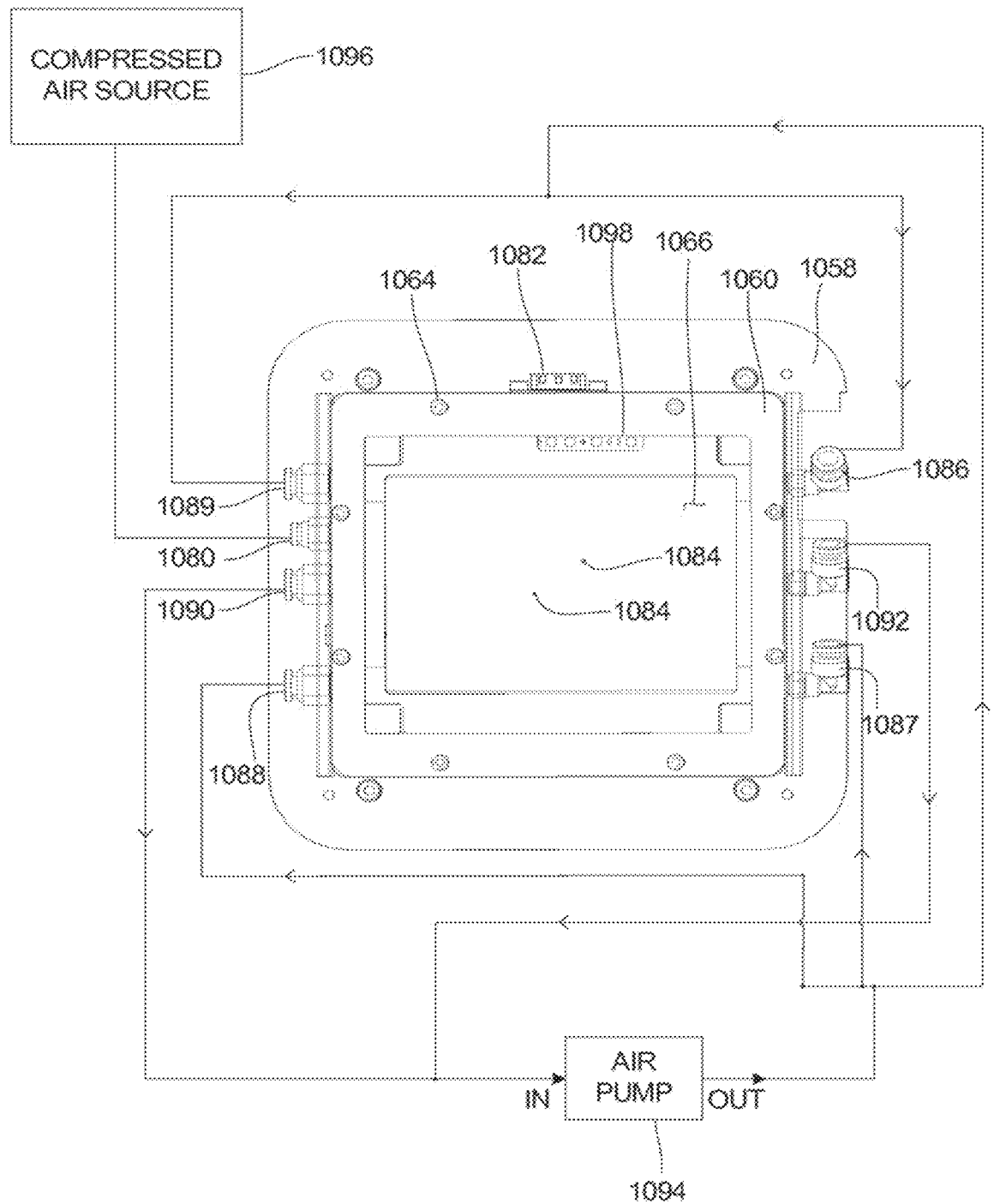

FIG. 52 is a top view of the heated pressure chamber.

Alternative Embodiments of the Overall Instrument

Figure 1A:
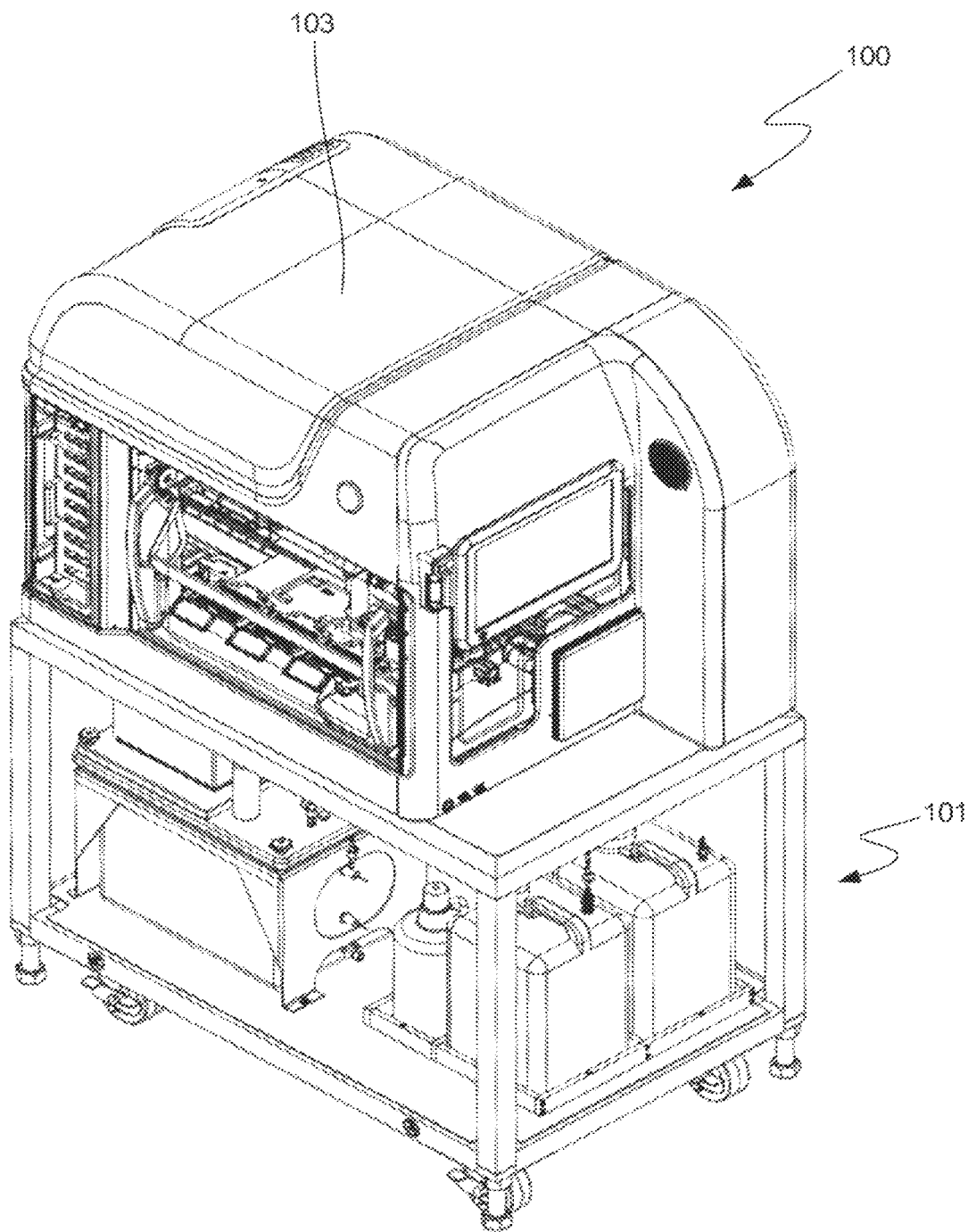
FIG. 1A is an isometric view of a cart top instrument for amplifying and analyzing a biological sample and reagent mixture.
Figure 53A:
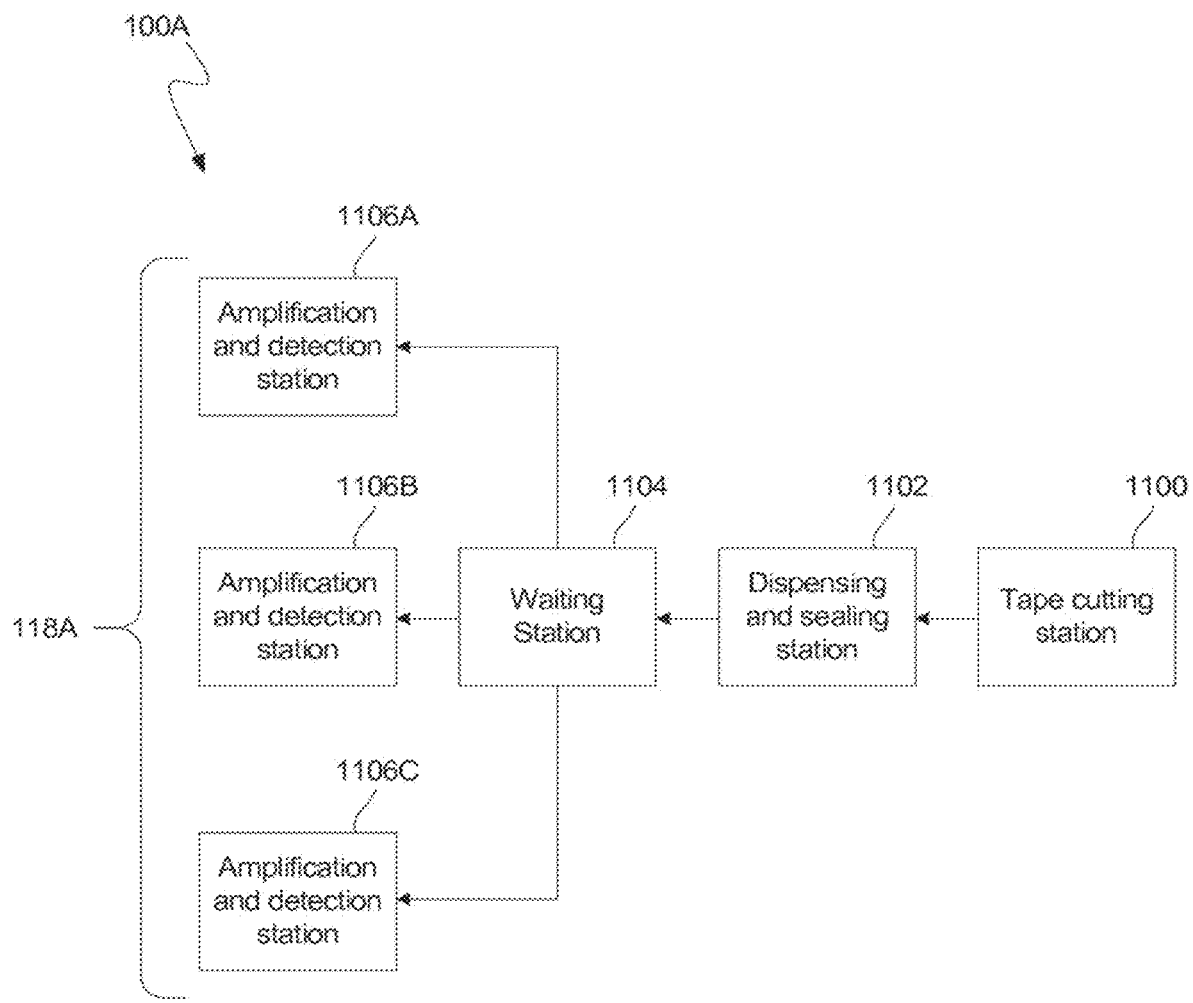

FIG. 53A is a schematic view of an alternative embodiment of the instrument seen in FIGS. 1A-52.

Figure 53B:
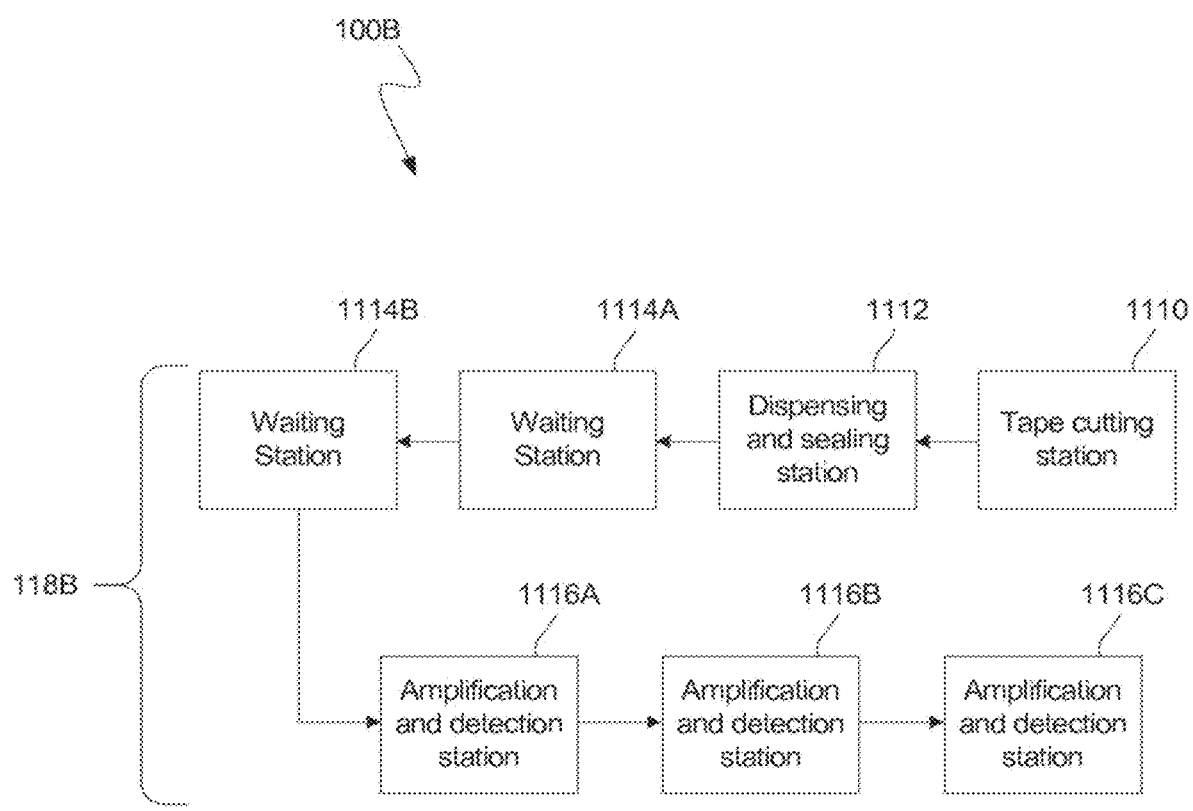

FIG. 53B is a schematic view of an alternative embodiment of the instrument seen in FIGS. 1A-52.

DETAILED DESCRIPTION

In general, the present disclosure relates to an instrument for analyzing biological sample and reagent mixtures. The instrument is an all-in-one instrument that is capable of dispensing, amplifying, and analyzing biological samples and reagents in a compact design. A tape containing a plurality of wells is automatically advanced through the instrument along a tape path assembly. The tape path assembly includes a first position, a second position, a third position, and a fourth position. At the first position, the tape can be cut so that a tape segment with a single array of wells proceeds through the instrument. Alternatively, the tape can advance through the first position to the second position without being cut. Further, the tape can advance without being cut until any number of arrays of wells have passed through the first position and the tape can then be cut. At the second position, a biological sample and a reagent are dispensed into the plurality of wells in the tape with a dispensing assembly to form a biological sample and reagent mixture. After the biological sample and the reagent are dispensed into the tape, a tape sealing assembly seals the tape with a seal, such as an optically clear cover seal. The tape then advances to the third position. At the third position, the tape containing the biological sample and reagent mixture can either be cooled to prevent the biological sample and reagent mixture from undergoing a chemical reaction or heated to incubate the biological sample and reagent mixture. The tape will then advance to the fourth position. At the fourth position, the biological sample and reagent mixture in the plurality of wells in the tape can be amplified and analyzed with a detection assembly. The all-in-one instrument is capable of amplifying nucleic acids in the biological sample and reagent mixture by thermal cycling the biological sample and reagent mixture (polymerase chain reaction) or by heating the biological sample and reagent mixture at a constant temperature (isothermal amplification). As the tape advances through the system, the second position, the third position, and the fourth position can function at the same time to allow the instrument to continuously dispense, amplify, and analyze the biological sample and reagent mixture in the tape.

The all-in-one instrument is advantageous, as it performs all of the functions needed to dispense, amplify, and analyze a biological sample and reagent mixture without the need for human intervention. A user can simply select parameters for the instrument and position a biological sample and a reagent in the instrument. The instrument can then aspirate the biological sample and the reagent, automatically advance tape through the instrument, dispense the biological sample and the reagent into the tape, and amplify and analyze the biological sample and reagent mixture in the tape. The instrument is further advantageous, as it has a compact design that supports all of the components necessary for performing the functions of the instrument on a single chassis. Further, the functions provided in the instrument allow the instrument to be used for large scale testing with high-throughput or small scale testing with low-throughput. The compact design, efficiency, and versatility of the instrument allow the instrument to be used in a large variety of settings and for a large number of different applications.

Overall Instrument

Figure 1B:
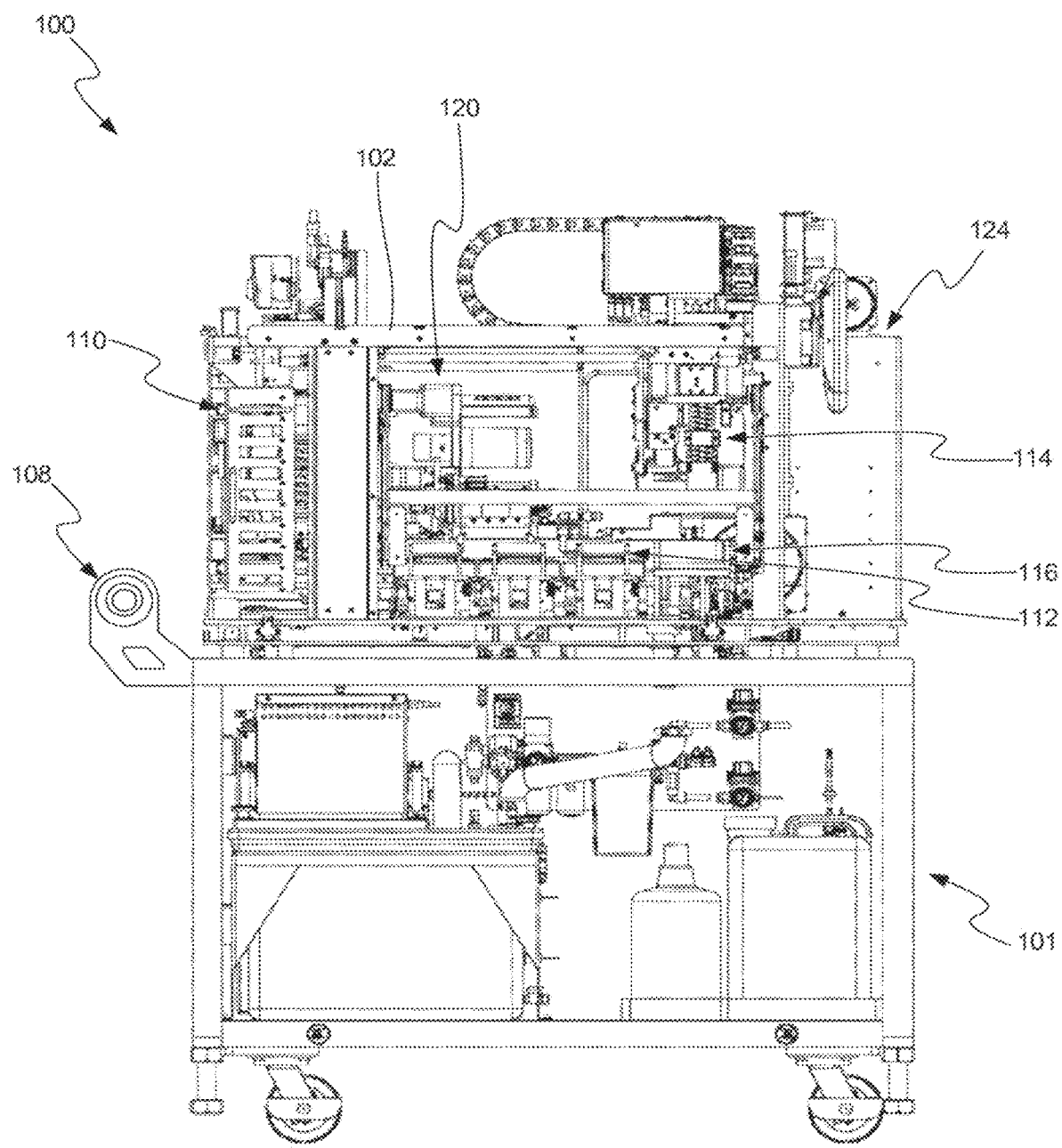
FIG. 1B is a side view of the instrument seen in FIG. 1A.
Figure 1C:
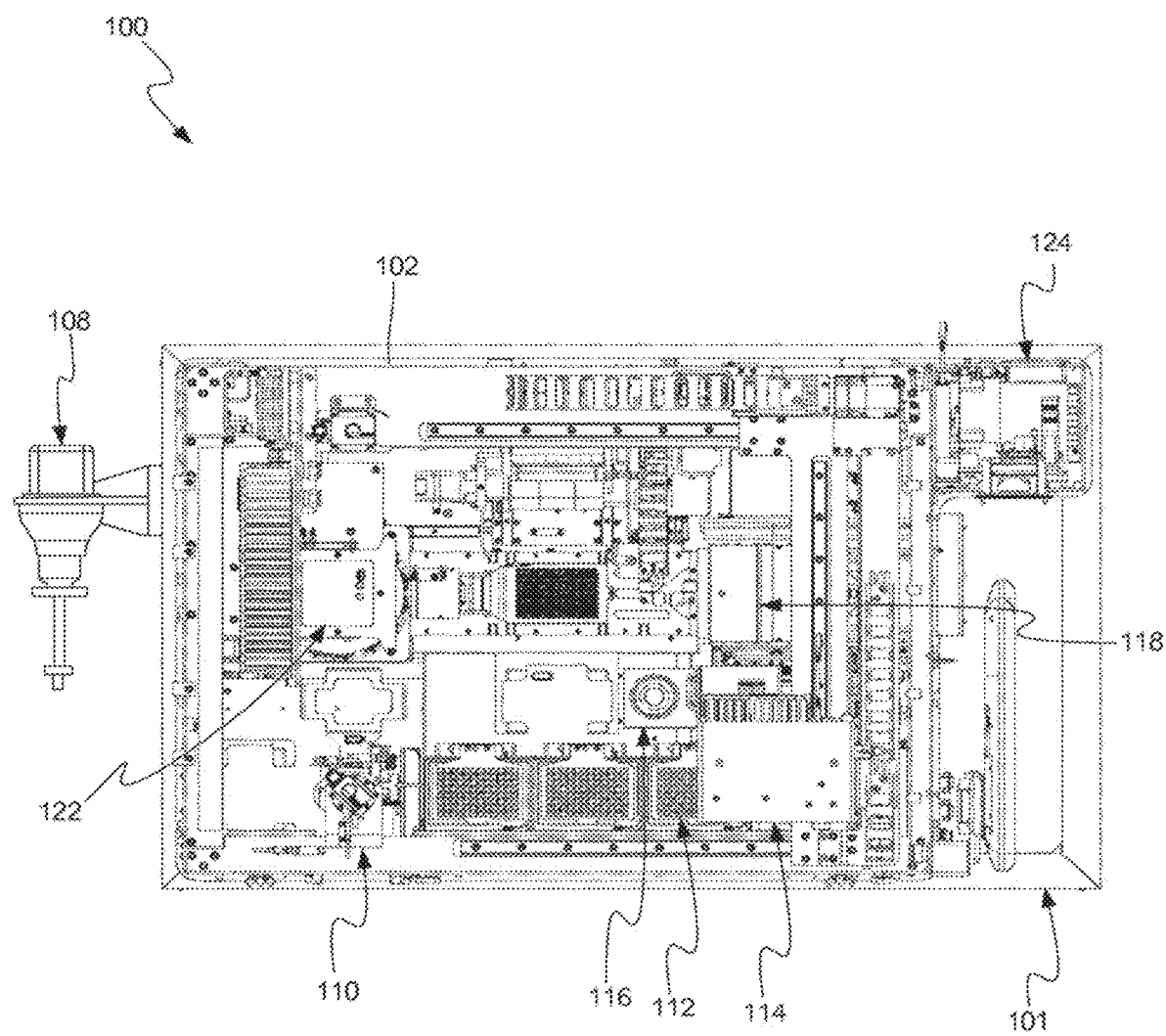
FIG. 1C is a top plan view of the instrument seen in FIG. 1A.
Figure 1D:
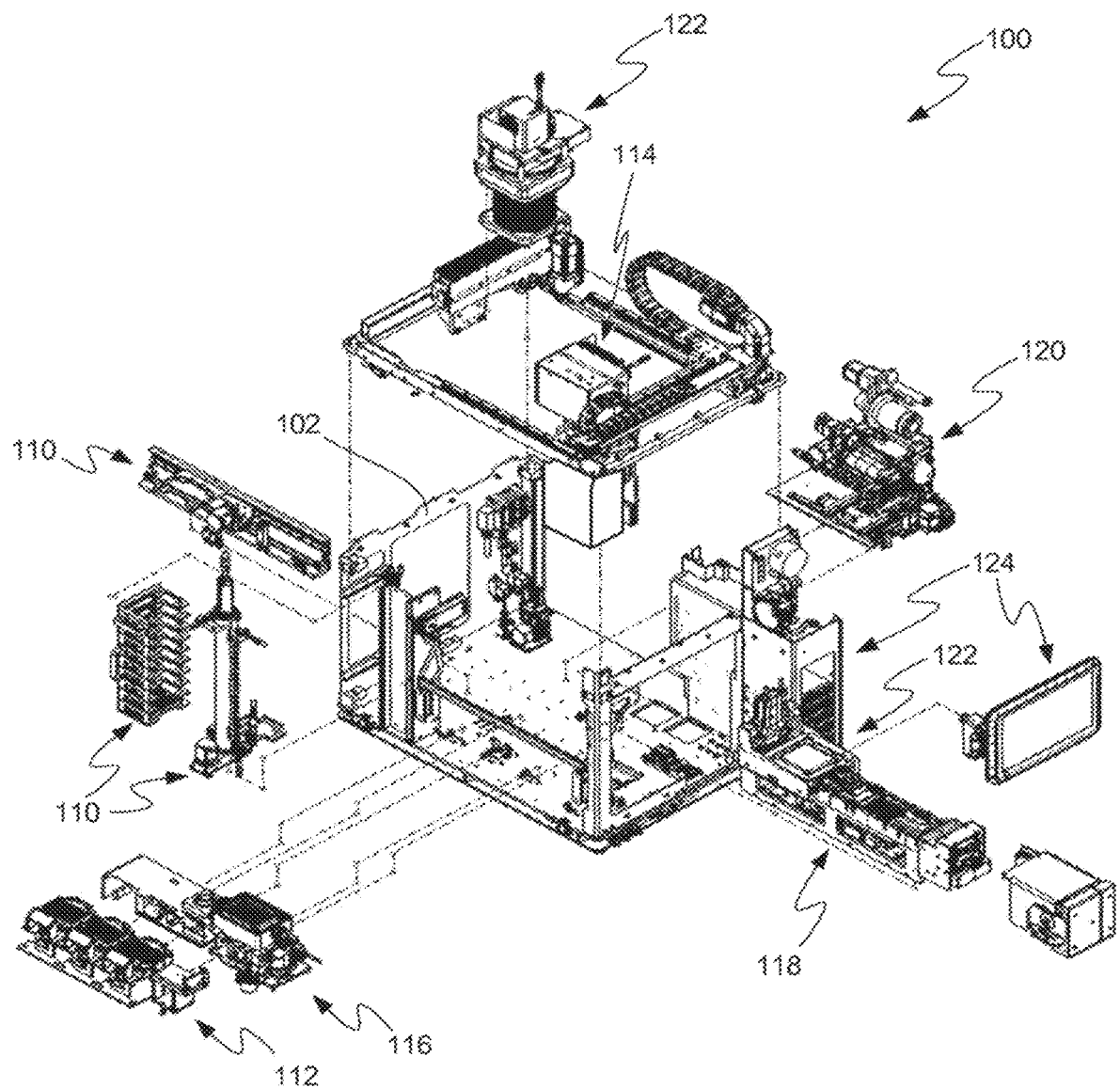
FIG. 1D is an exploded view of the instrument seen in FIG. 1A.
Figure 1E:
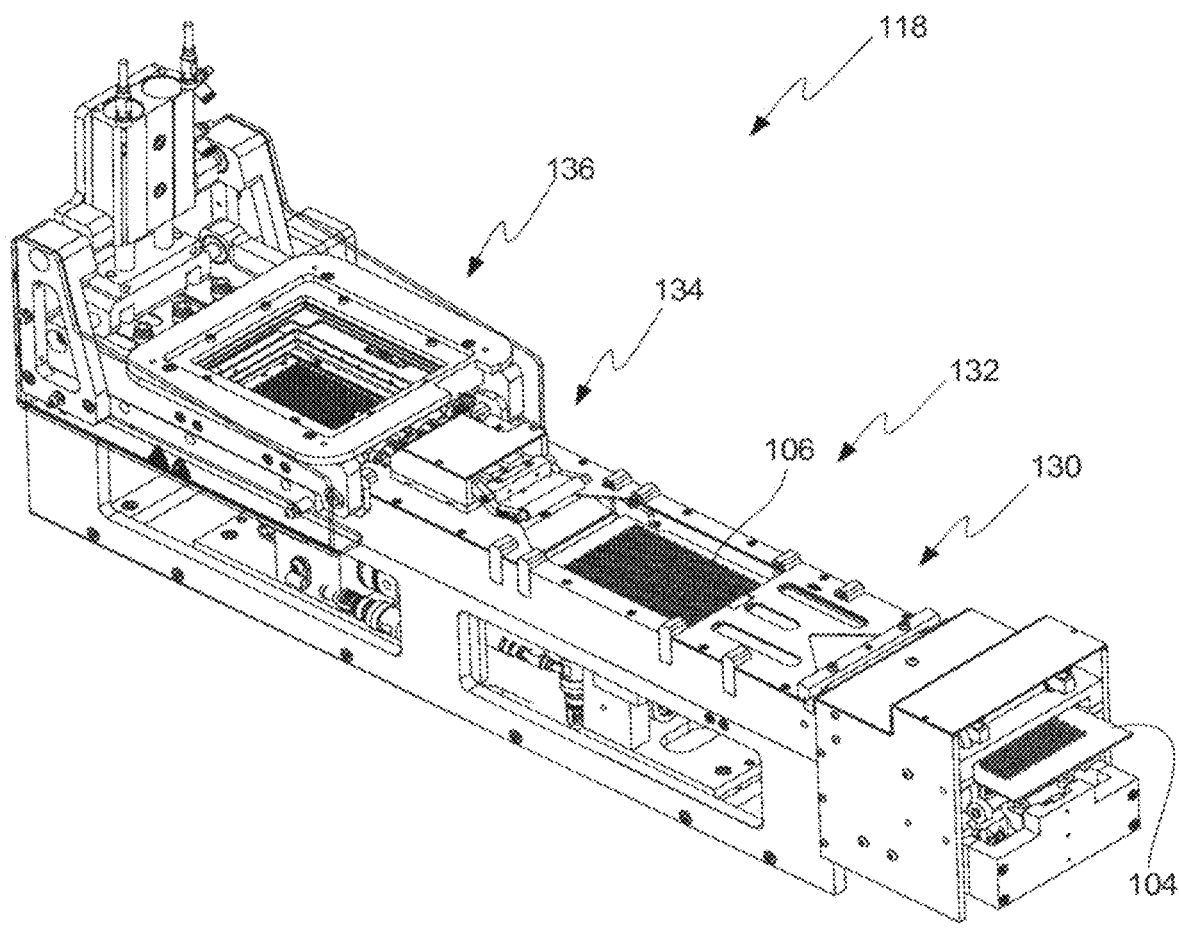
FIG. 1E is a front isometric view of a tape path assembly that runs through the instrument seen in FIG. 1A.
Figure 1F:
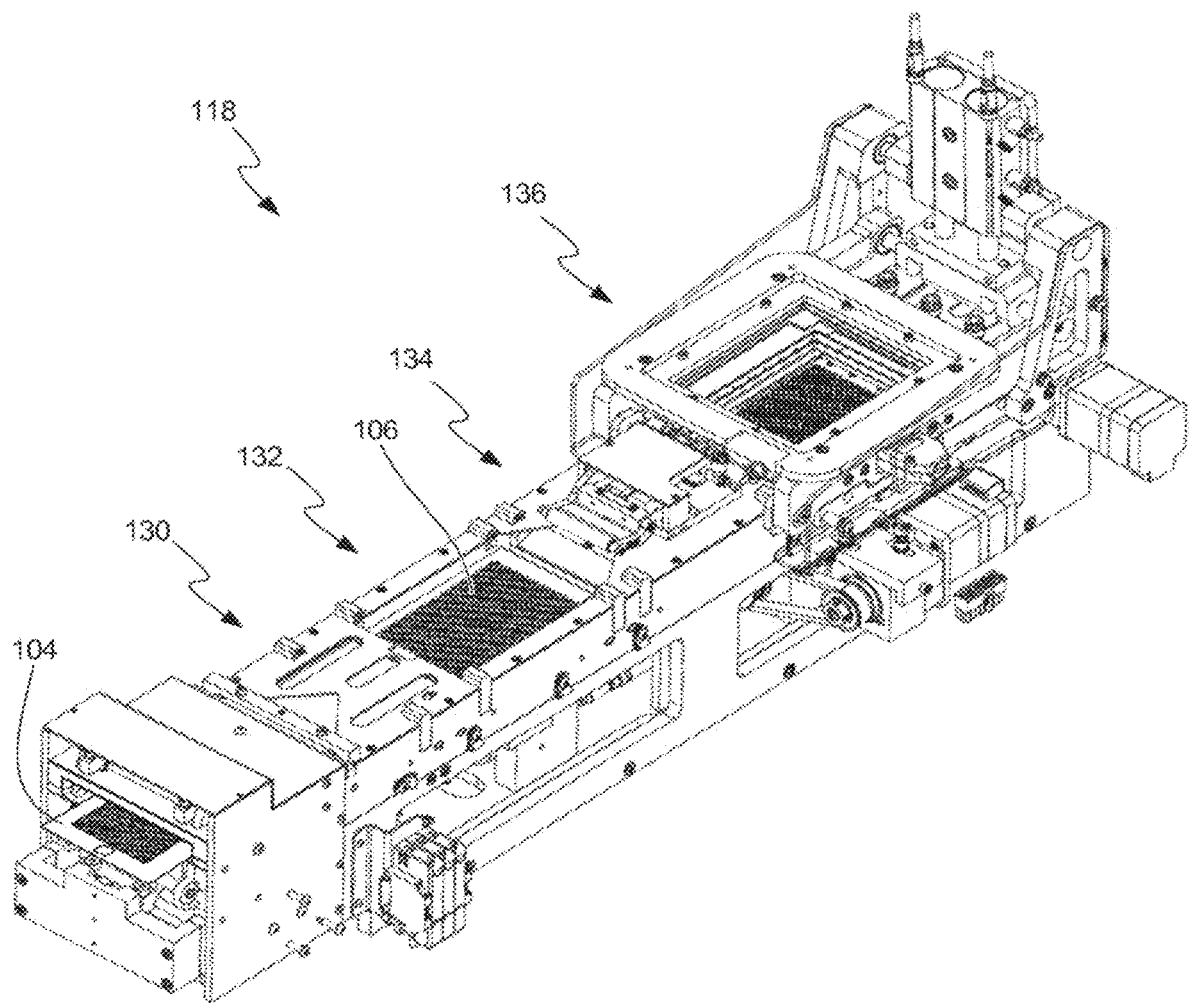
FIG. 1F is a back perspective view of the tape path assembly as seen in FIG. 1E.

FIG. 1A is an isometric view of instrument 100 mounted on cart assembly 101. FIG. 1B is a side view of instrument 100 on cart assembly 101 seen in FIG. 1A. FIG. 1C is a top plan view of instrument 100. FIG. 1D is an exploded view of instrument 100. FIG. 1E is a front isometric view of tape path assembly 118 that runs through instrument 100. FIG. 1F is a back perspective view of tape path assembly 118 as seen in FIG. 1D. Instrument 100 is mounted on cart assembly 101 and includes chassis 102, enclosure 103 (removed for clarity in subsequent figures), tape 104 (as shown in FIGS. 1E-1F), seal 106 (as shown in FIGS. 1E-1F), plate stacker assembly 110, deck plate assembly 112, dispensing assembly 114, wash assembly 116, tape path assembly 118, tape sealing assembly 120, detection assembly 122 (as shown in FIGS. 1C-1D), and electronic assembly 124. Enclosure 103 provides a controlled environment for a reaction to take place in instrument 100. Enclosure 103 includes intake filters, an exhaust filter, and an exhaust blower in order to control air quality within instrument 100.

Also mounted on cart assembly 101 is rewind assembly 108. Rewind assembly 108 is aligned with tape path assembly 118. Cart assembly 101 includes a bleach reservoir, a waste tank with an exhaust filter and an activated carbon filter for wash assembly 116. Cart assembly 101 also includes two water tanks for providing system fluid to dispensing assembly 114 and wash assembly 116. As shown in FIGS. 1E-1F, tape path assembly 118 includes first position 130, second position 132, third position 134, and fourth position 136.

Instrument 100 can be used to dispense, amplify, and analyze a biological sample and reagent mixture. Instrument 100 includes a plurality of assemblies that are all positioned on chassis 102. Tape 104 is advanced through instrument 100. Tape 104 has a plurality of wells that can receive a biological sample and a reagent for amplification and analysis. The plurality of wells on tape 104 are arranged in arrays, so that each array is spaced apart from adjacent arrays. In the embodiment shown, tape 104 is a white and opaque tape. In alternate embodiments, tape 104 can be black, white, or gray and transparent, semi-transparent, or opaque. Tape 104 can be made of a plastic material such as polypropylene or another suitable material such as metal foil.

As tape 104 advances through instrument 100, the plurality of assemblies in instrument 100 will interact with tape 104. The assemblies that are included on instrument 100 are plate stacker assembly 110, deck plate assembly 112, dispensing assembly 114, wash assembly 116, tape path assembly 118, tape sealing assembly 120, detection assembly 122, and electronic assembly 124. The plurality of assemblies are positioned on chassis 102 of instrument 100 to minimize the size of chassis 102 and instrument 100. Minimizing the size of chassis 102, and thus instrument 100, allows instrument 100 to have a compact design.

Each assembly in instrument 100 performs a function related to dispensing, amplifying, and/or analyzing a biological sample and reagent mixture so that instrument 100 can operate as an all-in-one assembly. Plate stacker assembly 110 is capable of receiving and moving plates containing a biological sample and/or a reagent in instrument 100. Deck plate assembly 112 is capable of receiving plates containing a biological sample and/or a reagent. Dispensing assembly 114 can aspirate a biological sample and/or a reagent from a plate in plate stacker assembly 110 and dispense the biological sample and/or the reagent into tape 104 in instrument 100. Dispensing assembly 114 can also aspirate a biological sample and/or a reagent from a plate in deck plate assembly 112 and dispense the biological sample and/or the reagent into tape 104 in instrument 100. Further, dispensing assembly 114 can aspirate a biological sample and/or reagent from any of a plate in plate stacker assembly 110, a plate in deck plate assembly 112, or tape 104, and can dispense the biological sample and/or reagent into a plate in plate stacker assembly 110, a plate in deck plate assembly 112, or tape 104. Wash assembly 116 is used to clean dispensing assembly 114 before and/or after dispensing assembly 114 is used to dispense the biological sample and the reagent into tape 104.

Tape 104 advances along tape path assembly 118 through instrument 100. Tape path assembly 118 extends through instrument 100 and provides a path along which tape 104 can advance. Tape path assembly 118 includes first position 130, second position 132, third position 134, and fourth position 136. Different functions are completed at each position along tape path assembly 118. At first position 130, tape 104 can be cut to singulate tape 104 into a tape segment with a single array of wells. Alternatively, tape 104 can advance as a web through first position 130 without being cut, or tape 104 can be cut after any number of arrays of wells have passed through first position 130. At second position 132, dispensing assembly 114 dispenses the biological sample and the reagent into tape 104 to form a biological sample and reagent mixture. Further, tape sealing assembly 120 is positioned adjacent second position 132 of tape path assembly 118 and seals an array on tape 104 with seal 106 after the biological sample and the reagent are dispensed into tape 104. Thermal management of tape 104 can occur at second position 132. For example, tape 104 can be cooled at second position 132 to prevent the biological sample and reagent mixture from undergoing a chemical reaction, or tape 104 can be heated at second position 132 to incubate the biological sample and reagent mixture. Thermal management of tape 104 can occur at third position 134 as well. At third position 134, tape 104 can again be cooled to prevent the biological sample and reagent mixture from undergoing a chemical reaction or heated to incubate the biological sample and reagent mixture. Tape 104 waits in third position 134 until instrument 100 is prepared to amplify and analyze the biological sample and reagent mixture in tape 104. At fourth position 136, tape 104 can be amplified and analyzed using detection assembly 122 that is positioned adjacent fourth position 136 of tape path assembly 118. Detection assembly 122 can heat the biological sample and reagent mixture in tape 104 and further includes a camera that can be used to analyze the biological sample and reagent mixture in tape 104. Electronic assembly 124 is included in instrument 100 to power instrument 100 and control the other assemblies in instrument 100.

Instrument 100 is advantageous for a number of reasons. First, each of the plurality of assemblies are positioned on a single chassis 102. This allows instrument 100 to have a compact design, thus making instrument 100 suitable for use in a variety of different settings. Second, instrument 100 is an all-in-one system that is capable of performing each step necessary to dispense, amplify, and analyze a biological sample and reagent mixture that is to be tested in instrument 100. This allows instrument 100 to be used without the need for additional equipment to perform different functions for dispensing, amplifying, and analyzing the biological sample and reagent mixture. Third, instrument 100 can be used for large scale or small scale testing. Instrument 100 includes all of the components necessary to test a large number of biological samples or a small number of biological samples. This versatility allows instrument 100 to be used in a wide range of settings and for a large number of different applications.

Figure 2A:
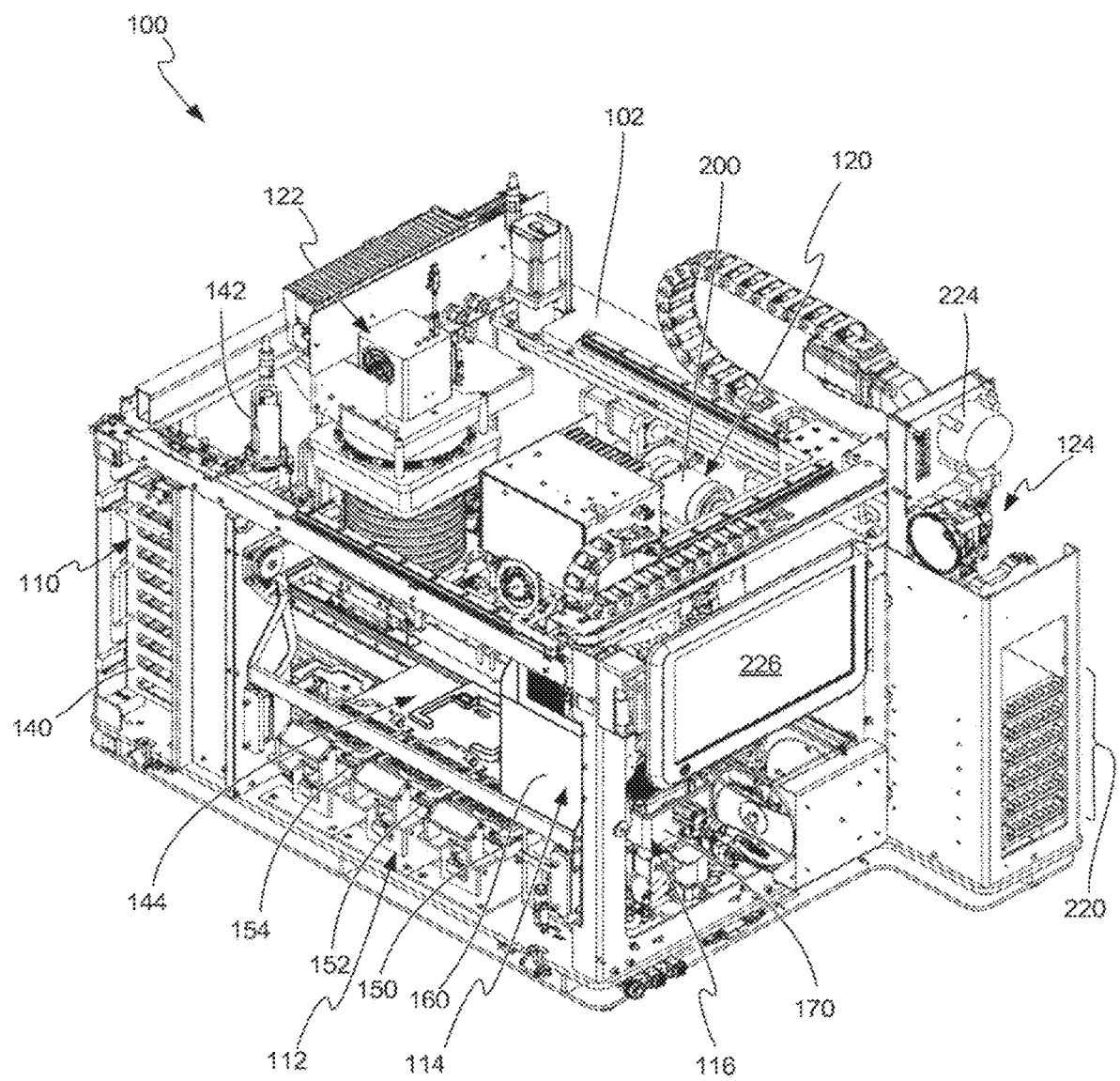
FIG. 2A is an isometric view of the instrument.
Figure 2B:
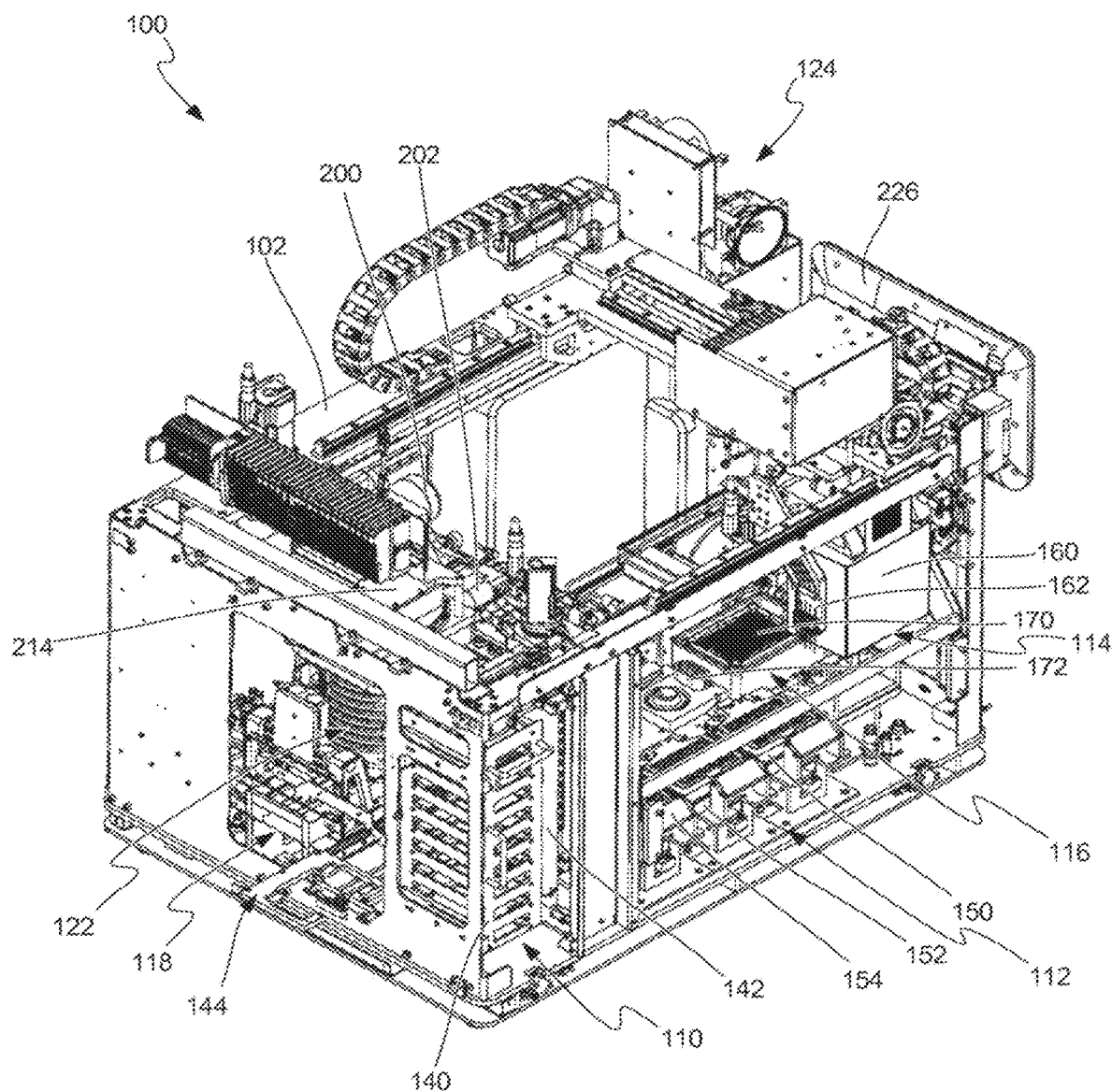
FIGS. 2B-2D are perspective views of the instrument.
Figure 2C:
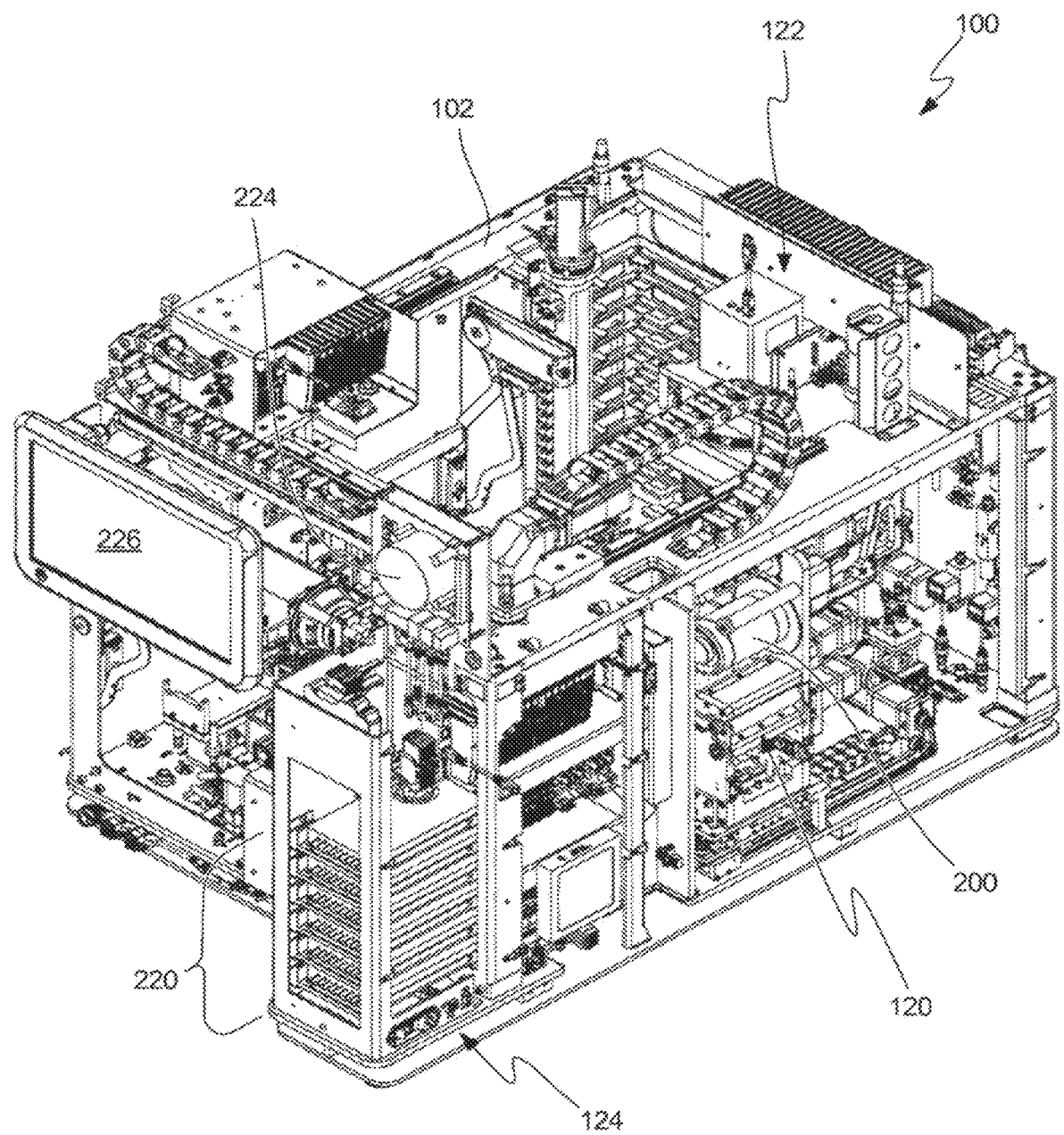
Figure 2D:
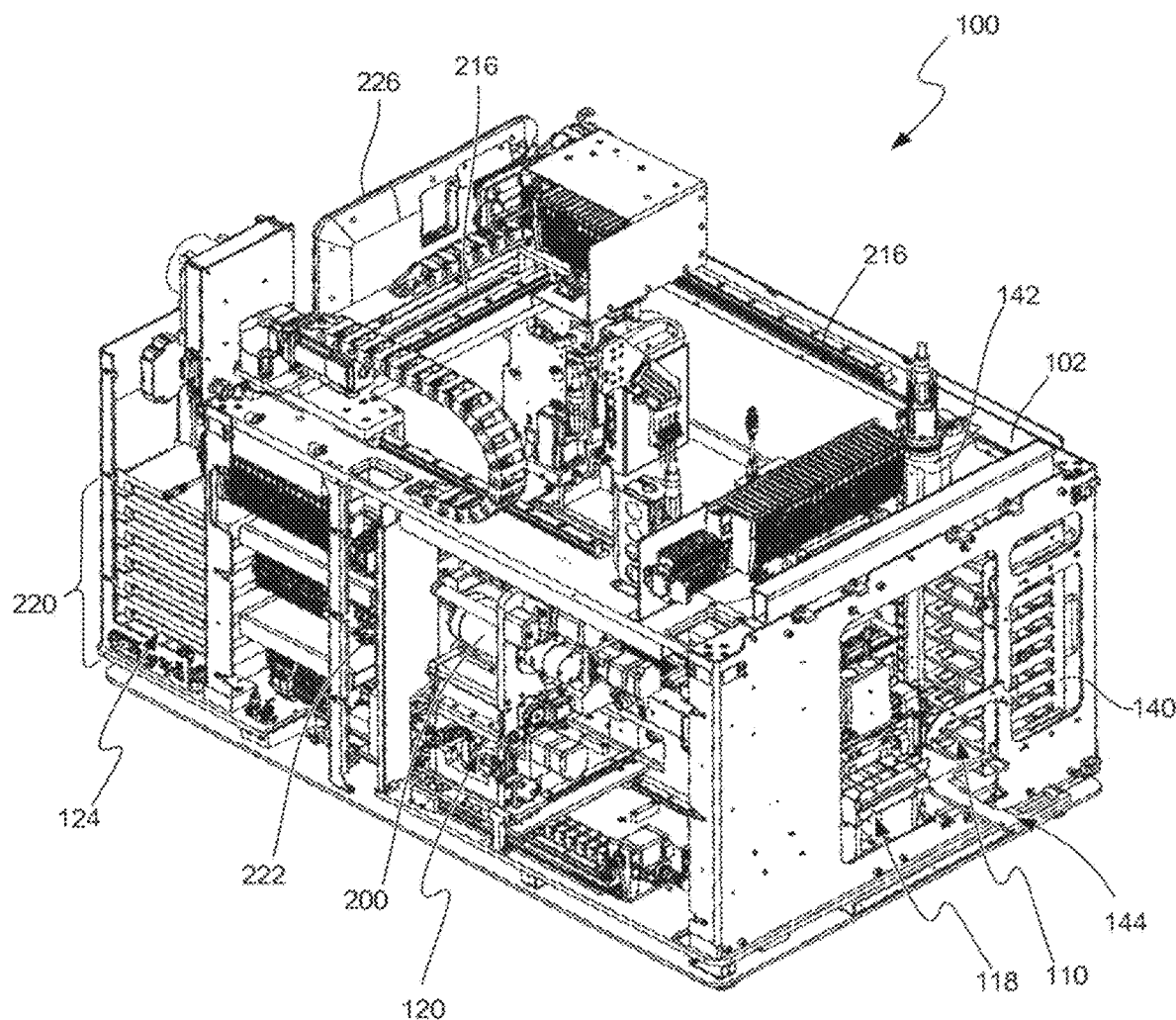
Figure 2E:
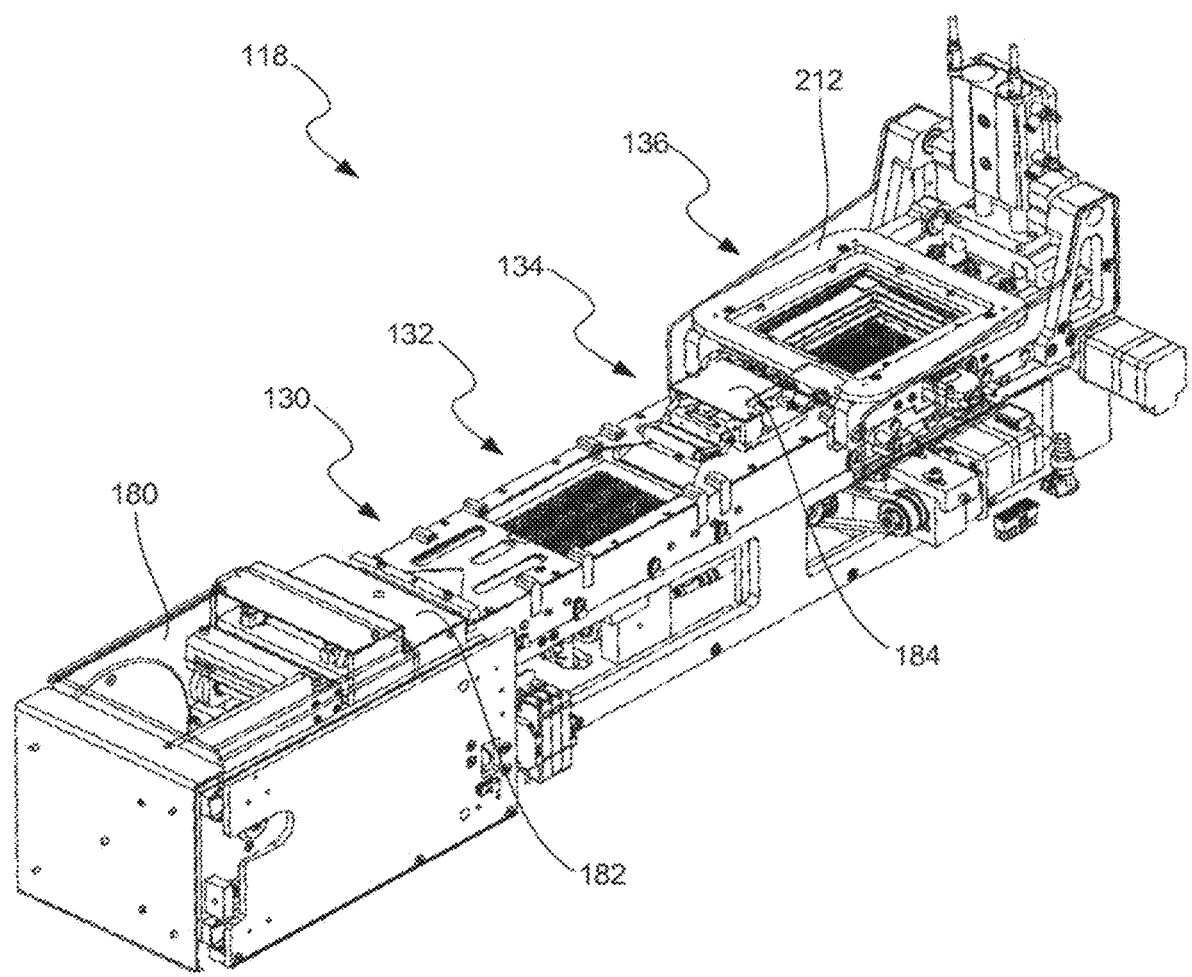
FIGS. 2E-2F are back perspective views of the tape path assembly that runs through the instrument.
Figure 2F:
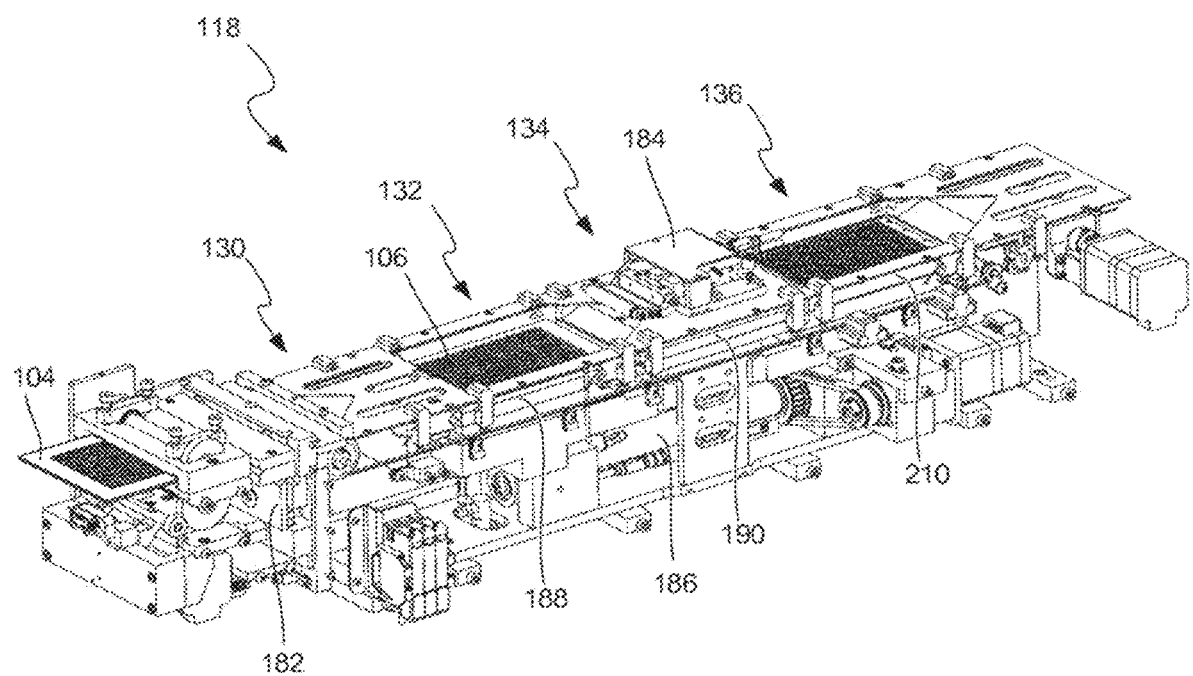

FIG. 2A is an isometric view of instrument 100. FIGS. 2B-2D are perspective views of instrument 100. FIGS. 2E-2F are back perspective views of tape path assembly 118 in instrument 100. Instrument 100 includes chassis 102, tape 104, seal 106, plate stacker assembly 110, deck plate assembly 112, dispensing assembly 114, wash assembly 116, tape path assembly 118, tape sealing assembly 120, detection assembly 122, and electronic assembly 124. Tape path assembly 118 includes first position 130, second position 132, third position 134, and fourth position 136.

Plate stacker assembly 110 includes plate rack 140, plate stacker 142, and plate shuttle 144. In the embodiment shown in FIGS. 2A-2D, plate stacker assembly 110 is used to receive, hold, and move plates containing a biological sample. In alternate embodiments, plate stacker assembly 110 could also be used to receive, hold, and move plates containing a reagent. Plate rack 140 is a chute or hotel that can receive and hold a plurality of plates. Plate rack 140 is attached to chassis 102 of instrument 100 and can be moved in and out of instrument 100 using any suitable mechanism, including having a user pull plate rack 140 out of instrument 100. Plate stacker 142 includes an arm with a spatula that can move up and down and rotate on a support structure. The spatula of plate stacker 142 can lift plates out of plate rack 140 and move them in instrument 100. Plate shuttle 144 includes a nest portion that can move horizontally along a support structure. Plates from plate rack 140 can be moved by plate stacker 142 to the nest portion of plate shuttle 144. When a plate is positioned on the nest portion of plate shuttle 144, the nest portion can move through instrument 100 to be positioned for aspiration or dispensing.

Plates containing a biological sample and/or a reagent can be placed in plate stacker assembly 110 in two ways. First, plate rack 140 can be pulled out of instrument 100 and plates can be positioned on plate rack 140. Second, the nest portion of plate shuttle 144 can extend out of instrument 100, as seen in FIGS. 2B and 2D. A plate can then be positioned on the nest portion of plate shuttle 144 and the nest portion can then move back into instrument 100. In alternate embodiments, plate stacker assembly 110 can further receive a tip tray holder containing tips for dispensing assembly 114, a matrix rack that holds a plurality of matrix tubes, a well trough, or any other container that is capable of containing a biological sample and/or a reagent.

Deck plate assembly 112 includes deck plate station 150, deck plate station 152, and deck plate station 154. In the embodiment shown in FIGS. 2A-2F, deck plate assembly 112 is used to receive and hold plates containing a reagent. In alternate embodiments, deck plate assembly 112 can be used to receive and hold plates containing a biological sample. Each of deck plate station 150, deck plate station 152, and deck plate station 154 can receive and hold a plate. Deck plate station 150, deck plate station 152, and deck plate station 154 each further include a hold down to hold the plate in place. Plates are positioned on deck plate station 150, deck plate station 152, and deck plate station 154 by lifting up the hold down, positioning the plate, and then lowering the hold down to secure the plate in place. In alternate embodiments, deck plate station 150, deck plate station 152, and deck plate station 154 can further receive a matrix rack that holds a plurality of matrix tubes, a well trough, or any other container that is capable of containing a biological sample and/or a reagent.

Dispensing assembly 114 includes sample dispenser 160 and reagent dispenser 162. Sample dispenser 160 and reagent dispenser 162 both include one or more tips that can be used to aspirate and dispense biological samples and reagents. In alternate embodiments, the tips could be pin tools that can be used to transfer the biological sample and/or the reagent. Reagent dispenser 162 is positioned on a side of sample dispenser 160. Sample dispenser 160 and reagent dispenser 162 move together in an x direction and a y direction on a gantry on a top end of instrument 100. In the embodiment shown, when sample dispenser 160 moves in a z direction, reagent dispenser 162 will move with sample dispenser 160. Reagent dispenser 162 can further move in a z direction relative to sample dispenser 160. In the embodiment shown in FIGS. 2A-2F, sample dispenser 160 is used to aspirate a biological sample from a plate in plate shuttle 144 and then dispense the biological sample into tape 104. Reagent dispenser 162 is used to aspirate a reagent from a plate in deck plate assembly 112 and then dispense the reagent into tape 104. In alternate embodiments, sample dispenser 160 can aspirate and dispense the reagent and reagent dispenser 162 can aspirate and dispense the biological sample.

Wash assembly 116 includes sample dispenser wash 170 and reagent dispenser wash 172. Sample dispenser wash 170 can be used to wash the tips on sample dispenser 160. Sample dispenser wash 170 is a vacuum based system that can use a cleaning solution and/or water with air flow to evacuate any residual biological sample or reagent from the tips to decontaminate them so they can be reused. An example of sample dispenser wash 170 is disclosed in published PCT application WO2014/179584, which is hereby incorporated by reference in its entirety. Reagent dispenser wash 172 is used to wash the tips on reagent dispenser 162. Reagent dispenser wash 172 uses water and air flow to clean the tips.

As shown in FIGS. 2E and 2F, tape path assembly 118 includes first position 130, second position 132, third position 134, and fourth position 136. Tape path assembly 118 also includes tape infeed 180, tape cutter 182, retractable hold down 184, actuating mechanism 186, thermal unit 188, and thermal unit 190. Tape infeed 180 is positioned near a first end of tape path assembly 118 upstream of first position 130. Tape infeed 180 includes a retractable spool that can hold a cartridge of tape 104. Tape infeed 180 is positioned near the first end of tape path assembly 118 so that tape 104 can be fed into tape path assembly 118. Tape 104 that is fed into tape path assembly 118 can then advance to first position 130. Positioned adjacent first position 130 is tape cutter 182. Tape cutter 182 includes a blade that can be actuated upward to cut tape 104 if desired. Tape 104 can also advance along tape path assembly 118 without being cut by tape cutter 182.

Tape 104 advances from first position 130 to second position 132 along tape path assembly 118. In second position 132, the biological sample and the reagent are dispensed into tape 104 with dispensing assembly 114 to form a biological sample and reagent mixture. To hold tape 104 flat during dispensing, retractable hold down 184 is positioned adjacent second position 132 (and on top of third position 134). Retractable hold down 184 includes a retractable bar that can be automatically actuated to hold tape 104 flat. Positioned beneath second position 132 is thermal unit 188. Thermal unit 188 includes one or more thermoelectric modules (TEMs) that can be used to either cool or heat the biological sample and reagent mixture in tape 104. Positioned adjacent second position 132 is tape sealing assembly 120. An array on tape 104 can be sealed with seal 106 using tape sealing assembly 120 when that array is positioned in second position 132.

After dispensing and sealing, tape 104 advances to third position 134. Positioned above third position 134 is retractable hold down 184 to hold tape 104 flat when tape 104 is in second position 132. Positioned beneath third position 134 is thermal unit 190. Thermal unit 190 includes one or more TEMs that can be used to either cool or heat the biological sample and reagent mixture in tape 104. Tape 104 can wait at third position 134 until instrument 100 is prepared to amplify and analyze the biological sample and reagent mixture in tape 104.

When instrument 100 is prepared to amplify and analyze the biological sample and reagent mixture, tape 104 can advance to fourth position 136. Positioned beneath fourth position 136 is thermal unit 210 to heat the biological sample and reagent mixture in tape 104. Positioned above fourth position 136 is heated pressure chamber 212 to pressurize an area above tape 104 to push down on and keep seal 106 on tape 104. The biological sample and reagent mixture in tape 104 is amplified using thermal unit 210 in fourth position 136. Either after or during amplification, the biological sample and reagent mixture can be analyzed using camera 214. Heated pressure chamber 212 further heats the biological sample and reagent mixture and prevents condensation on seal 106 on tape 104 to ensure accurate analysis with camera 214.

Tape 104 advances along tape path assembly 118 through instrument 100 with actuating mechanism 186. Actuating mechanism 186 is a belt that drives tape 104 with frictional engagement in the embodiment shown in FIGS. 2A-2F. In alternate embodiments, actuating mechanism 186 can drive tape 104 with any suitable mechanism. Tape 104 advances through instrument 100 along tape path assembly 118 until tape 104 exits instrument 100 at a second end of tape path assembly 118.

As shown in FIGS. 2A, 2C, and 2D, tape sealing assembly 120 includes spool 200 and applicator 202. Tape sealing assembly 120 is capable of movement in both the x and y directions in relation to instrument 100. Spool 200 can hold a web of seals 106 that can be used to seal tape 104 in instrument 100. Seals 106 are cover seals that can be applied to tape 104 to contain the biological sample and reagent mixture in tape 104 and prevent evaporation and contamination of the biological sample and reagent mixture in tape 104. Seals 106 that are held on spool 200 are routed through tape sealing assembly 120 so that applicator 202 can capture seal 106 as seal 106 is removed from the backing seal 106 is held on. Applicator 202 can then apply seal 106 to an array of tape 104. Tape sealing assembly 120 is positioned adjacent second position 132 of tape path assembly 118 so that tape 104 can be sealed with seal 106 at second position 132.

Detection assembly 122 includes thermal unit 210, heated pressure chamber 212, and camera 214. Detection assembly 122 is positioned at fourth position 136 to amplify and analyze the biological sample and reagent mixture in tape 104. Thermal unit 210 is positioned underneath fourth position 136 and includes one or more TEMs that can be used to hold the biological sample and reagent mixture at a constant temperature or cycle the biological sample and reagent mixture through multiple temperatures. Heated pressure chamber 212 is positioned above and around fourth position 136. Heated pressure chamber 212 seals, pressurizes, and heats the area above fourth position 136 so that the biological sample and reagent mixture in tape 104 can be analyzed. Heated pressure chamber 212 also prevents condensation on seal 106 so that camera 214 can properly detect a signal from the biological sample and reagent mixture in tape 104.

Detection assembly 122 dudes excitation light emitting diodes for illuminating the biological sample and reagent mixture in tape 104 to excite a dye or probe in the biological sample and reagent mixture. The dye or probe emits a signal, such as fluorescence, and an emission filter wheel filters the signal entering camera 214 to a desired wavelength. Camera 214 is positioned above fourth position 136 and heated pressure chamber 212 and can detect the signal emitted from the biological sample and reagent mixture in tape 104. Camera 214 is a CCD camera in the embodiment shown, but can be any suitable camera or other detection device in alternate embodiments.

As shown in FIGS. 2A-2D, electronic assembly 124 includes illumination strips 216, power supply 220, printed circuit boards 222, industrial PC 224, and display 226. Illumination strips 216 line chassis 102 and provide additional lighting during operation of instrument 100. In the embodiment shown, illumination strips 216 are light emitting diodes. In an alternate embodiment, illumination strips 216 can include an ultra violet light source to aid in decontamination of instrument 100. Power supply 220 powers instrument 100 and each of the plurality of assemblies positioned in instrument 100. Printed circuit boards 222 include electronic components that are used to control the operation of instrument 100. Printed circuit boards 222 are positioned in a back portion of instrument 100 and are further located throughout instrument 100 to control each of the plurality of assemblies in instrument 100. Industrial PC 224 is also positioned in a back portion of instrument 100 and further controls the operation of instrument 100. Industrial PC 224 can communicate with printed circuit boards 222 throughout instrument 100 to execute the functions of instrument 100. Display 226 is positioned on a first side of instrument 100 and is a touchscreen display that a user can use to control testing in instrument 100. Display 226 can also display data that is collected in instrument 100 during operation. Display 226 can be attached to a multidirectional arm so that a user can move display 226 to a position suitable for them. Instrument 100 further includes an analytics system to gather and analyze data that is collected during analysis of the biological sample and reagent mixture.

Instrument 100 is advantageous over prior art devices, as instrument 100 can test a large sample set or a small sample set. This versatility allows instrument 100 to be used in a variety of settings. The all-in-one function and compact design further allows instrument 100 to be used in a variety of different settings and for a wide range of different applications. Instrument 100 can amplify and analyze a biological sample and reagent mixture according to polymerase chain reaction (PCR) steps. This includes real-time PCR, end-point PCR, and other suitable PCR variations. Real-time PCR (or quantitative PCR) includes thermal cycling and amplifying the biological sample and reagent mixture and detecting a signal from the biological sample and reagent mixture at the same time. End-point PCR includes detecting a signal from the biological sample and reagent mixture after it has been amplified. The biological sample and reagent mixture can be amplified according to any suitable process with end-point PCR. Further, the biological sample and reagent mixture can be dispensed and sealed in tape 104 in instrument 100, removed from instrument 100 to undergo amplification using an external device, and then inserted back into instrument 100 for end-point detection with instrument 100. Instrument 100 can also amplify and analyze a biological sample and reagent mixture using isothermal amplification. Isothermal amplification includes amplifying the biological sample and reagent mixture at a constant temperature. Instrument 100 can also be used for other PCR processes or for any process that detects a signal from a biological sample and reagent mixture using a camera.

Figure 3A:
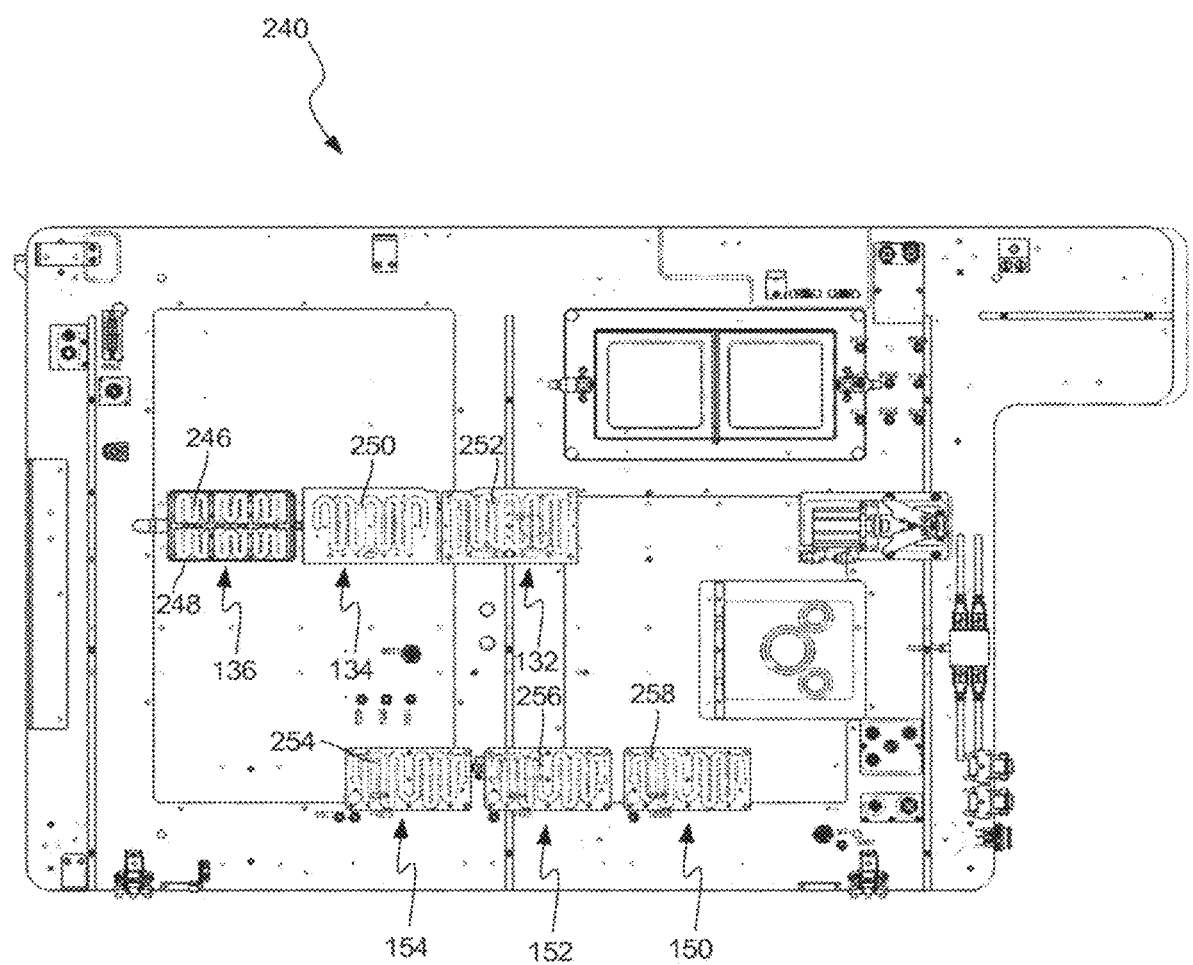
FIG. 3A is a top plan view of a thermal management system in the instrument.
Figure 3B:
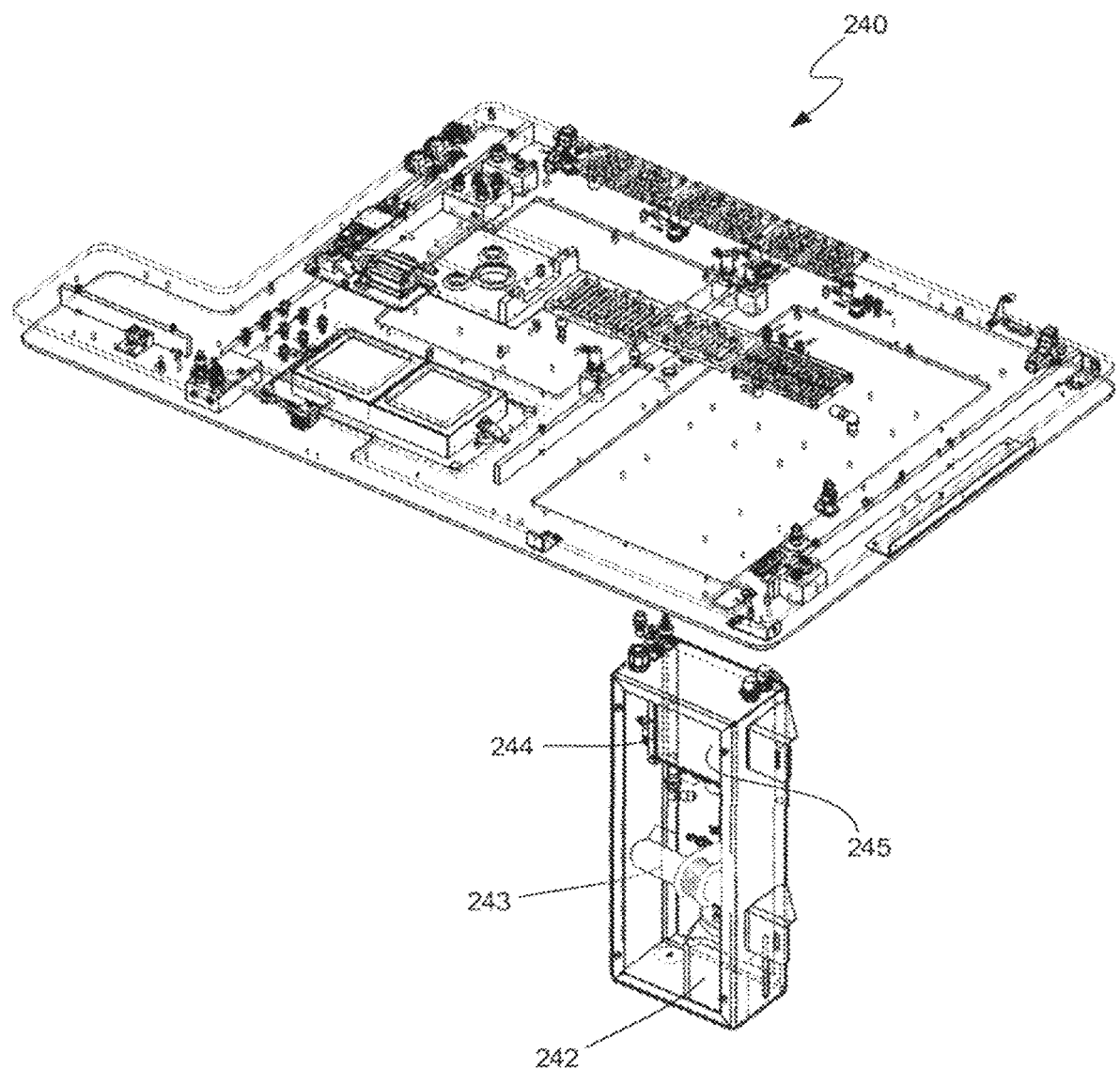
FIG. 3B is a perspective view of the thermal management system seen in FIG. 3A.
Figure 3C:
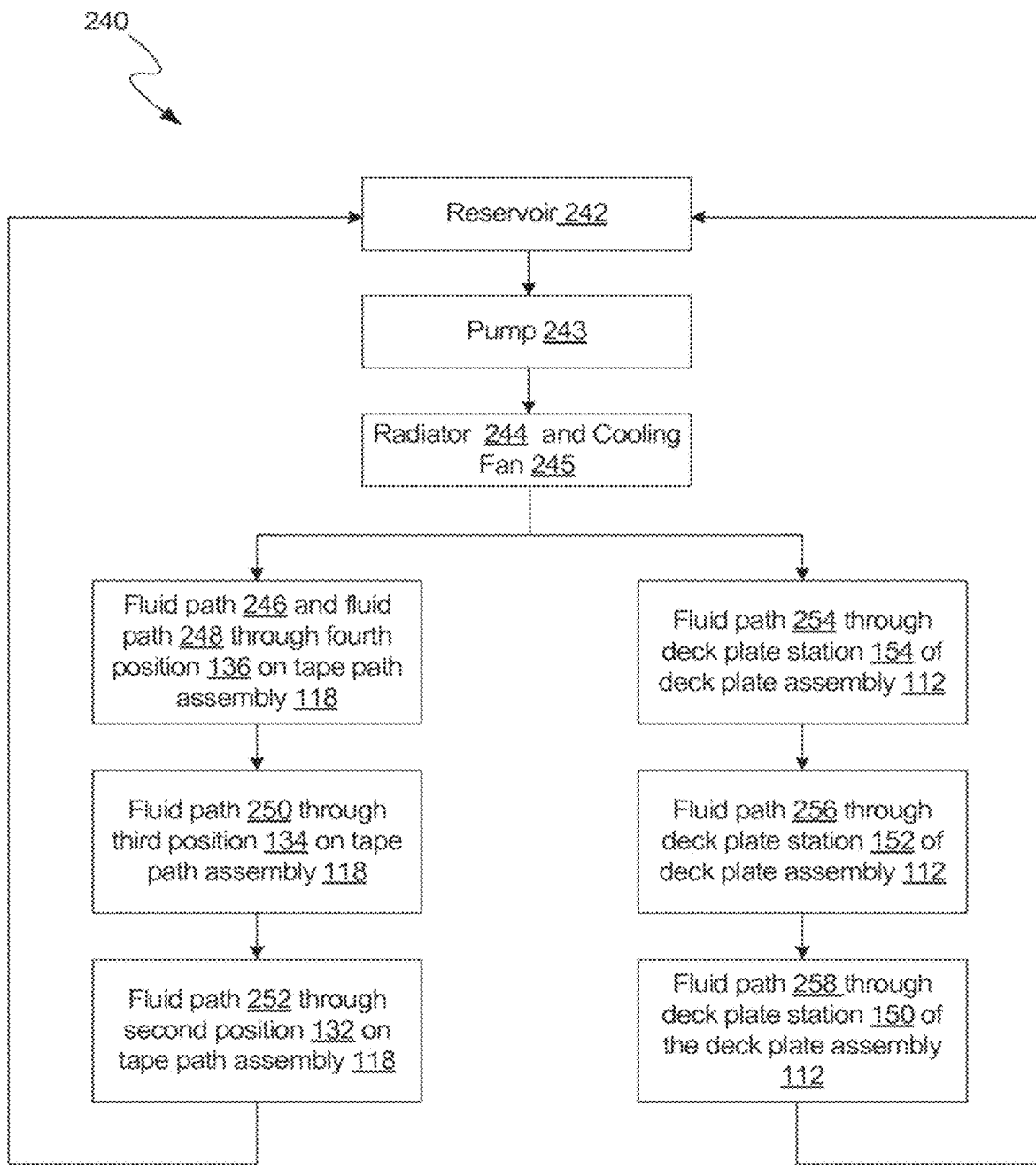
FIG. 3C is a schematic view of the thermal management system seen in FIGS. 3A and 3B.

FIG. 3A is a top plan view of thermal management system 240 in instrument 100. FIG. 3B is a perspective view of thermal management system 240. FIG. 3C is a schematic view of thermal management system 240. Instrument 100 includes deck plate assembly 112 (including deck plate station 150, deck plate station 152, and deck plate station 154) and tape path assembly 118 (including second position 132, third position 134, and fourth position 136). Thermal management system 240 includes reservoir 242, fluid pump 243, radiator 244, cooling fan 245, fluid path 246, fluid path 248, fluid path 250, fluid path 252, fluid path 254, fluid path 256, and fluid path 258.

Thermal management system 240 runs through instrument 100 to provide a heat exchange fluid to thermal units that are positioned in instrument 100. Thermal management system 240 is a closed-loop fluidic thermal management system. Fluid that is not being used to exchange heat can be stored in reservoir 242. Fluid that is being used to exchange heat can flow through radiator 244 so that the temperature of the fluid can be controlled. Cooling fan 245 aids in controlling the temperature of the fluid by blowing cooling air across radiator 244 in order to remove heat from fluid flowing through radiator 244. Fluid from radiator 244 can then flow through a plurality of fluid paths in instrument 100.

Fluid path 246 and fluid path 248 are both positioned beneath fourth position 136 of tape path assembly 118. Fluid path 246 runs on a first side of fourth position 136 and fluid path 248 runs on a second side of fourth position 136. Fluid path 250 is positioned beneath third position 134 of tape path assembly 118. Fluid path 252 is positioned beneath second position 132 of tape path assembly 118. Fluid path 254 is positioned beneath deck plate station 154 of deck plate assembly 112. Fluid path 256 is positioned beneath deck plate station 152 of deck plate assembly 112. Fluid path 258 is positioned beneath deck plate station 150 of deck plate assembly 112. Fluid paths 246-258 all include a cavity that curves back and forth through a block so that fluid can flow through the cavity and exchange heat with components that are positioned above the cavity.

When heat exchange is needed, fluid pump 243 pumps fluid from reservoir 242 to radiator 244. Radiator 244 and cooling fan 245 can adjust the temperature of the fluid for use in instrument 100. After the temperature of the fluid is regulated, the fluid flows through instrument 100 along two separate paths. The first path is through fluid path 246 and 248, fluid path 250, fluid path 252, and back to reservoir 242. The second path is through fluid path 254, fluid path 256, fluid path 258, and back to reservoir 242. The fluid that flows from radiator 244 to fluid paths 246, 248, and 254 is routed through a base portion of instrument 100. Further, fluid that flows from fluid paths 252 and 258 to reservoir 242 is routed through a base portion of instrument 100. Routing the fluid through a base portion of instrument 100 allows the space on the main surface of instrument 100 to hold other components. This allows for flexibility in the design of instrument 100 and allows instrument 100 to have a compact design.

Thermal management system 240 is advantageous as it is a closed-loop system. This means instrument 100 does not have to be connected to a fluid source to regulate the temperature of components in instrument 100, as the fluid is stored in thermal management system 240 and cycled through thermal management system 240 as needed. This allows instrument 100 to be used in settings where there is no access to a temperature controlled fluid source. Thermal management system 240 is further advantageous, as it can effectively and efficiently regulate the temperature of components that are positioned along thermal management system 240 using convective heat transfer.

Figure 4A:
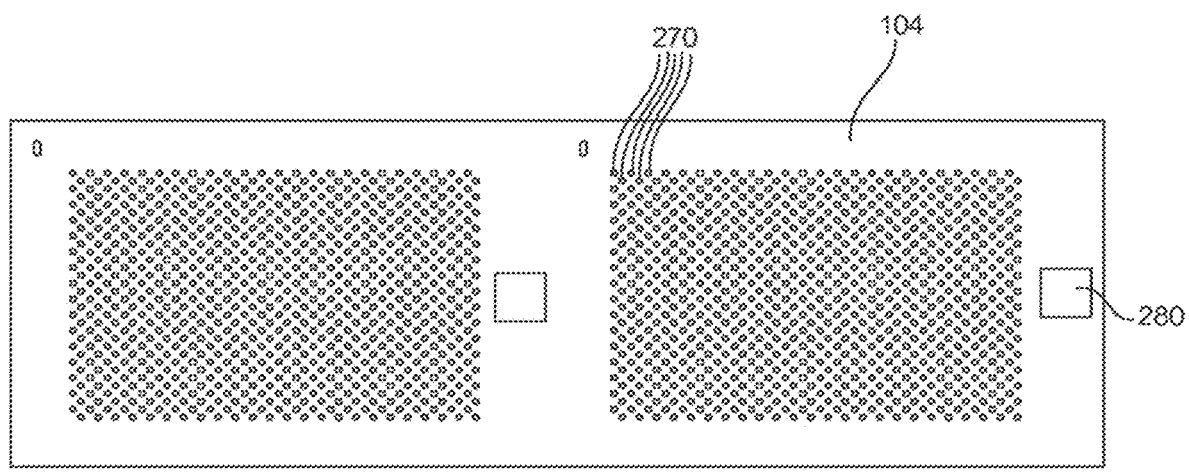
FIG. 4A is a top plan view of a tape with a plurality of wells.
Figure 4B:
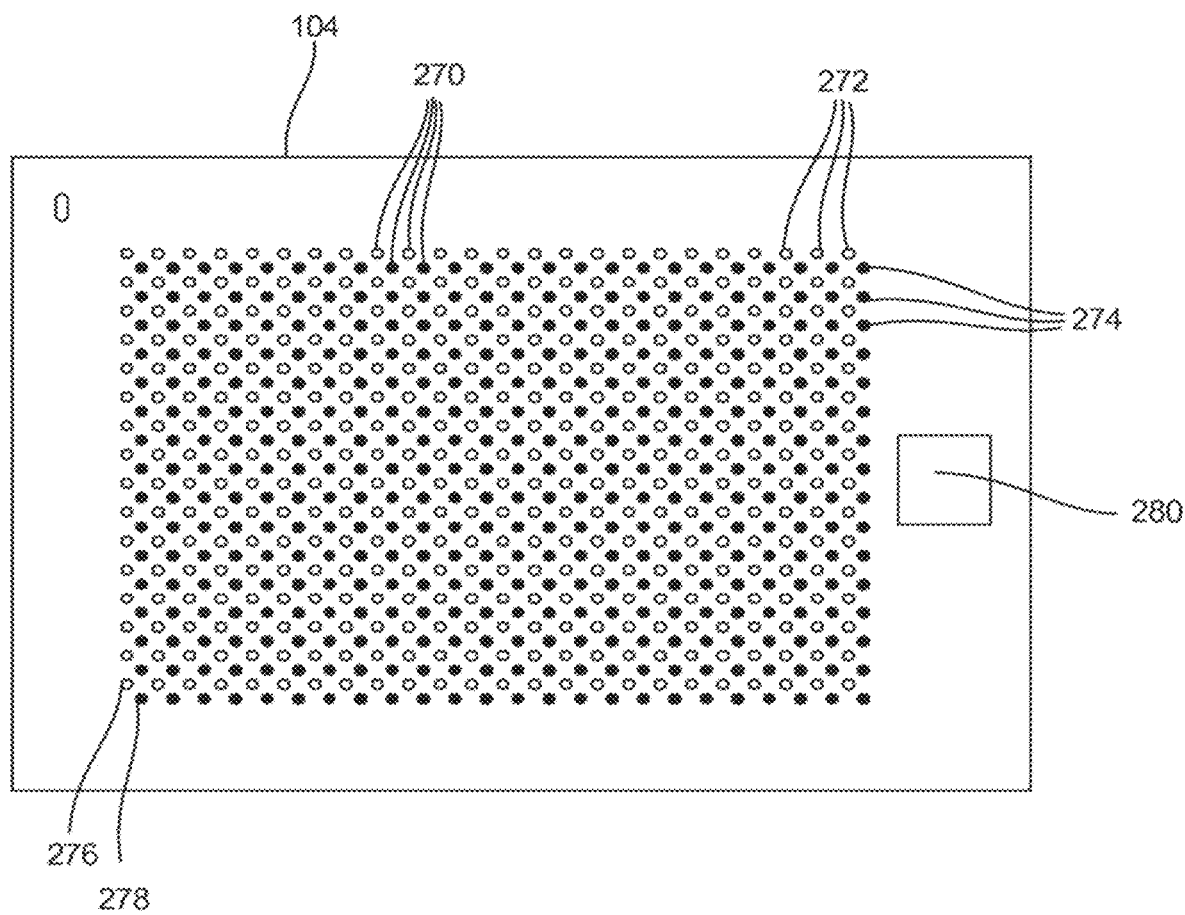
FIG. 4B is a schematic view of the tape seen in FIG. 4A with a first plurality of wells and a second plurality of wells.

FIG. 4A is a top plan view of tape 104 with wells 270. FIG. 4B is a schematic view of tape 104 with first plurality of wells 272 and second plurality of wells 274. Tape 104 includes wells 270, including first plurality of wells 272. (including well 276), second plurality of wells 274 (including well 278), and array identifier 280.

Tape 104 includes wells 270. Wells 270 are formed in tape 104 to receive and hold a biological sample and a reagent for amplification and analysis. Tape 104 can include any number of wells 270, including one well 270 or a plurality of wells 270. For example, tape 104 can include wells 270 arranged in a 96 well configuration, a 192 well configuration, a 384 well configuration, a 768 well configuration, or a 1536 well configuration. Array identifier 280 is an identifier, such as a barcode, which identifies the contents in wells 270. Tape 104 is made out of a polymer material and wells 270 are created by embossing in the embodiment shown, although they can be created using other suitable methods in alternate embodiments. In the embodiment shown, tape 104 is a white and opaque tape. In alternate embodiments, tape 104 can be black, white, or gray and transparent, semi-transparent, or opaque.

In the embodiment shown in FIGS. 4A-4B, wells 270 include first plurality of wells 272 and second plurality of wells 274 that are offset from and interlaced with first plurality of wells 272. As seen in FIG. 4B, first plurality of wells 272 are represented with white circles and second plurality of wells 274 are represented with black circles. Tape 104 includes 768 wells, with 384 wells making up first plurality of wells 272 and 384 wells making up second plurality of wells 274. In alternate embodiments, tape 104 can include any number and size of wells 270 with a first plurality of wells being interlaced with a second plurality of wells.

First plurality of wells 272 and second plurality of wells 274 are positioned on tape 104 so that the wells in first plurality of wells 272 and the wells in second plurality of wells 274 are offset from one another at a 45-degree angle. For example, well 276 of first plurality of wells 272 is offset from well 278 of second plurality of wells 274 at a 45-degree angle. Each well in first plurality of wells 272 is offset from each adjacent well in second plurality of wells 274 at a 45-degree angle. This allows first plurality of wells 272 and second plurality of wells 274 to be interlaced with one another in an offset pattern.

Interlacing first plurality of wells 272 and second plurality of wells 274 with each other on tape 104 is advantageous. If either first plurality of wells 272 or second plurality of wells 274 were removed, a 384-well format would be left on tape 104. Interlacing is advantageous for a number of reasons. First, tape 104 allows a standard 384-well format to be duplicated in essentially the same amount of space as previously required for the 384-well format. This doubles the number of results that can be collected when a single array of tape 104 is tested, increasing the efficiency and throughput of the testing device. Second, tape 104 can easily interact with standardized equipment, such as pipette tips, that is currently available for the 384-well or 96-well format. Third, interlacing first plurality of wells 272 and second plurality of wells 274 with one another allows for maximum spacing between wells 270, allowing for larger wells then would otherwise be possible. Fourth, the surface area between wells 270 is maximized on tape 104, which is advantageous when tape 104 is sealed. A larger surface area allows for a better seal, as there is more contact between tape 104 and seal 106.

Plate Stacker Assembly

FIG. 5A is an isometric view of plate stacker assembly 110 in instrument 100. FIG. 5B is a top cut away view of plate stacker assembly 110 in instrument 100. FIG. 5C is an isometric view of plate stacker assembly 110. Plate stacker assembly 110 is positioned in a first corner of instrument 100. Plate stacker assembly 110 is capable of receiving, holding, and moving plates in instrument 100. In the embodiment shown in FIGS. 5A-5C, plate stacker assembly 110 receives plates containing a biological sample. In alternate embodiments, plate stacker assembly 110 can receive plates containing other samples or reagents.

Plate stacker assembly 110 includes plate rack 302, plate stacker 304, and plate shuttle 306. Plate rack 302 is a chute or a hotel that can receive and hold a plurality of plates. Plate rack 302 is attached to instrument 100 and can be moved in and out of instrument 100 using any suitable mechanism. Plate stacker 304 includes an arm that can move up and down on and rotate around a support structure with a spatula attached to the arm. The spatula and the arm of plate stacker 304 can pick plates out of plate rack 302 and move them in instrument 100 with rotational and vertical movement. Plate shuttle 306 includes a nest portion that can move horizontally along a support structure. Plates from plate rack 302 can be moved by plate stacker 304 and placed on the nest portion of plate shuttle 306. When a plate is positioned on the nest portion of plate shuttle 306, the nest portion can move through instrument 100 to be positioned for aspiration and dispensing.

Plates containing a biological sample can be placed in plate stacker assembly 110 in two ways. First, plate rack 302 can be pulled out of instrument 100 and plates containing a biological sample can be positioned on plate rack 302. Second, the nest portion of plate shuttle 306 can extend out of instrument 100 (as seen in FIG. 8B). This allows instrument 100 to interface with plate storage units or plate lid removal equipment outside of instrument 100. A plate can then be positioned on the nest portion of plate shuttle 306 and the nest portion can then move back into instrument 100.

Plate stacker assembly 110 can receive, hold, and move plates or other components compatible with instrument 100, such as tip trays for dispensing assembly 114. Further, plate stacker assembly 110 can complete these functions in a small area. This makes plate stacker assembly 110 advantageous for use in instrument 100, which is a compact instrument with limited space.

FIG. 6A is an isometric view of plate rack 302. FIG. 6B is a top plan view of nest 312 of plate rack 302. Plate rack 302 includes frame 310, nests 312, rails 314, rails 315, handles 316, and contact 318, as shown in FIG. 6A. Each nest 312 includes frame 320, corner supports 322, opening 324, and slot 326, as shown in FIG. 6B.

Plate rack 302 includes frame 310 that forms a body portion of plate rack 302. As seen in the embodiment shown in FIGS. 6A-6B, attached to frame 310 are a plurality of nests 312. In alternate embodiments, one nest 312 or any number of nests 312 can attached to frame 310. Nests 312 are positioned in a vertical row on frame 310. Each nest 312 can receive and hold a plate. When a plate is needed for aspiration or dispensing, the plate can be picked from nest 312 that the plate is positioned in and moved through instrument 100 to be positioned for aspiration or dispensing.

Rails 314 are attached to frame 310 on an outer side surface of frame 310. Rails 314 are sliding rails in the embodiment shown in FIG. 6A that slide upon corresponding rails 315 that can be attached to instrument 100. Rails 314 and rails 315 allow plate rack 302 to slide in and out of instrument 100. In alternate embodiments, rails 314 and rails 315 can be any mechanism that holds plate rack 302 in instrument 100 and allows plate rack 302 to slide in and out of instrument 100. In some embodiments, when plate rack 302 is slid out of instrument 100 plate rack 302 can be fully removed. This allows a user to remove plate rack 302, load plate rack 302 with plates at a location away from instrument 100, and then reinsert plate rack 302 into instrument 100 once plates have been positioned on plate rack 302. Handles 316 are attached to an outer front surface of frame 310. Handles 316 can be grasped by a user to slide plate rack 302 out of instrument 100 along rails 314 and rails 315. Handles 316 can also be used to move plate rack 302 when plate rack 302 is removed from instrument 100.

Contact 318 is also attached to an outer side surface of frame 310. Contact 318 will abut a contact that is attached to instrument 100 when plate rack 302 is positioned in instrument 100. Contact 318 and the contact attached to instrument 100 act as a sensor to indicate to instrument 100 that plate rack 302 is positioned in instrument 100. Further, contact 318 can communicate to the contact attached to instrument 100 to indicate what configuration or size of plate rack 302 has been placed in instrument 100. In alternate embodiments, any identification mechanism can be positioned on plate rack 302 and any identification reader can be positioned on instrument 100. As a first example, a barcode affixed to frame 310 of plate rack 302 could be scanned by a camera on instrument 100 and used to indicate what configuration or size of plate rack 302 has been placed in instrument 100. As a second example, an RFID tag affixed to frame 310 of plate rack 302 could be scanned by an RFD reader on instrument 100 and used to indicate what configuration or size of plate rack 302 has been placed in instrument 100. This information can then be used by instrument 100 to indicate to components that interact with plate rack 302 what configuration and size of plate rack 302 is in instrument 100.

As seen in FIG. 6B, each nest 312 includes frame 320 that forms an outer body portion of nest 312. Frame 320 has a beveled inner edge to guide a plate being placed on nest 312 into the proper position. The beveled inner edge on frame 320 eliminates the need for a plate to be perfectly aligned with nest 312 before it is placed. Attached to each inner corner of frame 320 is a corner support 322. Corner supports 322 are flat support structures that are each capable of supporting a corner of a plate when a plate is positioned in nest 312. Positioned inwards of frame 320 and corner supports 322 is opening 324. Positioned on a side of frame 320 is slot 326. Opening 324 and slot 326 are provided in each nest 312 so that an arm can pass through nest 312 to place plates in nest 312 and to pick plates from nest 312. Slot 326 is positioned on the side of frame 320 through which the arm will pass. Allowing an arm to pass through opening 324 and slot 326 allows plate rack 302 to have a compact design.

Figure 7C:
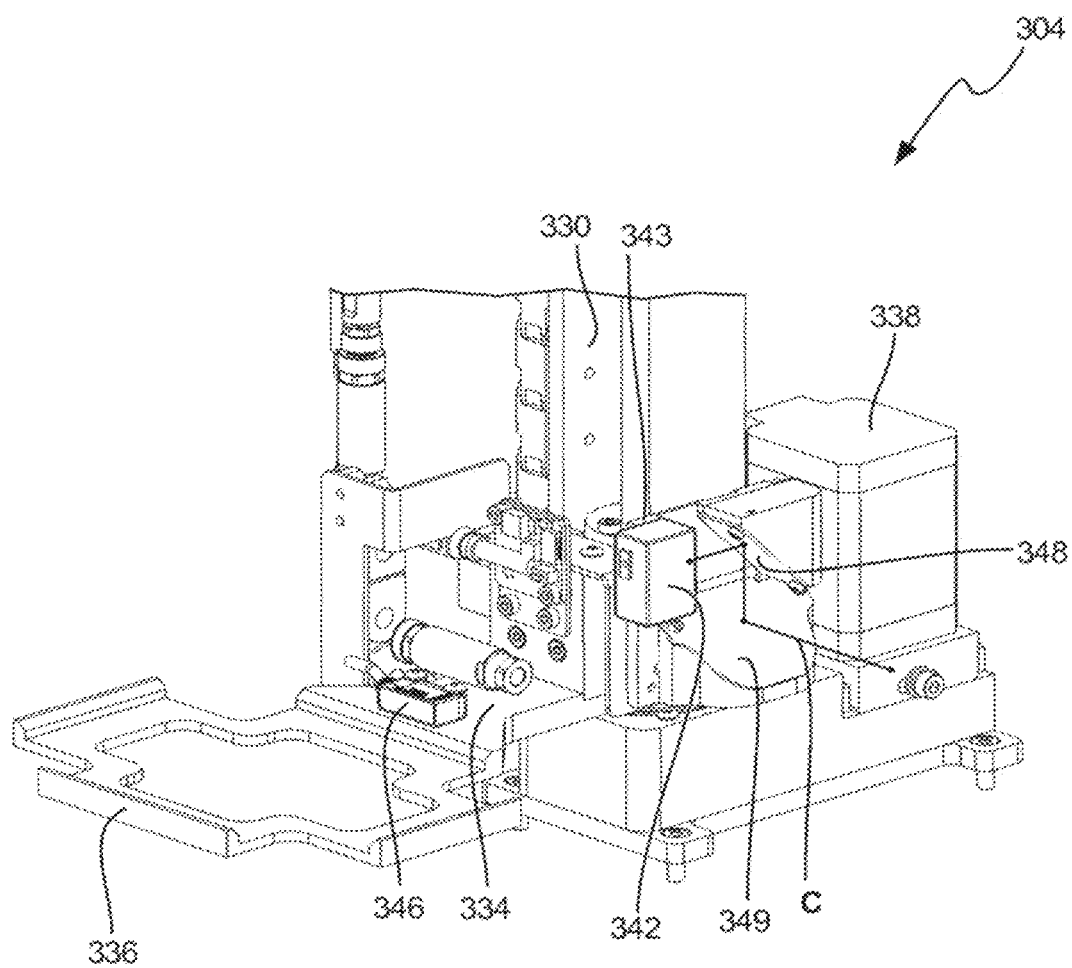

FIG. 7A is an isometric view of plate stacker 304. FIG. 7B is a perspective view of a portion of plate stacker 304 and a portion of plate rack 302. 7C is a perspective view of a portion of plate stacker 304. Plate stacker 304 includes column 330, screw rail 332, arm 334, spatula 336, actuator 338, actuator 340, camera 342, bracket 343, cable carrier 344, sensor 346, mirror 348, and mirror 349. Spatula 336 includes support member 350 and notches 352. Also shown in FIG. 7B is plate 390A positioned on plate rack 302. Also shown in FIGS. 7B and 7C is camera path C.

Plate stacker 304 includes column 330 that forms a support structure for plate stacker 304. Positioned inside column 330 is screw rail 332. Arm 334 is attached to screw rail 332. Arm 334 includes spatula 336 that can be used to pick and place plates in instrument 100. Arm 334 can move up and down in a vertical direction on screw rail 332. Arm 334 can also rotate with column 330 about a vertical axis. Actuator 338 is positioned on a base portion of plate stacker 304 and controls the rotational movement of column 330 and arm 334. Actuator 340 is positioned on a top end of column 330 and controls the vertical movement of arm 334 on screw rail 332. In the embodiment shown, actuator 340 includes a servo motor that tracks the vertical position of arm 334 on screw rail 332.

Camera 342 is attached to plate stacker 304 with bracket 343. Camera 342 is used to scan barcodes or other plate identifiers on plates that are positioned in instrument 100. In the embodiment shown in FIG. 7B, camera 342 is used to scan barcodes on plates positioned in plate rack 302. Camera 342 is attached to bracket 343 so that camera 342 moves up and down with arm 334 on screw rail 332. Camera path C shows the path from a barcode on plate 390A to camera 342. Camera 342 is positioned such that camera 342 captures the image of the barcode reflected in mirrors 348 and 349. Scanning barcodes with camera 342 allows instrument 100 to determine what plate should be moved with spatula 336. Cable carrier 344 is positioned adjacent column 330 and contains cables that connect camera 342 to a power source and other electronic components that are needed to communicate with instrument 100. Also attached to plate stacker 304 is sensor 346. Sensor 346 senses the presence of a plate on spatula 336.

Spatula 336 of arm 334 is used to pick and place plates in instrument 100. Spatula 336 includes support member 350 and notches 352. Support member 350 is a base portion with a plus shape. Notches 352 are open areas in each corner of spatula 336. Support member 350 and notches 352 are shaped so that spatula 336 can pass through nests in instrument 100. Support member 350 is used to engage a bottom of a plate in instrument 100. This engagement supports a plate and allows spatula 336 to move the plate in instrument 100. Support member 350 has a beveled inner edge to guide a plate being picked with spatula 336 into the proper position. The beveled inner edge on support member 350 eliminates the need for a plate to be perfectly aligned with spatula 336 before it is picked. Using spatula 336 to move plates in instrument 100 is advantageous, as support member 350 of spatula 336 fully supports a plate and eliminates concerns that the plate will be dropped as it is moved in instrument 100, FIG. 8A is an isometric view of plate shuttle 306. FIG. 8B is an isometric view of plate shuttle 306 in instrument 100. Plate shuttle 306 includes support 360, rail 362, nest 364, bracket 366, driving mechanism 368 (including drive belt 369 and actuator 370), clamp 372, home sensor 374, and plate sensor 378. Nest 364 includes frame 380, corner supports 382, opening 384, and slot 386.

Plate shuttle 306 includes support 360 that forms a support structure for plate shuttle 306. Support 360 extends in a horizontal direction through instrument 100. Attached to support 360 is rail 362. Rail 362 also extends in a horizontal direction through instrument 100 along support 360. Nest 364 can be attached to rail 362 with bracket 366. Nest 364 moves along rail 362 in a horizontal direction through instrument 100. Bracket 366 attaches nest 364 to rail 362. Bracket 366 attaches nest 364 to driving mechanism 368 with clamp 372. Driving mechanism 368 is a belt driven system in the embodiment shown in FIGS. 8A-8B, but can be any suitable driving mechanism in alternate embodiments. Actuator 370 is attached to support 360 and controls the movement of driving mechanism 368. Bracket 366 attaches to drive belt 369 of driving mechanism 368 with clamp 372. As drive belt 369 of driving mechanism 368 moves, clamp 372 will move with drive belt 369 and thus will move bracket 366. As bracket 366 moves with driving mechanism 368, bracket 366 will slide upon rail 362 and move nest 364 in instrument 100.

Also attached to support 360 are home sensor 374, and plate sensor 378. Home sensor 374 is positioned on a first end of support 360. Home sensor 374 senses when nest 364 is positioned near the first end of support 360. This is the home position for nest 364. As seen in FIG. 8B, nest 364 can extend out of instrument 100 through an opening in instrument 100. Plate sensor 378 is positioned between the middle portion and the first end of support 360. Plate sensor 378 senses when a plate is positioned on nest 364. When a plate is positioned on nest 364, plate sensor 378 will indicate to instrument 100 that there is a plate positioned on nest 364 to prevent instrument 100 from trying to place another plate on nest 364. When a plate is positioned on nest 364, plate sensor 378 will also indicate to instrument 100 that a plate is available for dispensing operations.

As seen in FIG. 8A, nest 364 includes frame 380 that forms an outer body portion of nest 364. Frame 380 has a beveled inner edge to guide a plate being placed on nest 364 into the proper position. The beveled inner edge on frame 380 eliminates the need for a plate to be perfectly aligned with nest 364 before the plate is placed. Attached to each inner corner of frame 380 is a corner support 382. Corner supports 382 are flat support structures that are each capable of supporting a corner of a plate when a plate is positioned in nest 364. Positioned inward of frame 380 and corner supports 382 is opening 384. Positioned on a side of frame 380 is slot 386. Opening 384 and slot 386 are provided in nest 364 so that arm 334 of plate stacker 304 can pass through nest 364 to place plates in nest 364 and to pick plates from nest 364. Slot 326 is positioned on the side of frame 320 through which arm 334 will pass. Allowing arm 334 to pass through opening 384 and slot 386 of nest 364 allows a plate to be easily picked from or placed into nest 364.

FIG. 9A is an isometric view of plate rack 302 and plate stacker 304 when spatula 336 is in a home position. FIG. 9B is an isometric view of plate rack 302 and plate stacker 304 when spatula 336 has been moved from the home position. FIG. 9C is an isometric view of plate rack 302 and plate stacker 304 when spatula 336 is positioned to pick plate 390A. FIG. 9D is a perspective view of plate stacker 304 and plate shuttle 306 when spatula 336 has placed plate 390A in nest 364 of plate shuttle 306. Plate rack 302 includes frame 310, plurality of nests 312 (including nest 312A), and rails 314. Each nest 312 includes frame 320, corner supports 322, opening 324, and slot 326 (as shown in FIG. 6B). Plate stacker 304 includes column 330, screw rail 332, arm 334, spatula 336, actuator 338, actuator 340, camera 342, cable carrier 344, and sensor 346. Spatula 336 includes support member 350 and notches 352. Plate shuttle 306 includes support 360, rail 362, nest 364, bracket 366, driving mechanism 368, home sensor 374, and plate sensor 378. Nest 364 includes frame 380. Also shown are plates 390 (including plate 390A).

As seen in FIG. 9A, plate stacker 304 is in a home position when arm 334 with spatula 336 is positioned over a top end of plate rack 302. To move arm 334 out of the home position, actuator 338 will rotate arm 334 and column 330 so that arm 334 is no longer positioned over plate rack 302. Actuator 340 can then move arm 334 up and down along screw rail 332.

As seen in FIG. 9B, arm 334 has been rotated and vertically moved away from the home position. This prepares plate stacker 304 to pick a plate out of plate rack 302. To pick a plate out of plate rack 302, actuator 340 moves arm 334 vertically so that arm 334 is aligned just below a bottom surface of nest 312 containing the plate that is to be picked. Actuator 338 then rotates arm 334 until spatula 336 is positioned underneath the plate that is to be picked. Spaces are left between each nest 312 in plate rack 302 to allow spatula 336 to move between nests 312.

As seen in FIG. 9C, spatula 336 is positioned underneath plate 390A in nest 312A at the bottom end of plate rack 302. After spatula 336 is rotated to this position, actuator 340 can move arm 334 upward so that spatula 336 engages and picks plate 390A positioned on nest 312A. Actuator 340 drives screw rail 332 to move arm 334 and spatula 336 upward to pick plate 390A so that plate 390A no longer touches nest 312A and so that plate 390A and spatula 336 are positioned just above a top surface of nest 312A. This allows actuator 338 to rotate arm 334 away from plate rack 302, thus moving plate 390A out of plate rack 302.

When spatula 336 engages plate 390A in nest 312A of plate rack 302, spatula 336 and arm 334 pass through opening 324 and slot 326 of nest 312A. Support member 350 engages a bottom side of plate 390 A and picks plate 390 A off of corner supports 322 of nest 312A. Notches 352 of spatula 336 are sized and shaped so that they pass next to corner supports 322. This allows spatula 336 to move through opening 324.

After plate 390 A has been picked out of plate rack 302, arm 334 and spatula 336 are rotated away from plate rack 302 and positioned above plate shuttle 306. Plate shuttle 306 then moves nest 364 into a position to receive plate 390A from plate stacker 304. Arm 334 and spatula 336 are then lowered. As arm 334 and spatula 336 are lowered, spatula 336 passes through opening 384 and slot 386 of nest 364. Notches 352 of spatula 336 pass around corner supports 382 of nest 364. As spatula 336 passes through nest 364, each corner of plate 390A on spatula 336 will come into contact with one corner support 382. This will pick plate 390A off of spatula 336 as spatula 336 passes through nest 364, as seen in FIG. 9D. Plate shuttle 306 can then move nest 364 into position for aspiration or dispensing and instrument 100 can aspirate or dispense a fluid from plate 390A on nest 364.

After aspiration, plate 390A can be picked from nest 364 with arm 334 of plate stacker 304. To pick plate 390A from nest 364, spatula 336 and arm 334 of plate stacker 304 first need to be positioned below the position where plate 390 A will be picked. Plate shuttle 306 can then move nest 364 so that nest 364 is positioned over spatula 336 and arm 334. Spatula 336 and arm 334 can then be driven upward by actuator 340. Spatula 336 and arm 334 will pass through nest 364 and engage and pick plate 390A that was positioned on nest 364. When spatula 336 engages plate 390A in nest 364 of plate shuttle 306, spatula 336 and arm 334 pass through opening 384 and slot 386 of nest 364 (shown in FIG. 8A). Support member 350 engages a bottom side of plate 390A and picks plate 390A off of corner supports 382 of nest 364. Notches 352 of spatula 336 are sized and shaped so that they pass next to corner supports 382. This allows spatula 336 to move through opening 384.

After plate 390 A has been picked out of nest 364 of plate shuttle 306, arm 334 and spatula 336 can be moved vertically until they are aligned just above a top surface one nest 312 in plate rack 302 in which plate 390A is to be placed. If nest 312 in which plate 390A is to be placed is lower than nest 364 of plate shuttle 306, plate shuttle 306 will need to move nest 364 out of the way before arm 334 and spatula 336 can be moved vertically into a position just above a top surface of one nest 312 in plate rack 302. Once arm 334 and spatula 336 are aligned just above one nest 312 in plate rack 302, actuator 338 can rotate arm 334 and spatula 336. This will position arm 334 and spatula 336 just over a top surface of nest 312 in which plate 390A is to be placed. Actuator 340 can then lower arm 334 and spatula 336. This will cause arm 334 and spatula 336 to pass through opening 324 and slot 326 of nest 312. As spatula 336 passes through nest 312, each corner of plate 390 A on spatula 336 will come into contact with one corner support 322. This will pick plate 390A off of spatula 336 as spatula 336 passes through nest 312. Spatula 336 will then be positioned just below a bottom surface of nest 312 and actuator 338 can rotate spatula 336 and arm 334 out of plate rack 302.

Plate rack 302 can hold any number of plates 390. When one plate 390 is needed, plate stacker 304 can use camera 342 to determine which plate 390 arm 334 should engage. This allows a user to place plates 390 on nests 312 of plate rack 302 in any order. This is advantageous, as it allows for great flexibility in using instrument 100. A user does not need to determine the order of testing before setting up instrument 100, as instrument 100 will be able to select and move plates 390 in any order.

Plate stacker assembly 110 is further advantageous, as arm 334 and spatula 336 provide firm contact and engagement with plates in instrument 100. Prior art systems grip plates with a robotic arm to move them in instrument 100. Picking plates 390 with spatula 336 provides better contact with plates 390, ensuring that plates 390 will move through instrument 100 without being dropped. This makes plate stacker assembly 110 more reliable than prior art systems.

Plate stacker assembly 110 is also advantageous, as it allows for rotational movement and vertical movement about a common z-axis. This movement around a common z-axis allows plate stacker assembly 110 to have a compact design. This saves space in instrument 100 while still allowing for a large range of motion for moving plates in instrument 100.

Deck Plate Assembly

FIG. 10 is an isometric view of deck plate assembly 112 within instrument 100. Deck plate assembly 112 includes deck plate station 402, deck plate station 404, and deck plate station 406. Deck plate station 402, deck plate station 404, and deck plate station 406 hold plates or racks containing reagents (reagent plates). Dispensing assembly 114 of instrument 100 dispenses the reagents into tape 104 proceeding through instrument 100. In alternate embodiments, deck plate station 402, deck plate station 404, and deck plate station 406 can be used to receive and hold plates or racks containing biological samples. In alternate embodiments, deck plate assembly 112 can include a single deck plate station, two deck plate stations, or four or more deck plate stations.

FIG. 11A is a partially transparent isometric view of deck plate station 406. FIGS. 11B-11D are perspective views of deck plate station 406. As shown in FIGS. 11A-11D, deck plate station 406 includes housing 408, deck cover 410 (shown transparent in FIG. 11A) with A1 position 412, thermoelectric modules (TEMs) 414, temperature sensor 416, spring-loaded clip 418, hold down 420 with clover leaf pattern 422, pivot 424, lock knob 426, drain port 428, fluid inlet port 430, fluid outlet port 432, hold down height adjustment screw 434, mirror 474, and camera 476. In the embodiment shown in FIGS. 11B and 11D, plate 442 with wells 444 rests on deck cover 410. In an alternative embodiment shown in FIG. 11C, rack 446 with plurality of matrix tubes 448 rests on deck cover 410. Plurality of matrix tubes 448 includes resealable caps. In alternative embodiments, any suitable plate or rack can rest on deck cover 410. Camera 476 captures an image of a barcode on plate 442 or rack 446 using mirror 474 (see FIG. 16 for more detail).

Housing 408 surrounds deck cover 410. TEMs 414 and temperature sensor 416 are located underneath deck cover 410. TEMs 414 provide thermal management of deck cover 410. For example, when plate 442 is placed on deck cover 410, deck cover 410 can cool plate 442 to a desired temperature. Plate 442 can be a plate containing reagents in wells 444, and deck cover 410 can cool plate 442 in order to prevent the reagents in wells 444 from denaturing, degrading, or otherwise reacting. Temperature sensor 416 provides feedback in order to maintain deck cover 410 at a desired temperature. Fluid inlet port 430 and fluid outlet port 432 are connected to thermal management system 240 of instrument 100 to provide a heat sink for TEMs 414 (see FIGS. 13-14 for more detail).

Plate 442 is secured and aligned in A1 position 412 on deck cover 410 with spring-loaded clip 418. Spring-loaded clip 418 is attached to deck cover 410 and can be retracted in order to place plate 442 onto deck cover 410. Spring-loaded clip 418 includes a spring that allows spring-loaded clip 418 to secure plate 442 on deck cover 410. When plate 442 is placed onto deck cover 410, spring-loaded clip 418 secures plate 442 such that the first well of wells 444 is aligned in A1 position 412. Aligning plate 442 in A1 position 412 aligns wells 444 of plate 442 such that the holes of clover leaf pattern 422 align with wells 444 of plate 442 such that dispensing assembly 114 of instrument 100 can accurately locate wells 444 and aspirate the contents of wells 444 from plate 442.

Drain 428 is located on housing 408. When plate 442 is cooled on deck cover 410, condensation may accumulate on plate 442 and on deck cover 410. Housing 408 is shaped with an angled trough such that condensation is directed away from plate 442 and deck cover 410 and exits deck plate station 406 through drain 428.

Hold down 420 is in the open position in FIGS. 11B and 11C and in the closed position in FIG. 11D. When hold down 420 is in the open position, plate 442 or rack 446 may be placed onto deck plate station 406. When hold down 420 is in the closed position, plate 442 or rack 446 is secured on deck cover 410 and the contents of wells 444 or plurality of matrix tubes 448 may be aspirated from plate 442. Plate 442 can include a seal over each well 444. Dispensing assembly 114 of instrument 100 uses tips to break the seal over each well 444 and aspirate a reagent from each well 444. Hold down 420 secures plate 442 on deck cover 410 such that plate 442 is not lifted off of deck plate station 406 when the tips are retracted after having punctured through the seal over each well 444.

Pivot 424 is connected to hold down 420 and allows a user to manually pivot hold down 420 between the open position and the closed position. Lock knob 426 is connected to pivot 424 and allows a user to manually secure hold down 420 in the open position or the closed position. In the embodiment shown, lock knob 426 is a spring-loaded retractable plunger. In order to lock or unlock hold down 420 and move hold down 420 to the open or closed position, the user pulls lock knob 426 away from pivot 424, turns lock knob 426 half a rotation, pivots hold down 420 up or down to the open or closed position, turns lock knob 426 a half rotation, and releases lock knob 426.

Hold down 420 includes clover leaf pattern 422 in order to accommodate variations in wells 444 of plate 442 and plurality of matrix tubes 448 of rack 446. Clover leaf pattern 422 includes 96 four-leaf clover-shaped holes. In the embodiment shown in FIG. 11D, plate 442 includes 96 wells. When hold down 420 is in the closed position, as shown in FIG. 11D, the center of each four-leaf clover-shaped hole of clover leaf pattern 422 is aligned with one of wells 444 such that each well 444 is accessible for dispensing. In an alternative embodiment, plate 442 may include 384 wells. In this alternative embodiment, when hold down 420 is in the closed position, each leaf of each four-leaf clover-shaped hole of clover leaf pattern 422 is aligned with one of wells 444 such that each well 444 is accessible for dispensing.

FIGS. 12A and 12B are partially transparent perspective views of deck plate station 406. Deck plate station 406 includes housing 408, deck cover 410, spring-loaded clip 418, hold down 420 with clover leaf pattern 422, pivot 424, lock knob 426, fluid outlet port 432, hold down height adjustment screw 434, rail clamp nut 436, guides 460, and rail 464 (shown partially transparent in FIGS. 12A and 12B).

Hold down height adjustment screw 434 is connected to rail clamp nut 436. Rail clamp nut 436 is installed into a groove of rail 464 so that rail clamp nut can slide freely. Rail clamp nut 436 and hold down height adjustment screw 434 cooperate to clamp rail 464 against one of guides 460 to keep hold down 420 at a desired height. Hold down height adjustment screw 434 allows the user to manually adjust the height of hold down 420 up and down in order to accommodate different heights of plate 442 or rack 446 and to vary how tightly hold down 420 is secured to plate 442 or rack 446.

When a user loosens hold down height adjustment screw 434 (using, for example, a hex key), rail clamp nut 436 releases rail 464 such that the user can manually adjust the height of hold down 420 up or down. Rail 464 slides up and down within guides 460. Once the desired height is selected based on the height of plate 442 or rack 446, the user tightens hold down adjustment screw 434 to secure the position of hold down 420. As hold down adjustment screw 434 is tightened, rail clamp nut 436 pulls rail 464 over to one of guides 460 to secure hold down 420 at the desired height. Hold down 420 is held in place on plate 442 or rack 446 with friction and gravity.

FIG. 13 is a partially transparent isometric view from underneath deck plate station 406. Deck plate station 406 includes housing 408, deck cover 410, hold down 420 with clover leaf pattern 422, lock knob 426, fluid inlet port 430, fluid outlet port 432, guides 460, and jacket 466 with fluid path 468.

Jacket 466 with fluid path 468 is located underneath deck cover 410 (shown in FIGS. 11A-11D). TEMs 414 are located between jacket 466 and deck cover 410. Housing 408 surrounds jacket 466. Fluid path 468 is connected to thermal management system 240 of instrument 100 through fluid inlet port 430 and fluid outlet port 432.

FIG. 14 is a bottom view of deck plate station 406. Deck plate station includes housing 408, TEMs 414 (shown in phantom), fluid inlet port 430, fluid outlet port 432, and jacket 466 with fluid path 468. As shown in FIGS. 13 and 14, fluid flows through fluid path 468 in order to provide thermal management, such as cooling, and can create a heat sink for the heat generated by TEMs 414.

Fluid path 468 is a cavity that snakes back forth within jacket 466. Fluid, such as cooling water, enters fluid path 468 through fluid inlet port 430, passes through fluid path 468, and exits fluid path 468 through fluid outlet port 432. Jacket 466 with fluid path 468 provides a heat sink that removes heat generated by TEMs 414 when TEMs 414 are operating to cool deck cover 410. Housing 408 is made of a phenolic material to provide insulation such that the heat from TEMs 414 does not reach deck cover 410. In alternate embodiments, housing 408 can be made of any other insulating material.

FIG. 15 is a partially transparent side view of deck plate station 406. Deck plate station 406 includes housing 408, drain port 428, hold down 420, pivot 424, and limit switch 470. Limit switch 470 detects the position of hold down 420, including whether hold down 420 is in the open position or in the closed position (FIGS. 11B and 11D). Limit switch 470 provides a signal to instrument 100 to prevent other assemblies such as dispensing assembly 114 from running into deck plate station 406.

FIG. 16 is a side view of deck plate station 406 of deck plate assembly 112 within instrument 100. Deck plate station 406 is representative of deck plate station 402 and deck plate station 404. Deck plate station 406 includes housing 408, hold down 420, plate 442 with barcode 472, mirror 474, and camera 476. Also shown in FIG. 16 is camera path P.

Barcode 472 is located on plate 442. Barcode 472 identifies the contents of plate 442. Plate 442 is positioned in deck plate assembly 406 such that barcode 472 is reflected in mirror 474. Camera path shows the path from barcode 472 to camera 476. Camera 476 is positioned such that camera 476 captures the image of barcode 472 reflected in mirror 474. Camera 476 captures the image of barcode 472, which allows instrument 100 to identify the contents of plate 442.

Tape Path Assembly

FIG. 17A is an isometric view of tape path assembly 118 in instrument 100. FIG. 17B is a front isometric view of tape path assembly 118. Tape path assembly 118 includes first position 130, second position 132, third position 134, fourth position 136, tape infeed 510, tape spool 512, drive mechanism 514, tape cutter 516, lift mechanism 518, retractable hold down 520, and covers 522. Covers 522 include tape receiving ends 524. Tape path assembly 118 also includes entrance ENT at a first end and exit EXT at a second end. Also shown in FIG. 17B is tape 104.

Tape path assembly 118 extends through instrument 100 and provides a path along which tape 104 having a plurality of wells can advance. Tape 104 moves through instrument 100 from entrance ENT to exit EXT of tape path assembly 118 through the different positions on tape path assembly 118. First position 130 is positioned between entrance ENT and second position 132; second position 132 is positioned between first position 130 and third position 134; third position 134 is positioned between second position 132 and fourth position 136; and fourth position 136 is positioned between third position 134 and exit EXT. Different functions are completed at each position along tape path assembly 118.

Tape infeed 510 is positioned adjacent entrance ENT and can be extended to a loading position (not shown in FIGS. 17A-17B) for loading tape spool 512. Tape infeed 510 can then be retracted to retracted position R, where tape infeed 510 and tape spool 512 can be enclosed within instrument 100. At retracted position R, tape 104 can be driven toward entrance ENT and advanced along tape path 118 toward exit EXT. In this manner, tape infeed 510 allows for manual loading of tape spool 512, while tape 104 can be automatically advanced within instrument 100, reducing the likelihood of contamination of the wells. Tape infeed 510 also allows for the continuous infeed of a desired length of tape 104 for processing and analysis. Specifically, tape 104 is guided between entrance ENT and exit EXT, tape 104 can be cut to a desired length, processed, and analyzed along a single, compact pathway.

After tape 104 has been fed into tape path assembly 118 with tape infeed 510, tape 104 can advance to first position 130. Tape 104 automatically advances along tape path assembly 118 using drive mechanism 514. Drive mechanism 514 is positioned under a top surface of tape path assembly 118 and includes a belt that can be used to drive tape 104 along tape path assembly 118. At first position 130, tape 104 can be cut with tape cutter 516 so any number of arrays of wells can advance through instrument 100, including a tape segment with a single array of wells.

Alternatively, tape 104 can advance as a web through first position 130 without being cut. At second position 132, dispensing assembly 114 (not shown in FIGS. 17A-17B) can dispense a biological sample and a reagent into tape 104 to form a biological sample and reagent mixture. Further, tape sealing assembly 120 (not shown in FIGS. 17A-17B) can be positioned adjacent to second position 132 to seal the biological sample and reagent mixture in tape 104. Positioned below second position 132 and fourth position 136 is lift mechanism 518. Lift mechanism 518 raises second position 132 and fourth position 136 when tape 104 is held in a stationary position on tape path assembly 118, but can lower second position 132 and fourth position 136 when tape 104 is being advanced along tape path assembly 118. Positioned adjacent to second position 132 and over third position 134 is retractable hold down 520. Retractable hold down 520 can extend toward second position 132 to hold tape 104 flat while in second position 132 during dispensing.

Tape 104 can also be cooled at second position 132 to prevent the biological sample and reagent mixture from undergoing a chemical reaction, or tape 104 can be heated at second position 132 to incubate the biological sample and reagent mixture. At third position 134, tape 104 can again be cooled to prevent the biological sample and reagent mixture from undergoing a chemical reaction or heated to incubate the biological sample and reagent mixture. At third position 134, tape 104 can be held in place while tape 104 downstream from third position 134 is processed at fourth position 136. At fourth position 136, the biological sample and reagent mixture in tape 104 can be amplified and analyzed using detection assembly 122 (not shown in FIGS. 17A-17B) that is positioned adjacent to fourth position 136. The biological sample and reagent mixture can undergo thermal cycling or be heated at a constant temperature at fourth position 136 with detection assembly 122. Detection assembly 122 further includes a camera (not shown in FIGS. 17A-17B) that can be used to analyze the biological sample and reagent mixture in tape 104. In this manner, tape path assembly 118 has a compact design, making the instrument suitable for use in a variety of different settings.

Covers 522 are located above first position 130, above third position 134, and between fourth position 136 and exit EXT. Covers 522 can span the width of tape 104 and include tape-receiving ends 524 at a first end of each cover 522. Covers 522 can be v-shaped at tape-receiving ends 524. In the embodiment shown in FIGS. 17A-17B, covers 522 are made from stainless steel. In alternate embodiments, covers 522 can be made from any suitable material. Covers 522 can prevent tape 104 from bending upward off of tape path assembly 118.

FIG. 18A is a front isometric view of tape path assembly 118 with tape infeed 510 in a retracted position R. FIG. 18B is a front isometric view of tape path assembly 118 seen in FIG. 18A with tape infeed 510 in an extended position E. Tape path assembly 118 includes first position 130, second position 132, third position 134, fourth position 136, tape infeed 510, and tape spool 512. Tape path assembly 118 also includes entrance ENT at a first end and exit EXT at a second end. Also shown in FIGS. 18A-18B is tape 104.

Tape infeed 510 is adjacent to entrance ENT. When tape infeed 510 is at retracted position R (as shown in FIG. 18A), tape 104 is advanced from tape spool 512 through tape infeed 510 toward first position 130 by a plurality of rollers (not shown in detail in FIGS. 18A-18B). When tape infeed 510 is at extended position E (as shown in FIG. 18B), tape spool 512 holding tape 104 can be loaded into tape infeed 510. In this manner, tape 104 can be manually loaded into instrument 100 but automatically advanced along tape path assembly 118 by tape infeed 510.

FIG. 19A is a back perspective view of tape path assembly 118 with drive mechanism 514. FIG. 19B is a back isometric view of drive mechanism 514. FIG. 19C is a perspective view of one of rollers 550 of tape path assembly 118. Tape path assembly 118 includes first position 130, second position 132, third position 134, fourth position 136, drive mechanism 514, and covers 522. Drive mechanism 514 includes shaft 532, idler pulleys 536, drive belts 538, actuator 540, actuator drive pulleys 542, idler guide pulleys 544, rollers 550, and springs 552. Tape path assembly 118 also includes entrance ENT at a first end and exit EXT at a second end. Also shown in FIG. 19A is tape 104.

Tape 104 advances along tape path assembly 118 through instrument 100 via drive mechanism 514. Drive mechanism 514 includes idler pulleys 536 positioned near entrance ENT of tape path assembly 118. Idler pulleys 536 are mounted on each side of tape path assembly 118. Drive mechanism 514 also includes actuator drive pulleys 542 and idler guide pulleys 544 positioned near exit EXT of tape path assembly 118. Actuator drive pulleys 542 and idler guide pulleys 544 are mounted on each side of tape path assembly 118. Actuator drive pulleys 542 are connected to one another with shaft 532. Drive belts 538 extend between and wrap around actuator drive pulleys 542 and idler pulleys 536. Idler guide pulleys 544 keep drive belts 538 aligned with actuator drive pulleys 542 and idler pulleys 536. In the embodiment shown, there are two idler pulleys 536, two actuator drive pulleys 542, four idler guide pulleys 544, and two drive belts 538. One idler pulley 536, one actuator drive pulley 542, two idler guide pulleys 544, and one drive belt 538 are positioned on each of a front side and a back side of tape path assembly 118 and are positioned in parallel at approximately a width of tape 104. On each side, actuator drive pulley 542 is aligned with idler pulley 536 so that drive belt 538 can wrap around each of actuator drive pulley 542 and idler pulley 536.

Drive belts 538 are driven by actuator 540. Actuator 540 is attached to shaft 532. Shaft 532 extends between actuator drive pulleys 542. In the embodiment shown in FIGS. 19A-19C, actuator 540 is a motor. In alternate embodiments, actuator 540 can actuate drive belts 538 with any suitable mechanism such as, for example, an electric motor, a pneumatic motor, or a hydraulic motor. Actuator 540 rotates shaft 532 and actuator drive pulleys 542, which transfer movement to drive belts 538. Drive belts 538 move around idler pulleys 536, drive pulleys 542, and idler guide pulleys 544. Idler guide pulleys 544 keep drive belts 538 aligned with actuator drive pulleys 542 and idler pulleys 536.

Rollers 550 are located along both sides of tape path assembly 118 between entrance ENT and exit EXT. Rollers 550 are located directly above drive belts 538. As seen in FIG. 19C, rollers 550 are spring-loaded with springs 552. Springs 552 hold rollers 550 in compression against drive belts 538. Tape 104 is positioned between rollers 550 and drive belts 538. As drive belts 538 are driven, tape 104 will move with drive belts 538 along tape path assembly 118 due to friction between tape 104 and drive belts 538. Rollers 550 hold tape 104 securely against drive belts 538 as tape 104 is advanced along tape path assembly 118. Further, covers 522 hold tape 104 flat across tape path assembly 118 and maintain contact with drive belts 538. Tape 104 is thus driven through instrument 100 along tape path assembly 118 via friction.

FIG. 20A is a front plan view of tape infeed 510 on tape path assembly 118, FIG. 20B is a front isometric view of tape infeed 510 on tape path assembly 118. Tape infeed 510 includes driven rollers 560, first tension rollers 562, actuator 564, pulley 566, drive belt 568, transfer rollers 570, extendable portion 572, extendable portion rollers 574, and second tension rollers 576. Tape path assembly 118 also includes entrance ENT. Also shown in FIG. 20B is tape 104.

Tape infeed 510 is attached to tape path assembly 118 adjacent to entrance ENT. Driven rollers 560, first tension rollers 562, transfer rollers 570, extendable portion rollers 574, and second tension rollers 576 all comprise a pair of rollers that are parallel to each other at approximately the width of tape 104. Driven rollers 560 comprise tacky rollers connected to tape path assembly 118 upstream of first position 130. First tension rollers 562 are positioned on top of driven rollers 560 and can be weighted, tensioned with springs, or otherwise compressed against driven rollers 560.

Driven rollers 560 are driven by actuator 564. In this embodiment, actuator 564 is a motor. In alternate embodiments, actuator 564 can drive driven rollers 560 with any suitable mechanism such as, for example, an electric motor, a pneumatic motor, or a hydraulic motor.

Actuator 564 is connected to driven rollers 560 via pulley 566 and drive belt 568. Transfer rollers 570 are positioned upstream of driven rollers 560 so as to be in contact with driven rollers 560. In this embodiment, transfer rollers 570 are held in tension against driven rollers 560 by springs. In alternate embodiments, transfer rollers 570 can be held in tension against driven rollers 560 with any suitable mechanism. Extendable portion 572 is positioned upstream of transfer rollers 570. Extendable portion 572 comprises extendable portion rollers 574 and second tension rollers 576. The rollers of second tension rollers 576 are positioned on top of extendable portion rollers 574 and can be weighted, tensioned with springs, or otherwise compressed against extendable portion rollers 574. Extendable portion rollers 574 are positioned such that when extendable portion 572 is in a retracted position (as shown in FIG. 20A), extendable portion rollers 574 contact transfer rollers 570. When extendable portion 572 is in an extended position, extendable portion rollers 574 do not contact transfer rollers 570.

When extendable portion 572 is in an extended position, tape spool 512 holding tape 104 can be manually loaded into extendable portion 572. Tape 104 can then be manually advanced and fed between extendable portion rollers 574 and second tension rollers 576, which are configured to capture and hold the leading edge of tape 104. When extendable portion 572 is in a retracted position, actuator 564 can rotate driven rollers 560 via pulley 566 and drive belt 568. Motion from driven rollers 560 is transferred to extendable portion rollers 574 via transfer rollers 570. The motion from driven rollers 560 transferred to extendable portion rollers 574 advances tape 104 until tape 104 is captured between driven rollers 560 and first tension rollers 562, which further advances tape 104 along tape path assembly 118. In this manner, tape spool 512 holding tape 104 can be manually loaded outside of the instrument, while tape 104 can be automatically advanced within the instrument, simplifying loading of tape spool 512 with tape 104.

FIG. 21A is a back perspective view of tape cutter 516 on tape path assembly 118. FIG. 21B is a plan view of a front side of tape cutter 516 having movable blade 580 in a retracted position. FIG. 21C is a plan view of a front side of tape cutter 516 having movable blade 580 in an extended position. FIG. 21D is a plan view at entrance ENT of tape path assembly 118 with tape cutter 516 having movable blade 580 in a retracted position. FIG. 21E is a partially transparent plan view at entrance ENT of tape path assembly 118 with tape cutter 516 having movable blade 580 in an extended position. Tape path assembly 118 includes first position 130, driven rollers 560, first tension rollers 562, and tape cutter 516. Tape cutter 516 includes sensor 578, movable blade 580, actuator 582, tape clamp 584 with tacky end 586, fixed blade 588, safety guard 590, fixed blade mount 592, movable blade mount 594, and ball spring detents 596. Tape path assembly 118 also includes entrance ENT. Also shown in FIGS. 21A-21E is tape 104.

Tape cutter 516 is located immediately before first position 130 and adjacent to entrance ENT. Tape 104 can be cut with tape cutter 516 or tape 104 can pass through tape cutter 516 without being cut. Tape 104 is advanced along tape path assembly 118, between first tension rollers 562 and driven rollers 560. Sensor 578 senses when tape spool 512 (shown in FIGS. 18A-18B) is out of tape 104. As tape 104 passes between movable blade 580 and fixed blade 588, a sensor (not shown) located downstream of tape cutter 516 can monitor the position of tape 104 to indicate to actuator 582 when a desired length of tape 104 has passed between movable blade 580 and fixed blade 588. Actuator 582 can then drive movable blade 580 upward to cut tape 104. In the embodiment shown in FIGS. 21A-21E, actuator 582 is a linear actuator. In alternate embodiments, actuator 582 can drive movable blade 580 with any suitable mechanism. Movable blade mount 594 can pivot slightly against a single point. Ball spring detents 596 are positioned against a bottom end of movable blade 580 and give movable blade 580 a slight angle with respect to fixed blade 588. This slight angle of movable blade 580 improves cutting with movable blade 580.

Tape clamp 584 is spring-loaded and moves upward with movable blade 580. Tape clamp 584 is configured to contact tape 104 before movable blade 580. Tacky end 586 of tape clamp 584 positively holds tape 104 against a bottom surface of fixed blade mount 592 while tape 104 is being cut between movable blade 580 and fixed blade 588. As movable blade 580 is driven upward, spring-loaded safety guard 590 is retracted to allow movable blade 580 to cross fixed blade 588 and cut tape 104. After tape 104 has been cut, movable blade 580 retracts with tape clamp 584, and safety guard 590 extends to contact a side surface of fixed blade mount 592. In this manner, tape cutter 516 can cleanly cut tape 104 to a desired length.

FIG. 22A is a partially transparent front perspective view of lift mechanism 518. FIG. 22B is a plan view of lift mechanism 518. Lift mechanism 518 includes platform 600, shaft 604, first linkage 606, second linkage 608, actuator 610, drive pulley 612, timing pulley 614, and drive belt 616. Lift mechanism 518 is positioned under a top surface of tape path assembly 118. Platform 600 is raised and lowered with shaft 604. Shaft 604 connects to platform 600 with first linkage 606 and second linkage 608.

Lift mechanism 518 is driven with actuator 610. Actuator 610 can be a motor, such as, for example, an electric motor, a pneumatic motor, or a hydraulic motor. Actuator 610 is connected to and can rotate drive pulley 612. Timing pulley 614 is positioned on shaft 604. Drive belt 616 extends between and wraps around drive pulley 612 and timing pulley 614. As actuator 610 rotates drive pulley 612, drive belt 616 will move with drive pulley 612 and rotate timing pulley 614. As timing pulley 614 is rotated, timing pulley 614 rotates shaft 604, moving first linkage 606 and second linkage 608 which then move platform 600. In this manner, actuator 610 can move platform 600 up and down. Platform 600 can be actuated up and down to move parts of tape path assembly 118 up and down.

FIG. 23A is a front plan view of lift mechanism 518 on tape path assembly 118 in a retracted position. FIG. 23B is a front plan view of lift mechanism 518 on tape path assembly 118 in an extended position. Tape path assembly 118 includes second position 132, third position 134, fourth position 136, and lift mechanism 518. Lift mechanism 518 includes platform 600, shaft 604, first linkage 606 (shown in FIGS. 22A-22B), second linkage 608 (shown in FIGS. 22A-22B), actuator 610, drive pulley 612, timing pulley 614, and drive belt 616. Also shown in FIGS. 23A-23B is tape level T.

Lift mechanism 518 is located underneath tape level T of tape path assembly 118. Platform 600 is positioned underneath second position 132, third position 134, and fourth position 136. Platform 600 is attached to third position 134.

When tape 104 (not shown in FIGS. 23A-23B) is advanced to second position 132 or fourth position 136, lift mechanism 518 can be driven upward to raise second position 132 and fourth position 136 to tape level T. Platform 600 is raised and lowered with shaft 604 extending between first linkage 606 and second linkage 608. In alternate embodiments, platform 600 could be split to allow portions beneath second position 132 and fourth position 136 to be raised and lowered separately.

Lift mechanism 518 is driven by actuator 610. Actuator 610 rotates drive pulley 612, which in turn rotates timing pulley 614 on shaft 604 with belt 616. In this manner, platform 600 can be driven upward (as seen in FIG. 23B) so that second position 132 and fourth position 136 are at tape level T. This supports tape 104 as tape 104 is processed at second position 132 and fourth position 136.

FIG. 24 is a front perspective view of thermal units 620 and 622 on tape path assembly 118. Tape path assembly 118 includes second position 132, third position 134, thermal unit 620, and thermal unit 622. Thermal unit 620 includes thermoelectric modules (TEMs) 624. Thermal unit 622 includes TEMs 626.

Thermal units 620 and 622 are positioned in tape path assembly 118. Thermal unit 620 is positioned at second position 132 and thermal unit 622 is positioned at third position 134. In the embodiment shown in FIG. 24, thermal unit 620 includes two TEMs 624 and thermal unit 622 includes two TEMs 626. In alternate embodiments, thermal units 620 and 622 can include any number of TEMs 624 or 626, or any other mechanism capable of heating or cooling second position 132 and third position 134. When heating or cooling is needed, electricity flows through TEMs 624 and 626 in one direction for heating and in the other direction for cooling. This allows thermal units 620 and 622 to either cool or heat the biological sample and reagent mixture in tape 104 in second position 132 and third position 134.

FIG. 25 is a bottom view of fluid paths 630 and 640 on tape path assembly 118. Tape path assembly 118 includes second position 132, third position 134, fourth position 136, thermal unit 620, thermal unit 622, fluid path 630, inlet port 632, outlet port 634, fluid path 640, inlet port 642, and outlet port 644.

Fluid paths 630 and 640 are positioned in tape path assembly 118. Fluid path 630 is positioned at second position 132 and fluid path 640 is positioned at third position 134. Fluid path 630 is connected to inlet port 632 at a first end and to outlet port 634 at a second end. Fluid path 640 is connected to inlet port 642 at a first end and to outlet port 644 at a second end. Fluid paths 630 and 640 are cavities that curve back and forth under second position 132 and third position 134. Fluid from a reservoir (not shown in FIG. 26) can be delivered into fluid paths 630 and 640 through inlet ports 632 and 642, respectively. This fluid can then flow through fluid paths 630 and 640 to exchange heat with components positioned above fluid paths 630 and 640 at second position 132 and third position 134, respectively. The fluid in fluid paths 630 and 640 can then flow out through outlet ports 634 and 644, respectively. Routing the fluid underneath second position 132 and third position 134 in this manner allows the space on the top surface of second position 132 and third position 134 to hold components that require regulated temperatures.

FIG. 26A is a partially transparent side view of retractable hold down 520. FIG. 26B is a back perspective view of retractable hold down 520 on tape path assembly 118 with retractable hold down 520 in a retracted position. FIG. 26C is a back perspective view of retractable hold down 520 on tape path assembly 118 with retractable hold down 520 in an extended position. Tape path assembly 118 includes second position 132, third position 134, fourth position 136, and retractable hold down 520. Retractable hold down 520 includes roller 650, arm 652, track roller 654, track 656, air cylinder 658, inlet port 660, inlet port 662, and bars 664.

Retractable hold down 520 is positioned over third position 134 and can be moved between an extended and a retracted position. Retractable hold down 520 includes roller 650 attached to a first end of arm 652. When retractable hold down 520 is in an extended position, arm 652 can be extended out and down so that roller 650 can hold down tape 104 in second position 132. A second end of arm 652 is attached to track roller 654. Track roller 654 is positioned in and rolls along track 656 to move arm 652 and roller 650 between an extended and a retracted position.

Retractable hold down 520 further includes air cylinder 658. Inlet port 660 and inlet port 662 are attached to air cylinder 658. Air can flow through inlet port 660 and inlet port 662 into air cylinder 658. A first end of bars 664 are positioned in air cylinder 658. Bars 664 slide in and out of air cylinder 658, moving air cylinder 658 between a retracted and extended position. A second end of bars 664 is attached to arm 652.

To move retractable hold down 520 from a retracted to an extended position, air can flow through inlet port 660 into air cylinder 658. As air from inlet port 660 flows into air cylinder 658 it causes bars 664 to extend out of air cylinder 658. This causes track roller 654 to slide along track 656 so that arm 652 can move to an extended position. Track 656 has a first end that is positioned at an elevation that is lower than the elevation of a second end of track 656. As track roller 654 moves from the first end to the second end of track 656, the second end of arm 652 will be driven upward. This in turn causes the first end of arm 652 to be driven down. This motion can force roller 650 on the first end of arm 652 down against tape 104 and/or second position 132 of tape path assembly 118.

To move retractable hold down 520 from an extended position to a retracted position, air can flow through inlet port 662 into air cylinder 658. As air from inlet port 662 flows into air cylinder 658 it causes bars 664 to retract back into air cylinder 658. This causes track roller 654 to slide along track 656 so that arm 652 can move to a retracted position. This motion will cause roller 650 on the first end of arm 652 to move up from tape 104 and/or second position 132 of tape path assembly 118.

When a leading edge, positioning hole, or other identifying mark of tape 104 (not shown) is detected by a sensor positioned along tape path assembly 118, retractable hold down 520 can extend roller 650 to hold down the leading edge or a middle portion of tape 104. Tape 104 can be processed when roller 650 of retractable hold down 520 is extended. After tape 104 is processed, retractable hold down 520 can retract and allow tape 104 to be further processed or advanced to third position 134. For example, roller 650 can be extended to hold down tape 104 at second position 132 while tape 104 is being dispensed into. After tape 104 has been dispensed into, roller 650 can be retracted and a sealing operation can be performed. In this manner, multiple operations, such as dispensing and sealing, can be performed on the same portion of tape 104 at the same location reducing the overall size of instrument 100.

FIG. 27 is a perspective view of rewind assembly 108. Rewind assembly 108 can be attached to cart assembly 101 and aligned with tape path assembly 118 to accumulate processed tape leaving tape path assembly 118 (see FIGS.

1B-1C). Rewind assembly 108 includes mounting bracket 670, motor 672, shaft 674, spool 676, retainer clips 678, and spool retainer 680. Mounting bracket 670 attaches rewind assembly 108 to cart assembly 101 (see FIGS. 1B-1C). Motor 672 is attached to shaft 674. Shaft 674 mechanically engages spool 676. Spool 676 is secured on shaft 674 with spool retainer 680. Rotation of motor 672 is synchronized with movement of tape 104 through tape path assembly 118. Once tape 104 begins to exit tape path assembly 118, tape 104 is attached to spool 676 using tape or another attaching means. Rotation of motor 672 causes spool 676 to rotate and accumulate tape 104 on spool 676. After processing of all arrays of tape 104 is complete, tape 104 is secured to spool 676 with retainer clips 678. Spool 676 can be removed from rewind assembly 108 by removing spool retainer 680 and sliding spool 676 off of shaft 674.

Dispensing Assembly

FIG. 28 is an isometric view of instrument 100 with dispensing assembly 114. Dispensing assembly 114 includes gantry x-axis track 702, gantry y-axis track 704, dispensing enclosure 706, and dispensing head 708. Gantry x-axis track 702 includes actuator 710, drive belt 712, and cable carrier 714. Gantry y-axis track 704 includes actuator 716, drive belt 718, and cable carrier 720. Actuator 710 is connected to drive belt 712, and actuator 716 is connected to drive belt 718.

Gantry x-axis track 702 and gantry y-axis track 704 allow dispensing enclosure 706 and dispensing head 708 to move in the x and y directions within instrument 100. Gantry y-axis track 704 is connected to cable carrier 714. Dispensing enclosure 706 sits on top of gantry y-axis track 704 and is connected to dispensing head 708 and cable carrier 720. Cable carrier 714 and cable carrier 720 guide wiring and tubing going to dispensing enclosure 706 and dispensing head 708. Dispensing head 708 sits underneath gantry y-axis track 704. Dispensing enclosure 706 and dispensing head 708 can move simultaneously along gantry y-axis track 704.

In order to move gantry y-axis track 704 with dispensing enclosure 706 and dispensing head 708 in the x direction along gantry x-axis track 702, actuator 710 drives drive belt 712. Drive belt 712 moves gantry y-axis track 704 along gantry x-axis track 702. Cable carrier 714 includes a stationary end that does not move and an end attached to gantry y-axis track 704 that moves along with gantry y-axis track 704. Cable carrier 714 holds all cabling and tubing required for dispensing assembly 114 properly aligned when gantry y-axis track 704 moves along gantry x-axis track 702. In the embodiment shown, actuator 710 is a servo motor, and the shaft rotation position of the servo motor is controlled by the control systems of instrument 100, including an industrial PC and associated interface cards in electronic assembly 124.

In order to move dispensing enclosure 706 and dispensing head 708 in the y direction along gantry y-axis track 704, actuator 716 drives drive belt 718. Drive belt 718 moves dispensing enclosure 706 and dispensing head 708 along gantry y-axis track 704. Cable carrier 720 includes a stationary end that does not move and an end attached to dispensing enclosure 706 that moves along with dispensing enclosure 706. Cable carrier 720 keeps all cables and tubes required for dispensing assembly 114 properly aligned when dispensing enclosure 706 and dispensing head 708 move in they direction along gantry y-axis track 704. In the embodiment shown, actuator 710 is a servo motor, and the shaft rotation position of the servo motor is controlled by the control systems of instrument 100, including an industrial PC and associated interface cards in electronic assembly 124.

Dispensing assembly 114 aspirates a sample or a reagent from a sample plate or a reagent plate and dispenses the sample or reagent into the wells of tape 104 positioned at second position 132 of tape path assembly 118. Dispensing assembly 114 moves dispensing enclosure 706 and dispensing head 708 in the x direction and in the y direction along gantry x-axis track 702 and gantry y-axis track 704 in order to position dispensing enclosure 706 and dispensing head 708 above a sample plate or reagent plate. Dispensing assembly 114 then extends dispensing head 708 in the z direction in order to aspirate a sample or reagent from the sample plate or reagent plate. Dispensing assembly 114 subsequently retracts dispensing head 708 in the z direction and again moves dispensing enclosure 706 and dispensing head 708 in the x direction and in the y direction in order to position dispensing enclosure 706 and dispensing head 708 above tape 104. Dispensing assembly 114 then extends dispensing head 708 in the z direction in order to dispense the sample or reagent into the wells of tape 104. While aspirating or dispensing, if necessary, dispensing assembly 114 can move dispensing head 708 in the x direction, y direction, and z direction to reposition dispensing head 708.

FIG. 29 is a schematic view of dispensing assembly 114 seen in FIG. 28. Dispensing assembly 114 includes gantry x-axis track 702, gantry y-axis track 704, dispensing enclosure 706, and dispensing head 708. Gantry x-axis track 702 includes actuator 710, drive belt 712, and cable carrier 714. Gantry y-axis track 704 includes actuator 716, drive belt 718, and cable carrier 720. Dispensing enclosure 706 includes pressure reservoir 722, metering pump 724, manifold 726, system fluid supply and waste 728, and electronics 730. Dispensing head 708 includes contact dispensing unit 732 and non-contact dispensing unit 734.

Dispensing assembly 114 combines multiple dispensing technologies into a single head by providing both contact and non-contact dispensing with dispensing head 708. Gantry x-axis track 702 and gantry y-axis track 704 provide shared x- and y-axes for dispensing head 708, which reduces cost and conserves space within instrument 100.

FIG. 30 is a perspective view of gantry y-axis track 704, dispensing enclosure 706, and dispensing head 708 of dispensing assembly 114 seen in FIG. 28. Gantry y-axis track 704 includes actuator 716, drive belt 718, and cable carrier 720. Dispensing enclosure 706 includes manifold 726 with channels 736. Dispensing head 708 includes contact dispensing unit 732 with pipette tips 738 and non-contact dispensing unit 734 with jet tips 740 and valves 742. Tubes 744 connect non-contact dispensing unit 734 to dispensing enclosure 706. Tubes 744 are attached to jet tips 740 and to channels 736 of manifold 726.

As shown in FIGS. 28-30, contact dispensing unit 732 dispenses a liquid into tape 104 (not shown). In an alternative embodiment, contact dispensing unit 732 can dispense a liquid into a plate with a plurality of wells, such as a microtiter plate. In an alternative embodiment, contact dispensing unit 732 may dispense onto a flat surface. Contact dispensing unit 732 can be a parallel channel pipettor. Contact dispensing unit 732 aspirates and dispenses liquid with pipette tips 738. The liquid can be a biological sample. In an alternative embodiment, the liquid can be a reagent. Contact dispensing unit 732 may include a single pipette tip 738. In alternative embodiments, contact dispensing unit 732 may include any number of pipette tips 738 including 96 pipette tips 738 or 384 pipette tips 738. Contact dispensing unit 732 dispenses a liquid while the liquid is still in tips 738. Tips 738 come into contact with the wells into which the liquid is dispensed.

Non-contact dispensing unit 734 dispenses a liquid into tape 104. In an alternative embodiment, non-contact dispensing unit 734 can dispense a liquid into a plate with a plurality of wells, such as a microtiter plate. In an alternative embodiment, non-contact dispensing unit 734 may dispense onto a flat surface. Non-contact dispensing unit 734 can be an independent channel non-contact jet dispenser. Non-contact dispensing unit 734 aspirates and dispenses liquid with jet tips 740. The liquid can be a reagent. In an alternative embodiment, the liquid can be a biological sample. Non-contact dispensing unit 734 may include a single jet tip 740. In alternative embodiments, non-contact dispensing unit 734 may include any number of jet tips 740, including two, four, eight, or sixteen jet tips 740. When non-contact dispensing unit 734 dispenses a liquid, the liquid separates from jet tips 740 and only the liquid comes into contact with the wells into which the liquid is dispensed.

In order to separate a liquid from jet tips 740, metering pump 724 of dispensing enclosure 706 pressurizes pressure reservoir 722, tubes 744 and jet tips 740 to a desired pressure based on dispense fluid viscosity and a desired dispensing volume. Pressure reservoir 722 is used to store pressure created by metering pump 724. Pressure reservoir 722 provides a constant pressure for dispensing. In order to dispense the liquid, electronics 730 actuates valves 742 to open valves 742, and the pressure in tubes 744 allows the liquid to shoot out from jet tips 740. In the embodiment shown, valves 742 are solenoid valves. Valves 742 may be opened one at a time in order to dispense liquid from jet tips 740 one at a time. In an alternative embodiment, valves 742 may be opened simultaneously in order to dispense liquid from jet tips 740 at the same time. As stated above in reference to FIG. 28, dispensing enclosure 706 and dispensing head 708 are connected and move simultaneously along gantry y-axis track 704. This prevents bending and stretching of tubes 744 during dispensing, thereby minimizing pressure fluctuations within tubes 744. Reducing pressure fluctuations in tubes 744 improves the dispensing accuracy of non-contact dispensing unit 734, especially at low dispensing volumes such as 800 nanoliters.

FIG. 31A is an isometric view of dispensing head 708 with contact dispensing unit 732 in an extended position and non-contact dispensing unit 734 with jet tips 740 in a retracted position. FIG. 31B is an isometric view of dispensing head 708 with contact dispensing unit 732 in a retracted position and non-contact dispensing unit 734 in an extended position. Non-contact dispensing unit 734 includes jet tips 740 and valves 742. In addition to contact dispensing unit 732 and non-contact dispensing unit 734, dispensing head 708 includes first z-axis track 746 with rails 748, spring 750, and actuator 752. Dispensing head 708 also includes second z-axis track 754 with rail 756, spring 758 (shown in FIG. 31C), and actuator 760. Actuator 752 moves contact dispensing unit 732 in the z direction along rails 748. Actuator 760 moves non-contact dispensing unit 734 in the z direction along rail 756.

FIG. 31C is a partially transparent perspective view of first z-axis track 746 and second z-axis track 754 of dispensing head 708 seen in FIGS. 31A-31B. Non-contact dispensing unit 734 with jet tips 740 is attached to second z-axis track 754. First z-axis track 746 includes rails 748, spring 750, actuator 752, attachment plate 762, fine pitch adjustment mechanism 764, pivot bolt 766, and identification mechanism 768. Second z-axis track 754 includes rail 756, spring 758, and actuator 760.

As shown in FIGS. 30, 31A, 31B, and 31C, in the embodiment shown, first z-axis track 746 is attached to gantry y-axis track 704. Contact dispensing unit 732 is attached to and moves along first z-axis track 746, and non-contact dispensing unit 734 is attached to and moves along second z-axis track 754. In the embodiment shown, second z-axis track 754 is attached to contact dispensing unit 732 such that second z-axis track 754 and non-contact dispensing unit 734 move in the z direction when contact dispensing unit 732 moves in the z direction along first z-axis track 746. In an alternative embodiment, second z-axis track 754 can be attached to gantry y-axis track 704 such that non-contact dispensing unit 734 moves in the z direction only along second z-axis track 754, independent from the z-axis motion of contact dispensing unit 732. In an another alternative embodiment, where second z-axis track 754 is attached to gantry y-axis track 704, first z-axis track 746 can be attached to non-contact dispensing unit 734 such that first z-axis track 746 and contact dispensing unit 732 move in the z direction when non-contact dispensing unit 734 moves in the z direction along second z-axis track 754. As shown in FIGS. 31A-31B, each individual valve 742 attached to a corresponding jet tip 740 can be mounted to an independent z-axis track 754' to enable each individual valve 742 and corresponding jet tip 740 to move independently in the z direction.

Contact dispensing unit 732 attaches to attachment plate 762 of first z-axis track 746. Prior to attaching contact dispensing unit 732, fine pitch adjustment mechanism 764 rotates attachment plate 762 around pivot bolt 766 in order to adjust the angle of attachment plate 762. This ensures that contact dispensing unit 732 is attached to attachment plate 762 such that pipette tips 738 are aligned and level with the matrix of wells of tape 104, sample plate, or reagent plate for aspiration and dispensing.

When contact dispensing unit 732 is in an extended position, spring 750 is compressed. In the event of a loss of power to actuator 752, spring 750 will hold the z direction position of contact dispensing unit 732 or retract contact dispensing unit 732 along first z-axis track 746. This prevents damage to pipette tips 738 and serves as a safety mechanism in the event a user is interacting with dispensing head 708 inside instrument 100. In alternative embodiments, a gas shock, alternate type of spring, or friction limit via a gear train can be used. Second z-axis track 754 include spring 758, which functions in the same manner as spring 750 in order to hold the z direction position of non-contact dispensing unit 734 or retract non-contact dispensing unit 734 in the event of a loss of power to actuator 760. This prevents damage to jet tips 740 and serves as a safety mechanism in the event an operator is interacting with dispensing head 708 inside instrument 100.

In order to aspirate and dispense, contact dispensing unit 732 moves along first z-axis track 746 to an extended position (FIG. 31A). Non-contact dispensing unit 734 remains in a retracted position along second z-axis track 754. In order to aspirate and dispense, non-contact dispensing unit 734 moves along second z-axis track 754 into an extended position (FIG. 31B) such that jet tips 740 extend past contact dispensing unit 732. Contact dispensing unit 732 can be in an extended position or a retracted position when non-contact dispensing unit 734 aspirates and dispenses. During or prior to aspiration or dispensing, identification mechanism 768 can read an identifier, such as a barcode, off of tape 104, a sample plate, or a reagent plate to identify the contents and configuration of tape 104, the sample plate, or the reagent plate. In one embodiment, identification mechanism 768 can be a camera. In an alternative embodiment, identification mechanism 768 can be a radio frequency identification reader used in combination with radio frequency identification tags on or in tape 104, a sample plate, or a reagent plate to identify the configuration and contents of tape 104, the sample plate, or the reagent plate.

FIG. 32A is a transparent isometric view of dispensing enclosure 706 of dispensing assembly 114 seen in FIGS. 28-30. FIG. 32B is a perspective view of dispensing enclosure 706. FIGS. 32A-32B are transparent to show the components enclosed in dispensing enclosure 706. Dispensing enclosure 706 includes pressure reservoir 722, metering pump 724, manifold 726 with channels 736, system fluid supply and waste 728, electronics 730, pressure reservoir valve 770, and pressure sensor 772. System fluid supply and waste 728 includes supply port 774, waste port 776, and system fluid valve 778. Supply port 774 is connected to a system fluid supply and waste port 776 is connected to a waste receptacle.

FIG. 33 is a schematic diagram of non-contact dispensing components of dispensing enclosure 706 and the dispensing head 708 seen in FIGS. 31A-31C and 32 A-32B. Dispensing enclosure 706 includes pressure reservoir 722, metering pump 724, manifold 726 with channels 736, system fluid supply and waste 728, pressure reservoir valve 770, pressure sensor 772, check valve 780, and filter 782. System fluid supply and waste 728 includes supply port 774, waste port 776, system fluid valve 778, and check valve 784. Non-contact dispensing unit 734 includes jet tips 740 and valves 742. Tubes 744 connect non-contact dispensing unit 734 to dispensing enclosure 706. Tubes 744 are attached to jet tips 740 and to channels 736 of manifold 726.

As shown in FIGS. 32A-32B and FIG. 33, dispensing enclosure 706 is connected to jet tips 740 with tubes 744. Tubes 744 are connected to manifold 726 through channels 736, and each of tubes 744 is connected to each of jet tips 740. Pressure sensor 772 measures the pressure in manifold 726, which is the same as the pressure in tubes 744. Valves 742 open and close jet tips 740. Electronics 730 provides power to and assists in the control of all components of dispensing enclosure 706 and dispensing head 708. In the embodiment shown, electronics 730 is a printed circuit board.

Metering pump 724 supplies the system fluid flow needed to wash and pressurize non-contact dispensing system 36 and dispensing enclosure 706. Metering pump 724 is connected to pressure reservoir valve 770 and system fluid valve 778. Supply port 774 is connected to a system fluid supply and waste port 776 is connected to a waste receptacle. System fluid, such as water, enters dispensing enclosure 706 through supply port 774 and system waste fluid leaves through waste port 776. System fluid valve 778 controls system fluid into and waste flow out of dispensing enclosure 706 and through metering pump 724. Pressure reservoir 722 is connected to pressure reservoir valve 770. Pressure reservoir valve 770 controls system fluid flow into and out of pressure reservoir 722. Pressure sensor 772 measures the pressure in pressure reservoir 722 in order to determine whether a desired pressure in pressure reservoir 722 has been reached. Check valve 780 allows ambient air into pressure reservoir 722 if the pressure in pressure reservoir 722 drops below atmospheric pressure. Filter 782 prevents any unwanted particles from entering pressure reservoir 722. Electronics 730 provides power to and controls all components of dispensing enclosure 706 and dispensing head 708 except for actuators. In the embodiment shown, electronics 730 is a printed circuit board.

In order to begin operation of dispensing enclosure 706 along with non-contact dispensing unit 734, non-contact dispensing unit 734 is moved into a wash position. Pressure reservoir valve 770 is closed and valves 742 and system fluid valve 778 are opened. Metering pump 724 is then run forward in order to pump system fluid through supply port 774, through check valve 784, into manifold 726, through channels 736, into tubes 744, and through jet tips 740 in order to purge any air or waste in jet tips 740. Jet tips 740 and tubes 744 are now filled with system fluid and valves 742 are closed.

Non-contact dispensing unit 734 is then moved into an aspiration position above a reagent plate. Valves 742 are opened and closed one at a time and metering pump 724 is run backwards in order to aspirate an air gap into each of jet tips 740. In this embodiment, the air gap is approximately 20,000 nanoliters. Jet tips 740 are subsequently lowered into the wells of the reagent plate, valves 742 are opened and closed one at a time, and metering pump 724 is run backwards in order to aspirate a reagent into jet tips 740. In this embodiment, jet tips 740 aspirate between 80,000 and 700,000 nanoliters of reagent into each of jet tips 740. In alternate embodiments, jet tips 740 can aspirate other amounts of reagent based on the size of tubes 744. The air gap prevents system fluid and the reagent from mixing. Once the reagent is aspirated into one or more of jet tips 740, pressure reservoir valve 770 is opened, metering pump 724 is run forward, and system fluid is pumped into pressure reservoir 722 through the bottom of pressure reservoir 722. This creates pressure by compressing the air above the system fluid in pressure reservoir 722 and pressurizing the system fluid in tubes 744, the air gap in between the system fluid and the reagent, and the reagent in tubes 744. Metering pump 724 is run until a desired pressure is reached, the pressure corresponding to the viscosity and the amount of reagent needed for dispensing. Pressure sensor 772 measures the pressure in pressure reservoir 722 and the components of manifold 726 in order to determine when the desired pressure is reached.

Non-contact dispensing unit 734 is then moved into a dispensing position above tape 104 or above a plate. Each of valves 742 is triggered by electronics 730 above a desired well. Once each of valves 742 is triggered, the pressure in tubes 744 and jet tips 740 causes the reagent to shoot out of each of jet tips 740 and into the wells of tape 104. Non-contact dispensing unit 734 is moved in the x and y directions along the matrix of wells of tape 104 and valves 742 are triggered repeatedly in order to dispense the reagent into each of the wells of tape 104. Jet tips 740 move across tape 104 in the x and y directions during dispensing. In the embodiment shown, jet tips 740 move continuously and dispense without having to stop above each well of tape 104. Non-contact dispensing unit 734 can dispense between 100 and 3,000 nanoliters of reagent. Valves 742 can be triggered one at a time in order to dispense the reagent from each of jet tips 740 one at a time. In an alternative embodiment, valves 742 can be triggered simultaneously in order to dispense reagent into multiple wells at once. Once the reagent is dispensed into the wells of tape 104, non-contact dispensing unit 734 can be moved back into a wash position and the process can be repeated.

As shown in FIGS. 28-33, dispensing head 708 can move along gantry x-axis track 702 and gantry y-axis track 704 to aspirate and dispense a reagent and/or a biological sample with contact dispensing unit 732 and non-contact dispensing unit 734 in a variety of sequences. In one embodiment, dispensing head 708 moves along gantry x-axis track 702 and gantry y-axis track 704 to a first aspiration position where contact dispensing unit 732 aspirates a first liquid into at least one of pipette tips 738. Dispensing head 708 subsequently moves to a second aspiration position where non-contact dispensing unit 734 aspirates a second liquid into at least one of jet tips 740. Dispensing head 708 then moves to a first dispensing position where contact dispensing unit 732 dispenses the first liquid with at least one of pipette tips 738. Finally dispensing head 708 moves to a second dispensing position where non-contact dispensing unit 734 dispenses the second liquid with at least one of jet tips 740. This aspirating and dispensing sequence minimizes evaporation of the first and second liquids during the sequence. In alternative embodiment that also minimizes evaporation of the first and second liquids, the sequence can be such that non-contact dispensing unit 734 aspirates, contact dispensing unit 732 aspirates, non-contact dispensing unit 734 dispenses, and contact dispensing unit 732 dispenses.

In another alternative embodiment, non-contact dispensing unit 734 aspirates, contact dispensing unit 732 aspirates, contact dispensing unit 732 dispenses, and non-contact dispensing unit 734 dispenses. This sequence minimizes the time a liquid is in pipette tips 738 of contact dispensing unit 732 before the liquid is dispensed. In another alternative embodiment, contact dispensing unit 732 aspirates, non-contact dispensing unit 734 aspirates, non-contact dispensing unit 734 dispenses, and contact dispensing unit 732 dispenses. This sequence minimizes the time a liquid is in jet tips 740 of non-contact dispensing unit 734 before the liquid is dispensed.

Tape Sealing Assembly

FIG. 34A is an isometric view of instrument 100 with tape sealing assembly 120. Tape sealing assembly 120 includes applicator 800 and locking mechanism 802. Seal web 804 is secured to seal assembly 120 with locking mechanism 802. FIG. 34B is a perspective view of seal web 804 with seals 106 on backer 806. Tape sealing assembly 120 peels seals 106 off of backer 806 of seal web 804. Applicator 800 of tape sealing assembly 120 seals tape 104 with seals 106 after a biological sample and a reagent have been dispensed into tape 104. Seals 106 contain the biological sample and reagent mixture in tape 104 and prevent spillage, evaporation, and contamination of the biological sample and reagent mixture in tape 104.

FIG. 35 is a perspective view of tape sealing assembly 120 positioned adjacent to tape path assembly 118. Tape path assembly 118 includes first position 130, second position 132, third position 134, and fourth position 136. Tape sealing assembly 120 includes head 808. Tape sealing assembly 120 can be moved in the y direction normal to tape path assembly 118 and in the x direction parallel to tape path assembly 118. Thus, tape sealing assembly 120 can be positioned adjacent to tape path assembly 118, with head 808 positioned at second position 132. Tape sealing assembly 120 seals tape 104 at second position 132 after the biological sample and reagent are dispensed.

FIG. 36A is a top view of tape sealing assembly 120 within instrument 100. FIGS. 36B and 36C are perspective views of tape sealing assembly 120. Tape sealing assembly 120 includes x-axis drive mechanism 810 with actuator 812 and drive belt 814, y-axis drive mechanism 816 with actuator 818 and drive belt 820, x-axis stage 822, x-axis rails 824, y-axis stage 826, and y-axis rails 828. X-axis drive mechanism 810 is connected to x-axis stage 822. Y-axis drive mechanism 816 is connected to y-axis stage 826. X-axis stage 822 is installed on x-axis rails 824, and y-axis stage 826 is installed on y-axis rails 828. Y-axis rails 828 are installed on x-axis stage 822.

X-axis drive mechanism 810 and y-axis drive mechanism 816 move tape sealing assembly 120 in the x and y directions in order to align tape sealing assembly 120 with tape path assembly 118 such that seal 106 can be properly applied to tape 104. To move tape sealing assembly 120 in the x direction, actuator 812 drives drive belt 814, transferring motion to x-axis stage 822 and moving x-axis stage across x-axis rails 824. In the embodiments shown in FIGS. 36A-36C, actuator 812 is a motor. In alternate embodiments, actuator 812 can drive belt 814 with any suitable mechanism such as, for example, an electric motor, a pneumatic motor, or a hydraulic motor. To move tape sealing assembly 120 in the y direction, actuator 818 drives drive belt 820, transferring motion to y-axis stage 826 and moving y-axis stage 826 across y-axis rails 828. In the embodiment shown in FIGS. 36A-36C, actuator 818 is a motor. In alternate embodiments, actuator 818 can drive belt 820 with any suitable mechanism such as, for example, an electric motor, a pneumatic motor, or a hydraulic motor.

FIG. 37A is an isometric view of a portion of tape sealing assembly 120. FIG. 37B is a side view of tape sealing assembly 120 with threading path B. Tape sealing assembly 120 includes seal web 804, head 808, spool holder 830 with locking mechanism 802, sensor 834, peel plate 836 with bottom edge 838, backer take-up mechanism 840, lever 862, and slip clutch 874. Backer take-up mechanism 840 includes in-feed guide 842, top guide 844, out-feed guide 846, drive roller 848, friction roller 849, tension bar 856, tension spring 857, shaft 858, shaft actuator 860, and fixed idler 864. Seal web 804 is installed on spool holder 830 and threaded through tape sealing assembly 120 along threading path B.

Prior to threading seal web 804 through tape sealing assembly 120, seal web 804 is placed on spool holder 830 and locking mechanism 802 secures seal web 804 in tape sealing assembly 120. In the embodiments shown in FIGS. 37A-37B, locking mechanism 802 is a knob locking mechanism (shown in further detail in FIGS. 39A-39B). In alternate embodiments, locking mechanism 802 can secure seal web 804 with any suitable mechanism, such as a cam lock and lever. Before seal web 804 is manually threaded through tape sealing assembly 120, a number of seals 106 can be removed such that only backer 806 is manually threaded.

Once seal web 804 is secured on spool holder 830, lever 862 is rotated clockwise approximately ninety degrees to open threading path B (see FIGS. 38B-38C for more detail), and seal web 804 can be manually threaded along threading path B through tape sealing assembly 120. Seal web 804 is first routed across peel plate 836 and around bottom edge 838 of peel plate 836. Seal web 804 enters backer take-up mechanism 840 through in-feed guide 842. Seal web 804 is manually advanced past in-feed guide 842, top guide 844, out-feed guide 846, and out the back of backer take-up mechanism 840. Seal web 804 is manually advanced past fixed idler 864 and fastened to shaft 858. Threading path B is then closed by rotating lever 862 counter-clockwise, returning lever 862 to its original position (see FIGS. 38A-38B for more detail). When threading path B is closed, friction roller 849 clamps backer 806 against drive roller 848. Tension spring 857 determines the amount of clamping force. In one embodiment, seal web 804 can be fastened to a disposable take-up core (not shown) attached to shaft 858. The use of a disposable take-up core simplifies removal of backer 806 from tape sealing assembly 120 after seals 106 have been removed from seal web 804, leaving backer 806 wound around the disposable take-up core (not shown).

Once seal web 804 has been manually threaded through tape sealing assembly 120, seal web 804 can be automatically advanced through tape sealing assembly 120 along threading path B. To automatically advance seal web 804, actuator 850 drives drive roller 848 to advance seal web 804 between friction roller 849 and drive roller 848. Slip clutch 874 of spool holder 830 maintains a desired level of tension in seal web 804 over bottom edge 838 of peel plate 836 and along threading path B between spool holder 830, drive roller 848, and friction roller 849. After tape sealing assembly 120 has automatically advanced seal web 804, shaft actuator 860 rotates shaft 858 to take up slack created in seal web 804 along threading path B between shaft 858 and drive roller 848 and friction roller 849. Shaft 858 can wind or rewind backer 806. As backer 806 from seal web 804 is wound around shaft 858, fixed idler 864 can come into contact with seal web 804. As seal web 804 progresses through tape sealing assembly 120 and seals 106 are removed from backer 806, backer 806 is wound around shaft 858. Backer 806 wound around shaft 858 can be disposed once shaft 858 is full.

As backer take-up mechanism 840 automatically advances seal web 804, sensor 834 detects the location of seal 106 on seal web 804 via sensor path S. Sensor 834 signals backer take-up mechanism 840 to stop advancing seal web 804 when seal 106 is positioned on peel plate 836. Bottom edge 838 of peel plate 836 can have a small radius to facilitate seal peeling when tape sealing assembly 120 is automatically advancing seal web 804. As seal web 804 moves across peel plate 836 and passes around bottom edge 838, sensor 834 signals backer take-up mechanism 840 to stop advancing seal web 804 just before seal 106 moves past bottom edge 838 of peel plate 836 and begins to separate from backer 806. Bottom edge 838 of peel plate 836 is angled such that when seal 106 moves past bottom edge 838, a leading edge of seal 106 is separated from backer 806. In alternate embodiments, a second sensor may be used to sense when a leading edge of seal 106 has passed by bottom edge 838 thereby indicating that the leading edge of seal 106 has separated from backer 806.

FIG. 38A is a perspective view of backer take-up mechanism 840. FIG. 38B is a side view of backer taker-up mechanism 840 with friction roller 849 in a closed position. FIG. 38C is a side view of backer taker-up mechanism 840 with friction roller 849 in an open position. Backer take-up mechanism 840 includes in-feed guide 842, top guide 844, mount 845, out-feed guide 846, drive roller 848, friction roller 849, actuator 850, pulley 852, drive belt 854, tension bar 856, tension spring 857, lever 862, and cam 863.

While seal web 804 is automatically advanced through backer take-up mechanism 840, seal web 804 is pinched between friction roller 849 and drive roller 848 such that friction roller 849 rotates at the same rate as drive roller 848. In order to allow seal web 804 to be manually threaded through threading path B (shown in FIG. 37B), lever 862 can be rotated approximately ninety degrees clockwise to rotate friction roller 849 away from drive roller 848. This moves friction roller 849 from the closed position seen in FIG. 38B to the open position seen in FIG. 38C. Once friction roller 849 is in an open position, seal web 804 can be manually threaded through threading path B, passing by in-feed guide 842 and top guide 844, between friction roller 849 and drive roller 848, and over out-feed guide 846. Lever 862 can then be rotated counter-clockwise to rotate friction roller 849 back to a closed position in which seal web 804 is pinched between drive roller 848 and friction roller 849.

Friction roller 849 is opened and closed by rotation of lever 862. Lever 862 is attached to cam 863 and tension bar 856 such that when lever 862 is rotated, cam 863 rotates as well. When lever 862 is rotated clockwise, cam 863 pushes against mount 845, rotating tension bar 856 clockwise to the position in FIG. 38C. The clockwise rotation of tension bar 856 moves friction roller 849 away from drive roller 848 such that friction roller 849 no longer contacts drive roller 848. This makes it possible for seal web 804 to be manually fed into backer take-up mechanism 840. After seal web 804 has been manually fed into backer take-up mechanism 840, lever 862 can be rotated counterclockwise to rotate cam 863 in the opposite direction to return tension bar 856 to the position in FIG. 38B. This allows spring 857, which pulls on tension bar 856, to pull friction roller 849 into drive roller 848 until seal web 804 is pinched between drive roller 848 and friction roller 849 with a determined amount of force. This makes it possible to automatically advance seal web 804.

FIGS. 39A-39B are cross-sectional views of spool holder 830, with locking mechanism 802 in an unlocked position in FIG. 39A, and locking mechanism 802 in a locked position in FIG. 39B. Spool holder 830 includes locking mechanism 802, compression piece 866, rubber roller 868, screw 870, spool 872, and slip clutch 874.

In order to prevent spool 872 from rotating independently of spool holder 830, spool holder 830 includes locking mechanism 802. Locking mechanism 802 is connected to compression piece 866, which is connected to rubber roller 868, such that when locking mechanism 802 is locked, locking mechanism 802 presses into compression piece 866, which in turn compresses rubber roller 868. Locking mechanism 802 can be locked or unlocked by manually rotating locking mechanism 802 around the end of screw 870. Locking mechanism 802 can be locked part way, thereby providing for a variable pressure on rubber roller 868 and thus a variable pressure on spool 872. When locking mechanism 802 is in the locked position, the maximum pressure is exerted by rubber roller 868 on spool 872. When locking mechanism 802 is in the unlocked position, no pressure is exerted by rubber roller 868 on spool 872. When locking mechanism 802 is in a partially locked position, a partial amount of pressure is exerted by rubber roller 868 on spool 872. In this manner, spool 872 rotates with rubber roller 868 as seal web 804 is automatically advanced through tape sealing assembly 120. Slip clutch 874 is adjustable to maintain a desired tension in backer 806 along threading path B (shown in FIG. 37B) as seal web 804 is manually or automatically advanced through tape sealing assembly 120.

FIG. 40 is a partially transparent perspective view of applicator 800 of tape sealing assembly 120. FIG. 41 is a bottom view of pad 876 of applicator 800. Applicator 800 includes head 808, pad 876 having vacuum holes 878, shaft 880, actuator 882, shaft 884, drive belt 886, pulleys 888, and vacuum chambers 890. Head 808 is connected to and rotates around shaft 880. Head 808 is connected to drive belt 886. Drive belt 886 wraps around pulleys 888 and shaft 884. Shaft 884 is connected to actuator 882. Head 808 includes applicator vacuum chambers 890, which form vacuum holes 878 in applicator pad 876. The convex face of head 808 is lined with pad 876, which can be made from vulcanized rubber to facilitate compression when head 808 presses seal 106 onto tape 104. In order to move head 808, actuator 882 drives shaft 884. Shaft 884 rotates head 808 around shaft 880 via drive belt 886 and pulleys 888. Head 808 rotates around shaft 880 to peel seal 106 from seal web 804 and press seal 106 onto tape 104.

FIGS. 42A-42B are partially transparent perspective views of a portion of tape sealing assembly 120 removing seal 106 from backer 806 of seal web 804. Seal 106 is in a peel position in FIG. 42A. Seal 106 is completely removed from backer 806 in FIG. 42B. Tape sealing assembly 120 includes applicator 800 (shown fully in FIG. 40), peel plate 836 with bottom edge 838 (seen in FIG. 37B), and backer take-up mechanism 840 with in-feed guide 842. Applicator 800 includes head 808 with first edge 892 and second edge 894, pad 876 with vacuum holes 878 (shown in FIGS. 40-41), shaft 880, and vacuum chambers 890 (shown in FIG. 40).

Applicator 800 moves head 808 such that pad 876 faces peel plate 836 with first edge 892 of head 808 near a leading edge of seal 106 in a position to be peeled. Head 808 rotates around shaft 880 at the same rate that seal web 804 is advanced by backer take-up mechanism 840. Vacuum chambers 890 can be activated in stages such that vacuum chambers 890 are activated gradually from first edge 892 to second edge 894 of head 808 as seal 106 is peeled from backer 806. Vacuum chambers 890 can be activated only for the portion of seal 106 peeled and in contact with pad 876. When seal 106 is completely removed from backer 806, all of vacuum chambers 890 can be activated. When seal 106 is completely removed from backer 806 and fully captured by head 808, head 808 moves into a position facing down toward tape 104.

Backer take-up mechanism 840 advances seal web 804 at the same rate as applicator 800 rotates head 808 around shaft 880 to pick up seal 106 from seal web 804. In this manner, backer take-up mechanism 840 can automatically advance seal web 804 around peel plate 836 and through in-teed guide 842, and backer take-up mechanism 840 can work in conjunction with applicator 800 to peel seal 106 from seal web 804.

FIGS. 43A-43B are side views of tape sealing assembly 120 applying seal 106 to tape 104 at second position 132 on tape path assembly 118. FIG. 43A is a side view of tape sealing assembly 120 just before seal 106 is applied. FIG. 43B is a side view of tape sealing assembly 120 just after seal 106 is applied. Tape sealing assembly 120 includes head 808, x-axis stage 822, x-axis rails 824, y-axis stage 826, and y-axis rails 828. Pad 876 is positioned on head 808 and includes vacuum holes 878 (shown in FIGS. 40A-40B), vacuum chambers 890 (shown in FIGS. 40A-40B), first edge 892, and second edge 894.

In order to apply seal 106 to tape 104, y-axis stage 826 moves along y-axis rails 828 toward tape path assembly 118. At the same time, head 808 rotates downward such that second edge 894 of pad 876 touches down on one side of tape 104, allowing seal 106 to make initial contact with tape 104 (shown in FIG. 43A). Y-axis stage 826 continues to advance along rails 828 in synchronized movement with the rotation of head 808. Head 808 rocks from second edge 894 to first edge 892 and then from second edge 894 to first edge 892 a first time as y-axis stage 826 advances and retracts, respectively, along y-axis rails 828. This rocking movement applies pressure to seal 106 and tape 104 to press seal 106 onto tape 104. In this embodiment, if 15 or more pounds of pressure per square inch is applied by head 808 to tape 104, pressure sensitive adhesive on seal 106 can be activated. In an alternate embodiment, the amount of pressure required is dependent on the pressure sensitive adhesive being used. While head 808 moves across tape 104 the first time, vacuum chambers 890 are deactivated and seal 106 is transferred to tape 104. In an alternative embodiment, vacuum chambers 890 are not deactivated and seal 106 is still transferred to tape 104.

After seal 106 has been applied, y-axis stage 826 moves back along y-axis rails 828, across tape 104, and actuator 812 drives x-axis stage 822 along x-axis rails 824 slightly downstream or upstream in the x direction. This motion shifts head 808 slightly downstream or upstream from where seal 106 was applied, and allows y-axis stage 826 to again move forward across tape 104 in synchronized movement with the rotation of head 808. Head 808 rocks from second edge 894 to first edge 892 and then from second edge 894 to first edge 892 a second time as y-axis stage 826 advances and retracts, respectively, along rails 828. This second rocking movement ensures the pressure sensitive adhesive is activated over the entire surface of seal 106, including where vacuum holes 878 were placed relative to tape 104 and seal 106 during the first rocking movement of head 808.

Thermal Unit and Heated Pressure Chamber

FIG. 44 is an isometric view of tape path assembly 118 that runs through instrument 100. Tape path assembly 118 includes first position 130, second position 132, third position 134, and fourth position 136. Also shown in FIG. 45 are tape 104, thermal unit 210, and heated pressure chamber 212.

Tape 104 includes a matrix of wells that can contain a biological sample and reagent mixture. Tape 104 is fed into tape path assembly 118 and then advances to first position 130. Positioned beneath first position 130 is a tape cutter. The tape cutter can be actuated upward to cut tape 104 if desired. Tape 104 can also advance along tape path assembly 118 without being cut. Tape 104 advances from first position 130 to second position 132 along tape path assembly 118. In section position 132, the biological sample and reagent mixture are dispensed into tape 104 with dispensing assembly 114 (not shown). The biological sample and reagent mixture mix together in the matrix of wells of tape 104 to create the biological sample and reagent mixture. The biological sample and reagent mixture in tape 104 can be heated or cooled at second position 132 with a thermal unit that is positioned underneath second position 132. Seal 106 can be also be placed over the matrix of wells of tape 104 to seal the biological sample and reagent mixture in the matrix of wells when tape 104 is in second position 132. After dispensing and sealing, tape 104 advances to third position 134. The biological sample and reagent mixture in tape 104 can be heated or cooled at third position 134 with a thermal unit that is positioned underneath third position 134. Tape 104 can wait at third position 134 until instrument 100 is prepared to analyze the biological sample and reagent mixture in tape 104.

When instrument 100 is ready to amplify and analyze the biological sample and reagent mixture, tape 104 can advance to fourth position 136. Positioned beneath fourth position 136 is thermal unit 210 to control the temperature of the biological sample and reagent mixture in tape 104. Positioned above fourth position 136 is heated pressure chamber 212 to create a constant pressure across the top of tape 104. Thermal unit 210 can be used to heat the biological sample and reagent mixture at a constant temperature or cycle the biological sample and reagent mixture through multiple temperatures. Heated pressure chamber 212 can be sealed off from the ambient air surrounding heated pressure chamber 212. Heated pressure chamber 212 pressurizes and heats the area above fourth position 136 so that the biological sample and reagent mixture in tape 104 can be analyzed.

Heated pressure chamber 212 further heats the biological sample and reagent mixture and prevents condensation on seal 106 covering the matrix of wells of tape 104 to ensure accurate analysis. Either after or during heating, the biological sample and reagent mixture can be analyzed using a camera that is positioned above fourth position 136.

Thermal unit 210 and heated pressure chamber 212 can also be utilized to improve application and adhesion of a bottom side of seal 106 to a top side of tape 104 when tape 104 is to be used external to instrument 100. In one embodiment, this use of tape 104 can be thermal cycling of tape 104 in a water bath. To improve application and adhesion of seal 106 on tape 104, tape 104 is advanced into fourth position 136, thermal unit 210 is raised, heat and pressure are applied to an enclosed space of heated pressure chamber 212, and an amount of time is allowed to elapse. In one embodiment, this time may be 60 seconds. In other embodiments, any reasonable amount of time may be used. When the operation is complete, thermal unit 210 is lowered, heated pressure chamber 212 is raised, and tape 104 can be advanced for use external to instrument 100.

In this embodiment, adhesive between seal 106 and tape 104 is optimally applied at greater than room temperature. Also, the force applied to seal 106 by pressurizing the enclosed space, and thereby pressing seal 106 against tape 104, is uniform across the entirety of seal 106. This force helps ensure that a bottom side of seal 106 of tape 104 that is not immediately over a well of tape 104 is in contact with a top side of tape 104. Thus, applying heat and pressure over time can greatly improve the adhesion of seal 106 to tape 104.

FIG. 45A is a perspective view of thermal unit 210 and heated pressure chamber 212, with heated pressure chamber 212 in a closed position. FIG. 45B is a perspective view of thermal unit 210 and heated pressure chamber 212, with heated pressure chamber 212 in an open position. FIG. 45C is an exploded view of thermal unit 210 and heated pressure chamber 212. Also shown in FIG. 45C are tape 104 and seal 106. FIG. 45D is an exploded view of thermal unit 210. FIG. 45E is an exploded view of heated pressure chamber 212.

Thermal unit 210 is used to control the temperature of the biological sample and reagent mixture in the matrix of wells of tape 104. Tape 104 can be positioned on a top side of thermal unit 210. Thermal unit 210 includes cavities that are configured to receive the matrix of wells of tape 104. The cavities of thermal unit 210 are slightly smaller than or the same size as the wells of tape 104 in order to form a solid contact between the interior surface of the cavities of thermal unit 210 and the exterior surface of the wells of tape 104. Thermal unit 210 can be used to heat and cool the biological sample and reagent mixture in tape 104. Thermal unit 210 can heat the biological sample and reagent mixture at a constant temperature or thermal unit 210 can cycle the biological sample and reagent mixture through multiple temperatures.

Positioned above thermal unit 210 and tape 104 is heated pressure chamber 212. When thermal unit 210 heats a mixture in tape 104, vapor pressure in the wells of tape 104 may cause seal 106 to delaminate from tape 104. Heated pressure chamber 212 pressurizes the space above seal 106 of tape 104 to create a force that pushes against seal 106. The pressure keeps seal 106 in contact with tape 104 and also presses the matrix of wells of tape 104 into the cavities of thermal unit 210 in order to provide better heat transfer between thermal unit 210 and the biological sample and reagent mixture in the matrix of wells of tape 104. Heated pressure chamber 212 also heats the area above tape 104 to prevent condensation from forming on seal 106 so that accurate detection can occur. Either during or after the biological sample and reagent mixture are heated with thermal unit 210, a camera, such as a CCD camera, positioned above heated pressure chamber 212 can analyze the biological sample and reagent mixture in the matrix of wells in tape 104.

Thermal unit 210 includes first housing portion 1002, second housing portion 1004, gasket 1006, mounting feature 1008, inlet ports 1010, outlet ports 1012, recess 1014, thermal block 1020, wells 1022, fluid path 1052 (not shown in FIGS. 45A-45E), and fluid path 1054 (not shown in FIGS. 45A-45E). Thermal block 1020 includes first plate 10'30, first sheet 1032, second plate 1034, second sheet 1036, thermoelectric modules (TEMs) 1038, heat transfer compound 1040 (not shown in FIGS. 45A-45E), and temperature sensor 1042. Thermal unit 210 will be discussed in more detail below in FIGS. 46A-49.

Stationary frame 990 is connected to tape path assembly 118. Movable frame 992 is connected to stationary frame 990 with hinge pins 994. Stationary frame 990 is connected to actuator 996 with vertical mounts 998. Actuator 996 is connected to movable frame 992 with pin 1000. Interface bracket 1058 of heated pressure chamber 212 connects heated pressure chamber 212 to movable frame 992. In the embodiment shown, actuator 996 is an air cylinder. In alternative embodiments, actuator 996 can be another type of actuator, such as a pneumatic, hydraulic, solenoid, or electromagnetic actuator. Actuator 996 moves heated pressure chamber 212 from a closed position (FIG. 45A) to an open position (FIG. 45B) by rotating movable frame 992 around hinge pins 994.

Heated pressure chamber 212 includes interface bracket 1058, clamp 1060, housing 1062, bolts 1064, glass cover plate 1066, gasket 1068, gasket 1070, insulator plate 1071, gasket 1072, gasket 1073, enclosed space 1074 (not shown in FIGS. 45A-45B), heater plenum 1076 with air distribution orifices 1077, heating element 1078, compressed air fitting 1080, electrical connection 1082 (not shown in FIGS. 45A-45E), mask 1084 (not shown in FIGS. 45A-45E), air pump fitting 1086, air pump fitting 1087, air pump fitting 1088, air pump fitting 1089, air pump fitting 1090, air pump fitting 1092, air pump 1094 (not shown in FIGS. 45A-45E), compressed air source 1096 (not shown in FIGS. 45A-45E), and temperature sensor 1098 (not shown in FIGS. 45A-45E). Heated pressure chamber 212 will be discussed in more detail below in FIGS. 50-52.

FIG. 46A is a perspective view of thermal unit 210. FIG. 46B is a perspective view of the bottom of thermal unit 210. FIG. 46C is a top view of thermal unit 210. FIG. 46D is an isometric view of an array of tape 104 on thermal unit 210. Thermal unit 210 includes first housing portion 1002, second housing portion 1004, gasket 1006, mounting feature 1008, inlet ports 1010, outlet ports 1012, recess 1014, thermal block 1020, and cavities 1022. Also shown in FIG. 46D is tape 104.

Thermal unit 210 is positioned along tape path assembly 118 in instrument 100. Thermal unit 210 includes first housing portion 1002 positioned above second housing portion 1004. Gasket 1006 is positioned between first housing portion 1002 and second housing portion 1004. Mounting feature 1008 is positioned around second housing portion 1004. Second housing portion 1004 includes mounting feature 1008, which can be used to mount thermal unit 210 in tape path assembly 118.

Thermal unit 210 also includes two inlet ports 1010 and two outlet ports 1012. Inlet ports 1010 are positioned on a first end of thermal unit 210 and can receive a fluid. That fluid can flow through a thermal management system in first housing portion 1002. Outlet ports 1012 are positioned on a second end of thermal unit 210 and can expel the fluid from the thermal management system in first housing portion 1002. Thermal unit 210 further includes recess 1014. Recess 1014 is positioned on a first side of first housing portion 1002 and extends into first housing portion 1002.

Thermal unit 210 further includes thermal block 1020. Thermal block 1020 is positioned in recess 1014 and does not directly contact first housing portion 1002. Thermal block 1020 includes a heat pump that can be used to heat or cool a biological sample and reagent mixture in a matrix of wells of tape 104. Thermal block 1020 further includes cavities 1022. Cavities 1022 are configured to receive the matrix of wells of tape 104. Each cavity 1022 is sized slightly smaller than or the same as the size of one well on tape 104. This allows an exterior surface of each of the wells in the matrix of wells of tape 104 to form a solid contact with an interior surface of one cavity 1022. Forming a solid contact between an interior surface of each cavity 1022 and an exterior surface of one of the wells in the matrix of wells of tape 104 provides for better heat transfer. The solid contact between each cavity 1022 on thermal block 1020 with a well in the matrix of wells of tape 104 provides better heat transfer between the heat pump in thermal block 1020 and the biological sample and reagent mixture in the matrix of wells of tape 104. Better heat transfer allows for more precise control of the temperature of the biological sample and reagent mixture in the matrix of wells of tape 104.

As seen in the embodiment shown in FIGS. 46A-46C, thermal unit 210 includes 768 cavities 1022. The 768 cavities 1022 include two matrices of 384 cavities 1022 that are arranged in an offset and interlaced pattern. This allows cavities 1022 to receive tape 104 that has a matrix of 768 wells. In alternate embodiments, thermal unit 210 can includes any number of cavities 1022 and cavities 1022 can be arranged in any suitable pattern.

FIG. 47A is a cross-sectional side view of thermal unit 210. FIG. 47B is a cutaway cross-sectional side view of thermal unit 210. FIG. 47C is a schematic view of a cross-section of thermal unit 210. Thermal unit 210 includes first housing portion 1002, second housing portion 1004, gasket 1006, mounting feature 1008, inlet ports 1010, outlet ports 1012, recess 1014, thermal block 1020, and cavities 1022. Thermal block 1020 includes first plate 1030, first sheet 1032, second plate 1034, second sheet 1036, TEMs 1038, and heat transfer compound 1040.

Thermal unit 210 includes first housing portion 1002 that is connected to second housing portion 1004 with gasket 1006. Mounting feature 1008 is part of second housing portion 1004 and can be used to mount second housing portion 1004 in tape path assembly 118. Inlet ports 1010 are connected to a first end of thermal unit 210 and outlet ports 1012 are connected to a second end of thermal unit 210 so that a fluid can be routed through thermal unit 210. Recess 1014 is positioned on a first side of first housing portion 1002. Thermal unit 210 further includes thermal block 1020 positioned in recess 1014 of first housing portion 1002. Thermal block 1020 includes a plurality of cavities 1022 that are configured to receive a matrix of wells of tape 104.

Thermal block 1020 includes first plate 1030, first sheet 1032, second plate 1034, second sheet 1036, TEMs 1038, and heat transfer compound 1040. First plate 1030 is an aluminum plate that is configured to spread heat throughout first plate 1030 in the embodiment shown. In alternate embodiments, first plate 1030 can be made out of any material that is capable of transferring and spreading heat. First plate 1030 is between 1 millimeter (0.039 inches) and 10 millimeters (0.394 inches) thick. More preferable, first plate 1030 is between 1 millimeter (0.039 inches) and 3 millimeters (0.118 inches) thick. First plate 1030 contains cavities 1022 of thermal block 1020. Cavities 1022 are cavities that extend a distance into first plate 1030.

A bottom side of first plate 1030 is attached to a top side of first sheet 1032. A bottom side of first sheet 1032 is attached to a top side of second plate 1034. In this embodiment, first sheet 1032 is a pyrolytic graphite sheet that is used to attach and conduct heat between first plate 1030 and second plate 1034. In other embodiments, first sheet 1032 can be a heat transfer compound or any other heat transfer medium.

Second plate 1034 is a copper plate that is configured to transfer heat in the embodiment shown. In alternate embodiments, second plate 1034 can be made out of any material that is capable of transferring and spreading heat. Second plate 1034 is between 0.5 millimeters (0.019 inches) and 5 millimeters (0.197 inches) thick. More preferably, second plate 1034 is between 0.5 (0.019 inches) millimeters and 2 millimeters (0.079 inches) thick.

A bottom side of second plate 1034 is attached to a top side of second sheet 1036. A bottom side of second sheet 1036 is attached to a top side of TEMs 1038. In this embodiment, second sheet 1036 is a pyrolytic graphite sheet that is used to attach and conduct heat between second plate 1034 and TEMs 1038. In other embodiments, second sheet 1036 can be a heat transfer paste or any other suitable heat transfer medium.

TEMs 1038 are positioned below first plate 1030 and second plate 1034. TEMs 1038 make up the heat pump of thermal block 1020. TEMs 1038 generate heat that can be transferred and spread through second plate 1034 and first plate 1030 into a biological sample and reagent mixture held in a matrix of wells in tape 104. In alternate embodiments, any suitable heat pump can be used in place of TEMs 1038.

Heat transfer compound 1040 is used to attach a bottom side of TEMs 1038 to first housing portion 1002. A portion of a thermal management system is positioned in a lower half of first housing portion 1002 beneath the cavity that holds thermal block 1020. The portion of the thermal management system is used to exchange heat with TEMs 1038. In the embodiment shown, heat transfer compound 1040 is a silicon based compound used to improve heat transfer between the portion of the thermal management system and TEMs 1038. In alternate embodiments, heat transfer compound 1040 can be a pyrolytic graphite sheet or any other suitable heat transfer medium.

Thermal unit 210 is advantageous, as it is compact system that is capable of being placed within tape path assembly 118 in instrument 100. Further, the configuration of thermal unit 210 with multiple layers of plates allows different materials to be used to ensure that the transfer and spread of heat from TEMs 1038 through thermal block 1020 is efficient and effective. Using copper, which has a higher thermal conductivity than aluminum, for second plate 1034 allows heat from TEMs 1038 to spread and transfer uniformly through second plate 1034 to first plate 1030. Using aluminum, which has a lesser density than copper, for first plate 1030 increases the rate of temperature change in first plate 1030 and second plate 1034 for the same amount of energy from TEMs 1038. Combined, the materials used in first plate 1030, first sheet 1032, second plate 1034, and second sheet 1036 ensure that heat is transferred and spread throughout first plate 1030 to rapidly and uniformly heat or cool the biological sample and reagent mixture in the matrix of wells of tape 104 positioned on thermal unit 210. Uniformly heating or cooling the biological sample and reagent mixture is necessary to obtain consistent and accurate results when analyzing the biological sample and reagent mixture, in this context, heating or cooling should be understood to be inclusive of thermal cycling.

FIG. 48 is a top plan see-through view of a top side of thermal unit 210. Thermal unit 210 includes first housing portion 1002, thermal block 1020, and cavities 1022. Thermal block 1020 includes TEMs 1038 and temperature sensor 1042.

First housing portion 1002 of thermal unit 210 houses thermal block 1020. Cavities 1022 are positioned on a top side of thermal block 1020 and are configured to receive a matrix of wells of tape 104. Thermal block 1020 includes TEMs 1038. In the embodiment shown in FIG. 48, thermal block 1020 includes six different TEMs 1038. In alternate embodiments, thermal block 1020 can include any number of TEMs 1038. Further, TEMs 1038 can be any heat source that is capable of heating and cooling a biological sample and a reagent.

TEMs 1038 are arranged to uniformly heat or cool thermal block 1020. As seen in the embodiment shown in FIG. 48, three TEMs 1038 are positioned on a first side of thermal unit 210 and the remaining three TEMs 1038 are positioned on a second side of thermal unit 210. Heat that is generated in TEMs 1038 can transfer through thermal block 1020 to heat or cool a biological sample and reagent mixture in the matrix of wells of tape 104 that are positioned in cavities 1022 of thermal unit 210. Temperature sensor 1042 measures the temperature of thermal unit block 1020. In the embodiment shown, temperature sensor 1042 is a resistance temperature detector that monitors the temperature of thermal block 1020 and provides feedback to the control system of instrument 100 such that the control system either heats, cools, or maintains a set point temperature of thermal block 1020.

FIG. 49 is a bottom plan see-through view of thermal unit 210. Thermal unit 210 includes first housing portion 1002, fluid path 1052, and fluid path 1054. Fluid path 1052 and fluid path 1054 are positioned in a bottom half of first housing portion 1002.

Fluid path 1052 is a cavity that runs from a first end of thermal unit 210 to a second end of thermal unit 210. Fluid path 1052 snakes back and forth between the first end and the second end of thermal unit 210 on a first side of thermal unit 210. A fluid can run through fluid path 1052 to exchange heat with thermal block 1020. Fluid flows through an inlet port (see FIGS. 45A-45B) on a first end of thermal unit 210, through fluid path 1052, and out of an outlet port (see FIGS. 45A-45B) on a second end of thermal unit 210.

Fluid path 1054 is a cavity that runs from a first end of thermal unit 210 to a second end of thermal unit 210. Fluid path 1054 snakes back and forth between the first end and the second end of thermal unit 210 on a second side of thermal unit 210. A fluid can run through fluid path 1054 to exchange heat with thermal block 1020. Fluid flows through an inlet port (see FIGS. 45A-45B) on a first end of thermal unit 210, through fluid path 1054, and out of an outlet port (see FIGS. 45A-45B) on a second end of thermal unit 210.

Fluid path 1052 and fluid path 1054 are part of a thermal management system in instrument 100. The thermal management system is a closed loop system and fluid that flows through fluid path 1052 and fluid path 1054 flows through a radiator (not shown in FIG. 49) to be cooled or heated as needed. That fluid can then flow through fluid path 1052 and fluid path 1054 again to exchange heat with thermal unit 210. The thermal management system is advantageous, as it is an efficient and compact way to control the temperature of thermal block 1020 in thermal unit 210.

FIG. 50 is a cross-sectional view of tape 104 with seal 106 sealed between thermal unit 210 and heated pressure chamber 212. Heated pressure chamber 212 includes interface bracket 1058, clamp 1060, housing 1062, bolts 1064, glass cover plate 1066, gasket 1068, gasket 1070, insulator plate 1071, gasket 1072, gasket 1073, enclosed space 1074, heater plenum 1076 with distribution orifices 1077, heating element 1078, compressed air fitting 1080, and multi-pin electrical connector 1082 (seen in FIG. 51). Clamp 1060 can be made of aluminum and is connected to housing 1062 with bolts 1064. Housing 1062 can be a low thermal conductivity thermoplastic polymer such as polyether ether ketone (PEEK) such that housing 1062 does not absorb heat generated within enclosed space 1074. In alternative embodiments, housing 1062 can be any heat resistant material or material with low thermal conductivity.

Glass cover plate 1066 is clamped in between gasket 1068 and gasket 1070. Clamp 1060 holds glass cover plate 1066 in place so that glass cover plate 1066 does not move when pressure is applied to glass cover plate 1066. Gasket 1068 creates a seal between glass cover plate 1066 and clamp 1060. Gasket 1070 creates a seal between glass cover plate 1066 and housing 1062. Gaskets 1068 and 1070 prevent chipping and cracking of glass cover plate 1066 and facilitate even pressure distribution across glass cover plate 1066. Gasket 1072 creates a seal between housing 1062 and tape 104.

Clamp 1060, housing 1062, bolts 1064, glass cover plate 1066, gasket 1068, gasket 1070, and gasket 1072 create enclosed space 1074. Enclosed space 1074 is a sealed, enclosed space above tape 104 and seal 106 that can be heated and pressurized. Insulator plate 1071, gasket 1073, heater plenum 1076, and heating element 1078 are located within enclosed space 1074. Insulator plate 1071 insulates heating element 1078 and heater plenum 1076, minimizing heat loss from enclosed space 1074. Heating element 1078 heats enclosed space 1074 to prevent condensation on seal 106 in the wells of tape 104. Heater plenum 1076 includes air distribution orifices 1077, which circulate air within enclosed space 1074 to facilitate uniform heat distribution within enclosed space 1074. Gasket 1073 creates a seal between heater plenum 1076 and housing 1062. Heater plenum 1076 can be aluminum. In alternative embodiments, heater plenum 1076 can be any other suitable material with high thermal conductivity, such as stainless steel. Compressed air fitting 1080 is attached to housing 1062 and can be connected to a compressed air source to provide compressed air for pressurizing enclosed space 1074. Multi-pin electrical connector 1082 is attached to housing 1062 and powers heating element 1078.

In order to amplify and analyze a biological sample and reagent mixture, tape 104 with seal 106 is positioned between thermal unit 210 and heated pressure chamber 212 such that a matrix of wells of tape 104 is aligned with the matrix of wells of thermal unit 210. Thermal unit 210 is raised and heated pressure chamber 212 is lowered such that tape 104 is pressed against gasket 1072 and the matrix of wells of tape 104 is pressed into the matrix of wells of thermal unit 210. Heated pressure chamber 212 is sealed by raising the lift to which thermal unit 210 is attached, which in turn causes a top surface of first housing portion 1002 of thermal unit 210 to come into contact with a bottom surface of tape 104. This pushes a top surface of tape 104 up against a bottom surface of gasket 1072 of the heated pressure chamber 212. Compressed air is fed through compressed air fitting 1080 into enclosed space 1074 above tape 104 and seal 106. Compressed air pressurizes enclosed space 1074 to between 5 psi and 20 psi. Heating element 1078 heats the air in enclosed space 1074. Depending on the temperature of thermal unit 210 during amplification, the air temperature within enclosed space 1074 may be between 70 and 120 degrees Celsius. Heater plenum 1076 with air distribution orifices 1077 accelerates heating and facilitates uniform heat distribution within enclosed space 1074.

A desired pressure and temperature is maintained in enclosed space 1074 while a biological sample and reagent mixture is amplified and detected in the matrix of wells of tape 104. When amplification and detection is complete, thermal unit 210 is lowered, heated pressure chamber 212 is raised, and tape 104 advances along tape path 118 such that a new matrix of wells of tape 104 is positioned between thermal unit 210 and heated pressure chamber 212.

FIG. 51 is an isometric view of heated pressure chamber 212. Heated pressure chamber 212 includes interface bracket 1058, clamp 1060, housing 1062, heater plenum 1076 with air distribution orifices 1077, glass cover plate 1066 with mask 1084, compressed air fitting 1080, multi-pin electrical connector 1082, and air pump fittings 1086. Air pump fittings 1086 can be connected to an air pump for pumping air into and out of enclosed space 1074 to facilitate uniform temperature distribution within enclosed space 1074.

Glass cover plate 1066 with mask 1084 allows accurate detection of the mixture in the matrix of wells of tape 104. Mask 1084 is two dots on glass cover plate 1066 and allows instrument 100 to recognize that an array of tape 104 is present in thermal unit 210. Mask 1084 can be etched or printed onto a bottom surface of glass cover plate 1066. Glass cover plate 1066 can be a ten millimeter thick anti-reflective coated glass cover plate to allow the camera to see the entire matrix of wells during detection.

FIG. 52 is a top view of heated pressure chamber 212. Heated pressure chamber 212 includes clamp 1060, bolts 1064, glass cover plate 1066 with mask 1084, heater plenum 1076 (shown in FIGS. 50-51), heating element 1078 (shown in FIG. 50), compressed air fitting 1080, multi-pin electrical connector 1082, air pump fitting 1086, air pump fitting 1087, air pump fitting 1088, air pump fitting 1089, air pump fitting 1090, and air pump fitting 1092, air pump 1094, compressed air source 1096, and temperature sensor 1098. Compressed air source 1096 pumps compressed air into enclosed space 1074 through compressed air fitting 1080 for pressurizing enclosed space 1074.

Air pump fitting 1086, air pump fitting 1087, air pump fitting 1088, air pump fitting 1089, air pump fitting 1090, and air pump fitting 1092 are connected to air pump 1094, forming a closed circuit of air flow. Air flows out of air pump 1094, through air pump fittings 1086, 1087, 1088, and 1089, across enclosed space 1074, out of air pump fittings 1090 and 1092, and back into air pump 1094. The closed circuit of air flow moves the air at approximately four liters per minute within enclosed space 1074 to facilitate uniform temperature distribution within enclosed space 1074. In alternative embodiments, air can flow into any four of air pump fittings 1086, 1087, 1088, 1089, 1090, and 1092 and out of any two of air pump fittings 1086, 1087, 1088, 1089, 1090, and 1092.

Heating element 1078 is embedded in a heat-tolerant media and connected to heater plenum 1076 with an adhesive. In one embodiment, the heat-tolerant media can be a polyamide. In an alternative embodiment, the heat-tolerant media can be a silicone rubber media. Heating element 1078 is connected to heater plenum 1076 with adhesive. The adhesive sticks to heater plenum 1076 and the heat-tolerant media in which heating element 1078 is embedded. In one embodiment, heating element 1078 can be a copper-based resistive heater, such as a copper alloy heater. In alternative embodiments, heating element 1078 is a heater that fits within the space constraints of enclosed space 1074. Heating element 1078 heats the air in enclosed space 1074 to a desired temperature and heater plenum 1076 absorbs and transfers the heat to facilitate uniform temperature distribution within enclosed space 1074.

Multi-pin electrical connector 1082 provides power to heating element 1078 and power to and sensor values from temperature sensor 1098 while maintaining a pressure-type connection to housing 1062. Temperature sensor 1098 senses the temperature of heater plenum 1076 such that the temperature within enclosed space 1074 can be controlled. In one embodiment, heater plenum 1076 is maintained at 115 degrees Celsius such that the temperature in enclosed space 1074 is approximately 105 degrees Celsius. In alternative embodiments, heater plenum 1076 is maintained at a temperature such that the air temperature within enclosed space 1074 is maintained at a desired temperature between 70 and 120 degrees Celsius.

Alternative Embodiments of the Overall Instrument

FIG. 53A is a schematic of instrument 100A. FIG. 53B is a schematic of instrument 100B. Instrument 100A and instrument 100B are alternative embodiments of instrument 100 seen in FIGS. 1-52. Instrument 100A includes tape path assembly 118A, which includes tape cutting station 1100, dispensing and sealing station 1102, waiting station 1104, and a plurality of amplification and detection stations 1106 (including amplification and detection station 1106A, amplification and detection station 1106B, and amplification and detection station 1106C). Instrument 100B includes tape path assembly 118B, which includes tape cutting station 1110, dispensing and sealing station 1112, a plurality of waiting stations 1114 (including waiting station 1114A and waiting station 1114B), and a plurality of amplification and detection stations 1116 (including amplification and detection station 1116A, amplification and detection station 1116B, and amplification and detection station 1116C).

Tape path assemblies 118A and 118B extend through instruments 100 A and 100B, respectively, and provide a path along which tape 104 having a plurality of wells can advance. Tape 104 moves through instruments 100A and 100B from an entrance to an exit of tape path assemblies 118A and 118B through the different stations on tape path assemblies 118A and 118B.

Instrument 100A includes tape cutting station 1100 that is positioned between an entrance of tape path assembly 118A and dispensing and sealing station 1102; dispensing and sealing station 1102 is positioned between tape cutting station 1100 and waiting station 1104; waiting station 1104 is positioned between dispensing and sealing station 1102 and the plurality of amplification and detections stations 1106; and the plurality of amplification and detection stations 1106 are positioned between waiting station 1104 and an exit of tape path assembly 118 A. The plurality of amplification and detection stations 1106 include three different amplification and detection stations in the embodiment shown in FIG. 53A, but can include any number of amplification and detection stations in alternate embodiments.

Amplification and detection stations 1106 are arranged in parallel with one another in instrument 100A. Tape 104 that enters instrument 100 A can be cut into a first tape segment with a single array of wells at tape cutting station 1100. The first tape segment can then move to dispensing and sealing station 1102, where a biological sample and a reagent can be dispensed into the first tape segment to form a biological sample and reagent mixture. The biological sample and reagent mixture can then be sealed in the first tape segment at dispensing and sealing station 1102. Further, the first tape segment can be cooled to prevent the biological sample and reagent mixture from undergoing a chemical reaction or heated to incubate the biological sample and reagent mixture at dispensing and sealing station 1102. The first tape segment can then move to waiting station 1104 where the first tape segment can again be cooled to prevent the biological sample and reagent mixture from undergoing a chemical reaction or heated to incubate the biological sample and reagent mixture.

From waiting station 1104, the first tape segment can be routed to amplification and detection station 1106 A, amplification and detection station 1106B, or amplification and detection station 1106C. At any of the plurality of amplification and detection stations 1106, the biological sample and reagent mixture can undergo thermal cycling or be heated at a constant temperature. The biological sample and reagent mixture can also be analyzed at amplification and detection stations 1106.

After first tape segment has moved from dispensing and sealing station 1102 to waiting station 1104, a second tape segment can be cut from tape 104 and moved to dispensing and sealing station 1102. The second tape segment will undergo the same processing as the first tape segment but it can be moved to a different one of the plurality of amplification and detection stations 1106. Further, a third tape segment can be cut from tape 104 and moved to dispensing and sealing station 1102. The third tape segment will undergo the same processing as the first and second tape segments and moved to the final of the plurality of amplification and detection stations 1106. Having a plurality of amplification and detection stations 1106 allows instrument 100 A to analyze multiple arrays of tape 104 at the same time. Amplification and detection stations 1106 can begin the processing of tape 104 when tape 104 reaches each amplification and detection station 1106, or amplification and detection stations 1106 can be run at the same time. In an alternate embodiment, waiting station 1104 can be eliminated and the tape segments can pass from dispensing and sealing station 1102 to one of the plurality of amplification and detection stations 1106.

Each of the plurality of amplification and detection stations 1106 can include the same means for analysis or different means for analysis. For example, amplification and detection stations 1106 can all analyze the biological sample and reagent mixture using polymerize chain reaction analysis. Alternatively, amplification and detection station 1106A can analyze the biological sample and reagent mixture using polymerize chain reaction analysis, amplification and detection station 1106B can analyze the biological sample and reagent mixture using melt curve analysis, and amplification and detection station 1106C can analyze the biological sample and reagent mixture using isothermal amplification analysis. Having different means of analysis at each amplification and detection station 1106 allows a sample to undergo different analysis at the same time.

Instrument 100B includes tape cutting station 1110 that is positioned between an entrance of tape path assembly 118B and dispensing and sealing station 1112; dispensing and sealing station 1112 is positioned between tape cutting station 1110 and waiting station 1114A, waiting station 1114A is positioned between dispending and sealing station 1112 and waiting station 1114B; waiting station 1114B is positioned between waiting station 1114A and amplification and detection station 1116A; amplification and detection station 1116A is positioned between waiting station 1114B and amplification and detection station 1116B; amplification and detection station 1116B is positioned between amplification and detection station 1116A and amplification and detection station 1116C; and amplification and detection station 1116C is positioned between amplification and detection stations 1116B and an exit of tape path assembly 118A. The plurality of amplification and detection stations 1116 include three different amplification and detection stations in the embodiment shown in FIG. 53B, but can include any number of amplification and detection stations in alternate embodiments.

Amplification and detection stations 1116 are arranged in series with one another in instrument 100B. Tape 104 that enters instrument 100B can be cut into a first tape segment with a single array of wells at tape cutting station 1100 or tape 104 can advance as a web through tape cutting station 1110 without being cut. A first array of tape 104 can then move to dispensing and sealing station 1112, where a biological sample and a reagent can be dispensed into the first array of tape 104 to form a biological sample and reagent mixture. The biological sample and reagent mixture can be then be sealed in the first array of tape 104 at dispensing and sealing station 1112. Further, the first array of tape 104 can be cooled to prevent the biological sample and reagent mixture from undergoing a chemical reaction or heated to incubate the biological sample and reagent mixture at dispensing and sealing station 1112. The first array of tape 104 can then move to waiting station 1114A where the first array of tape 104 can again be cooled to prevent the biological sample and reagent mixture from undergoing a chemical reaction or heated to incubate the biological sample and reagent mixture.

When the first array of tape 104 advances to waiting station 1114A, a second array of tape 104 can move to dispensing and sealing station 1112. The second array of tape 104 can then undergo the same processing as the first array of tape 104 at dispensing and sealing station 1112. After this, the first array of tape 104 can move to waiting station 1114B and the second array of tape 104 can move to waiting station 1114A. Both waiting stations 1114A and 1114B can cool or heat the biological sample and reagent mixture. A third array of tape 104 can then move to dispensing and sealing station 1112. The third array of tape 104 can then undergo the same processing as the first array of tape 104 at dispensing and sealing station 1112. At this point, tape 104 can move through instrument 100B so that the first array of tape 104 is positioned in amplification and detection station 1116C, the second array of tape 104 is positioned in amplification and detection station 1116B, and the third array of tape 104 is positioned in amplification and detection station 1116C. At any of the plurality of amplification and detection stations 1116, the biological sample and reagent mixture can undergo thermal cycling or be heated at a constant temperature. The biological sample and reagent mixture can also be analyzed at amplification and detection stations 1116. Having a plurality of amplification and detection stations 1116 allows instrument 100B to analyze multiple arrays at a single time. In an alternate embodiment, waiting stations 1114A and 1114B can be eliminated and tape 104 can move from dispensing and sealing station 1112 to the plurality of amplification and detection stations 1116.

Each of the plurality of amplification and detection stations 1116 can include the same means for analysis or different means for analysis. For example, amplification and detection stations 1116 can all analyze the biological sample and reagent mixture using polymerize chain reaction analysis. Alternatively, amplification and detection station 1116A can analyze the biological sample and reagent mixture using polymerize chain reaction analysis, amplification and detection station 1116B can analyze the biological sample and reagent mixture using melt curve analysis, and amplification and detection station 1116C can analyze the biological sample and reagent mixture using isothermal amplification analysis.

Instrument 100A and instrument 100B are example alternate embodiments of instrument 100. It is appreciated that there can be any number of alternate embodiments of instrument 100. For example, instrument 100 can include any number of amplification and detection stations arranged in series, parallel, or both. Further, instrument 100 could include any number of dispensing stations arranged in series, parallel, or both. Instrument 100 can also include any number of waiting stations or no waiting stations. Additionally, instrument 100 could also include any number of tape path assemblies. Having different means of analysis at each amplification and detection station 1116 allows a sample to undergo different analysis at the same time.

The preceding description is a non-exclusive description of possible embodiments of the present disclosure. It is contemplated that the elements disclosed can be combined in any manner. The instrument described can optionally include, additionally and/or alternatively, any one or more of the features, configurations and/or components described in the preceding description.

While the invention has been described with reference to an exemplary embodiment(s), it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment(s) disclosed, but that the invention will include all embodiments falling within the scope of the appended claims.

The invention claimed is:

1. A dispensing assembly comprising:
    a gantry with an x-axis track and a y-axis track, the y-axis track of the gantry configured to move along the x-axis track of the gantry;
    a dispensing head attached to and configured to move along the y-axis track of the gantry, the dispensing head comprising:
        a first z-axis track;
        a second z-axis track;
        a contact dispensing unit attached to an configured to move along the first z-axis track, the contact dispensing unit comprising one or more pipette tips; and
        a non-contact dispensing unit attached to and configured to move along the second z-axis track, the non-contact dispensing unit comprising a plurlity of jet tips and respective valves;
    a dispensing enclosure attached to the y-axis track of the gantry, the dispensing enclosure having a pressure reservoir, a metering pump for pressurizing the pressure reservoir to provide a constant pressure, and electronics configured to actuate the respective valves of the non-contact dispensing unit for dispensing; and
    one or more tubes connecting respective jet tips of the non-contact dispensing unit to the pressure reservoir of the dispensing enclosure.

2. The dispensing assembly of claim 1, wherein the dispensing head and the dispensing enclosure are configured to move simultaneously along the y-axis track of the gantry.

3. The dispensing assembly of claim 1, wherein the contact dispensing unit comprises a plurality of pipette tips.

4. The dispensing assembly of claim 1, wherein the second z-axis track comprises a plurality of independent z-axis tracks, each of the plurality of jet tips and the respective valves are attached to one of the plurality of independent z-axis tracks.

5. The dispensing assembly of claim 1, wherein the x-axis track of the gantry comprises a cable carrier having one end that is attached to the y-axis track of the gantry, and the y-axis track of the gantry comprises a cable carrier having one end that is attached to the dispensing enclosure.

6. The dispensing assembly of claim 1, wherein the first z-axis track and the second z-axis track each comprise a safety mechanism configured to hold or retract the respective contact or non-contact dispensing unit in the event of a loss of power.

* * * * *

UNITED STATES PATENT AND TRADEMARK OFFICE
CERTIFICATE OF CORRECTION

PATENT NO. : 11,231,430 B2
APPLICATION NO. : 16/799584
DATED : January 25, 2022
INVENTOR(S) : Darren Lynn Cook et al.

It is certified that error appears in the above-identified patent and that said Letters Patent is hereby corrected as shown below:

In the Claims

In Claim 1:
Column 56, Line 16, the text "non-contact dispensing unit comprising a plurlity of" should read
-- non-contact dispensing unit comprising a plurality of --

Signed and Sealed this
Twelfth Day of April, 2022

Drew Hirshfeld
*Performing the Functions and Duties of the*
*Under Secretary of Commerce for Intellectual Property and*
*Director of the United States Patent and Trademark Office*